United States Patent
Reitman et al.

(10) Patent No.: US 8,691,960 B2
(45) Date of Patent: Apr. 8, 2014

(54) OXIDOREDUCTASES FOR ENANTIOSELECTIVE REACTIONS

(71) Applicant: Duke University, Durham, NC (US)

(72) Inventors: Zachary James Reitman, Durham, NC (US); Hai Yan, Chapel Hill, NC (US); Bryan Daehahn Choi, Durham, NC (US); John Howard Sampson, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/778,167

(22) Filed: Feb. 27, 2013

(65) Prior Publication Data

US 2013/0266998 A1    Oct. 10, 2013

Related U.S. Application Data

(60) Provisional application No. 61/604,630, filed on Feb. 29, 2012.

(51) Int. Cl.
 *C12N 15/53*  (2006.01)
 *C12N 15/52*  (2006.01)

(52) U.S. Cl.
 CPC ..................................... *C12N 15/52* (2013.01)
 USPC ....... 536/23.2; 435/189; 435/142; 435/320.1; 435/325; 435/252.3; 435/252.33; 435/254.11; 435/254.21; 435/254.23; 435/254.22; 435/254.2

(58) Field of Classification Search
 None
 See application file for complete search history.

(56) References Cited

U.S. PATENT DOCUMENTS

| | | | |
|---|---|---|---|
| 5,487,987 A | 1/1996 | Frost et al. | |
| 6,365,376 B1 | 4/2002 | Brzostowicz et al. | |
| 7,799,545 B2 | 9/2010 | Burgard et al. | |
| 8,227,237 B2* | 7/2012 | Reppas et al. | 435/257.2 |
| 2008/0229451 A1 | 9/2008 | Cao et al. | |
| 2009/0139134 A1* | 6/2009 | Yoshikuni et al. | 44/307 |
| 2009/0155873 A1* | 6/2009 | Kashiyama et al. | 435/165 |

(Continued)

FOREIGN PATENT DOCUMENTS

WO    WO 2010/104391 A2    9/2010

OTHER PUBLICATIONS

Suzuki et al., "Enhancement of the latent 3-isopropylmalate dehydrogenase activity of promiscuous homoisocitrate dehydrogenase by directed evolution", Biochemical Journal, vol. 431, pp. 401-410, 2010.*

(Continued)

*Primary Examiner* — Rebecca Prouty
*Assistant Examiner* — Richard Ekstrom
(74) *Attorney, Agent, or Firm* — Womble Carlyle Sandridge & Rice, LLP

(57) ABSTRACT

Described herein are compositions and methods for generating oxidoreductases for enantioselective reactions. Described herein are compositions and methods for generating neomorphic (R)-2-hydroxyacid dehydrogenases capable of enzymatically converting a 1-carboxy-2-ketoacid to a 1-carboxy-(R)-2-hydroxyacid, or the reverse reaction. Illustrative examples include (a) (R)-2-hydroxyadipate dehydrogenase and uses thereof for converting 2-oxoadipate to (R)-2-hydroxyadipate, or the reverse reaction; and (b) (R)-2-hydroxyglutarate dehydrogenase and uses thereof for converting 2-oxoglutarate to (R)-2-hydroxyglutarate, or the reverse reaction. Also described herein are compositions and methods for generating non-natural microbial organisms to enzymatically convert 2-oxoadipate to (E)-2-hexenedioate or adipate, or to enzymatically convert 2-oxoglutarate to (E)-2-pentenedioate or glutarate, or the respective reverse reactions.

20 Claims, 21 Drawing Sheets

(56) References Cited

U.S. PATENT DOCUMENTS

| | | |
|---|---|---|
| 2010/0151536 A1 | 6/2010 | Baynes et al. |
| 2010/0317069 A1 | 12/2010 | Burk et al. |
| 2010/0330626 A1 | 12/2010 | Burgard et al. |
| 2011/0091944 A1 | 4/2011 | Wu et al. |
| 2011/0195466 A1 | 8/2011 | Burgard et al. |
| 2012/0021472 A1 | 1/2012 | Zelder et al. |
| 2012/0028320 A1* | 2/2012 | Raemakers-Franken et al. ............... 435/135 |

OTHER PUBLICATIONS

Tracewell et al., "Directed enzyme evolution: climbing fitness peaks one amino acid at a time", Current Opinion in Chemical Biology, vol. 13, pp. 3-9, 2009.*
Miyazaki, "Identification of a novel trifunctional homoisocitrate dehydrogenase and modulation of the broad substrate specificity through site-directed mutagenesis", Biochemical and Biophysical Research Communications, vol. 336, pp. 596-602, 2005.*
Miyazaki et al., "Crystal structure of tetrameric homoisocitrate dehydrogenase from an extreme thermophile, *Thermus thermophilus*: Involvement of hydrophobic dimer-dimer interaction in extremely high thermotolerance", Journal of Bacteriology, vol. 187, No. 19, pp. 6779-6788.*
Clarke et al., Rational construction of a 2-hyroxyacid dehydrogenase with new substrate specificity. Biochem. Biophys. Res. Comm. 148(1): 15-23 (1987).
Aktas and Cook, "A Lysine-Tyrosine Pair Carries Out Acid-Base Chemistry in the Metal Ion-Dependent Pyridine Dinucleotide-Linked . . . " Biochemistry 48(16):3565-3577 (2009).
Bleeker et al., "IDH1 Mutations at Residue p.R132 (IDH1 R132) Occur Frequently in High-Grade Gliomas But Not in Other Solid Tumors," Human Mutation 30(1): 7-11 (2009).
Bulfer et al., "Crystal structure of homoisocitrate dehydrogenase from *Schizosaccharomyces pombe*," Proteins. Oct. 24, 2011. doi: 10.1002/prot.23231 661-666 (2011).
Chattoo and Sherman, "Selection of Lys2 Mutants of the Yeast *Saccharomyces cerevesiae* by the Utilization of α-aminoadipate," Genetics 93: 51-65 (1979).
Dang et al., "Cancer-associated IDH1 mutations produce 2-hydroxyglutarate," Nature 462:739-744 (2009).
Dang, "A biocatalyst inspired by cancer," Nature Chemical Biology 8:874-875 (2012).
Goh et al., "Characterization of the human gene encoding α-aminoadipate aminotransferase (AADAT)," Mol. Genetics Metabol. 76: 172-180 (2002).
Gross et al., "Cancer-associated metabolite 2-hydroxyglutarate accumulates in acute myelogenous leukemia with isocitrate . . . " J. Exp. Medicine 207(2): 339-344 (2010).
Jin et al., "2-Hydroxyglutarate Production, but Not Dominant Negative Function, Is Conferred by Glioma-Derived NADP+-Dependent Isocitrate . . . " PloS one 6(2)e16812: 1-8 (2011).
Lin et al., "Chemical Mechanism of Homoisocitrate Dehydrogenase from *Saccharomyces cereVisiae*," Biochemistry 47(13):4169-4180 (2008).
Lin et al., "Complete Kinetic Mechanism of Homoisocitrate Dehydrogenase from *Saccharomyces cereVisiae*," Biochemistry 46(3):890-898 (2007).
Lin et al., "Site-Directed Mutagenesis as a Probe of the Acid-Base Catalytic Mechanism of Homoisocitrate Dehydrogenase from . . . ," Biochemistry 48(30): 7305-7312 (2009).
Mardis et al., "Recurring Mutations Found by Sequencing an Acute Myeloid Leukemia Genome," New Eng. J. Med. 361: 1058-1066 (2009).
Miyazaki et al., "Characterization of Homoisocitrate Dehydrogenase Involved in Lysine Biosynthesis of an Extremely Thermophilic . . . " J. Biol. Chem. 278(3): 1864-1871 (2003).
Nango et al., "Structure of *Thermus thermophilus* homoisocitrate dehydrogenase in complex with a designed inhibitor," J. Biochem 150(6): 607-614 (2011).
Nature Research Highlight, "Enzyme design inspired by cancer," Nature 489: 744 (2012).
Niu et al., "Benzene-Free Synthesis of Adipic Acid," Biotechnology Progress 18: 201-211 (2002).
Northrop and Cleland, "The Kinetics of Pig Heart Triphosphopyridine Nucleotide-Isocitrate Dehydrogenase," J. Biol. Chem. 249(9):2928-2931 (1974).
Parthasarathy et al., "Substrate Specificity of 2-Hydroxyglutaryl-CoA Dehydratase from *Clostridium symbiosum*: Toward a Bio-Based . . . " Biochemistry 50:3540-3550 (2011).
Pietrak et al., "A Tale of Two Subunits: How the Neomorphic R132H IDH1 Mutation Enhances Production of rHG," Biochemistry 50: 4804-4812 (2011).
Polen et al., "Toward biotechnological production of adipic acid and precursors from biorenewables," J. Biotechnology: 1-10 (2012).
Reitman et al., "Enzyme redesign guided by cancer-derived IDH1 mutations," Nature Chemical Biology 8: 887-889 (2012).
Ro et al., Induction of multiple pleiotropic drug resistance genes in yeast engineered to produce an increased level of . . . , BMC Biotechnology 8:83 1-14 (2008).
Sato et al., "A "Green" Route to Adipic Acid: Direct Oxidation of Cyclohexenes with 30 Percent Hydrogen Peroxide," Science 281: 1646-1647 (1998).
Struys et al., Measurement of Urinary D- and L-2-Hydroxyglutarate Enantiomers by Stable-Isotope-dilution Liquid Chromatography . . . Clin. Chemistry 50(8): 1391-1395 (2004).
Suda et al., "Purification and Properties of α-Ketoadipate Reductase, a Newly Discovered Enzyme from Human Placenta," Arch. Biochem. Biophys. 176: 610-620 (1976).
Suda et al., "Subcellular Localization and Tissue Distribution of α-Ketoadipate Reduction and Oxidation in the Rat," Biochem. Biophys. Res. Comm. 77(2): 586-591 (1977).
Tanaka et al., *Desulfovirga adipica* gen. nov., sp. nov., an adipate-degrading, Gram-negative, sulfate-reducing bacterium, Int. J. Systemat. Evol. Microbiol. 50:639-644 (2000).
Uhr et al., "The Kinetics of Pig Heart Triphosphopyridine Nucleotide-Isocitrate Dehydrogenase," J. Biol. Chem. 249(9):2920-2927 (1974).
Ward et al., "Identification of additional IDH mutations associated with oncometabolite R(−)-2-hydroxyglutarate production," Oncogene (2011) 1-8 (2011).
Ward et al., "The Common Feature of Leukemia-Associated IDH1 and IDH2 Mutations is a Neomorphic Enzyme Activity Converting α-Ketoglutarate . . . " Cancer Cell 17:225-234 (2010).
Wischgoll et al., "Decarboxylating and Nondecarboxylating Glutaryl-Coenzyme A Dehydrogenases in the Aromatic . . ." J. Bacteriology 191(13): 4401-4409 (2009).
Wischgoll et al., "Structural Basis for Promoting and Preventing Decarboxylation in Glutaryl-Coenzyme A Dehydrogenases," Biochemistry 49(25): 5350-5357 (2010).
Xu et al., "Structures of Human Cytosolic NADP-dependent Isocitrate Dehydrogenase Reveal a Novel Self-regulatory Mechanism . . . ," J. Biol. Chem 279(32):33946-33957 (2004).
Xu et al., "The α-Aminoadipate Pathway for Lysine Biosynthesis in Fungi," Cell Biochem. and Biophys. 46:43-64 (2006).
Yan et al., "IDH1 and IDH2 Mutations in Gliomas," New Eng. J. Med. 360:765-73 (2009).

* cited by examiner

FIG. 1
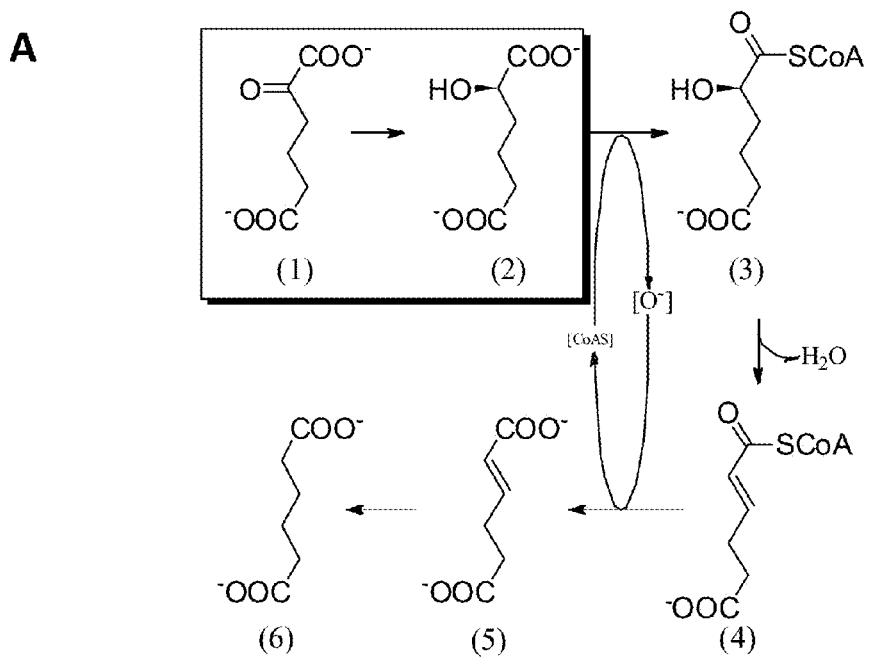
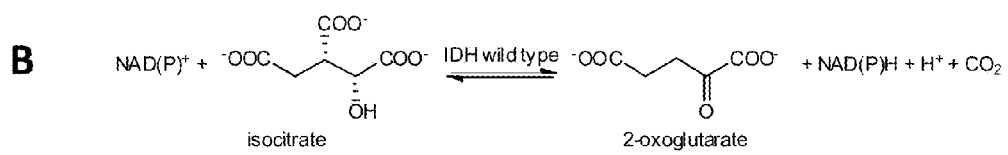
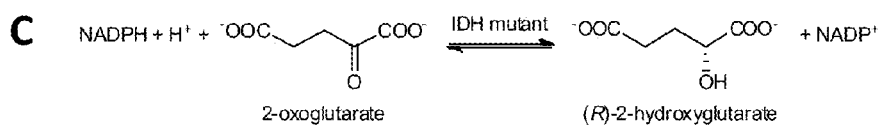
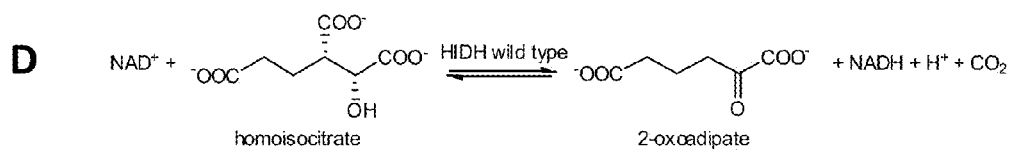
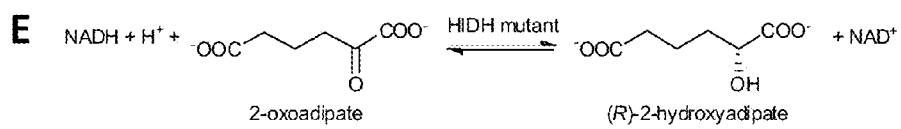

FIG. 2

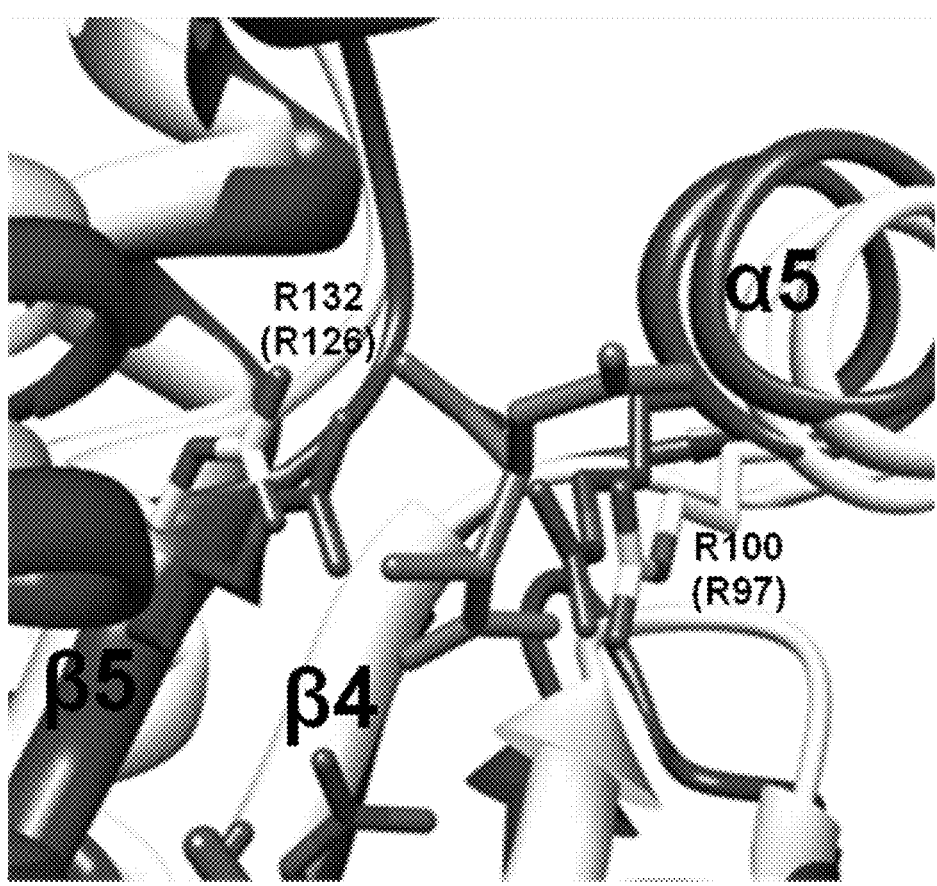

```
B
HsIDH1   (97-139)    GTIRNILGGTVF-REAIICKNIP--------RLVSGWVKPIIIGRHAYGDQY
HsIDH2   (137-179)   GTIRNILGGTVF-REPIICKNIP--------RLVPGWTKPITIGRHAHGDQY
SpHIDH   (94-133)    VALRKKMGLYANVRPV---KSLD--------GAKGKP-VDLVIVRENTECLY
ScHIDH   (111-150)   VALRREMGLFANVRPV---KSVE--------GEKGKP-IDMVIVRENTEDLY
TtHIDH   (85-125)    RYLRRRLDLYANVRPA---KSRP--------VPGSRPGVDLVIVRENTEGLY
TtIPMDH  (91-139)    LSLRKSQDLFANLRPA---KVFPGLERLSPLKEEIARGVDVLIVRELTGGIY
ScIPMDH  (94-143)    LKIRKELQLYANLRP---CNFASDSLLDLSPIKPQFAKGTDFVVVRELVGGIY
EcTDH    (94-140)    LKFRREFDQYVNLRPV---RLFPGVPC--PLAGKQPGDIDFYVVRENTEGEY
```

FIG. 3

```
Sy_IDH       MAK-----------------------------------------IKVKNPVVEIDGDEMTR
Hs_IDH1      MSKKI---------SGGS--------------------------VVEMQGDEMTR
Hs_IDH2      MAGYLRVVRSLCRASGSRPAWAPAALTAPTSQEQPRREYADKRIKVAKPVVEMDGDEMTR
Ec_IDH       M------ESKVVVPAQGKKITLQNGKLN----------------VPENPIIPYIEGDGIGV
Bs_IDH       M-------------AQGEKITVSNGVLN----------------VPNNPIIPFIEGDGTGP
Hs_IDH_NAD   MAGPAWISKVSRLLGAFHNPKQVTRGF-----------------TGGVQTVTLIPGDGIGP
Sp_HIDH      M-------------------S-----------------------ATRRIVLGLIPADGIGK
Sc_HIDH      MFRSVATRLSACRGLA-SNA------------------------ARKSLTIGLIPDGIGK
Ca_HIDH      M---LAARSSIRRCFSTSST------------------------TLKSLKIGLISGDGIGR
Tt_HIDH      M-------------------------------------------AYRICLIEGDGIGH
Ec_TDH       M-----------------------------------------MKTMRIAAIPGDGIGK
Pp_TDH       M-----------------------------------------SKPFRIAAIPGDGIGN
Tt_IPMDH     M-----------------------------------------KVAVLPGDGIGP
Af_IPMDH     M-----------------------------------------KKIAIFAGDGIGP
Sc_IPMDH     M-----------------------------------------SGPKKIVVLPGDHVGQ
Consensus    *                                            :   : .*

Sy_IDH       IIWEWIRERLILP--------YLDVDLKYYD-LSVEKRDETSD--QITIDAANAI-KEYG
Hs_IDH1      IIWELIKEKLIFP--------YVELDLHSYD-LGIENRDATND--QVTKDAAEAI-KKHN
Hs_IDH2      IIWQFIKEKLILP--------HVDIQLKYFD-LGLPNRDQTDD--QVTIDSALAT-QKYS
Ec_IDH       DVTPAMLKVVDAA-VEKAYKGERKISWMEIY-TGEKSTQVYGQDVWLPAETLDLI-REYR
Bs_IDH       DIWNAASKVLEAA-VEKAYKGEKKITWKEVY-AGEKAYNKTGE--WLPAETLDVI-REYF
Hs_IDH_NAD   EISAAVMKIFDAA--------KAPIQWEERN-VTAIQGPGGKW--MIPSEAKESM-DKNK
Sp_HIDH      EVVPAARRLMENL-FAKH---KLKFDFIDLD-AGWGTFERTGK--ALPERTVERLKTECN
Sc_HIDH      EVIPAGKQVLENL-NSKH---GLSFNFIDLY-AGFQTFQETGK--ALPDETVKVLKEQCQ
Ca_HIDH      EVIPAGKAVLENL-PSKH---DLQFEFVNLD-AGFELFKKTGT--ALPDETVDVLKKECD
Tt_HIDH      EVIPAARRVLE-----AT---GLPLEFVEAE-AGWETFERRGT--SVPEETVEKI-LSCH
Ec_TDH       EVLPEGIRVLQAA-AERW---GFALSFEQMEWASCEYYSHHGK--MMPDDWHEQL-SRFD
Pp_TDH       EVLPEGIRVVEAA-ARKH---GLDISFEFFEWASCDYYLAHGK--MMPDDWFEQL-KGFD
Tt_IPMDH     EVTEAALKVLRAL-DEAE---GLGLAYEVFP-FGGAAIDAFGE--PFPEPTRKGV-EEAE
Af_IPMDH     EIVAAARQVLDAV-DQAA---RLGLHCSEGL-VGGAALDASDD--PLPAASLQLA-LEAD
Sc_IPMDH     EITAEAIKVLKAISDVRS---NVKFDFENHL-IGGAAIDATGV--PLPDEALEAS-KKAD
Consensus    :             .                .

Sy_IDH       VGVKCATITPDEARVEEFGLKKMWKSPNGTIRNILGGVVFREPIVIKNVPRLVPGWTDP-
Hs_IDH1      VGVKCATITPDEKRVEEFKLQMWKSPNGTIRNILGGTVFREAIICKNIPRLVSGWVKP-
Hs_IDH2      VAVKCATITPDEARVEEFKLKKMWKSPNGTIRNILGGTVFREPIICKNIPRLVPGWTKP-
Ec_IDH       VAIKGPLTTPVGG---------GIRSLNVALRQELDLYICLRPV------RYYQGTPSPV
Bs_IDH       IAIKGPLTTPVGG---------GIRSLNVALRQELDLFVCLRPV------RYFTGVPSPV
Hs_IDH_NAD   MGLKGPLKTPI---AA------GHPSMNLLLRKTFDLYANVRPC------VSIEGYKTPY
Sp_HIDH      AALFGAVQSPT-HKVA------GYSSPIVALRKKMGLYANVRPV------KSLDG-----
Sc_HIDH      GALFGAVQSPT-TKVE------GYSSPIVALRREMGLFANVRPV------KSVEG-----
Ca_HIDH      GALFGAVSSPT-TKVA------GYSSPIVALRKKLGLYANVRPV------KSVEG-----
Tt_HIDH      ATLFGAATSPT-RKVP------GFFGAIRYLRRRLDLYANVRPA------KSRPV-----
Ec_TDH       AIYFGAVGWP--DTVPD---HISLWGSLLKFRREFDQYVNLRPV------RLFPGVPCPL
Pp_TDH       ALYFGAVGWP--DKVPD---HISLWGSLLKFRRDFDQYVNIRPV------RLFPGVPCPL
Tt_IPMDH     AVLLGSVGGPKWDGLPR---KIRPETGLLSLRKSQDLFANLRPA------KVFP-GLERL
Af_IPMDH     AVILGAVGGPRWDAYPP---AKRPEQGLLRLRKGLDLYANLRPA------QIFP-QLLDA
Sc_IPMDH     AVLLGAVGGPKWGT--G---SVRPEQGLLKIRKELQLYANLRPC------NFASDSLLDL
Consensus           .  *                        :*.            ..
```

FIG. 3, continued

```
Sy_IDH       --------------IVVGRHAFGDQYKATDFKVPGAGTLTMKWVGTNGEE-LEYEVFEF-PS
Hs_IDH1      --------------IIIGRHAYGDQYRATDFVVPGPGKVEMTYTPSDGTQKVTYLVHNFEEG
Hs_IDH2      --------------ITIGRHAHGDQYKATDFVADRAGTFKMVFTPKDGSGVKEWEVYNF-PA
Ec_IDH       K--HP---ELTDMVIFRENSEDIYAGIEWKA-DSADAE-KVIKFLREE-MGVKKIRFPEH
Bs_IDH       K--RP---EDTDMVIFRENTEDIYAGIEYAK-GSEEVQ-KLISFLQNE-LNVNKIRFPET
Hs_IDH_NAD   T--------DVNIVTIRENTEGEYSGIEHVIVD------GVVQ-----------------
Sp_HIDH      AKGKP-----VDLVIVRENTECLYVKEERMV-QNTPGK-RVAE-----------------
Sc_HIDH      EKGKP-----IDMVIVRENTEDLYIKIEKTYIDKATGT-RVAD-----------------
Ca_HIDH      -IGRP-----VDMVIVRENTEDLYIKEERVY-KKEDGT-KVAE-----------------
Tt_HIDH      PGSRP---G-VDLVIVRENTEGLYVEQERRYLDVA-----IAD-----------------
Ec_TDH       AGKQP---GDIDFYVVRENTEGEYSSLGGRVNEGTEHEVVIQE-----------------
Pp_TDH       AGREP---GDIDFVVIRENTEGEYSSLGGRMFEGTENEFVLQE-----------------
Tt_IPMDH     SPLKEEIARGVDVLIVRELTGGIYFGEPRGM-----SE-AEAW-----------------
Af_IPMDH     SPLRPELVRDVDILVVRELTGDIYFGQPRGL-EVVDGK-RRGF-----------------
Sc_IPMDH     SPIKPQFAKGTDFVVVRELVGGIYFGKRKE----DDGD-GVAW-----------------
Consensus            .   *.       *

Sy_IDH       AGVAMGMYNLDESIRDFAKASFNYGLNR--------------GWPV--YLSTKNTILKAY
Hs_IDH1      GGVAMGMYNQDKSIEDFAHSSFQMALSK--------------GWPL--YLSTKNTILKKY
Hs_IDH2      GGVGMGMYNTDESISGFAHSCFQYAIQK--------------KWPL--YMSTKNTILKAY
Ec_IDH       CGIGIKPCS-EEGTKRLVRAAIEYAIAN--------------DRDSV--TLVHKGNIMKFT
Bs_IDH       SGIGIKPVS-EEGTSRLVRAAIDYAIEH--------------GRKSV--TLVHKGNIMKFT
Hs_IDH_NAD   ---SIKLIT-EGVSKRIAEFAFEYARNN--------------HRSNV--TAVHKANIMRMS
Sp_HIDH      ---AIRRIS-EEASTKIGKMAFEIAKSRQKIRE-SGTYSIHKKPLV--TIIHKSNVMSVT
Sc_HIDH      ---ATKRIS-EIATRRIATIALDIALKRLQTRG---------QATL--TVTHKSNVLSQS
Ca_HIDH      ---AIKRIT-ETASTRIAKMAYEIALQREAVRKGTSGKQLHEKPSV--TVTHKSNVLSQS
Tt_HIDH      ---AV--IS-KKASERIGRAALRIAEGR--------------PRKTL--HIAHKANVLPLT
Ec_TDH       ---SV--FT-RRGVDRILRYAFELAQSR--------------PRKTL--TSATKSNGLAIS
Pp_TDH       ---SV--FT-RRGVDRILKYAFDVAQTR--------------ERKHV--TSATKSNGMAVS
Tt_IPMDH     ---NTERYS-KPEVERVARVAFFAARKR--------------RKHV--VSVDKANVLEVG
Af_IPMDH     ---NTMVYD-EDEIRRIAHVAFRAAQGR--------------RKQL--CSVDKANVLETT
Sc_IPMDH     ---DSEQYT-VPEVQRITRMAAFMALQH--------------EPPLPIWSLDKANVLASS
Consensus            .   .   .                    :       *  . :

Sy_IDH       DGRFKDLFQE-VFDAEFAD----------------------------KFKAAGIVYEHRLID
Hs_IDH1      DGRFKDIFQE-IYDKQYKS----------------------------QFEAQKIWYEHRLID
Hs_IDH2      DGRFKDIFQE-IFDKHYKT----------------------------DFDKNKIWYEHRLID
Ec_IDH       EGAFKDWGYE-LAREEFGGELIDGGPWLKV-------------KNPNTGKEIVIKDVIAD
Bs_IDH       EGAFKNWGYE-LAEKEYGDKVFTWAQYDRIAEEQGKDAANKAQSEAEAAGKIIIKDSIAD
Hs_IDH_NAD   DGLFLQKCRE-V-----------------------------------AESCKDIKFNEMYLD
Sp_HIDH      DGLFRESCRH-A-Q---------------------------------SLDPSYASINVDEQIVD
Sc_HIDH      DGLFREICKE-VYE---------------------------------SNKDKYGQIKYNEQIVD
Ca_HIDH      DGLFRETCRA-VYD---------------------------------ANANEYGGIEYKEQIVD
Tt_HIDH      QGLFLDTVKE-V-----------------------------------AKDFPLVNVQDIIVD
Ec_TDH       MPYWDERVEA-M-----------------------------------AENYPEIRWDKQHID
Pp_TDH       MPYWDERTAA-M-----------------------------------AANYPEISWDKQHID
Tt_IPMDH     E-FWRKTVEE-V-----------------------------------GRGYPDVALEHQYVD
Af_IPMDH     R-LWREVVTE-V-----------------------------------AQDYPDVQLSHMYVD
Sc_IPMDH     R-LWRKTVEETI-----------------------------------KNEFPTLKVQHQLID
Consensus            :  .                                            :  ..  *
```

FIG. 3, continued

```
Sy_IDH       DMVASALKWSGKF--VWACKNYDGDVQSDTVAQGFGSLGLMTSVLLSP----DGKT---V
Hs_IDH1      DMVAQAMKSEGGF--IWACKNYDGDVQSDSVAQGYGSLGMMTSVLVCP----DGKT---V
Hs_IDH2      DMVAQVLKSSGGF--VWACKNYDGDVQSDILAQGFGSLGLMTSVLVCP----DGKT---I
Ec_IDH       AFLQQILLRPAEYD-VIACMNLNGDYISDALAAQVGGIGIAPGANIGD------EC---A
Bs_IDH       IFLQQILTRPNEFD-VVATMNLNGDYISDALAAQVGGIGIAPGANINY------ETGH-A
Hs_IDH_NAD   TVCLNMVQDPSQFD-VLVMPNLYGDILSDLCAGLIGGLGVTPSGNIGA------NGV---A
Sp_HIDH      SMVYRLFREPECFD-VVVAPNLYGDILSDGAASLIGSLGLVPSANVGD------NF---V
Sc_HIDH      SMVYRLFREPQCFD-VIVAPNLYGDILSDGAAALVGSLGVVPSANVGP------EI---V
Ca_HIDH      SMVYRMFREPEIFD-VVVAPNLYGDILSDGAAALVGSLGVVPSANVGD------NF---A
Tt_HIDH      NCAMQLVMRPERFD-VIVTTNLLGDILSDLAAGLVGGLGLAPSGNIGD------TT---A
Ec_TDH       ILCARFVMQPERFD-VVVASNLFGDILSDLGPACTGTIGIAPSANLNP------ERTFPS
Pp_TDH       ILCARFVLQPDRFD-VVVASNLFGDILSDLGPACAGTIGIAPSANLNP------ERKFPS
Tt_IPMDH     AMAMHLVRSPARFD-VVVTGNIFGDILSDLASVLPGSLGLLPSASLGR------GT---P
Af_IPMDH     NAAMQLIRAPAQFD-VLLTGNMFGDILSDEASQLTGSIGMLPSASLGE------GR---A
Sc_IPMDH     SAAMILVKNPTHLNGIIITSNMFGDIISDEASVIPGSLGLLPSASLASLPDKNTAF---G
Consensus                .   :    *  **  **   .   * :*:  ..   :

Sy_IDH       EAEAAHGTVTRHYRQHQQGKATSTNPIASIFAWTQGLSF-RGKFDDTPDVVKFAETLEQV
Hs_IDH1      EAEAAHGTVTRHYRMYQKGQETSTNPIASIFAWTRGLAH-RAKLDNNKELAFFANALEEV
Hs_IDH2      EAEAAHGTVTRHYREHQKGRPTSTNPIASIFAWTRGLEH-RGKLDGNQDLIRFAQMLEKV
Ec_IDH       LFEATHGTAP------KYAGQDKVNPGSIILSAEMMLRH-MGW--------TEAADLIVKG
Bs_IDH       IFEATHGTAP------KYAGLDKVNPSSVILSGVLLLEH-LGW--------NEAADLVIKS
Hs_IDH_NAD   IFESVHGTAP------DIAGKDMANPTALLLSAVMMLRH-MGL--------FDHAARIEAA
Sp_HIDH      MSEPVHGSAP------DIAGRGIANPVATFKSVALMLEF-MGH--------QDAAADIYTA
Sc_HIDH      IGEPCHGSAP------DIAGKGIANPIATIRSTALMLEF-LGH--------NEAAQDIYKA
Ca_HIDH      IGEPCHGSAP------DIEGKGISNPVATIRSTALMLEF-MGY--------PEAAATIYQA
Tt_HIDH      VFEPVHGSAP------DIAGKGIANPTAAILSAAMMLDY-LGE--------KEAAKRVEKA
Ec_TDH       LFEPVHGSAP------DIYGKNIANPIATIWAGAMMLDF-LGN--GDERFQQAHNGILAV
Pp_TDH       LFEPVHGSAP------DIYGKNIANPIAMIWSGALMLDF-LGNDGADFRYRAAHDDILKA
Tt_IPMDH     VFEPVHGSAP------DIAGKGIANPTAAILSAAMMLEHAFGL--------VELARKVEDA
Af_IPMDH     MYEPIHGSAP------DIAGQDKANPLATILSVAMMLRYSLGA--------ELWAQRVEAA
Sc_IPMDH     LYEPCHGSAP------DLP-KNKVNPIATILSAAMMLKLSLNL--------PEEGKAIEDA
Consensus      *. **:..         .    **   : : :   *                  :

Sy_IDH       CIKTVEGGA-MTKDLALLIGP------DQAWMTTEQFFEAIRVNLEAEMAKWA-
Hs_IDH1      SIETIEAGF-MTKDLAACIKGLPNVQRSD-YLNTFEFMDKLGENLKIKLAQAKL
Hs_IDH2      CVETVESGA-MTKDLAGCIHGLSNVKLNEHFLNTTDFLDTIKSNLDRALGRQ--
Ec_IDH       MEGAINAKT-VTYDFERLMEG--------AKLLKCSEFGDAIIKNM---------
Bs_IDH       MEKTIASKV-VTYDFARLMDG--------ATEVKCSEFGEELIKNMD--------
Hs_IDH_NAD   CFATIKDGKSLTKD----LGG--------NA--KCSDFTEEICRRVKDLD-----
Sp_HIDH      VDKVLTEGKVLTPD----LGG--------KS--GTNEITDAVLANIHN-------
Sc_HIDH      VDANLREGSIKTPD----LGG--------KA--STQQVVDDVLSRL---------
Ca_HIDH      VDANLAEDKIKTPD----LGG--------NS--TTQEVIDDIIRRF---------
Tt_HIDH      VDLVLERGP-RTPD----LGG--------DA--TTEAFTEAVVEALKSL------
Ec_TDH       IEEVIAHGP-KTPD----MKG--------SA--TTPQVADAICKIILR-------
Pp_TDH       IEQVIAAGD-VTRD----MGG--------QQ--STQQVGQAITALVEA-------
Tt_IPMDH     VAKAL---L-ETPPPD--LGG--------SA--GTEAFTATVLRHLA--------
Af_IPMDH     VQRVLDQGL-RTADIA--APG--------APVIGTKAMGAAVVDALN-FKD----
Sc_IPMDH     VKKVLDAGI-RTGD----APG--------SN--STTEVGDAVAEEVKKILA----
Consensus              :         *                .    :    .
```

| HIDH mutation | V111D | R114Q | R115Q | R143C | R143H | R143K | Y150D |
|---|---|---|---|---|---|---|---|
| Analagous Human Mutation | IDH1-G97D | IDH2-R140Q | IDH2-N141Q | IDH1-R132C | IDH1-R132C | IDH2-R172K | IDH1-Y139D |
| Mutation Locus | cell lines | leukemia | structural position* | glioma, leukemia | glioma, leukemia | glioma, leukemia | in vitro |
| Reference | Bleeker, 2009 | Ward, 2010 | | Yan, 2009 | Yan, 2009 | Yan, 2009 | Ward, 2011 |

*Due to its position next to Arg114, we hypothesized that Arg115 may also lead to neomorphic HIDH activity FIG. 9
A 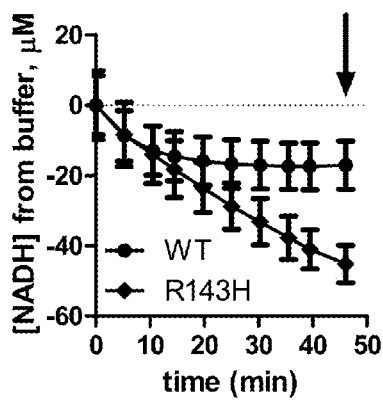
B 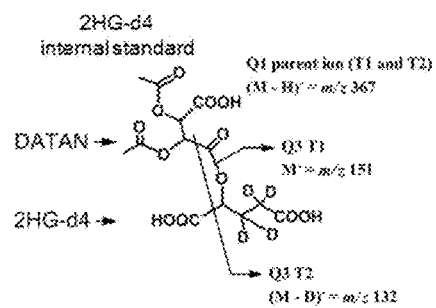
C 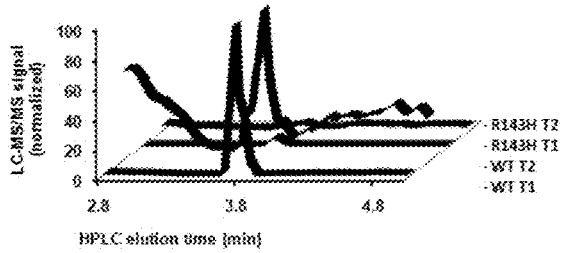 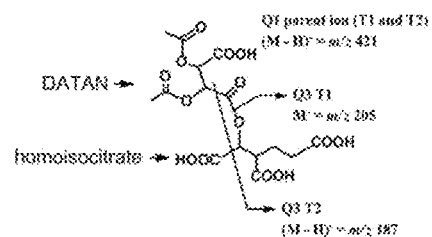
D 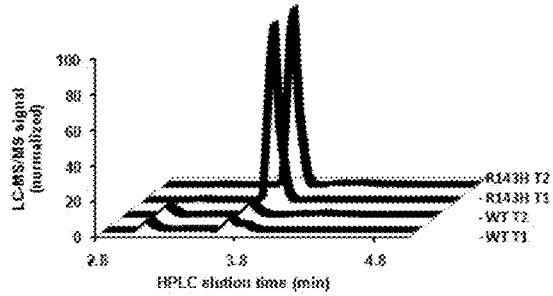 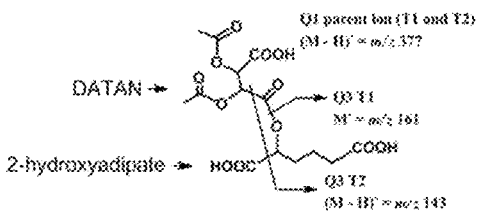

FIG. 10
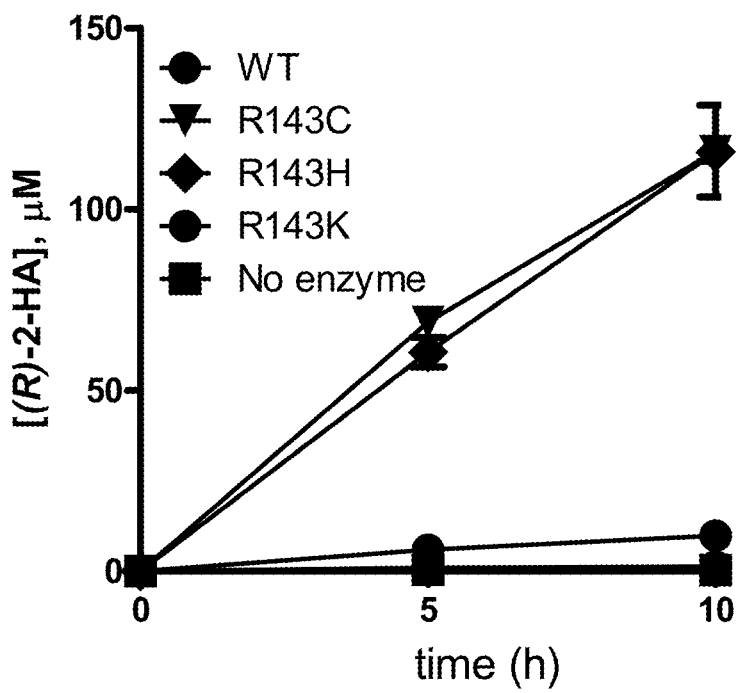
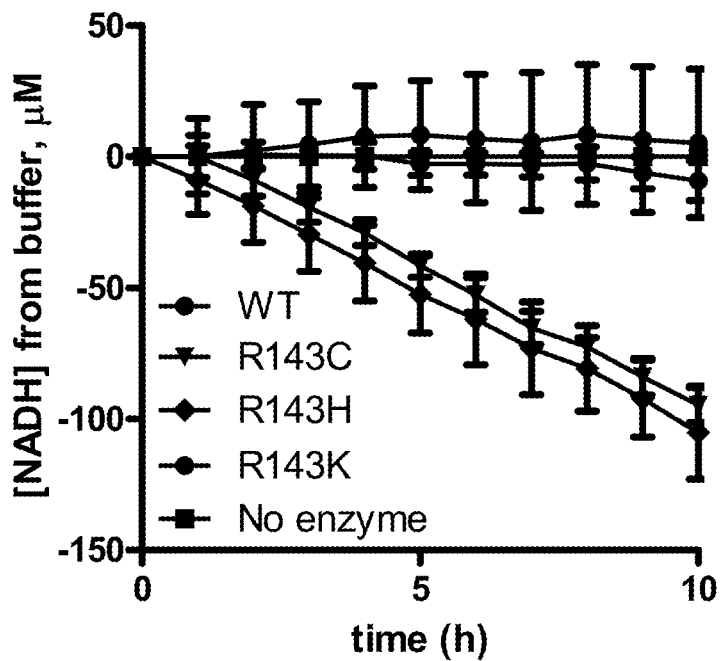

FIG. 17
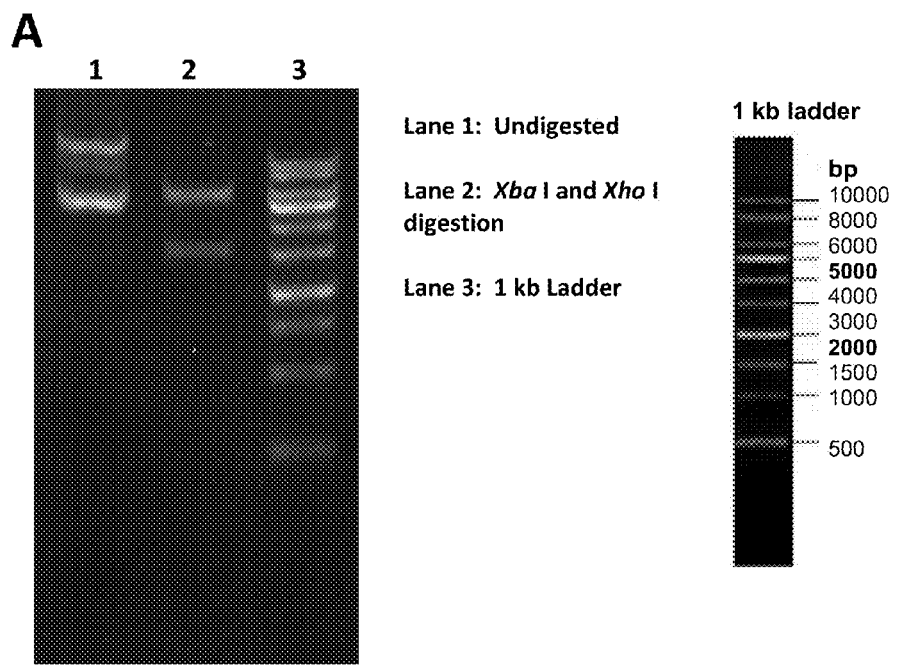
Lane 1: Undigested
Lane 2: *Xba* I and *Xho* I digestion
Lane 3: 1 kb Ladder
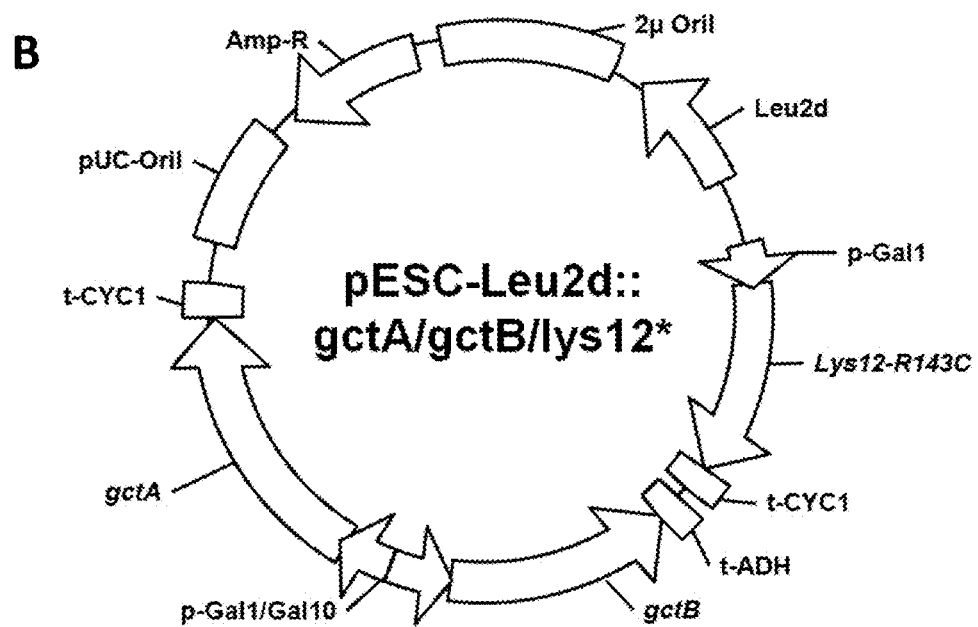

FIG. 18
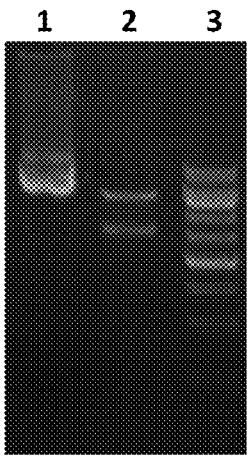
Lane 1: Undigested
Lane 2: Kpn I digestion
Lane 3: 1 kb Ladder
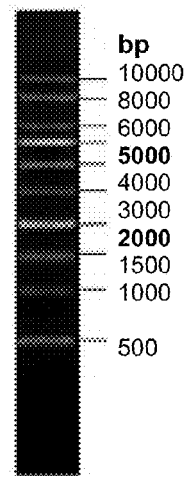
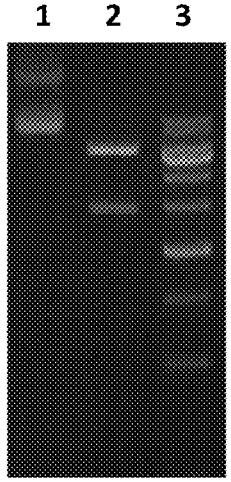
Lane 1: Undigested
Lane 2: Sac I and Sal I digestion
Lane 3: 1 kb Ladder
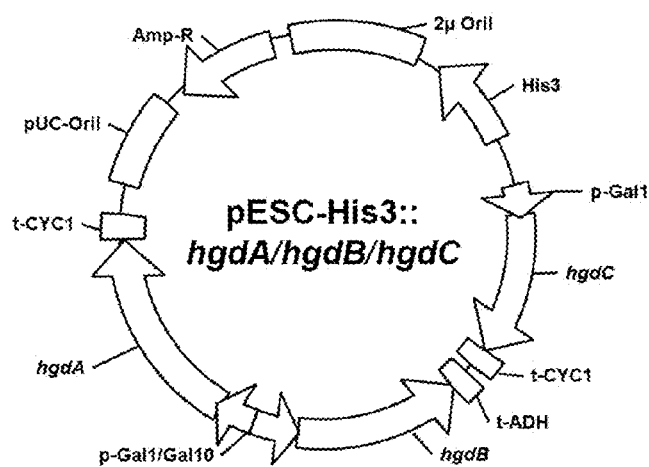

US 8,691,960 B2

OXIDOREDUCTASES FOR ENANTIOSELECTIVE REACTIONS

RELATED APPLICATIONS

This application is a non-provisional application that claims benefit of priority to U.S. Provisional Patent Application No. 61/604,630, filed Feb. 29, 2012, and which is hereby incorporated by reference in its entirety. This application is related to International Patent Application No. PCT/US2013/27836, filed Feb. 27, 2013, which is also hereby incorporated by reference in its entirety.

FEDERALLY SPONSORED RESEARCH

The research described herein was supported in part by U.S. National Institutes of Health grant R01 CA1403160.

REFERENCE TO SEQUENCE LISTING

This application is filed with a Computer Readable Form of a Sequence Listing in accord with 37 C.F.R. §1.821(c). The text file submitted by EFS, "D118_1090US1_sequence_listing_ST25.txt," was created on Feb. 7, 2013, has a file size of 483 Kbytes, and is hereby incorporated by reference in its entirety.

TECHNICAL FIELD

Described herein are compositions and methods for generating oxidoreductases for enantioselective reactions. Described herein are compositions and methods for generating neomorphic (R)-2-hydroxyacid dehydrogenases capable of enzymatically converting a 1-carboxy-2-ketoacid (i.e., 1-carboxy-2-oxoacid, α-ketocarboxylic acid, α-oxoacid) to a 1-carboxy-(R)-2-hydroxyacid (i.e., 1-carboxy-D-2-hydroxyacid, (R)-α-hydroxycarboxylic acid), or the reverse reaction. Illustrative examples include (a) (R)-2-hydroxyadipate dehydrogenase and uses thereof for converting 2-oxoadipate to (R)-2-hydroxyadipate, or the reverse reaction; and (b) (R)-2-hydroxyglutarate dehydrogenase and uses thereof for converting 2-oxoglutarate to (R)-2-hydroxyglutarate, or the reverse reaction. Also described herein are compositions and methods for generating non-natural microbial organisms to enzymatically convert 2-oxoadipate to (E)-2-hexenedioate or adipate, or to enzymatically convert 2-oxoglutarate to (E)-2-pentenedioate or glutarate, or the respective reverse reactions.

BACKGROUND

Adipic acid, i.e., 1,4-butanedicarboxylic acid; COOH$(CH_2)_4$COOH, is among the most-produced chemicals worldwide, with approximately 2.5 billion kilograms synthesized annually and a global market of 8 billion USD. The most typical use for adipic acid is for the synthesis of nylon-6,6 used in upholstery, auto parts, apparel, and other products. Standard industrial methods for adipic acid synthesis are costly and have major drawbacks including consumption of fossil fuels, inefficient yields, and production of greenhouse gases. To address this need, "greener" methods for adipic acid production have been demonstrated, but these methods have not been widely adopted, in part because they depend on large-scale hydrogen peroxide oxidation, or because they couple otherwise environmentally friendly fermentation reactions with non-biological synthetic reactions. Sato et al. *Science* 281: 1646-1647 (1998); Niu et al, *Biotechnol. Prog.* 18: 201-211 (2002).

A biological method for adipic acid synthesis by a series of recombinant enzymes in bacteria has been discussed. Burgard et al, U.S. Pat. No. 7,799,545; Burgard et al., U.S. Pat. App. Publication Nos. US 2009/0305364; US 2010/0330626; and US 2011/0195466. This biosynthetic pathway has the potential to lower the amounts and costs of input materials, reduce the need for fossil fuel substrates, and reduce the release of pollutants. In this method, genes encoding glutamate-fermenting enzymes from *Clostridia symbiosum* are expressed in a suitable bacteria such as *Escherichia coli* to convert 2-oxoadipate, via (R)-2-hydroxyadipate, (R)-2-hydroxyadipoyl-CoA, 2-hexenedioyl-CoA, and 2-hexendioic acid, to adipic acid (FIG. 1A). Parthasarathy et al., *Biochemistry* 50: 3540-3550 (2011). The compound, 2-oxoadipate (i.e., 2-oxohexanedioic acid), is a natural metabolic intermediate in several organisms (i.e., in lysine catabolism) and experiments show that adipate can be synthesized in bacteria supplied with glucose. Goh et al., *Mol. Genet. Metab.* 76: 172-180 (2002). In other examples, glutamate is converted to glutarate via (R)-2-hydroxyglutarate, (R)-2-hydroxyglutaryl-CoA, (E)-glutaconyl-CoA), (E)-glutaconate (i.e., (E)-pentenedioic acid), and glutarate, (i.e., pentanedioic acid).

Although other biosynthetic methods have become technically possible, an enzyme for efficient conversion of 2-oxoadipate to (R)-2-hydroxyadipic acid has not been established. *Acidaminococcus fermentans* 2-hydroxyglutarate dehydrogenase (HghH) was suggested as an enzyme for the conversion of 2-oxoadipate to (R)-2-hydroxyadipate (i.e., (R)-2-hydroxyhexanedioate). Parthasarathy et al., *Biochemistry* 50: 3540-3550 (2011). However, a drawback of HghH and of 2-hydroxyglutarate dehydrogenases, in general, is that their native substrate is 2-oxoglutarate, the 5-carbon analog of 2-oxoadipate. Consequently, conversion of 2-oxoadipate by HghH is performed 20-times less efficiently than 2-oxoglutarate. Thus, an enzyme that specifically converts 2-oxoadipate to (R)-2-hydroxyadipate, termed an (R)-2-hydroxyadipate dehydrogenase, is needed to overcome the inefficient 2-oxoadipate catalysis and undesired 2-oxoglutarate catalysis associated with HghHs. While 2-hydroxyadipate dehydrogenase activity is observed in nature, the gene that encodes this enzyme has not been identified. Furthermore, this enzyme is not ideal for this method because its substrate specificity is promiscuous and the stereochemistry of the 2-carbon of the product is unknown. Suda, et al., *Arch. Biochem. Biophys.* 176(2): 610-620 (1976); Suda et al., *Biochem. Biophys. Res. Comm.* 77(2): 586-591 (1977); Suda et al. *Pediatric Res.* 12(4): 297-300 (1978).

Isocitrate dehydrogenases (IDHs) are β-hydroxyacid oxidative decarboxylases that convert isocitrate to 2-oxoglutarate (α-ketoglutarate) (FIG. 1B) and are ubiquitous throughout life. Northrop and Cleland, *J. Biol. Chem.* 249: 2928-2931 (1974); Uhr et al., *J. Biol. Chem.* 249: 2920-2927 (1974).

Homoisocitrate dehydrogenases (HIDHs) are β-hydroxyacid oxidative decarboxylases from the same subfamily as IDHs that convert homoisocitrate, the 7-carbon analog of isocitrate, to 2-oxoadipate (2-oxohexanedioic acid) (FIG. 1D). HIDHs are involved in an alternative lysine synthetic pathway in yeasts, thermophilic bacteria, and archaea. Miyazaki et al. *J. Biol. Chem.* 278: 1864-1871 (2003); Xu et al., *Cell Biochem. Biophys.* 46: 43-64 (2006). Recent exome sequencing revealed missense mutations in $NADP^+$-dependent IDHs that mutate an arginine residue responsible for contacting the β-carboxyl of isocitrate during catalysis. Yan et al., *N. Engl. J. Med.* 360: 765-773 (2009); Mardis et al., *N. Engl. J. Med.* 361: 1058-1066 (2009). These mutations cause IDH enzymes to lose their native isocitrate dehydrogenase activity and to gain a neomorphic activity to convert 2-oxoglutarate (α-ketoglutarate) to 2-hydroxyglutarate (2-hydroxypentanedioate) (FIG. 1C). Dang et al., *Nature* 462: 739-744 (2009); Ward et al., *Cancer Cell* 17, 225-234 (2010).

The compound 2-hydroxyglutarate is a small biochemical of current interest due to its association with cancer and inborn errors of metabolism. It is of interest to detect and quantify this compound, especially in an enantioselective fashion (i.e., to discriminate the (R)-enantiomer from (S)-2-hydroxyglutarate). This would be useful for research or diagnostics for cancer and inborn errors of metabolism. Mass spectrometry is currently used quantify this compound but this type of instrumentation is specialized and expensive. Therefore, a more accessible quantification method would be useful.

An enzyme that links (R)-2-hydroxyglutarate to $NAD^+$/NADH would allow the development of an NADH-linked assay to quantify (R)-2-hydroxyglutarate. The principle behind this assay would be to add a sample with an unknown amount of (R)-2-hydroxyglutarate to a reaction mix containing a (R)-2-hydroxyglutarate dehydrogenase and $NAD^+$. Then, the (R)-2-hydroxyglutarate dehydrogenase enzyme would convert an equal amount of (R)-2-hydroxyglutarate and $NAD^+$ stoichiometrically to NADH and 2-oxoglutarate. The amount of NADH, which is exactly equal to the amount of input (R)-2-hydroxyglutarate in the sample, can then be measured by UV absorbance (e.g., 340 nm) or fluorescence (e.g., 340 nm excitation; 450 nm emission), or be detected by converting a secondary probe such as resazurin. This type of "enzyme-linked colorimetric assay" scheme is already in place for numerous common biochemicals such as glucose, glutamate, and so forth. This would be useful to lower the cost of (R)-2-hydroxyglutarate quantification, which currently requires mass spectrometry. It could be implemented in research labs, or even provide a diagnostic test in a clinical setting by measuring (R)-2-hydroxyglutarate in tumors, tissue samples, blood, and so forth.

HIDHs from the yeast *S. cerevisiae* and the thermophilic bacteria *T. thermophilus* have been studied. Miyazaki et al. *J. Biol. Chem.* 278: 1864-1871 (2003); Lin et al., *Biochemistry* 46: 890-898 (2007); Lin et al., *Biochemistry* 47: 4169-4180 (2008); Lin et al., *Biochemistry* 48: 7305-7312 (2009); Aktas and Cook, *Biochemistry* 48: 3565-3577 (2009).

Because IDHs and HIDHs are homologous and functionally related, analogous mutations to HIDHs can cause them to lose their native HIDH activity and to gain the ability to convert 2-oxoadipate to (R)-2-hydroxyadipate (FIG. 1E). Mutations to active site residues of other β-hydroxyacid oxidative decarboxylases can convert these enzymes to 2-hydroxyacid dehydrogenases. That is, instead of catalyzing the removal of a 3-carboxyl group and oxidation of a 2-alcohol group from a substrate to generate a 2-ketone product, the mutants instead catalyze reduction of the same 2-ketone product to the corresponding 2-alcohol. The enzymes also catalyze the reverse reaction (i.e., the oxidation of a 2-alcohol to a 2-ketone).

Alignments of human IDH1 or IDH2 and homoisocitrate dehydrogenases have been performed that show apparent homology among these enzymes. See Aktas and Cook, *Biochemistry* 48: 3565-3577 (2009). However, correct alignment of these proteins is not trivial. For example, Aktas and Cook incorrectly aligned human IDH1. See Aktas and Cook, FIG. 3 at 3569. The fourth entry in the alignment, Human_ICDH_NADP (i.e., HsIDH1), is not aligned correctly; the sequence should be shifted 8-residues to the right. This mistake was discovered when comparing Human_ICDH_NADP and *S. cerevisiae*_HICDH in FIG. 3 from Aktas and Cook.

In the correct alignment, the functionally critical residues are aligned with each other (see FIGS. 2B and 3). Residue HsIDH1-R132 is aligned with ScHIDH-R143. HsIDH1-R100, -R109, and -R132, which are important for substrate binding, and -Y139, which is essential for catalysis are aligned with ScHIDH-R114, -R124 and -R143, and Y150, respectively. In contrast, the alignment of Aktas and Cook aligned HsIDH1-R132 with a gap between E132 and K133 in the ScHIDH sequence. This alignment is also incorrect because HsIDH1-G148 was aligned with ScHIDH-R143. It is unlikely that the critical arginine residue could be replaced by a glycine. In addition, there is a conserved branched chain amino acid (e.g., Ile or Leu) before HsIDH1-R100 and ScHIDH-R114 and there are six intervening amino acids between the critical catalytic arginine and tyrosine residues, i.e., HsIDH1-R132/ScHIDH-R143 and HsIDH1-R139/ScHIDH-Y150. Moreover, the experimental evidence described herein robustly supports the alignment in FIGS. 2B and 3. Mutations to positionally aligned residues such as HsIDH1-R132H and ScHIDH-R143H have analogous functional changes. These examples demonstrate that the correct alignment of homologous residues in the IDH and HIDH sequences, inter alia, is unpredictable and requires experimental verification.

Described herein are mutations to residues of the HIDH active site responsible for creating a (R)-2-hydroxyadipate dehydrogenase enzyme (i.e., oxidoreductase) that catalyzes the conversion of 2-oxoadipate to (R)-2-hydroxyadipate. The method used to create such mutants has also been performed for a variety of HIDH enzymes from multiple species. Unique nucleotide and protein sequences were generated using the methods described herein. The method for generating these enzyme constructs was confirmed by biochemical assays that showed catalytic activity in the HIDH mutants (in this case, 2-hydroxyadipate dehydrogenase activity). The HIDH mutants were incorporated into vectors to generate a non-natural microbial organism (e.g., *Saccharomyces cerevisiae*, yeast). The transformed yeast can be used for the conversion of 2-oxoadipate to commercially useful (E)-2-hexenedioic acid and/or adipic acid products from the metabolism of that organism.

Isopropylmalate dehydrogenases (IPMDHs) and tartarate dehydrogenases (TDHs) are also β-hydroxyacid oxidative decarboxylases that can be mutated to change the activity using the methods described herein. Mutant IPMDHs reduce 4-methyl-2-ketopentanoate to 4-methyl-2-hydroxypentanoate. Mutant TDHs reduce 3-hydroxy-2-oxopropanoic acid (β-hydroxypyruvic acid) to 2,3-dihydroxypropanoic acid.

SUMMARY

Described herein are compositions and methods for generating oxidoreductases for enantioselective reactions. Described herein are compositions and methods for generating neomorphic (R)-2-hydroxyacid dehydrogenases capable of enzymatically converting a 1-carboxy-2-ketoacid (i.e., 1-carboxy-2-oxoacid, α-ketocarboxylic acid, α-oxoacid) to a 1-carboxy-(R)-2-hydroxyacid (i.e., 1-carboxy-D-2-hydroxy-acid, (R)-α-hydroxycarboxylic acid), or the reverse reaction. Illustrative examples include (a) (R)-2-hydroxyadipate dehydrogenase and uses thereof for converting 2-oxoadipate to (R)-2-hydroxyadipate, or the reverse reaction; and (b) (R)-2-hydroxyglutarate dehydrogenase and uses thereof for converting 2-oxoglutarate to (R)-2-hydroxyglutarate, or the reverse reaction. Also described herein are compositions and methods for generating non-natural microbial organisms to enzymatically convert 2-oxoadipate to (E)-2-hexenedioate or adipate, or to enzymatically convert 2-oxoglutarate to (E)-2-pentenedioate or glutarate, or the respective reverse reactions.

One embodiment described herein is a functional oxidoreductase (i.e., (R)-2-hydroxyacid dehydrogenase) capable of enzymatically converting a 1-carboxy-2-ketoacid (i.e., 1-carboxy-2-oxoacid, α-ketocarboxylic acid, α-oxoacid) to a 1-carboxy-(R)-2-hydroxyacid (i.e., 1-carboxy-D-2-hydroxyacid, (R)-α-hydroxycarboxylic acid), or the reverse reaction.

Another embodiment described herein is a functional (R)-2-hydroxyadipate dehydrogenase.

One aspect described herein is a polynucleotide comprising a nucleotide sequence encoding a polypeptide comprising a functional (R)-2-hydroxyadipate dehydrogenase useful for catalyzing the conversion of 2-oxoadipate to (R)-2-hydroxyadipate, or the reverse reaction, wherein the polynucleotide is any one of SEQ ID NOs: 3, 5, 7, 9, 11, 13, 17, 21, 25, 29, or 33, or a degenerate, homologous, or codon-optimized variant thereof.

Another aspect described herein is a polynucleotide comprising a nucleotide sequence encoding a polypeptide comprising a functional (R)-2-hydroxyadipate dehydrogenase useful for catalyzing the conversion of 2-oxoadipate to (R)-2-hydroxyadipate, or the reverse reaction, wherein the polypeptide is any one of SEQ ID NOs: 4, 6, 8, 10, 12, 14, 16, 18, 22, 26, 30, 34, or 35-153, or a degenerate or homologous variant thereof.

Another aspect described herein is a polynucleotide comprising a nucleotide sequence encoding a polypeptide comprising a functional (R)-2-hydroxyadipate dehydrogenase useful for catalyzing the conversion of 2-oxoadipate to (R)-2-hydroxyadipate, or the reverse reaction, wherein the polynucleotide is at least 90% identical to the polynucleotide sequence shown in SEQ ID NOs: 1, 3, 5, 7, 9, 11, 13, 17, 21, 25, 29, or 33; with the proviso that the encoded polypeptide has at least one or more mutations to the active site at positions V111, R114, R115, R124, R143, or Y150 of SEQ ID NO: 2; wherein the one or more mutations disrupt oxidative decarboxylation but do not disrupt oxidoreductase activity.

Another aspect described herein is a polynucleotide comprising a nucleotide sequence encoding a polypeptide comprising a functional (R)-2-hydroxyadipate dehydrogenase useful for catalyzing the conversion of 2-oxoadipate to (R)-2-hydroxyadipate, or the reverse reaction, wherein the polynucleotide is the sequence shown in SEQ ID NO: 1, 3, 5, 7, 9, 11, 13, 17, 21, 25, 29, or 33, with no more than 120 nucleotide substitutions; with the proviso that the encoded polypeptide has at least one or more mutations to the active site at positions analogous to V111, R114, R115, R124, R143, or Y150 of SEQ ID NO: 2; wherein the one or more mutations disrupt oxidative decarboxylation but do not disrupt oxidoreductase activity.

Another aspect described herein is a vector comprising the polynucleotides comprising a nucleotide sequence encoding a polypeptide comprising a functional (R)-2-hydroxyadipate dehydrogenase.

Another aspect described herein is a cultured cell comprising any of the vectors comprising the polynucleotides comprising a nucleotide sequence encoding a polypeptide comprising a functional (R)-2-hydroxyadipate dehydrogenase.

Another aspect described herein is a polypeptide comprising a functional (R)-2-hydroxyadipate dehydrogenase useful for catalyzing the conversion of 2-oxoadipate to (R)-2-hydroxyadipate, or the reverse reaction, wherein the polypeptide is at least 90% identical to the polypeptide sequence shown in SEQ ID NOs: 2, 4, 6, 8, 10, 12, 14, 16, 18, 20, 22, 24, 26, 28, 30, 32, 34, or 35-153; with the proviso that the polypeptide has at least one or more mutations to the active site at positions V111, R114, R115, R124, R143, or Y150 of SEQ ID NO: 2; wherein the one or more mutations disrupt oxidative decarboxylation but do not disrupt oxidoreductase activity.

Another aspect described herein is a polypeptide comprising a functional (R)-2-hydroxyadipate dehydrogenase useful for catalyzing the conversion of 2-oxoadipate to (R)-2-hydroxyadipate, or the reverse reaction, wherein the polypeptide is the sequence shown in SEQ ID NOs: 2, 4, 6, 8, 10, 12, 14, 16, 18, 20, 22, 24, 26, 28, 30, 32, 34, or 35-153 with no more than 40 amino acid substitutions; with the proviso that the polypeptide has at least one or more mutations to the active site at positions analogous to V111, R114, R115, R124, R143, or Y150 of SEQ ID NO: 2; wherein the one or more mutations disrupt oxidative decarboxylation but do not disrupt oxidoreductase activity.

Another aspect described herein is a composition useful for catalyzing the conversion of 2-oxoadipate to (R)-2-hydroxyadipate, or the reverse reaction, comprising: (a) a polynucleotide comprising a nucleotide sequence encoding a polypeptide comprising a functional (R)-2-hydroxyadipate dehydrogenase; (b) a polynucleotide comprising a nucleotide sequence capable of hybridizing to the complement of (a) under hybridization conditions comprising 7% sodium dodecyl sulfate, 0.5 M $Na_2HPO_4$, 1 mM EDTA at 60° C. with washing in 1×SSC, 0.1% SDS at 60° C. encoding a polypeptide comprising a functional (R)-2-hydroxyadipate dehydrogenase; (c) a polypeptide comprising an amino acid sequence comprising a functional oxidoreductase; (d) a vector comprising (a) or (b) or capable of expressing (c); or (e) an organism transformed with (d); and with the proviso that the polypeptide has one or more mutations to the active site at positions analogous to V111, R114, R115, R124, R143, or Y150 of the *Saccharomyces cerevisiae* homoisocitrate dehydrogenase (ScHIDH), i.e., SEQ ID NO: 2; and wherein the polypeptide catalyzes the conversion of 2-oxoadipate to (R)-2-hydroxyadipate in the presence of NADH.

In some aspects described herein, the polynucleotide is any one of SEQ ID NOs: 1, 3, 5, 7, 9, 11, 13, 15, 17, 19, 21, 23, 25, 27, 29, 31, 33, or a degenerate, homologous, or codon-optimized variant thereof.

In some aspects described herein, the polypeptide is any one of SEQ ID NOs: 2, 4, 6, 8, 10, 12, 14, 16, 18, 20, 22, 24, 26, 28, 30, 32, 34, 35-153, or degenerate or homologous variant thereof.

In some aspects described herein, the polynucleotide is any one of SEQ ID NOs: 11, 13, 17, or a degenerate, homologous, or codon-optimized variant thereof.

In some aspects described herein, the polypeptide is SEQ ID NO: 12, 14, 18, or a degenerate or homologous variant thereof.

In some aspects described herein, the organism is *Escherichia coli, Sacchromyces cerevisia, Pichia pastoris, Geotrichum candidum, Candida albicans, Rhodotorula rubra*, or *Rhodosporidium* sp.

Another aspect described herein is a method for enzymatically converting 2-oxoadipate to (R)-2-hydroxyadipate comprising a (R)-2-hydroxyadipate dehydrogenase, or the reverse reaction, comprising (a) a polynucleotide comprising a nucleotide sequence encoding a polypeptide comprising a functional (R)-2-hydroxyadipate dehydrogenase, wherein the polynucleotide is any one of SEQ ID NOs: 1, 3, 5, 7, 9, 11, 13, 15, 17, 19, 21, or a degenerate, homologous, or codon-optimized variant thereof; (b) a polynucleotide comprising a nucleotide sequence capable of hybridizing to the complement of (a) under hybridization conditions comprising 7% sodium dodecyl sulfate, 0.5 M Na$_2$HPO$_4$, 1 mM EDTA at 60° C. with washing in 1×SSC, 0.1% SDS at 65° C. encoding a polypeptide comprising a functional (R)-2-hydroxyadipate dehydrogenase; (c) a polypeptide comprising an amino acid sequence comprising a functional (R)-2-hydroxyadipate dehydrogenase, wherein the polypeptide is any one of SEQ ID NOs: 2, 4, 6, 8, 10, 12, 14, 16, 18, 20, 22, 35-153 or degenerate or homologous variant thereof; (d) a vector comprising (a) or (b) or capable of expressing (c); or (e) an organism transformed with (d); and with the proviso that the (R)-2-hydroxyadipate dehydrogenase has one or more mutations to the active site at positions analogous to V111, R114, R115, R124, R143, or Y150 of the *Saccharomyces cerevisiae* homoisocitrate dehydrogenase (ScHIDH), SEQ ID NO: 2; and wherein the (R)-2-hydroxyadipate dehydrogenase catalyzes the conversion of 2-oxoadipate to (R)-2-hydroxyadipate in the presence of NADH, or the reverse reaction.

Another aspect described herein is a method for enzymatically converting 2-oxoadipate to (R)-2-hydroxyadipate comprising a (R)-2-hydroxyadipate dehydrogenase, or the reverse reaction, comprising (a) selecting a polypeptide 2, 4, 6, 8, 10, 12, 14, 16, 18, 20, 22, 24, 26, 28, 30, 32, 34, or 35-153); (b) mutating one or more arginine residue in the active site to an amino acid selected from the group of His, Lys, Gln, Asn, Leu, Ile, Val, Tyr, Phe, Trp, Cys, Ser, Thr, Met, Glu, Asp, Ala, Gly, and Pro; with the proviso that the polypeptide has one or more mutations to the active site at positions analogous to R114, R115, R124, or R143, of the *Saccharomyces cerevisiae* homoisocitrate dehydrogenase (ScHIDH), SEQ ID NO: 2; and (c) assessing the oxidoreductase enzymatic activity; wherein the polypeptide catalyzes the conversion of 2-oxoadipate to (R)-2-hydroxyadipate in the presence of NADH, or the reverse reaction.

Another aspect described herein is a use of a (R)-2-hydroxyadipate dehydrogenase to convert 2-oxoadipate to (R)-2-hydroxyadipate, or the reverse reaction, comprising: (a) a polynucleotide comprising a nucleotide sequence encoding a polypeptide comprising a functional (R)-2-hydroxyadipate dehydrogenase, wherein the polynucleotide is any one of SEQ ID NOs: 1, 3, 5, 7, 9, 11, 13, 15, 17, 19, 21, or a degenerate, homologous, or codon-optimized variant thereof; (b) a polynucleotide comprising a nucleotide sequence capable of hybridizing to the complement of (a) under hybridization conditions comprising 7% sodium dodecyl sulfate, 0.5 M Na$_2$HPO$_4$, 1 mM EDTA at 60° C. with washing in 1×SSC, 0.1% SDS at 65° C. encoding a polypeptide comprising a functional (R)-2-hydroxyadipate dehydrogenase; (c) a polypeptide comprising an amino acid sequence comprising a functional (R)-2-hydroxyadipate dehydrogenase, wherein the polypeptide is any one of SEQ ID NOs: 2, 4, 6, 8, 10, 12, 14, 16, 18, 20, 22, 35-153 or degenerate or homologous variant thereof; (d) a vector comprising (a) or (b) or capable of expressing (c); or (e) an organism transformed with (d); and with the proviso that the (R)-2-hydroxyadipate dehydrogenase has one or more mutations to the active site at positions analogous to V111, R114, R115, R124, R143, or Y150 of the *Saccharomyces cerevisiae* homoisocitrate dehydrogenase (ScHIDH), SEQ ID NO: 2; and wherein the (R)-2-hydroxyadipate dehydrogenase catalyzes the conversion of 2-oxoadipate to (R)-2-hydroxyadipate in the presence of NADH, or the reverse reaction.

Another aspect described herein is a polynucleotide comprising a nucleotide sequence encoding a polypeptide comprising a functional (R)-2-hydroxyadipate dehydrogenase useful for catalyzing the conversion of 2-oxoadipate to (R)-2-hydroxyadipate, or the reverse reaction, wherein the polynucleotide sequence is shown in SEQ ID NO: 11 or 13.

Another aspect described herein is a polypeptide comprising a functional (R)-2-hydroxyadipate dehydrogenase useful for catalyzing the conversion of 2-oxoadipate to (R)-2-hydroxyadipate, or the reverse reaction, wherein the polypeptide sequence is shown in SEQ ID NO: 12 or 14.

Another aspect described herein is a method for enzymatically converting 2-oxoadipate to (R)-2-hydroxyadipate comprising a (R)-2-hydroxyadipate dehydrogenase, or the reverse reaction, comprising (a) a polynucleotide comprising a nucleotide sequence encoding a polypeptide comprising a functional (R)-2-hydroxyadipate dehydrogenase, wherein the polynucleotide is SEQ ID NO: 11 or 13; (b) a polynucleotide comprising a nucleotide sequence capable of hybridizing to the complement of (a) under hybridization conditions comprising 7% sodium dodecyl sulfate, 0.5 M Na$_2$HPO$_4$, 1 mM EDTA at 60° C. with washing in 1×SSC, 0.1% SDS at 65° C. encoding a polypeptide comprising a functional (R)-2-hydroxyadipate dehydrogenase; (c) a polypeptide comprising an amino acid sequence comprising a functional (R)-2-hydroxyadipate dehydrogenase, wherein the polypeptide is SEQ ID NO: 12 or 14; (d) a vector comprising (a) or (b) or capable of expressing (c); or (e) an organism transformed with (d); and wherein the (R)-2-hydroxyadipate dehydrogenase catalyzes the conversion of 2-oxoadipate to (R)-2-hydroxyadipate in the presence of NADH, or the reverse reaction.

Another aspect described herein is a use of a (R)-2-hydroxyadipate dehydrogenase to convert 2-oxoadipate to (R)-2-hydroxyadipate, or the reverse reaction, comprising: (a) a polynucleotide comprising a nucleotide sequence encoding a polypeptide comprising a functional (R)-2-hydroxyadipate dehydrogenase, wherein the polynucleotide is SEQ ID NO: 11 or 13; (b) a polynucleotide comprising a nucleotide sequence capable of hybridizing to the complement of (a) under hybridization conditions comprising 7% sodium dodecyl sulfate, 0.5 M Na$_2$HPO$_4$, 1 mM EDTA at 60° C. with washing in 1×SSC, 0.1% SDS at 65° C. encoding a polypeptide comprising a functional (R)-2-hydroxyadipate dehydrogenase; (c) a polypeptide comprising an amino acid sequence comprising a functional (R)-2-hydroxyadipate dehydrogenase, wherein the polypeptide is SEQ ID NO: 12 or 14; (d) a vector comprising (a) or (b) or capable of expressing (c); or (e) an organism transformed with (d); and wherein the (R)-2-hydroxyadipate dehydrogenase catalyzes the conversion of 2-oxoadipate to (R)-2-hydroxyadipate in the presence of NADH, or the reverse reaction.

Another aspect described herein is a method for enzymatically converting 2-oxoadipate to adipate, or the reverse reaction, comprising a non-natural organism comprising a microbial organism transformed with exogenous nucleic acids encoding: (a) (R)-2-hydroxyadipate dehydrogenase (producing (R)-2-hydroxyadipate); (b) adipate Co-A transferase (producing (R)-hydroxyadipoyl-CoA); (c) hydroxyadipoyl-CoA dehydratase (producing (E)-2-hexedioyl-CoA); (d) adipate Co-A transferase (producing (E)-2-hexendioic acid); (e) 2-hexenedioic acid dehydrogenase (producing adipic acid); wherein (a)-(e) comprise enzymes catalyzing the conversion of 2-oxoadipate to adipate, or the reverse reaction, when supplied with either 2-oxoadipate and NADH or adipate and NAD$^+$ and other appropriate cofactors or feedstocks.

Another aspect described herein is a method for enzymatically converting 2-oxoadipate to (E)-2-hexenedioate, or the reverse reaction, comprising a non-natural organism comprising a microbial organism transformed with exogenous nucleic acids encoding: (a) (R)-2-hydroxyadipate dehydrogenase (producing (R)-2-hydroxyadipate); (b) adipate Co-A transferase (producing (R)-hydroxyadipoyl-CoA); (c) hydroxyadipoyl-CoA dehydratase (producing (E)-2-hexedioyl-CoA); (d) adipate Co-A transferase (producing (E)-2-hexendioic acid); wherein (a)-(d) comprise enzymes catalyzing the conversion of 2-oxoadipate to (E)-2-hexenedioate, or the reverse reaction, when supplied with either 2-oxoadipate and NADH or (E)-2-hexenedioate and NAD+ and other appropriate cofactors or feedstocks.

Another aspect described herein is a method for enzymatically converting 2-oxoglutarate to glutarate, or the reverse reaction, comprising a non-natural organism comprising a microbial organism transformed with exogenous nucleic acids encoding: (a) (R)-2-hydroxyglutarate dehydrogenase (producing (R)-2-hydroxyglutarate); (b) gluconate Co-A transferase (producing (R)-2-hydroxyglutaryl-CoA); (c) hydroxyadipoyl-CoA dehydratase (producing (E)-glutaconyl-CoA)(d) gluconate Co-A transferase (producing (E)-glutaconate i.e., (E)-pentenedioic acid); (e) pentenedioic acid dehydrogenase (producing glutarate, i.e., pentanedioic acid); wherein (a)-(e) comprise enzymes catalyzing the conversion of 2-oxoglutarate to glutarate or the reverse reaction, when supplied with either 2-oxoglutarate and NADH or gluconate and NAD+ and other appropriate cofactors or feedstocks.

Another aspect described herein is a method for enzymatically converting 2-oxoadipate to adipate, or the reverse reaction, comprising a non-natural organism comprising a microbial organism comprising: (a) SEQ ID NOs: 154 (Lys12) encoding an (R)-2-hydroxyadipate dehydrogenase comprising SEQ ID NO: 155 (HIDH) (producing (R)-2-hydroxyadipate); (b) SEQ ID NOs: 156 or 157 (gctA) and SEQ ID NOs: 159 or 160 (gctB) encoding an adipate Co-A transferase comprising SEQ ID NOs: 158 (gctA) and 161 (gctB) (producing (R)-hydroxyadipoyl-CoA); (c) SEQ ID NOs: 162 or 163 (hgdA) and SEQ ID NOs: 162 or 163 (hgdB) and SEQ ID NOs: 168 or 169 (hgdc) encoding an hydroxyadipoyl-CoA dehydratase comprising SEQ ID NO: 164 (hgdA), 167 (hgdB), and 170 (hgdc) (producing (E)-2-hexedioyl-CoA); (d) SEQ ID NOs: 156 or 157 (gctA) and SEQ ID NOs: 159 or 160 (gctB) encoding an adipate Co-A transferase comprising SEQ ID NOs: 158 (gctA) and 161 (gctB) (producing (E)-2-hexendioic acid); (e) SEQ ID NOs: 171 or 172 (gdh) encoding an 2-hexenedioic acid dehydrogenase comprising SEQ ID NO: 173 (gdh) (producing adipic acid); wherein (a)-(e) comprise enzymes catalyzing the conversion of 2-oxoadipate to adipate, or the reverse reaction, when supplied with either 2-oxoadipate and NADH or adipate and NAD+ and other appropriate cofactors or feedstocks.

Another aspect described herein is a method for enzymatically converting 2-oxoadipate to (E)-2-hexenedioate, or the reverse reaction, comprising a non-natural organism comprising a microbial organism transformed with exogenous nucleic acids encoding: (a) SEQ ID NOs: 154 (Lys12) encoding an (R)-2-hydroxyadipate dehydrogenase comprising SEQ ID NO: 155 (HIDH) (producing (R)-2-hydroxyadipate); (b) SEQ ID NOs: 156 or 157 (gctA) and SEQ ID NOs: 159 or 160 (gctB) encoding an adipate Co-A transferase comprising SEQ ID NOs: 158 (gctA) and 161 (gctB) (producing (R)-hydroxyadipoyl-CoA); (c) SEQ ID NOs: 162 or 163 (hgdA) and SEQ ID NOs: 162 or 163 (hgdB) and SEQ ID NOs: 168 or 169 (hgdc) encoding an hydroxyadipoyl-CoA dehydratase comprising SEQ ID NO: 164 (hgdA), 167 (hgdB), and 170 (hgdc) (producing (E)-2-hexedioyl-CoA); (d) SEQ ID NOs: 156 or 157 (gctA) and SEQ ID NOs: 159 or 160 (gctB) encoding an adipate Co-A transferase comprising SEQ ID NOs: 158 (gctA) and 161 (gctB) (producing (E)-2-hexendioic acid); wherein (a)-(d) comprise enzymes catalyzing the conversion of 2-oxoadipate to (E)-2-hexenedioate, or the reverse reaction, when supplied with either 2-oxoadipate and NADH or (E)-2-hexenedioate and NAD+ and other appropriate cofactors or feedstocks.

Another aspect described herein is a method for enzymatically converting 2-oxoadipate to adipate, or the reverse reaction, comprising a non-natural organism comprising a microbial organism comprising: (a) SEQ ID NOs: 154 (Lys12) encoding an (R)-2-hydroxyadipate dehydrogenase comprising SEQ ID NO: 155 (HIDH) (producing (R)-2-hydroxyadipate); (b) SEQ ID NOs: 156 or 157 (gctA) and SEQ ID NOs: 159 or 160 (gctB) encoding an adipate Co-A transferase comprising SEQ ID NOs: 158 (gctA) and 161 (gctB) (producing (R)-hydroxyadipoyl-CoA); (c) SEQ ID NOs: 162 or 163 (hgdA) and SEQ ID NOs: 162 or 163 (hgdB) and SEQ ID NOs: 168 or 169 (hgdc) encoding an hydroxyadipoyl-CoA dehydratase comprising SEQ ID NO: 164 (hgdA), 167 (hgdB), and 170 (hgdc) (producing (E)-2-hexedioyl-CoA); (d) SEQ ID NOs: 171 or 172 (gdh) encoding an 2-hexenedioic acid dehydrogenase comprising SEQ ID NO: 173 (gdh) (producing adipoyl-CoA); (e) SEQ ID NOs: 156 or 157 (gctA) and SEQ ID NOs: 159 or 160 (gctB) encoding an adipate Co-A transferase comprising SEQ ID NOs: 158 (gctA) and 161 (gctB) (producing adipic acid); wherein (a)-(e) comprise enzymes catalyzing the conversion of 2-oxoadipate to adipate, or the reverse reaction, when supplied with either 2-oxoadipate and NADH or adipate and NAD+ and other appropriate cofactors or feedstocks.

Another embodiment described herein is a functional (R)-2-hydroxyglutarate dehydrogenase.

One aspect described herein is a polynucleotide comprising a nucleotide sequence encoding a polypeptide comprising a functional (R)-2-hydroxyglutarate dehydrogenase useful for catalyzing the conversion of 2-oxoglutarate to (R)-2-hydroxyglutarate, or the reverse reaction, wherein the polynucleotide is any one of SEQ ID NOs: 3, 5, 7, 9, 11, 13, 17, 21, 25, 29, or 33, or a degenerate, homologous, or codon-optimized variant thereof.

Another aspect described herein is a polynucleotide comprising a nucleotide sequence encoding a polypeptide comprising a functional (R)-2-hydroxyglutarate dehydrogenase useful for catalyzing the conversion of 2-oxoglutarate to (R)-2-hydroxyglutarate, or the reverse reaction, wherein the polypeptide is any one of SEQ ID NOs: 4, 6, 8, 10, 12, 14, 16, 18, 22, 26, 30, 34, or 35-153, or a degenerate or homologous variant thereof.

Another aspect described herein is a polynucleotide comprising a nucleotide sequence encoding a polypeptide comprising a functional (R)-2-hydroxyglutarate dehydrogenase useful for catalyzing the conversion of 2-oxoglutarate to (R)-2-hydroxyglutarate, or the reverse reaction, wherein the polynucleotide is at least 90% identical to the polynucleotide sequence shown in SEQ ID NOs: 1, 3, 5, 7, 9, 11, 13, 17, 21, 25, 29, or 33; with the proviso that the encoded polypeptide has at least one or more mutations to the active site at positions V111, R114, R115, R124, R143, or Y150 of SEQ ID NO: 2; wherein the one or more mutations disrupt oxidative decarboxylation but do not disrupt oxidoreductase activity.

Another aspect described herein is a polynucleotide comprising a nucleotide sequence encoding a polypeptide comprising a functional (R)-2-hydroxyglutarate dehydrogenase useful for catalyzing the conversion of 2-oxoglutarate to (R)-2-hydroxyglutarate, or the reverse reaction, wherein the polynucleotide is the sequence shown in SEQ ID NO: 1, 3, 5, 7, 9, 11, 13, 17, 21, 25, 29, or 33, with no more than 120 nucleotide substitutions; with the proviso that the encoded polypeptide has at least one or more mutations to the active site at positions analogous to V111, R114, R115, R124, R143, or Y150 of SEQ ID NO: 2; wherein the one or more mutations disrupt oxidative decarboxylation but do not disrupt oxidoreductase activity.

In some aspects, vectors comprise the polynucleotides comprising a nucleotide sequence encoding a polypeptide comprising a functional (R)-2-hydroxyglutarate dehydrogenase.

In some aspects, cultured cells comprise vectors comprising the polynucleotides comprising a nucleotide sequence encoding a polypeptide comprising a functional (R)-2-hydroxyglutarate dehydrogenase.

Another aspect described herein is a polypeptide comprising a functional (R)-2-hydroxyglutarate dehydrogenase useful for catalyzing the conversion of 2-oxoglutarate to (R)-2-hydroxyglutarate, or the reverse reaction, wherein the polypeptide is at least 90% identical to the polypeptide sequence shown in SEQ ID NOs: 2, 4, 6, 8, 10, 12, 14, 16, 18, 20, 22, 24, 26, 28, 30, 32, 34, or 35-153; with the proviso that the polypeptide has at least one or more mutations to the active site at positions V111, R114, R115, R124, R143, or Y150 of SEQ ID NO: 2; wherein the one or more mutations disrupt oxidative decarboxylation but do not disrupt oxidoreductase activity.

Another aspect described herein is a polypeptide comprising a functional (R)-2-hydroxyglutarate dehydrogenase useful for catalyzing the conversion of 2-oxoglutarate to (R)-2-hydroxyglutarate, or the reverse reaction, wherein the polypeptide is the sequence shown in SEQ ID NOs: 2, 4, 6, 8, 10, 12, 14, 16, 18, 20, 22, 24, 26, 28, 30, 32, 34, or 35-153 with no more than 40 amino acid substitutions; with the proviso that the polypeptide has at least one or more mutations to the active site at positions analogous to V111, R114, R115, R124, R143, or Y150 of SEQ ID NO: 2; wherein the one or more mutations disrupt oxidative decarboxylation but do not disrupt oxidoreductase activity.

Another aspect described herein is a composition useful for catalyzing the conversion of 2-oxoglutarate to (R)-2-hydroxyglutarate, or the reverse reaction, comprising: (a) a polynucleotide comprising a nucleotide sequence encoding a polypeptide comprising a functional (R)-2-hydroxyglutarate dehydrogenase; (b) a polynucleotide comprising a nucleotide sequence capable of hybridizing to the complement of (a) under hybridization conditions comprising 7% sodium dodecyl sulfate, 0.5 M $Na_2HPO_4$, 1 mM EDTA at 60° C. with washing in 1×SSC, 0.1% SDS at 60° C. encoding a polypeptide comprising a functional (R)-2-hydroxyglutarate dehydrogenase; (c) a polypeptide comprising an amino acid sequence comprising a functional oxidoreductase; (d) a vector comprising (a) or (b) or capable of expressing (c); or (e) an organism transformed with (d); and with the proviso that the polypeptide has one or more mutations to the active site at positions analogous to V111, R114, R115, R124, R143, or Y150 of the *Saccharomyces cerevisiae* homoisocitrate dehydrogenase (ScHIDH), i.e., SEQ ID NO: 2; and wherein the polypeptide catalyzes the conversion of 2-oxoglutarate to (R)-2-hydroxyglutarate in the presence of NADH.

In some aspects, the polynucleotide is any one of SEQ ID NOs: 1, 3, 5, 7, 9, 11, 13, 15, 17, 19, 21, 23, 25, 27, 29, 31, 33, or a degenerate, homologous, or codon-optimized variant thereof.

In some aspects, the polypeptide is any one of SEQ ID NOs: 2, 4, 6, 8, 10, 12, 14, 16, 18, 20, 22, 24, 26, 28, 30, 32, 34, 35-153, or degenerate or homologous variant thereof.

In some aspects, the polynucleotide is any one of SEQ ID NOs: 11, 13, 17, or a degenerate, homologous, or codon-optimized variant thereof.

In some aspects, the polypeptide is SEQ ID NO: 12, 14, 18, or a degenerate or homologous variant thereof.

In some aspects, the organism is *Escherichia coli, Sacchromyces cerevisia, Pichia pastoris, Geotrichum candidum, Candida albicans, Rhodotorula rubra,* or *Rhodosporidium* sp.

Another aspect described herein is a method for enzymatically converting 2-oxoglutarate to (R)-2-hydroxyglutarate comprising a (R)-2-hydroxyglutarate dehydrogenase, or the reverse reaction, comprising (a) a polynucleotide comprising a nucleotide sequence encoding a polypeptide comprising a functional (R)-2-hydroxyglutarate dehydrogenase, wherein the polynucleotide is any one of SEQ ID NOs: 1, 3, 5, 7, 9, 11, 13, 15, 17, 19, 21, or a degenerate, homologous, or codon-optimized variant thereof; (b) a polynucleotide comprising a nucleotide sequence capable of hybridizing to the complement of (a) under hybridization conditions comprising 7% sodium dodecyl sulfate, 0.5 M $Na_2HPO_4$, 1 mM EDTA at 60° C. with washing in 1×SSC, 0.1% SDS at 65° C. encoding a polypeptide comprising a functional (R)-2-hydroxyglutarate dehydrogenase; (c) a polypeptide comprising an amino acid sequence comprising a functional (R)-2-hydroxyglutarate dehydrogenase, wherein the polypeptide is any one of SEQ ID NOs: 2, 4, 6, 8, 10, 12, 14, 16, 18, 20, 22, 35-153 or degenerate or homologous variant thereof; (d) a vector comprising (a) or (b) or capable of expressing (c); or (e) an organism transformed with (d); and with the proviso that the (R)-2-hydroxyglutarate dehydrogenase has one or more mutations to the active site at positions analogous to V111, R114, R115, R124, R143, or Y150 of the *Saccharomyces cerevisiae* homoisocitrate dehydrogenase (ScHIDH), SEQ ID NO: 2; and wherein the (R)-2-hydroxyglutarate dehydrogenase catalyzes the conversion of 2-oxoglutarate to (R)-2-hydroxyglutarate in the presence of NADH, or the reverse reaction.

Another aspect described herein is a method for enzymatically converting 2-oxoglutarate to (R)-2-hydroxyglutarate comprising a (R)-2-hydroxyglutarate dehydrogenase, or the reverse reaction, comprising (a) selecting a polypeptide 2, 4, 6, 8, 10, 12, 14, 16, 18, 20, 22, 24, 26, 28, 30, 32, 34, or 35-153; (b) mutating one or more arginine residue in the active site to an amino acid selected from the group of His, Lys, Gln, Asn, Leu, Ile, Val, Tyr, Phe, Trp, Cys, Ser, Thr, Met, Glu, Asp, Ala, Gly, and Pro; with the proviso that the polypeptide has one or more mutations to the active site at positions analogous to R114, R115, R124, or R143, of the *Saccharomyces cerevisiae* homoisocitrate dehydrogenase (ScHIDH), SEQ ID NO: 2; and (c) assessing the oxidoreductase enzymatic activity; wherein the polypeptide catalyzes the conversion of 2-oxoglutarate to (R)-2-hydroxyglutarate in the presence of NADH, or the reverse reaction.

Another aspect described herein is a use of a (R)-2-hydroxyglutarate dehydrogenase to convert 2-oxoglutarate to (R)-2-hydroxyglutarate, or the reverse reaction, comprising: (a) a polynucleotide comprising a nucleotide sequence encoding a polypeptide comprising a functional (R)-2-hydroxyglutarate dehydrogenase, wherein the polynucleotide is any one of SEQ ID NOs: 1, 3, 5, 7, 9, 11, 13, 15, 17, 19, 21, or a degenerate, homologous, or codon-optimized variant thereof; (b) a polynucleotide comprising a nucleotide sequence capable of hybridizing to the complement of (a) under hybridization conditions comprising 7% sodium dodecyl sulfate, 0.5 M $Na_2HPO_4$, 1 mM EDTA at 60° C. with washing in 1×SSC, 0.1% SDS at 65° C. encoding a polypeptide comprising a functional (R)-2-hydroxyglutarate dehydrogenase; (c) a polypeptide comprising an amino acid sequence comprising a functional (R)-2-hydroxyglutarate dehydrogenase, wherein the polypeptide is any one of SEQ ID NOs: 2, 4, 6, 8, 10, 12, 14, 16, 18, 20, 22, 35-153 or degenerate or homologous variant thereof; (d) a vector comprising (a) or (b) or capable of expressing (c); or (e) an organism transformed with (d); and with the proviso that the (R)-2-hydroxyglutarate dehydrogenase has one or more mutations to the active site at positions analogous to V111, R114, R115, R124, R143, or Y150 of the *Saccharomyces cerevisiae* homoisocitrate dehydrogenase (ScHIDH), SEQ ID NO: 2; and wherein the (R)-2-hydroxyglutarate dehydrogenase catalyzes the conversion of 2-oxoglutarate to (R)-2-hydroxyglutarate in the presence of NADH, or the reverse reaction.

Another aspect described herein is a polynucleotide comprising a nucleotide sequence encoding a polypeptide comprising a functional (R)-2-hydroxyglutarate dehydrogenase useful for catalyzing the conversion of 2-oxoglutarate to (R)-2-hydroxyglutarate, or the reverse reaction, wherein the polynucleotide sequence is shown in SEQ ID NO: 11 or 13.

Another aspect described herein is a polypeptide comprising a functional (R)-2-hydroxyglutarate dehydrogenase useful for catalyzing the conversion of 2-oxoglutarate to (R)-2-hydroxyglutarate, or the reverse reaction, wherein the polypeptide sequence is shown in SEQ ID NO: 12 or 14.

Another aspect described herein is a method for enzymatically converting 2-oxoglutarate to (R)-2-hydroxyglutarate comprising a (R)-2-hydroxyglutarate dehydrogenase, or the reverse reaction, comprising (a) a polynucleotide comprising a nucleotide sequence encoding a polypeptide comprising a functional (R)-2-hydroxyglutarate dehydrogenase, wherein the polynucleotide is SEQ ID NO: 11 or 13; (b) a polynucleotide comprising a nucleotide sequence capable of hybridizing to the complement of (a) under hybridization conditions comprising 7% sodium dodecyl sulfate, 0.5 M Na$_2$HPO$_4$, 1 mM EDTA at 60° C. with washing in 1×SSC, 0.1% SDS at 65° C. encoding a polypeptide comprising a functional (R)-2-hydroxyglutarate dehydrogenase; (c) a polypeptide comprising an amino acid sequence comprising a functional (R)-2-hydroxyglutarate dehydrogenase, wherein the polypeptide is SEQ ID NO: 12 or 14; (d) a vector comprising (a) or (b) or capable of expressing (c); or (e) an organism transformed with (d); and wherein the (R)-2-hydroxyglutarate dehydrogenase catalyzes the conversion of 2-oxoglutarate to (R)-2-hydroxyglutarate in the presence of NADH, or the reverse reaction.

Another aspect described herein is a use of a (R)-2-hydroxyglutarate dehydrogenase to convert 2-oxoglutarate to (R)-2-hydroxyglutarate, or the reverse reaction, comprising: (a) a polynucleotide comprising a nucleotide sequence encoding a polypeptide comprising a functional (R)-2-hydroxyglutarate dehydrogenase, wherein the polynucleotide is SEQ ID NO: 11 or 13; (b) a polynucleotide comprising a nucleotide sequence capable of hybridizing to the complement of (a) under hybridization conditions comprising 7% sodium dodecyl sulfate, 0.5 M Na$_2$HPO$_4$, 1 mM EDTA at 60° C. with washing in 1×SSC, 0.1% SDS at 65° C. encoding a polypeptide comprising a functional (R)-2-hydroxyglutarate dehydrogenase; (c) a polypeptide comprising an amino acid sequence comprising a functional (R)-2-hydroxyglutarate dehydrogenase, wherein the polypeptide is SEQ ID NO: 12 or 14; (d) a vector comprising (a) or (b) or capable of expressing (c); or (e) an organism transformed with (d); and wherein the (R)-2-hydroxyglutarate dehydrogenase catalyzes the conversion of 2-oxoglutarate to (R)-2-hydroxyglutarate in the presence of NADH, or the reverse reaction.

Another embodiment described herein is a functional oxidoreductase (i.e., (R)-2-hydroxyacid dehydrogenase) capable of enzymatically converting a 1-carboxy-2-ketoacid (i.e., 1-carboxy-2-oxoacid, α-ketocarboxylic acid, α-oxoacid) to a 1-carboxy-(R)-2-hydroxyacid (i.e., 1-carboxy-D-2-hydroxyacid, (R)-α-hydroxycarboxylic acid), or the reverse reaction.

One aspect described herein is a polynucleotide comprising a nucleotide sequence encoding a polypeptide comprising a functional oxidoreductase (i.e., (R)-2-hydroxyacid dehydrogenase) capable of enzymatically converting a 1-carboxy-2-ketoacid (i.e., 1-carboxy-2-oxoacid, α-ketocarboxylic acid, α-oxoacid) to a 1-carboxy-(R)-2-hydroxyacid (i.e., 1-carboxy-D-2-hydroxyacid, (R)-α-hydroxycarboxylic acid), or the reverse reaction, wherein the polynucleotide is any one of SEQ ID NOs: 1, 3, 5, 7, 9, 11, 13, 15, 17, 19, 21, 23, 25, 27, 29, 31, 33, or a degenerate, homologous, or codon-optimized variant thereof.

Another aspect described herein is a polypeptide comprising a functional oxidoreductase capable of enzymatically converting a 1-carboxy-2-ketoacid to a 1-carboxy-(R)-2-hydroxyacid, wherein the polypeptide is any one of SEQ ID NOs: 2, 4, 6, 8, 10, 12, 14, 16, 18, 20, 22, 24, 26, 28, 30, 32, 34, or a degenerate, homologous, or codon-optimized variant thereof.

One aspect described herein is a polypeptide comprising a functional oxidoreductase capable of enzymatically converting a 1-carboxy-2-ketoacid to a 1-carboxy-(R)-2-hydroxyacid, wherein the polypeptide is any one of SEQ ID NOs: 35-153 or a degenerate, homologous, or codon-optimized variant thereof.

Another aspect described herein is a vector comprising a polynucleotide comprising a nucleotide sequence encoding a polypeptide comprising a functional oxidoreductase capable of enzymatically converting a 1-carboxy-2-ketoacid to a 1-carboxy-(R)-2-hydroxyacid, wherein the polynucleotide is any one of SEQ ID NOs: 1, 3, 5, 7, 9, 11, 13, 15, 17, 19, 21, 23, 25, 27, 29, 31, 33, or a degenerate, homologous, or codon-optimized variant thereof.

Another aspect described herein is a vector comprising a polynucleotide comprising a nucleotide sequence encoding a polypeptide comprising a functional oxidoreductase capable of enzymatically converting a 1-carboxy-2-ketoacid to a 1-carboxy-(R)-2-hydroxyacid, wherein the encoded polypeptide is any one of SEQ ID NOs: 2, 4, 6, 8, 10, 12, 14, 16, 18, 20, 22, 24, 26, 28, 30, 32, 34, or 35-153, or a degenerate or homologous variant thereof.

Another aspect described herein is a cultured cell comprising the vectors comprising functional oxidoreductase capable of enzymatically converting a 1-carboxy-2-ketoacid to a 1-carboxy-(R)-2-hydroxyacids.

Another aspect described herein is a polynucleotide comprising a nucleotide sequence encoding a polypeptide comprising a functional oxidoreductase capable of enzymatically converting a 1-carboxy-2-ketoacid to a 1-carboxy-(R)-2-hydroxyacid, wherein the nucleotide sequence is at least 90% identical to the polynucleotide sequences shown in SEQ ID NOs: 1, 3, 5, 7, 9, 11, 13, 15, 17, 19, 21, 23, 25, 27, 29, 31, or 33; with the proviso that the encoded polypeptide has at least one or more mutations to the active site at positions analogous to V111, R114, R115, R124, R143, or Y150 of the *Saccharomyces cerevisiae* homoisocitrate dehydrogenase (ScHIDH), i.e., SEQ ID NO: 2; wherein the one or more mutations disrupt oxidative decarboxylation but do not disrupt oxidoreductase activity.

Another aspect described herein is a polynucleotide comprising a nucleotide sequence encoding a polypeptide comprising a functional oxidoreductase capable of enzymatically converting a 1-carboxy-2-ketoacid to a 1-carboxy-(R)-2-hydroxyacid, wherein the nucleotide sequence is one of the sequences shown in SEQ ID NOs: 1, 3, 5, 7, 9, 11, 13, 15, 17, 19, 21, 23, 25, 27, 29, 31, or 33 with no more than 120 nucleotide substitutions; with the proviso that encoded polypeptide has at least one or more mutations to the active site at positions analogous to V111, R114, R115, R124, R143, or Y150 of the *Saccharomyces cerevisiae* homoisocitrate dehydrogenase (ScHIDH), i.e., SEQ ID NO: 2; wherein the one or more mutations disrupt oxidative decarboxylation but do not disrupt oxidoreductase activity.

One aspect described herein is a polynucleotide comprising a nucleotide sequence encoding a polypeptide comprising a functional oxidoreductase capable of enzymatically converting a 1-carboxy-2-ketoacid to a 1-carboxy-(R)-2-hydroxyacid, wherein the encoded polypeptide is at least 90% identical to the polypeptide sequences shown in SEQ ID NOs: 2, 4, 6, 8, 10, 12, 14, 16, 18, 20, 22, 24, 26, 28, 30, 32, 34, or 35-153; with the proviso that the encoded polypeptide has at least one or more mutations to the active site at positions analogous to V111, R114, R115, R124, R143, or Y150 of the *Saccharomyces cerevisiae* homoisocitrate dehydrogenase (ScHIDH), i.e., SEQ ID NO: 2; wherein the one or more mutations disrupt oxidative decarboxylation but do not disrupt oxidoreductase activity.

Another aspect described herein is a polynucleotide comprising a nucleotide sequence encoding a polypeptide comprising a functional oxidoreductase capable of enzymatically converting a 1-carboxy-2-ketoacid to a 1-carboxy-(R)-2-hydroxyacid, wherein the encoded polypeptide is one of the polypeptide sequence shown in SEQ ID NOs: 2, 4, 6, 8, 10, 12, 14, 16, 18, 20, 22, 24, 26, 28, 30, 32, 34, or 35-153 with no more than 40 amino acid substitutions; with the proviso that polypeptide has at least one or more mutations to the active site at positions analogous to V111, R114, R115, R124, R143, or Y150 of the *Saccharomyces cerevisiae* homoisocitrate dehydrogenase (ScHIDH), i.e., SEQ ID NO: 2; wherein the one or more mutations disrupt oxidative decarboxylation but do not disrupt oxidoreductase activity.

In some aspects, vectors comprise the polynucleotides comprising a nucleotide sequence encoding a polypeptide comprising a functional oxidoreductase capable of enzymatically converting a 1-carboxy-2-ketoacid to a 1-carboxy-(R)-2-hydroxyacid.

Another aspect described herein is a cultured cell comprising any of the vectors comprising polynucleotides comprising a nucleotide sequence encoding a polypeptide comprising a functional oxidoreductase capable of enzymatically converting a 1-carboxy-2-ketoacid to a 1-carboxy-(R)-2-hydroxyacid.

Another aspect described herein is a polypeptide comprising a functional oxidoreductase capable of enzymatically converting a 1-carboxy-2-ketoacid to a 1-carboxy-(R)-2-hydroxyacid, wherein the polypeptide is at least 90% identical to the polypeptide sequences shown in SEQ ID NOs: 2, 4, 6, 8, 10, 12, 14, 16, 18, 20, 22, 24, 26, 28, 30, 32, 34, or 35-153; with the proviso that the polypeptide has at least one or more mutations to the active site at positions analogous to V111, R114, R115, R124, R143, or Y150 of the *Saccharomyces cerevisiae* homoisocitrate dehydrogenase (ScHIDH), i.e., SEQ ID NO: 2; wherein the one or more mutations disrupt oxidative decarboxylation but do not disrupt oxidoreductase activity.

Another aspect described herein is a polypeptide comprising a functional oxidoreductase capable of enzymatically converting a 1-carboxy-2-ketoacid to a 1-carboxy-(R)-2-hydroxyacid, wherein the encoded polypeptide is one of the polypeptide sequence shown in SEQ ID NOs: 2, 4, 6, 8, 10, 12, 14, 16, 18, 20, 22, 24, 26, 28, 30, 32, 34, or 35-153 with no more than 40 amino acid substitutions; with the proviso that the polypeptide has at least one or more mutations to the active site at positions analogous to V111, R114, R115, R124, R143, or Y150 of the *Saccharomyces cerevisiae* homoisocitrate dehydrogenase (ScHIDH), i.e., SEQ ID NO: 2; wherein the one or more mutations disrupt oxidative decarboxylation but do not disrupt oxidoreductase activity.

Another aspect described herein is a polynucleotide comprising a nucleotide sequence encoding a polypeptide comprising a functional (R)-2-hydroxyacid dehydrogenase useful for catalyzing the enantioselective conversion of a 1-carboxy-2-ketoacid to a 1-carboxy-(R)-2-hydroxyacid, or the reverse reaction, wherein the polynucleotide is any one of SEQ ID NOs: 3, 5, 7, 9, 11, 13, 17, 21, 25, 29, or 33, or a degenerate, homologous, or codon-optimized variant thereof.

Another aspect described herein is a polynucleotide comprising a nucleotide sequence encoding a polypeptide comprising a functional (R)-2-hydroxyacid dehydrogenase useful for catalyzing the enantioselective conversion of a 1-carboxy-2-ketoacid to a 1-carboxy-(R)-2-hydroxyacid, or the reverse reaction, wherein the polypeptide is any one of SEQ ID NOs: 4, 6, 8, 10, 12, 14, 16, 18, 22, 26, 30, 34, or 35-153, or a degenerate or homologous variant thereof.

Another aspect described herein is a polynucleotide comprising a nucleotide sequence encoding a polypeptide comprising a functional (R)-2-hydroxyacid dehydrogenase useful for catalyzing the enantioselective conversion of a 1-carboxy-2-ketoacid to a 1-carboxy-(R)-2-hydroxyacid, or the reverse reaction, wherein the polynucleotide is at least 90% identical to the polynucleotide sequence shown in SEQ ID NOs: 3, 5, 7, 9, 11, 13, 17, 21, 25, 29, or 33; with the proviso that the encoded polypeptide has at least one or more mutations to the active site at positions V111, R114, R115, R124, R143, or Y150 of SEQ ID NO: 2; wherein the one or more mutations disrupt oxidative decarboxylation but do not disrupt oxidoreductase activity.

Another aspect described herein is a polynucleotide comprising a nucleotide sequence encoding a polypeptide comprising a functional (R)-2-hydroxyacid dehydrogenase useful for catalyzing the enantioselective conversion of a 1-carboxy-2-ketoacid to a 1-carboxy-(R)-2-hydroxyacid, or the reverse reaction, wherein the polynucleotide is the sequence shown in SEQ ID NO: 3, 5, 7, 9, 11, 13, 17, 21, 25, 29, or 33, with no more than 120 nucleotide substitutions; with the proviso that the encoded polypeptide has at least one or more mutations to the active site at positions analogous to V111, R114, R115, R124, R143, or Y150 of SEQ ID NO: 2; wherein the one or more mutations disrupt oxidative decarboxylation but do not disrupt oxidoreductase activity.

In some aspects, vectors comprise the polynucleotides comprising a functional (R)-2-hydroxyacid dehydrogenase In some aspects, cultured cells comprise vectors comprising the polynucleotides comprising a functional (R)-2-hydroxyacid dehydrogenase.

Another aspect described herein is a polypeptide comprising a functional (R)-2-hydroxyacid dehydrogenase useful for catalyzing the enantioselective conversion of a 1-carboxy-2-ketoacid to a 1-carboxy-(R)-2-hydroxyacid, or the reverse reaction, wherein the polypeptide is at least 90% identical to the polypeptide sequence shown in SEQ ID NOs: 2, 4, 6, 8, 10, 12, 14, 16, 18, 20, 22, 24, 26, 28, 30, 32, 34, or 35-153; with the proviso that the polypeptide has at least one or more mutations to the active site at positions V111, R114, R115, R124, R143, or Y150 of SEQ ID NO: 2; wherein the one or more mutations disrupt oxidative decarboxylation but do not disrupt oxidoreductase activity.

Another aspect described herein is a polypeptide comprising a functional (R)-2-hydroxyacid dehydrogenase useful for catalyzing the enantioselective conversion of a 1-carboxy-2-ketoacid to a 1-carboxy-(R)-2-hydroxyacid, or the reverse reaction, wherein the polypeptide is the sequence shown in SEQ ID NOs: 2, 4, 6, 8, 10, 12, 14, 16, 18, 20, 22, 24, 26, 28, 30, 32, 34, or 35-153 with no more than 40 amino acid substitutions; with the proviso that the polypeptide has at least one or more mutations to the active site at positions analogous to V111, R114, R115, R124, R143, or Y150 of SEQ ID NO: 2; wherein the one or more mutations disrupt oxidative decarboxylation but do not disrupt oxidoreductase activity.

Another aspect described herein is a composition useful for catalyzing the conversion of a 1-carboxy-2-ketoacid to a 1-carboxy-(R)-2-hydroxyacid, or the reverse reaction, comprising: (a) a polynucleotide comprising a nucleotide sequence encoding a polypeptide comprising a functional (R)-2-hydroxyacid dehydrogenase; (b) a polynucleotide comprising a nucleotide sequence capable of hybridizing to the complement of (a) under hybridization conditions comprising 7% sodium dodecyl sulfate, 0.5 M $Na_2HPO_4$, 1 mM EDTA at 60° C. with washing in 1×SSC, 0.1% SDS at 60° C. encoding a polypeptide comprising a functional (R)-2-hydroxyglutarate dehydrogenase; (c) a polypeptide comprising an amino acid sequence comprising a functional oxidoreductase; (d) a vector comprising (a) or (b) or capable of expressing (c); or (e) an organism transformed with (d); and with the proviso that the polypeptide has one or more mutations to the active site at positions analogous to V111, R114, R115, R124, R143, or Y150 of the *Saccharomyces cerevisiae* homoisocitrate dehydrogenase (ScHIDH), i.e., SEQ ID NO: 2; and wherein the polypeptide catalyzes the conversion of 1-carboxy-2-ketoacid to a 1-carboxy-(R)-2-hydroxyacid, in the presence of NADH.

In one aspect described herein, the polynucleotide is any one of SEQ ID NOs: 1, 3, 5, 7, 9, 11, 13, 15, 17, 19, 21, 23, 25, 27, 29, 31, 33, or a degenerate, homologous, or codon-optimized variant thereof.

In one aspect described herein, the polypeptide is any one of SEQ ID NOs: 2, 4, 6, 8, 10, 12, 14, 16, 18, 20, 22, 24, 26, 28, 30, 32, 34, 35-153, or degenerate or homologous variant thereof.

In one aspect described herein, the polynucleotide is any one of SEQ ID NOs: 11, 13, 17, or a degenerate, homologous, or codon-optimized variant thereof.

In one aspect described herein, the polypeptide is SEQ ID NO: 12, 14, 18, or a degenerate or homologous variant thereof.

In one aspect described herein, the organism is *Escherichia coli, Sacchromyces cerevisia, Pichia pastoris, Geotrichum candidum, Candida albicans, Rhodotorula rubra*, or *Rhodosporidium* sp.

Another aspect described herein is a method for enzymatically converting a 1-carboxy-2-ketoacid to a 1-carboxy-(R)-2-hydroxyacid, comprising a (R)-2-hydroxyacid dehydrogenase, or the reverse reaction, comprising (a) a polynucleotide comprising a nucleotide sequence encoding a polypeptide comprising a functional (R)-2-hydroxyacid dehydrogenase, wherein the polynucleotide is any one of SEQ ID NOs: 1, 3, 5, 7, 9, 11, 13, 15, 17, 19, 21, or a degenerate, homologous, or codon-optimized variant thereof; (b) a polynucleotide comprising a nucleotide sequence capable of hybridizing to the complement of (a) under hybridization conditions comprising 7% sodium dodecyl sulfate, 0.5 M $Na_2HPO_4$, 1 mM EDTA at 60° C. with washing in 1×SSC, 0.1% SDS at 65° C. encoding a polypeptide comprising a functional (R)-2-hydroxyacid dehydrogenase; (c) a polypeptide comprising an amino acid sequence comprising a functional (R)-2-hydroxyacid dehydrogenase, wherein the polypeptide is any one of SEQ ID NOs: 2, 4, 6, 8, 10, 12, 14, 16, 18, 20, 22, 35-153 or degenerate or homologous variant thereof; (d) a vector comprising (a) or (b) or capable of expressing (c); or (e) an organism transformed with (d); and with the proviso that the (R)-2-hydroxyacid dehydrogenase has one or more mutations to the active site at positions analogous to V111, R114, R115, R124, R143, or Y150 of the *Saccharomyces cerevisiae* homoisocitrate dehydrogenase (ScHIDH), SEQ ID NO: 2; and wherein the (R)-2-hydroxyacid dehydrogenase catalyzes the conversion of a 1-carboxy-2-ketoacid to a 1-carboxy-(R)-2-hydroxyacid, in the presence of NADH, or the reverse reaction.

Another aspect described herein is a method for enzymatically converting a 1-carboxy-2-ketoacid to a 1-carboxy-(R)-2-hydroxyacid, comprising a (R)-2-hydroxyacid dehydrogenase, or the reverse reaction, comprising (a) selecting a polypeptide 2, 4, 6, 8, 10, 12, 14, 16, 18, 20, 22, 24, 26, 28, 30, 32, 34, or 35-153; (b) mutating one or more arginine residue in the active site to an amino acid selected from the group of His, Lys, Gln, Asn, Leu, Ile, Val, Tyr, Phe, Trp, Cys, Ser, Thr, Met, Glu, Asp, Ala, Gly, and Pro; with the proviso that the polypeptide has one or more mutations to the active site at positions analogous to R114, R115, R124, or R143, of the *Saccharomyces cerevisiae* homoisocitrate dehydrogenase (ScHIDH), SEQ ID NO: 2; and (c) assessing the oxidoreductase enzymatic activity; wherein the polypeptide catalyzes the conversion of a 1-carboxy-2-ketoacid to a 1-carboxy-(R)-2-hydroxyacid, in the presence of NADH, or the reverse reaction.

Another aspect described herein is a use of a (R)-2-hydroxyacid dehydrogenase to convert a 1-carboxy-2-ketoacid to a 1-carboxy-(R)-2-hydroxyacid, or the reverse reaction, comprising: (a) a polynucleotide comprising a nucleotide sequence encoding a polypeptide comprising a functional (R)-2-hydroxyacid dehydrogenase, wherein the polynucleotide is any one of SEQ ID NOs: 1, 3, 5, 7, 9, 11, 13, 15, 17, 19, 21, or a degenerate, homologous, or codon-optimized variant thereof; (b) a polynucleotide comprising a nucleotide sequence capable of hybridizing to the complement of (a) under hybridization conditions comprising 7% sodium dodecyl sulfate, 0.5 M $Na_2HPO_4$, 1 mM EDTA at 60° C. with washing in 1×SSC, 0.1% SDS at 65° C. encoding a polypeptide comprising a functional (R)-2-hydroxyacid dehydrogenase; (c) a polypeptide comprising an amino acid sequence comprising a functional (R)-2-hydroxyacid dehydrogenase, wherein the polypeptide is any one of SEQ ID NOs: 2, 4, 6, 8, 10, 12, 14, 16, 18, 20, 22, 35-153 or degenerate or homologous variant thereof; (d) a vector comprising (a) or (b) or capable of expressing (c); or (e) an organism transformed with (d); and with the proviso that the (R)-2-hydroxyacid dehydrogenase has one or more mutations to the active site at positions analogous to V111, R114, R115, R124, R143, or Y150 of the *Saccharomyces cerevisiae* homoisocitrate dehydrogenase (ScHIDH), SEQ ID NO: 2; and wherein the (R)-2-hydroxyacid dehydrogenase catalyzes the conversion of a 1-carboxy-2-ketoacid to a 1-carboxy-(R)-2-hydroxyacid, in the presence of NADH, or the reverse reaction.

Another aspect described herein is a polynucleotide comprising a nucleotide sequence encoding a polypeptide comprising a functional (R)-2-hydroxyacid dehydrogenase useful for catalyzing the conversion of 2-oxoglutarate to (R)-2-hydroxyglutarate, or the reverse reaction, wherein the polynucleotide sequence is shown in SEQ ID NO: 11 or 13.

Another aspect described herein is a polypeptide comprising a functional (R)-2-hydroxyacid dehydrogenase useful for catalyzing the conversion of a 1-carboxy-2-ketoacid to a 1-carboxy-(R)-2-hydroxyacid, or the reverse reaction, wherein the polypeptide sequence is shown in SEQ ID NO: 12 or 14.

Another aspect described herein is a method for enzymatically converting a 1-carboxy-2-ketoacid to a 1-carboxy-(R)-2-hydroxyacid, comprising a (R)-2-hydroxyacid dehydrogenase, or the reverse reaction, comprising (a) a polynucleotide comprising a nucleotide sequence encoding a polypeptide comprising a functional (R)-2-hydroxyacid dehydrogenase, wherein the polynucleotide is SEQ ID NO: 11 or 13; (b) a polynucleotide comprising a nucleotide sequence capable of hybridizing to the complement of (a) under hybridization conditions comprising 7% sodium dodecyl sulfate, 0.5 M Na$_2$HPO$_4$, 1 mM EDTA at 60° C. with washing in 1×SSC, 0.1% SDS at 65° C. encoding a polypeptide comprising a functional (R)-2-hydroxyacid dehydrogenase; (c) a polypeptide comprising an amino acid sequence comprising a functional (R)-2-hydroxyacid dehydrogenase, wherein the polypeptide is SEQ ID NO: 12 or 14; (d) a vector comprising (a) or (b) or capable of expressing (c); or (e) an organism transformed with (d); and wherein the (R)-2-hydroxyacid dehydrogenase catalyzes the conversion of a 1-carboxy-2-ketoacid to a 1-carboxy-(R)-2-hydroxyacid in the presence of NADH, or the reverse reaction.

Another aspect described herein is a use of a (R)-2-hydroxyacid dehydrogenase to convert a 1-carboxy-2-ketoacid to a 1-carboxy-(R)-2-hydroxyacid, or the reverse reaction, comprising: (a) a polynucleotide comprising a nucleotide sequence encoding a polypeptide comprising a functional (R)-2-hydroxyacid dehydrogenase, wherein the polynucleotide is SEQ ID NO: 11 or 13; (b) a polynucleotide comprising a nucleotide sequence capable of hybridizing to the complement of (a) under hybridization conditions comprising 7% sodium dodecyl sulfate, 0.5 M Na$_2$HPO$_4$, 1 mM EDTA at 60° C. with washing in 1×SSC, 0.1% SDS at 65° C. encoding a polypeptide comprising a functional (R)-2-hydroxyacid dehydrogenase; (c) a polypeptide comprising an amino acid sequence comprising a functional (R)-2-hydroxyacid dehydrogenase, wherein the polypeptide is SEQ ID NO: 12 or 14; (d) a vector comprising (a) or (b) or capable of expressing (c); or (e) an organism transformed with (d); and wherein the (R)-2-hydroxyacid dehydrogenase catalyzes the conversion of a 1-carboxy-2-ketoacid to a 1-carboxy-(R)-2-hydroxyacid in the presence of NADH, or the reverse reaction.

Another embodiment described herein is a functional oxidoreductase.

One aspect described herein is a polynucleotide comprising a nucleotide sequence encoding a polypeptide comprising a functional oxidoreductase, wherein the polynucleotide is any one of SEQ ID NOs: 1, 3, 5, 7, 9, 11, 13, 15, 17, 19, 21, 23, 25, 27, 29, 31, 33, or a degenerate, homologous, or codon-optimized variant thereof.

Another aspect described herein is a polypeptide comprising a functional oxidoreductase, wherein the polypeptide is any one of SEQ ID NOs: 2, 4, 6, 8, 10, 12, 14, 16, 18, 20, 22, 24, 26, 28, 30, 32, 34, or a degenerate, homologous, or codon-optimized variant thereof.

One aspect described herein is a polypeptide comprising a functional oxidoreductase, wherein the polypeptide is any one of SEQ ID NOs: 35-153 or a degenerate or homologous variant thereof.

One aspect described herein is a vector comprising a polynucleotide comprising a nucleotide sequence encoding a polypeptide comprising a functional oxidoreductase, wherein the polynucleotide is any one of SEQ ID NOs: 1, 3, 5, 7, 9, 11, 13, 15, 17, 19, 21, 23, 25, 27, 29, 31, 33, or a degenerate, homologous, or codon-optimized variant thereof.

Another aspect described herein is a vector comprising a polynucleotide comprising a nucleotide sequence encoding a polypeptide comprising a functional oxidoreductase, wherein the encoded polypeptide is any one of SEQ ID NOs: 2, 4, 6, 8, 10, 12, 14, 16, 18, 20, 22, 24, 26, 28, 30, 32, 34, or 35-153, or a degenerate or homologous variant thereof.

Another aspect described herein is a cultured cell comprising the vectors comprising a polynucleotide comprising a nucleotide sequence encoding a polypeptide comprising a functional oxidoreductase.

Another aspect described herein is a polynucleotide comprising a nucleotide sequence encoding a polypeptide comprising a functional oxidoreductase, wherein the nucleotide sequence is at least 90% identical to the polynucleotide sequences shown in SEQ ID NOs: 1, 3, 5, 7, 9, 11, 13, 15, 17, 19, 21, 23, 25, 27, 29, 31, or 33; with the proviso that the encoded polypeptide has at least one or more mutations to the active site at positions analogous to V111, R114, R115, R124, R143, or Y150 of the *Saccharomyces cerevisiae* homoisocitrate dehydrogenase (ScHIDH), i.e., SEQ ID NO: 2; wherein the one or more mutations disrupt oxidative decarboxylation but do not disrupt oxidoreductase activity.

Another aspect described herein is a polynucleotide comprising a nucleotide sequence encoding a polypeptide comprising a functional oxidoreductase, wherein the nucleotide sequence is one of the sequences shown in SEQ ID NOs: 1, 3, 5, 7, 9, 11, 13, 15, 17, 19, 21, 23, 25, 27, 29, 31, or 33 with no more than 120 nucleotide substitutions; with the proviso that encoded polypeptide has at least one or more mutations to the active site at positions analogous to V111, R114, R115, R124, R143, or Y150 of the *Saccharomyces cerevisiae* homoisocitrate dehydrogenase (ScHIDH), i.e., SEQ ID NO: 2; wherein the one or more mutations disrupt oxidative decarboxylation but do not disrupt oxidoreductase activity.

Another aspect described herein is a polynucleotide comprising a nucleotide sequence encoding a polypeptide comprising a functional oxidoreductase, wherein the encoded polypeptide is at least 90% identical to the polypeptide sequences shown in SEQ ID NOs: 2, 4, 6, 8, 10, 12, 14, 16, 18, 20, 22, 24, 26, 28, 30, 32, 34, or 35-153; with the proviso that the encoded polypeptide has at least one or more mutations to the active site at positions analogous to V111, R114, R115, R124, R143, or Y150 of the *Saccharomyces cerevisiae* homoisocitrate dehydrogenase (ScHIDH), i.e., SEQ ID NO: 2; wherein the one or more mutations disrupt oxidative decarboxylation but do not disrupt oxidoreductase activity.

Another aspect described herein is a polynucleotide comprising a nucleotide sequence encoding a polypeptide comprising a functional oxidoreductase, wherein the encoded polypeptide is one of the polypeptide sequence shown in SEQ ID NOs: 2, 4, 6, 8, 10, 12, 14, 16, 18, 20, 22, 24, 26, 28, 30, 32, 34, or 35-153 with no more than 40 amino acid substitutions; with the proviso that polypeptide has at least one or more mutations to the active site at positions analogous to V111, R114, R115, R124, R143, or Y150 of the *Saccharomyces cerevisiae* homoisocitrate dehydrogenase (ScHIDH), i.e., SEQ ID NO: 2; wherein the one or more mutations disrupt oxidative decarboxylation but do not disrupt oxidoreductase activity.

Another aspect described herein is a vector comprising the polynucleotides vector comprising a polynucleotide comprising a nucleotide sequence encoding a polypeptide comprising a functional oxidoreductase. In some aspects, the polynucleotide is a codon-optimized nucleotide sequence encoding a polypeptide comprising a functional oxidoreductase.

Another aspect described herein is a cultured cell comprising any of the vectors comprising a polynucleotide comprising a nucleotide sequence encoding a polypeptide comprising a functional oxidoreductase.

Another aspect described herein is a polypeptide comprising a functional oxidoreductase, wherein the polypeptide is at least 90% identical to the polypeptide sequences shown in SEQ ID NOs: 2, 4, 6, 8, 10, 12, 14, 16, 18, 20, 22, 24, 26, 28, 30, 32, 34, or 35-153; with the proviso that the polypeptide has at least one or more mutations to the active site at positions analogous to V111, R114, R115, R124, R143, or Y150 of the *Saccharomyces cerevisiae* homoisocitrate dehydrogenase (ScHIDH), i.e., SEQ ID NO: 2; wherein the one or more mutations disrupt oxidative decarboxylation but do not disrupt oxidoreductase activity.

Another aspect described herein is a polypeptide comprising a functional oxidoreductase, wherein the encoded polypeptide is one of the polypeptide sequence shown in SEQ ID NOs: 2, 4, 6, 8, 10, 12, 14, 16, 18, 20, 22, 24, 26, 28, 30, 32, 34, or 35-153 with no more than 40 amino acid substitutions; with the proviso that the polypeptide has at least one or more mutations to the active site at positions analogous to V111, R114, R115, R124, R143, or Y150 of the *Saccharomyces cerevisiae* homoisocitrate dehydrogenase (ScHIDH), i.e., SEQ ID NO: 2; wherein the one or more mutations disrupt oxidative decarboxylation but do not disrupt oxidoreductase activity.

BRIEF DESCRIPTION OF THE DRAWINGS

FIG. 1: Biosynthetic method for conversion of 2-oxoadipate to adipate. (A) (1) 2-oxoadipate from general metabolism is converted to (2) (R)-2-hydroxyadipate by (R)-2-hydroxyadipate dehydrogenase and NADH; (3) (E)-2-hydroxyladipoyl-CoA by gluconate Co-A transferase and CoA; (4) (E)-2-hexenedioyl-CoA by hydroxyadipoyl-CoA dehydratase; (5) (E)-2-hexenedioate by gluconate Co-A transferase and CoA; and (6) adipate by (E)-2-hexenedioic acid dehydrogenase and NADH in bacteria. (B) IDHs catalyze the NAD(P)$^+$-linked reversible oxidative decarboxylation of isocitrate to form 2-oxoglutarate and $CO_2$. (C) In human cancer, IDH1 mutants (e.g., HsIDH1-R132H, HsIDH2-R140Q) catalyze the non-carboxylating reduction of 2-oxoglutarate to (R)-2-hydroxyglutarate. (D) HIDHs catalyze the NAD$^+$-linked reversible oxidative decarboxylation of homoisocitrate to form 2-oxoadipate and $CO_2$. (E) HIDH mutants catalyze the non-carboxylating reduction of 2-oxoadipate to (R)-2-hydroxyadipate.

FIG. 2: (A) Superimposition of three-dimensional structure of the active site for TtHIDH (light gray; PDB Accession No. 3ASJ; Miyazaki et al. *J. Biol. Chem.* 278, 1864-1871 (2003)) onto the HsIDH1 complex with isocitrate (dark gray; PDB Accession No. 1TOL; Xu et al., *J. Biol. Chem.* 279, 33946-33957 (2004)). The corresponding residues for TtHIDH are shown in parentheses. (B) Active site sequence alignments for isocitrate dehydrogenases (IDH), homoisocitrate dehydrogenases (HIDH), isopropylmalate dehydrogenases (IPMDHs) and tartarate dehydrogenases (TDHs), from *Homo sapiens* (Hs); *Saccharomyces cerevisiae* (Sc); *Schizosaccharomyces pombe* (Sp); *Thermus thermophilus* (Tt); and *Escherichia coli* (Ec) are shown with conserved arginine residues bolded as follows: HsIDH1, HsIDH2, ScHIDH, SpHIDH, TtHIDH, TtIPMDH, ScIPMDH, and EcTDH.

FIG. 3: Alignment of isocitrate dehydrogenases (IDH), homoisocitrate dehydrogenases (HIDH), isopropylmalate dehydrogenases (IPMDHs) and tartarate dehydrogenases (TDHs) from various species.

| Identifier | Organism and Enzyme | NCBI GI Number | SEQ ID No. |
| --- | --- | --- | --- |
| Sy_IDH | *Sphingobium yanoikuyae* isocitrate dehydrogenase | GI No. 1052977 | SEQ ID NO: 139 |
| Hs_IDH1 | *Homo sapiens* isocitrate dehydrogenase 1 | GI No. 49168486 | SEQ ID NO: 140 |
| Hs_IDH2 | *Homo sapiens* isocitrate dehydrogenase 2 | GI No. 28178832 | SEQ ID NO: 141 |
| Ec_IDH | *Escherichia coli* isocitrate dehydrogenase | GI No. 209772816 | SEQ ID NO: 142 |
| Bs_IDH | *Bacillus subtilis* isocitrate dehydrogenase | GI No. 729813 | SEQ ID NO: 143 |
| Hs_IDH_NAD | *Homo sapiens* isocitrate dehydrogenase 3 | GI No. 62897507 | SEQ ID NO: 144 |
| Sp_HIDH | *Schizosaccharomyces pombe* homoisocitrate dehydrogenase | GI No. 2388955 | SEQ ID NO: 145 |
| Sc_HIDH | *Saccharomyces cerevisiae* homoisocitrate dehydrogenase | GI No. 731845 | SEQ ID NO: 146 |
| Ca_HIDH | *Candida albicans* homoisocitrate dehydrogenase | GI No. 238879624 | SEQ ID NO: 147 |
| Tt_HIDH | *Thermus thermophilus* homoisocitrate dehydrogenase | GI No. 46199314 | SEQ ID NO: 148 |
| Ec_TDH | *Escherichia coli* tartarate dehydrogenase | GI No. 320668365 | SEQ ID NO: 149 |
| Pp_TDH | *Pseudomonas putida* tartarate dehydrogenase | GI No. 167033202 | SEQ ID NO: 150 |
| Tt_IPMDH | *Thermus thermophilus* isopropylmalate dehydrogenase | GI No. 66773874 | SEQ ID NO: 151 |
| Af_IPMDH | *Acidithiobacillus ferrooxidans* isopropylmalate dehydrogenase | GI No. 198283840 | SEQ ID NO: 152 |
| Sc_IPMDH | *Saccharomyces cerevisiae* isopropylmalate dehydrogenase | GI No. 151943807 | SEQ ID NO: 153 |

Legend for FIG. 3:
Alignment of native sequences of isocitrate dehydrogenases (IDH),
homoisocitrate dehydrogenases (HIDH),
isopropylmalate dehydrogenases (IPMDHs), and
tartarate dehydrogenases (TDHs) from various species.

Figure 4:
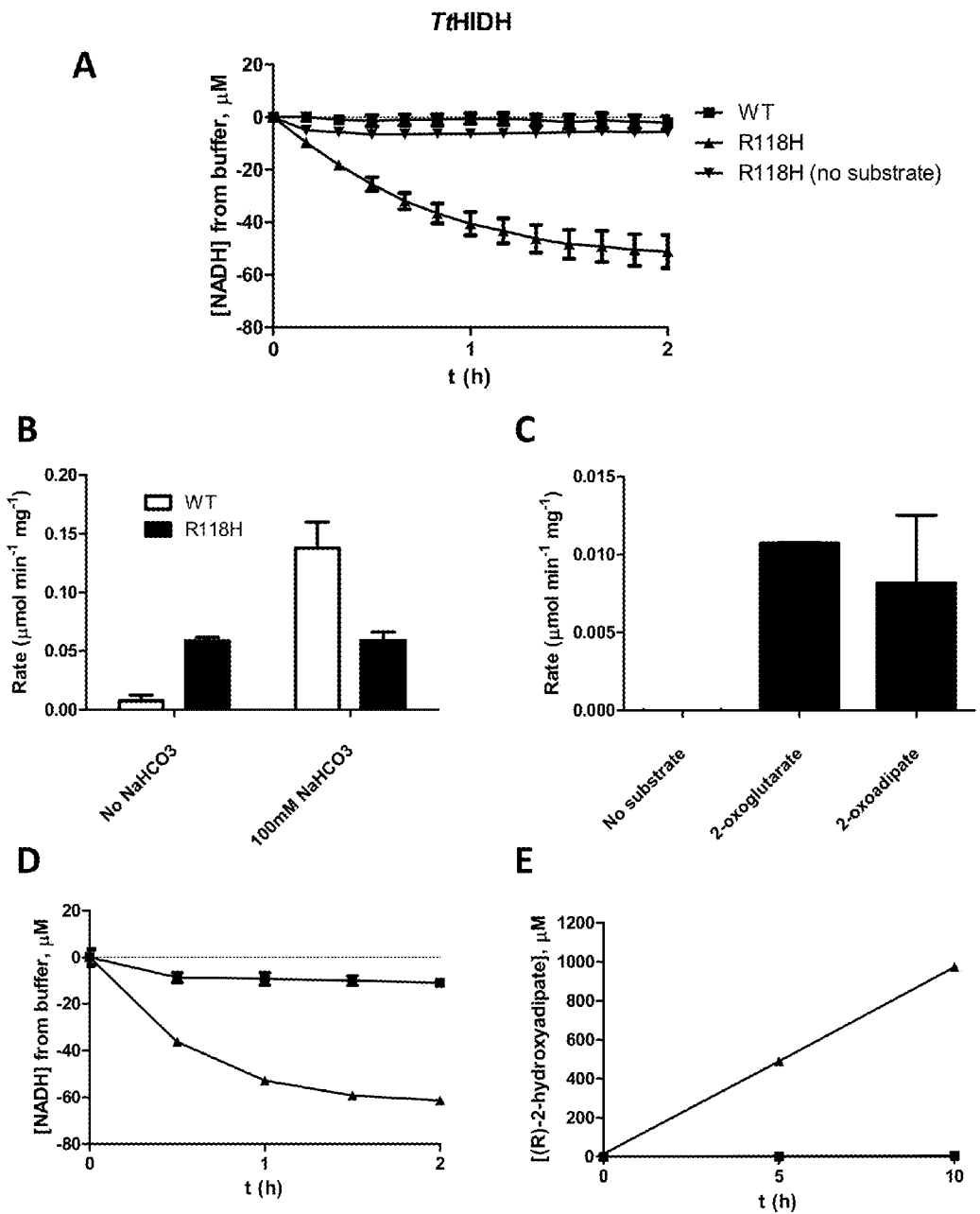

FIG. 4: Activity and product analysis of TtHIDH-R118H. (A) Decrease in NADH over time in a standard reaction initially containing 5 µg TtHIDH-R118H, 100 µM NADH, and 15 mM 2-oxoadipate. Minimal NADH oxidation is observed in control reactions containing TtHIDH-WT instead of TtHIDH-R118H, and in a control reaction containing TtHIDH-R118H with no 2-oxoadipate substrate. (B) Addition of $CO_2$ to the reaction as $NaHCO_3$ stimulates NADH oxidation in the presence of TtHIDH-WT, but not TtHIDH-R118H. (C) TtHIDH-R118H is also stimulated by 2-oxoglutarate. (D) Reactions containing BSA, TtHIDH-WT, or TtHIDH-R118H were monitored for NADH concentration for 2-hours. The concentration of (R)-2-hydroxyadipate was measured immediately after the reaction was mixed and again after 2-hours as shown in (E). Reactions were performed at 45° C. with 100 μM NADH and 15 mM 2-oxoadipate. The mean and standard error of the mean (SEM) for n=2 reactions are shown for each data point, and are representative of three independent experiments.

Figure 5:
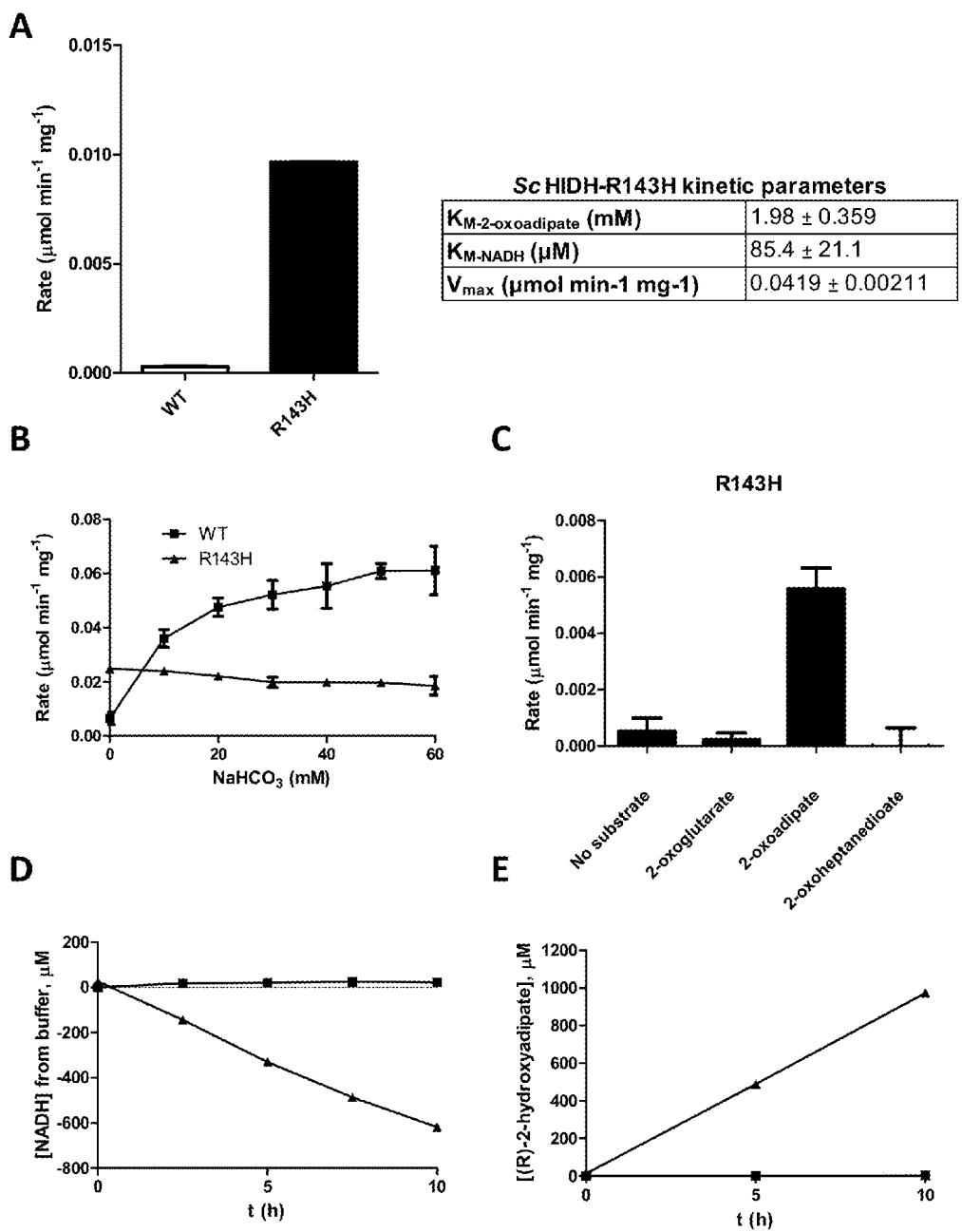

FIG. 5: Activity and product analysis of ScHIDH-R143H. Reactions were carried out with 100 μM NADH, 15 mM 2-oxoadipate, and 0.4 μg of purified ScHIDH-R143H or controls, in standard reaction buffer, unless indicated otherwise. (A) Initial rate of NADH decrease in the presence of BSA (protein control), ScHIDH-WT, or ScHIDH-R143H. (B) Initial rate of NADH decrease catalyzed by ScHIDH-WT or ScHIDH-R143H the presence of 0-60 mM $NaHCO_3$. (C) Initial rate of NADH decrease catalyzed by ScHIDH-R143H with 15 mM of the 5-carbon, 6-carbon, and 7-carbon diacids 2-oxoglutarate, 2-oxoadipate, and 2-oxoheptandioate, respectively, as substrate. (D) NADH concentration as assessed by UV absorbance at 340 nm. (E) (R)-2-hydroxyadipate concentration as quantified by LC-MS/MS, for a reaction containing 2 mM NADH and 2 mM 2-oxoadipate at 0, 5, and 10 h. Mean and SEM (if large enough to be shown) from n=2 reactions are shown and are representative of three independent experiments.

Figure 6:
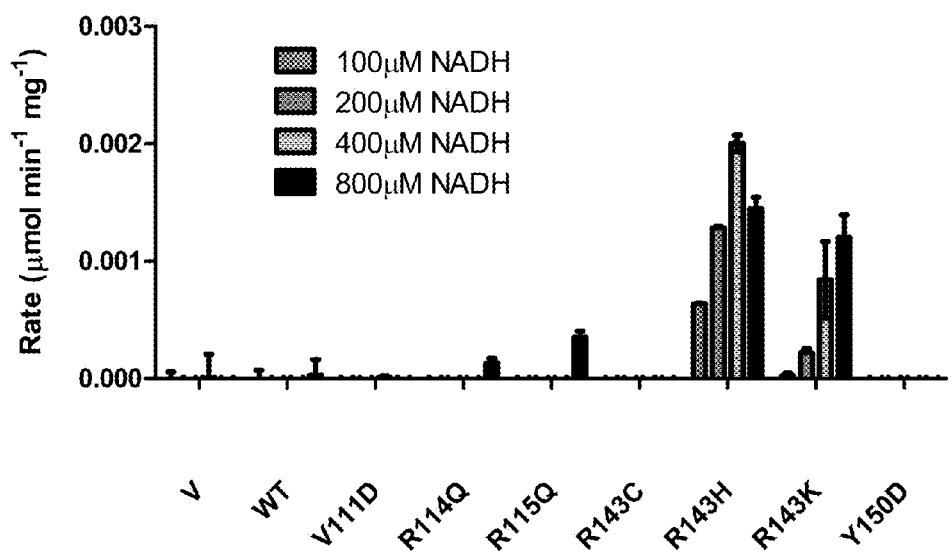

FIG. 6: Activity for a panel of ScHIDH mutants. The mutated human gene (IDH1 or IDH2) and mutation are shown, as well as a reference that identified that mutation in cancer or identified neomorphic function for that mutation in vitro. Crude lysates overexpressing ScHIDH-WT, -V111D, -R114Q, -R115Q, -R143C, -R143H, -R143K, and -Y150D were added to a reaction mix containing 15 mM 2-oxoadipate and 100-800 μM NADH. Mean and SEM (n=2) for the rate of decrease in NADH in the presence of lysates containing the various mutants is shown.

Figure 7:
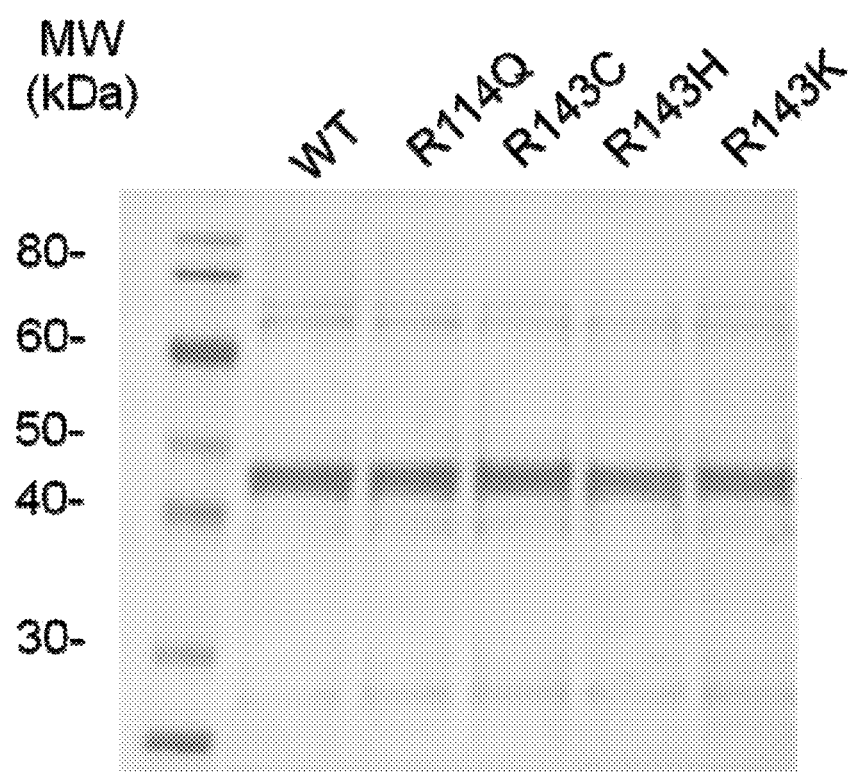

FIG. 7: Purification of ScHIDH mutants. SDS-PAGE with silver staining of purified ScHIDH mutants. A 15 μg aliquot of each purified protein was loaded.

Figure 8:
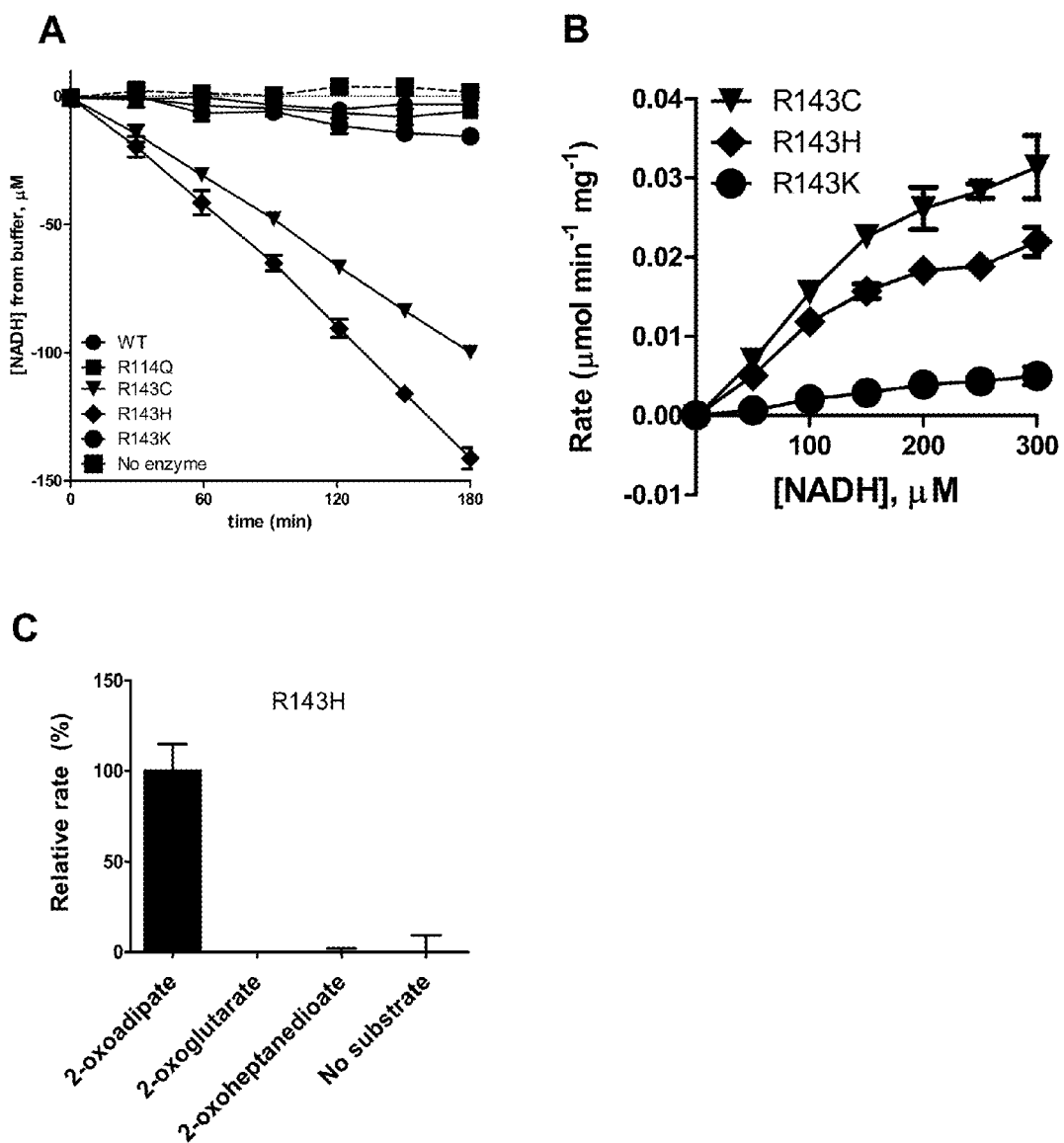

FIG. 8: Rate analysis of ScHIDH mutants. (A) Decrease in NADH over time in reactions containing 10 mM 2-oxoadipate, 300 μM NADH, and the indicated ScHIDH mutant. (B) Initial rate of NADH decrease in reactions containing the indicated ScHIDH mutant and 0-300 μM NADH. (C) Initial rate of NADH decrease in reactions containing ScHIDH-R143H and 15 mM of 2-oxoadipate, 2-oxoglutarate, or 2-oxoheptanedioate. Reactions contained 40 ng/μL of the indicated purified enzyme, 15 mM 2-oxoadipate, 100 mM HEPES, pH 7.3, 20 mM $MgCl_2$, and 100 μM NADH unless otherwise specified. Rates are expressed either in μmol NADH $min^{-1}$ $mg^{-1}$ enzyme, or in arbitrary relative rate of NADH decrease (oxidation) per unit time per unit of enzyme mass. Data are mean±s.d. (n=2) and are representative of three independent experiments.

FIG. 9: LC-MS/MS analysis of ScHIDH reactions. (A) NADH oxidation was monitored in reactions containing 50 mM HEPES, pH 7.3, 5 mM $MgCl_2$, 50 mM $NaHCO_3$, 5 mM 2-oxoadipate, 100 μM NADH. After 45 min (arrow), [3,3,4,4-$^2H_4$]-2-hydroxyglutarate (2HG-d4) internal standard was added and reactions were derivatized with diacetyl-L-tartaric anhydride (DATAN) and subjected to LC-MS/MS. (B) Fragmentation pattern for 2HG-d4, which was used as an internal standard to normalize the ion counts between different reactions. T1: Q1/Q3 (m/z)=367.0/151.0, T2: Q1/Q3 (m/z)= 367.0/132.0. (C) Transitions (denoted T1 and T2) corresponding to homoisocitrate. T1: Q1/Q3 (m/z)=421.3/205.1, T2: Q1/Q3 (m/z)=421.3/187.0 as shown by the mass fragmentation diagram on the right. (d) Transitions corresponding to 2-hydroxyadipate. T1: Q1/Q3 (m/z)=377.0/161.2, T2: Q1/Q3 (m/z)=377.0/143.2 as shown in the mass fragmentation diagram on the right. Results are representative of two independent experiments. Data in (A) are mean±s.d. from two independent experiments FIG. 10: ScHIDH mutants stoichiometrically produce (R)-2-hydroxyadipate. (A) (R)-2-hydroxyadipate concentration as quantified by LC-MS/MS for reactions initially containing 40 ng/μL of the indicated ScHIDH mutant, 2 mM NADH, 2 mM 2-oxoadipate, 20 mM $MgCl_2$, and 500 mM HEPES. (B) NADH concentration as assessed by absorbance at 340 nm for the same reactions. Data points are mean±s.d. from n=3 independent experiments.

Figure 11:
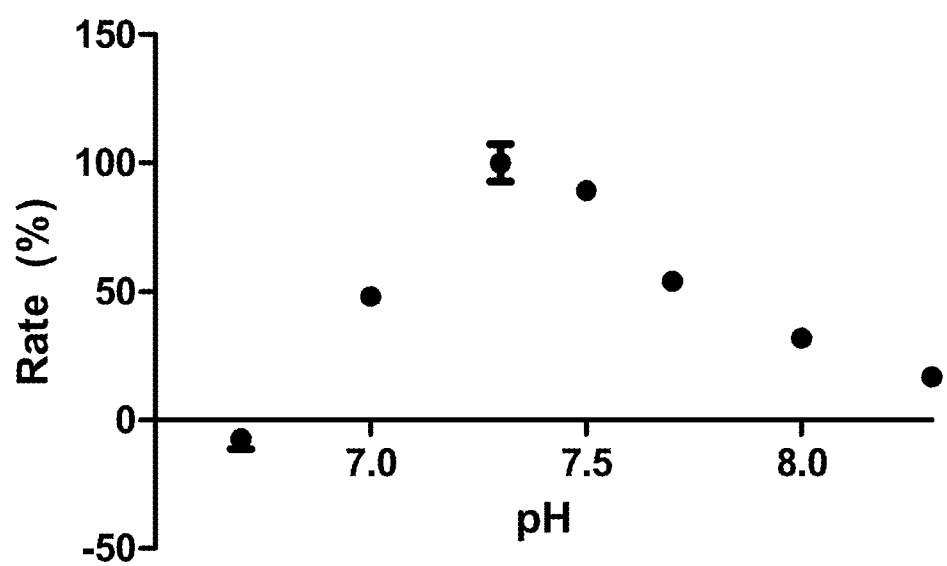

FIG. 11: pH dependence of ScHIDH-R143H. ScHIDH-R143H activity was assayed in HEPES buffer at various pHs under standard conditions. Rate is relative to the rate at pH 7.4. The pH optimum was estimated to be 7.4, similar to the wild type enzyme. Importantly for use in bio-based chemical production, this is compatible with the cytosol of most organisms.

Figure 12:
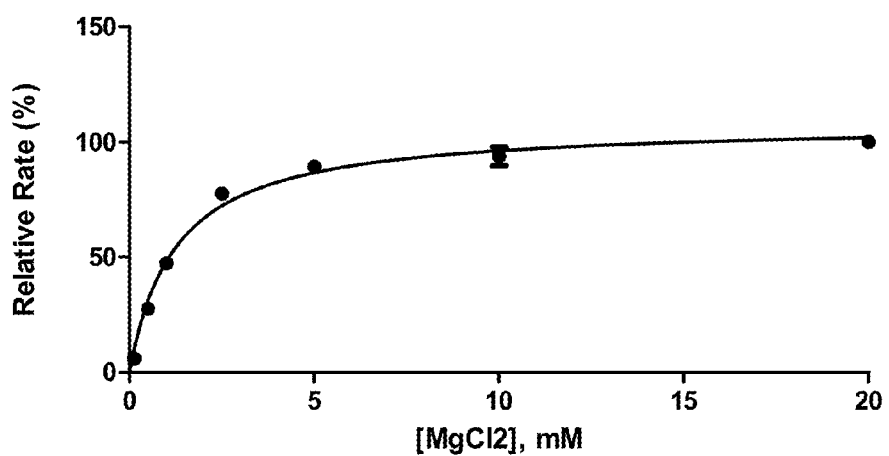

FIG. 12: Magnesium dependence of ScHIDH-R143H. ScHIDH-R143H activity was assayed at various $MgCl_2$ concentrations under standard conditions. The reaction rate is relative to the rate at 20 mM $MgCl_2$. The $K_M$ for $MgCl_2$ was estimated to be 1.1 mM, similar to the wild type HIDH enzyme.

Figure 13:
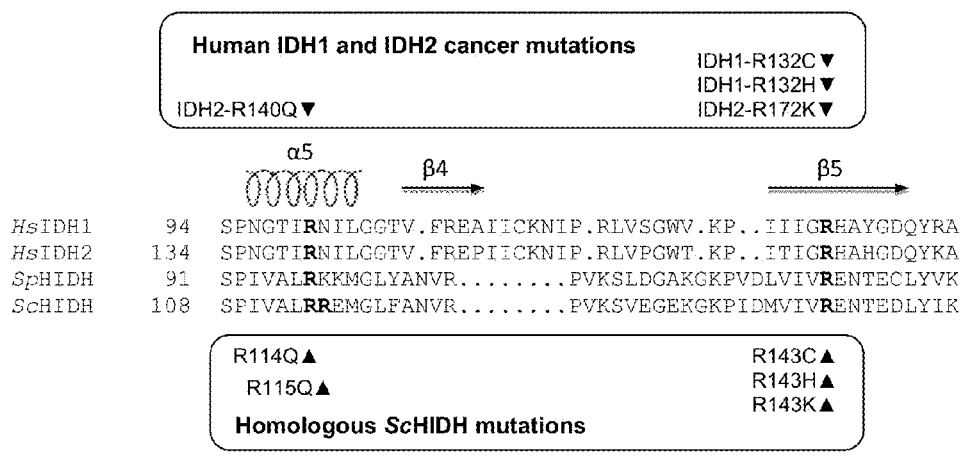

FIG. 13: Alignment of HsIDH1, HsIDH2, SpHIDH, and ScHIDH. The alignment shows the secondary structure of the respective proteins and the location of the conserved arginine residues in humans (Hs), *Saccharomyes pombe* (Sp), and *Saccaromyces cerevisiae* (Sc). Specific mutations in human IDH1 and IDH2 that are associated with cancer ares indicated in the top panel. Homologous mutations in ScHIDH as described herein are shown in the bottom panel.

Figure 14:
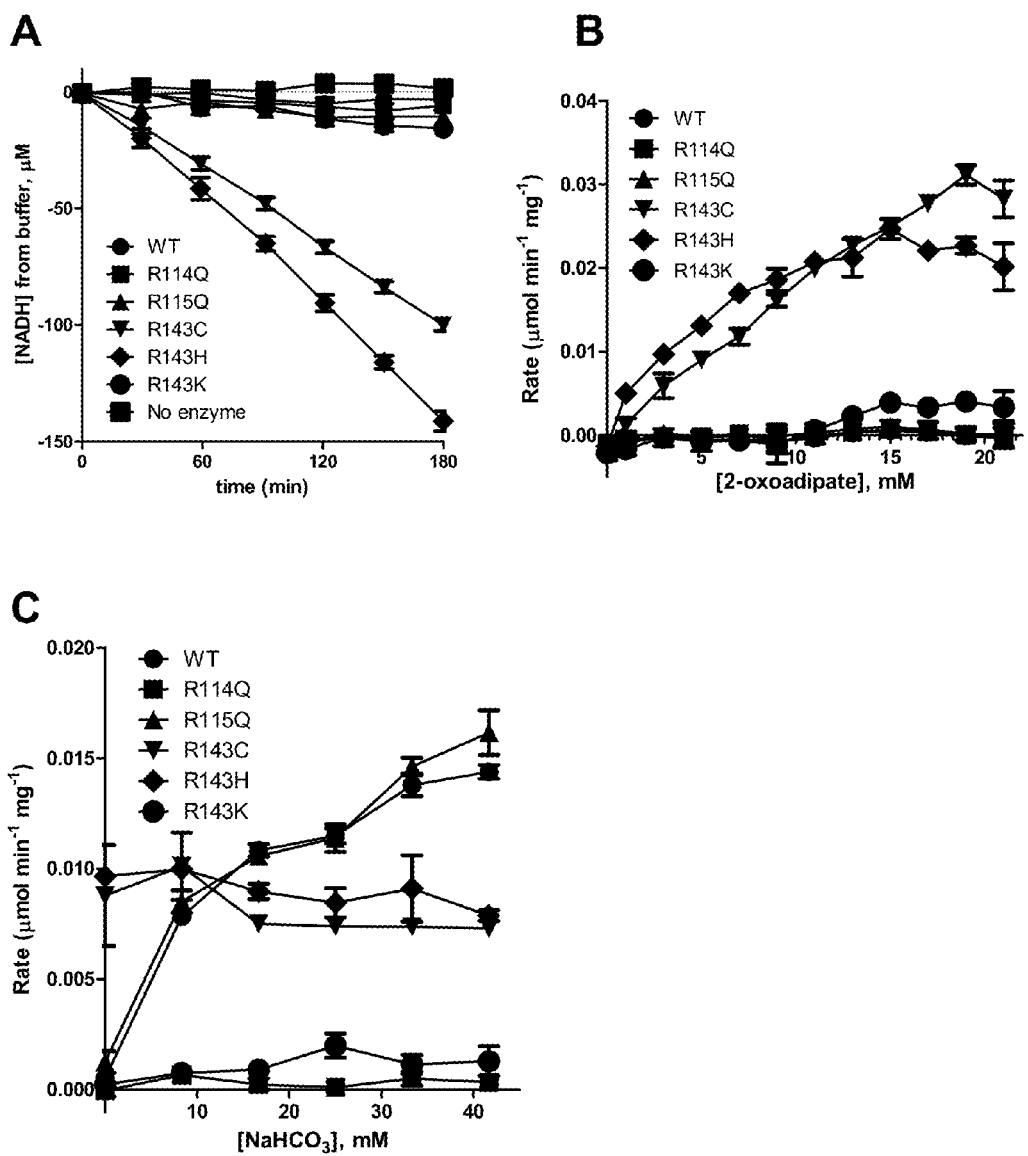

FIG. 14: Activity for ScHIDH-R115Q. (A) Decrease in NADH over time in reactions containing 10 mM 2-oxoadipate, 300 μM NADH, and the indicated ScHIDH mutant. (B) Initial rates of NADH-oxidation catalyzed by the indicated ScHIDH mutant at 0-22 mM 2-oxoadipate as indicated on the x-axis, and 300 μM NADH. (C) Initial rates of NADH-decrease catalyzed by the indicated ScHIDH mutant in the presence of 0-42 mM NaHCO3 as indicated on the x-axis, as well as 15 mM 2-oxoadipate and 100 μM NADH. NADH concentrations were determined by fluorescence spectroscopy (excitation wavelength: 340 nm; emission wavelength: 450 nm). All reactions contained 20 mM $MgCl_2$, 40 ng/μL of purified enzyme, and 100 mM HEPES, pH 7.3 unless otherwise specified. The mean±s.d. is shown for n=2 reactions and plots are representative of three independent experiments. Wild type ScHIDH, and the ScHIDH-R114Q, -R143K, -R143C, and -R143H mutants are shown for comparison.

Figure 15:
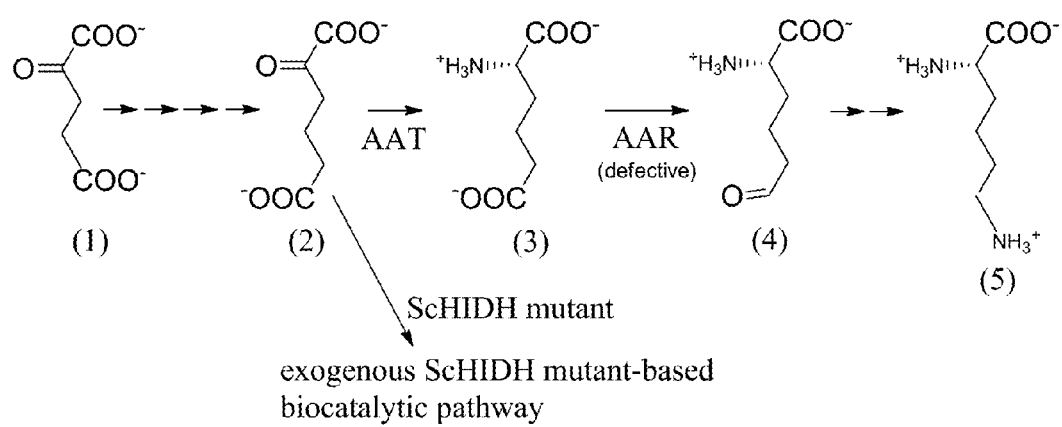

FIG. 15: Diversion of 2-oxoadipate from a lysine α-aminoadipate biosynthetic pathway for exogenous biocatalytic routes. In fungi and some bacteria, an alternative enzyme-catalyzed biosynthetic route for lysine biosynthesis exists. In this alternative lysine biosynthesis pathway, 2-oxoglutarate (1) (also known as α-ketoglutarate) from the general metabolism is converted to 2-oxoadipate through several enzymatic steps (2). 2-oxoadipate is then converted to 2-aminoadipate (3) (also known as α-aminoadipate) by α-aminoadipate aminotransferase (AAT). 2-aminoadipate is converted to the 2-aminoadipate semialdehyde (4) by α-aminoadipate reductase (AAR), which is then converted by two additional steps to yield lysine (5). Yeast strains with lys2-801 mutation lack AAR activity, leading to buildup of (3), and were used as microbial hosts. This leads to feedback buildup of 2-oxoadipate (2) for diversion into the exogenous ScHIDH mutant mediated biocatalytic pathway by mutant ScHIDH. Cofactors are not shown. Steps leading to (2) occur in the mitochondria, while steps following formation of (3) occur in the cytosol, with (2) likely transferred between compartments to since AAT isoforms are expressed in either compartment. The detailed pathway was discussed previously See Xu et al., *Cell Biochem. and Biophys.* 46(1): 43-64 (2006).

Figure 16:
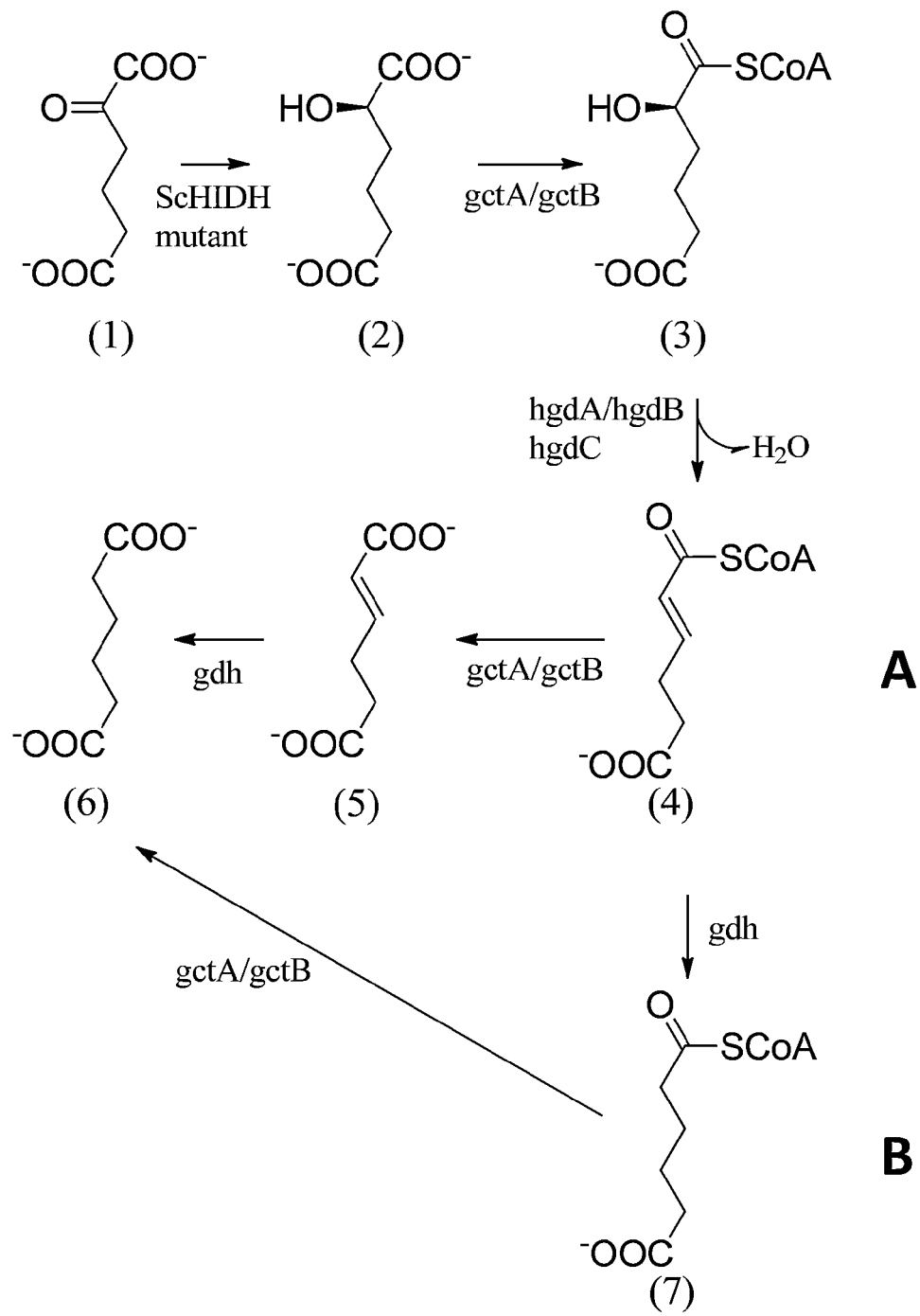

FIG. 16: Exogenous adipic acid biosynthetic route enabled by mutant ScHIDH. (1) 2-oxoadipate; (2) (R)-2-hydroxyadipate; (3) (R)-2-hydroxyadipoyl-CoA; (4) (E)-2-hexenedioyl-CoA; (5) (E)-2-hexenedioate; (6) adipic acid; (7) adipoyl-CoA. Not all cofactors are shown. ScHIDH and likely gdh use NADH as a cofactor while gctA/gctB exchange CoASH and $O_2$ in their reactions. The route from (1), (2), (3), (4), (5) was developed for yeast expression to yield (E)-2-hexenedioate and to serve as the basis for an adipic acid pathway. Two possible metabolic pathways for adipic acid biosynthesis exist: (A) saturation of the (E)-2-hexenedioyl-CoA double bond or (B) saturation of the (E)-2-hexenedioate double bond In (A), the biosynthetic route is (1), (2), (3), (4), (5), (6), and in (B) the biosynthetic route is (1), (2), (3), (4), (7), (6).

FIG. 17: pESC-leu2d-gctA/gctB/lys12* plasmid and cloning intermediates. (A) Analytical digest of pESC-leu2d-gctA/gctB. (B) pESC-leu2d-gctA/gctB/lys12* plasmid map. Inserts were confirmed by sequencing.

FIG. 18: pESC-His-hgdA/hgdB/hgdC plasmid and intermediates. (A) pESC-Leu2d-hgdB. (B) pESC-His-hgdA/hgdC analytical digest. (C) pESC-His-hgdA/hgdB/hgdC plasmid map. Inserts were confirmed by sequencing.

Figure 19:
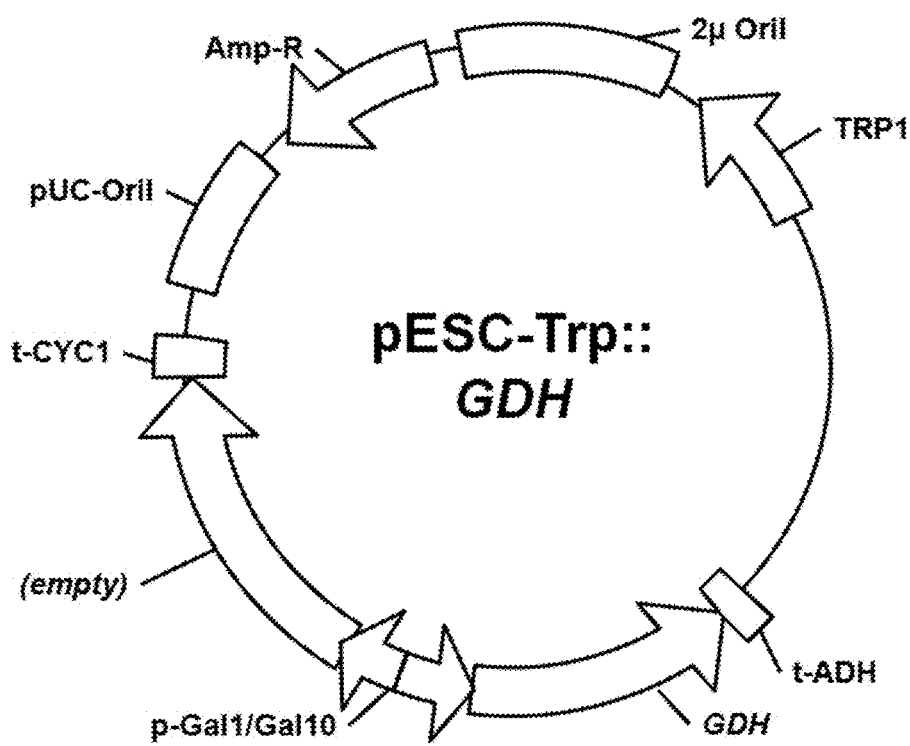

FIG. 19: pESC-Trp-gdh plasmid map.

DETAILED DESCRIPTION

The most mutated IDH residues in some human cancers is Arg132 of human cytosolic $NADP^+$-dependent isocitrate dehydrogenase (HsIDH1) in gliomas and Arg140 of human mitochondrial $NADP^+$-dependent IDH (HsIDH2) in human leukemias. Yan et al., *N. Engl. J. Med.* 360: 765-773 (2009); Ward et al., *Cancer Cell* 1: 225-243 (2010). These mutated arginine residues disrupt interactions with the β-carboxylate group of the natural isocitrate substrate and cause neomorphic enzymatic function. Dang et al., *Nature* 462: 739-744 (2009); Ward et al., *Cancer Cell* 17: 225-243 (2010); Pietrak et al., *Biochemistry* 50L 4804-4812 (2011).

The active sites of human cytosolic NADP-dependent IDH (HsIDH1) and *T. thermophilus* HIDH (TtHIDH) were compared to identify similar residue positions. Xu et al., *J. Biol. Chem.* 279: 33946-33957 (2004); Miyazaki et al. *J. Biol. Chem.* 278: 1864-1871 (2003). Although a structure for HIDH in complex with the homoisocitrate substrate is not available, a structure exists for HIDH in complex with the homoisocitrate analog, (2S,3S)-thiahomoisocitrate; this analog differs from homoisocitrate by replacement of C-4 with a sulfur atom. Nango et al., *J. Biochem.* 150(6): 607-614, (2011). Based on the crystal structures of HsIDH1 and TtHIDH, the relative topography and specific amino acid residues responsible for interaction with the common carboxylate moiety in the substrates were analyzed (FIG. 2A). Alignments of the enzymes were used to identify similarities in primary sequence, secondary structure, and residues around the active sites (FIG. 2B). These included β-strand 5 of HsIDH1 (residues 128-133) aligning with a corresponding β-strand (residues 114-119) in TtHIDH, and α-helix 5 (residues 95-103) of HsIDH1 aligning with a corresponding α-helix (residues 83-91) in TtHIDH.

The Arg132 residue contained within β-strand 5 of HsIDH1 has similar relative topography to Arg118 of TtHIDH. Additionally, α-helix 5 of HsIDH1 contains Arg100—the homologue of cancer mutant HsIDH2-R140—that corresponds in the same manner to Arg88 of TtHIDH. These observations led to the proposal that Arg88 and Arg118 of TtHIDH normally function to contact the β-carboxyl of the homoisocitrate substrate in an analogous manner to how Arg100 and Arg132 of HsIDH1 contact the β-carboxyl of the isocitrate substrate. Nango et al., *J. Biochem.* 150(6): 607-614 (2011). Given that analogous structural positions may suggest analogous functions, it was thought that these mutation-hotspot residues from human cancers could transform the catalytic activity. Because R132H converts HsIDH into an (R)-2-hydroxyglutarate dehydrogenase, the analogous TtHIDH mutation, R118H, converted TtHIDH into an (R)-2-hydroxyadipate dehydrogenase. Yan et al., *N. Engl. J. Med.* 360: 765 (2009); Dang et al., *Nature* 462: 739 (2009).

TtHIDH-R118H Produces R-2-Hydroxyadipate.

To investigate the function of the TtHIDH-R118H mutant, TtHIDH-WT and TtHIDH-R118H were expressed and purified and their activity was monitored via the rates of NADH oxidation. TtHIDH-R118H oxidized NADH in the presence of 15 mM 2-oxoadipate with an initial rate of 0.058±0.0031 U (μmol NADH $min^{-1}$ $mg^{-1}$) (FIG. 4A). In contrast, minimal NADH oxidation was observed in the presence of TtHIDH-WT or in the presence of TtHIDH-R118H without 2-oxoadipate (<0.01 U). HIDH-WT can normally carry out the reverse reductive carboxylation reaction in which $CO_2$ is required as a substrate to carboxylate 2-oxoadipate and form homoisocitrate. As expected, when $CO_2$ was added to the reaction containing 2-oxoadipate and NADH in the form of $NaHCO_3$, TtHIDH-WT was able to consume NADH at a rate of 0.14±0.022 U (FIG. 4B). However, the addition of $NaHCO_3$ did not stimulate TtHIDH-R118H activity compared to the reaction without $NaHCO_3$ (0.059 vs. 0.058 U, p=0.95). These results indicate that TtHIDH-WT performs the expected reverse reaction involving reductive carboxylation, and that TtHIDH-R118H is able to catalyze a reductive reaction that does not involve carboxylation.

Analysis of NADH-oxidation activity by TtHIDH-R118H indicated that a hydride ion was transferred from NADH to the 2-oxoadipate substrate. This hydride transfer, along with addition of a proton from solution, was hypothesized to result in the hydrogenation of the α-keto group of 2-oxoadipate to form 2-hydroxyadipate. Because β-hydroxyacid oxidative decarboxylases and their cancer associated mutants are stereospecific for (R)-hydroxyacids as their substrates/products, the product was expected to be the (R) enantiomer of 2-hydroxyadipate. Dang et al., *Nature* 462: 739-744 (2009); Aktas and Cook, *Biochemistry* 48: 3565-3577 (2009). To test this hypothesis, a high performance liquid chromatography tandem mass spectrometry (LC-MS/MS) method was developed for targeted quantification of 2-hydroxyadipate that discriminates between the (R)- and (S)-enantiomers. This method utilizes a derivation step with diacetyl-L-tartaric anhydride to generate derivatives of the (R)- and (S)-2-hydroxyadipate enantiomers that elute from the LC column at different times.

The product (R)-2-hydroxyadipate increased in a reaction mixture containing TtHIDH-R118H in the presence of NADH and 2-oxoadipate. After 2 h of reaction, the NADH concentration decreased by 61.3 µM, and the (R)-2-hydroxyadipate concentration increased by 61.3 µM, remarkably consistent with 1:1 stoichiometric production of (R)-2-hydroxyadipate (FIG. 4D). Background levels of 2-hydroxyadipate were seen in all reactions containing 2-oxoadipate (approximately 10 µM in reactions containing 15 mM 2-oxoadipate), but not in controls that did not contain 2-oxoadipate. This is due to a small level of contamination of 2-oxoadipate with a racemic mixture of R/S-2-hydroxyadipate (0.061% w/w), likely from a minor amount of spontaneous reduction in the 2-oxoadipate chemical stock. No increase of (S)-2-hydroxyadipate was observed, establishing that the reaction is specific for production of the (R)-enantiomer. This increase in (R)-2-hydroxyadipate was not observed in reactions performed in the presence of TtHIDH-WT or a buffer control. Thus, TtHIDH-R118H is an (R)-2-hydroxyadipic acid dehydrogenase that produces (R)-2-hydroxyadipate.

The substrate specificity of TtHIDH-R118H was also investigated. Although TtHIDH is thought to be the source of HIDH activity for a lysine catabolic pathway in *T. thermophilus*, the enzyme is actually 20 times more efficient for 5-carbon, 2-oxoglutarate than for 6-carbon, 2-oxoadipate. Miyazaki et al. *J. Biol. Chem.* 278: 1864 (2003). TtHIDH-R118H oxidized NADH at a 1.3-fold faster rate in the presence of 15 mM 2-oxoglutarate than in the presence of 15 mM 2-oxoadipate (FIG. 4C), suggestion that 2-oxoglutarate is probably a more preferable substrate of TtHIDH-R118H.

ScHIDH-R143H Produces (R)-2-hydroxyadipate.

In contrast to TtHIDH, which favors isocitrate over homoisocitrate, HIDH from *S. cerevisiae* (encoded by LYS12) has a 216-fold faster rate for homoisocitrate compared to isocitrate. Lin et al., *Biochemistry* 46: 890-898 (2007). The (R)-2-hydroxyadipic acid dehydrogenase from ScHIDH was thought have greater specificity for 2-oxoadipate than for 2-oxoglutarate and could potentially be a useful 2-hydroxyadipate dehydrogenase for bio-based adipate production. Because no structural information is available for ScHIDH, alignments between TtHIDH and ScHIDH were examined (FIGS. 2B and 3). Arg143 of ScHIDH is analogous to Arg118 of TtHIDH, supporting the hypothesis that ScHIDH-R143H is the analog of TtHIDH-R118H and therefore also of HsIDH1-R132H. Miyazaki et al. *J. Biol. Chem.* 278: 1864-1871 (2003).

ScHIDH-R143H was expressed and purified from bacteria and its enzymatic properties were investigated. ScHIDH-R143H oxidized NADH in the presence of 2-oxoadipate (0.0096±0.000014 U), but ScHIDH-WT had minimal activity (<0.001 U) (FIG. 5A). ScHIDH-R143H had Michaelis constants for NADH ($K_{M,NADH}$) of 85±21 µM and a $K_{M,2-oxoadipate}$ of 1.4±0.25 mM, with a maximal velocity ($V_{max}$) of 0.020±0.0027 U. As was the case for TtHIDH, ScHIDH-WT demonstrated robust activity when $CO_2$ was added to the reaction mixture as $HCO_3$ (0.061±0.0090 U; FIG. 5B), consistent with the reductive, carboxylating reverse reaction catalyzed by this enzyme. Lin et al., *Biochemistry* 46: 890-898 (2007). ScHIDH-WT had a $K_{M,HCO_3}$ of 10±3.7 mM, which is comparable to the previous observation of a $K_{M,HCO_3}$ of 16.3 mM for that enzyme. Similar to TtHIDH-R118H, ScHIDH-R143H was not stimulated by addition of up to 60 mM $NaHCO_3$.

ScHIDH-WT catalyzes the oxidative decarboxylation of isocitrate, albeit at a rate 216-fold slower than homoisocitrate, which implied that ScHIDHs may act on other substrates. Lin et al., *Biochemistry* 46: 890-898 (2007). Mutant ScHIDH-R143H was tested to determine if the protein could utilize other dicarboxylic keto-acids as substrates (FIG. 5C). However, a significant increase in NADH oxidation rate in the presence of 15 mM 2-oxoglutarate, compared to a reaction containing no substrate, was undetectable (<0.001 U for both, p=0.58). Additionally, a significant increase in NADH oxidation in the presence of 15 mM 2-oxoheptanedioic acid, the 7-carbon analog of α-ketoadipate (<0.001 U, p=0.47 for the comparison with no substrate) was also not detectable. Thus, ScHIDH-R143H has minimal or no promiscuous activity for other α-keto dicarboxylic acids that are similar to 2-oxoadipate.

It was confirmed that (R)-2-hydroxyadipate was the product of ScHIDH-R143H (FIG. 5I)). A reaction initially containing 2 mM of NADH and 2 mM 2-oxoadipate was assembled. After 10 h, the concentration of (R)-2-hydroxyadipate increased to 0.97 mM, while the NADH concentration decreased by 0.62 mM compared to a buffer control. This approaches the expected stoichiometry of a reaction in which equimolar amounts of NADH, $H^+$, and α-ketoadipate are converted to $NAD^+$ and 2-hydroxyadipate. The 2-hydroxyadipate product was the (R)-enantiomer, and no 2-hydroxyadipate accumulation was observed in control reactions containing ScHIDH-WT.

Multiple ScHIDH Mutants have 2-Hydroxyadipate Dehydrogenase Activity.

Experiments were conducted to determine whether other IDH mutations observed in cancers might also confer neomorphic function to HIDH. ScHIDH analogues to HsIDH1-G97D, HsIDH1-R132C, HsIDH1-Y139D, HsIDH2-R140Q, and HsIDH2-R172K were prepared. These mutants have been observed in cancer cell lines, observed in primary cancers, or have been shown to confer neomorphic 2-hydroxyglutarate activity in vitro. Bleeker et al., *Hum. Mut.* 30:1-11 (2009); Yan et al., *N. Engl. J. Med.* 360: 765-773 (2009); Ward et al., *Cancer Cell* 17: 225-234 (2010); Ward et al., *Oncogene* 2011: 1-8 (2011). The analogous ScHIDH mutants, as determined by structure-based alignment between HsIDH1 and ScHIDH (FIGS. 2B and 3), are V111D, R114Q, R143K, R143C, and Y150D. ScHIDH-R115Q was also generated by mutating an arginine residue to glutamate. Crude lysates of bacteria expressing these mutants had 2-hydroxyadipate activity when assayed at high NADH concentrations (200-800 µM) (FIG. 6). Notably, ScHIDH-R143K was able to elicit a reaction rate 83.0±0.03% as fast as ScHIDH-R143H at the relatively high NADH concentration of 800 µM, although it only elicited negligible activity (3.6±0.3% of ScHIDH-R143H) at standard conditions of 100 µM NADH. Thus, multiple cancer-associated mutations can result in an HIDH gain-of-function.

HIDH mutants that are analogous to IDH mutants observed in human cancer can catalyze the NADH-dependent conversion of 2-oxoadipate to (R)-2-hydroxyadipate. This is the case for HIDHs from disparate phylogenies, indicating that the introduction of (R)-2-hydroxyadipate dehydrogenase activity by specific mutations is possible. The studies herein show that the active site arginine residues that are hotspots for IDH cancer mutations are conserved not only among $NADP^+$-dependent IDHs but also among distantly related enzymes of the subfamily of β-hydroxyacid oxidative decarboxylases that act on (R)-hydroxyacids. Pietrak et al., *Biochemistry* 50: 4804-4812 (2011). These arginine residues therefore appear to "mask" a non-carboxylating catalytic function of enzymes that are specific for a decarboxylating catalytic process. A recent study found that tight isocitrate binding leads to competitive inhibition of a non-decarboxylating activity of IDH, and that the R132H mutation disrupts isocitrate binding and releases this inhibition. Pietrak et al., Biochemistry 50: 4804-4812 (2011). Results herein show that this is also the case for the HIDH and homoisocitrate. Mutation of critical arginine residues can have similar effects in other β-hydroxyacid oxidative decarboxylases that act on (R)-hydroxyacid substrates, such as isopropylmalate dehydrogenases (SEQ ID NOs: 23-30) or tartrate dehydrogenases (SEQ ID NOs: 31-34).

Enzymatic conversion of 2-oxoadipate to (R)-2-hydroxyadipate is a critical step in a proposed method for biosynthetic adipic acid production, but this step was previously thwarted by the lack of a specific enzyme to carry out the reaction. Parthasarathy et al., *Biochemistry* 50: 3540-3550 (2011). Studies herein show that a ScHIDH mutant can be created to address this problem. ScHIDH-R143H has minimal or no activity for 2-oxoglutarate as a substrate, solving the problem of undesired 2-oxoglutarate reduction that arises when HghH is used for this step, as was done in initial studies of this process. Parthasarathy et al., *Biochemistry* 50: 3540-3550 (2011). TtHIDH mutants are probably not optimal for this application because they have promiscuous substrate specificity for 2-oxoglutarate and because of their extremely high temperature optima.

Mutations analogous to HsIDH1-R132H and to HsIDH2-R172K resulted in the most active ScHIDH mutants. These are the most frequent mutations at their respective codons in cancer, which may indicate that they are selected more frequently due to improved neomorphic function. The failure to detect activity with ScHIDH-R143C in contrast to robust activity for ScHIDH-R143H is consistent with the fact that HsIDH1-R132C results in a 2-fold lower $V_{max}$ for neomorphic activity than does HsIDH1-R132H. Dang et al., *Nature* 462: 739-744 (2009); Gross et al., *J. Exp. Med.* 207: 339-344 (2010). The absence of detectable ScHIDH-R114Q activity is consistent with mutations at this residue providing less neomorphic activity. Alternatively, the presence of two arginine residues at this location (R114 and R115) in ScHIDH may provide redundancy at this location such that even when R114Q is introduced, R115 can complement its function of "masking" non-carboxylating catalytic function.

The following mutations were generated and assayed in crude bacterial lysates, but did not demonstrate 2-hydroxyadipate dehydrogenase activity in these initial assays at 100 µM NADH substrate (or minimal activity at higher NADH substrate levels): ScHIDH-V111D; ScHIDH-R114Q; ScHIDH-R115Q; ScHIDH-R143C; and ScHIDH-Y150D. Some of these mutations actually have 2-hydroxyadipate dehydrogenase activity that was undetectable under these assay conditions (e.g., ScHIDH-R143C).

It was surprising that the ScHIDH-R114Q and -R115Q mutants have much less activity than other mutations (i.e., R114H or R115H) because HsIDH2-R140 and HsIDH2-R172 mutations are about equally common in human leukemias. HsIDH1-R132 mutations, which are more frequent in gliomas, are homologous to HsIDH2-R172 mutations. Current studies have not found a difference between 2-hydroxyglutarate levels in cancer tissues that have HsIDH2-R140, HsIDH2-R172, or HsIDH1-R132 mutants. These results suggest that R140 and R172 mutations in HsIDH2 result in similar gain-of-function 2-hydroxyglutarate dehydrogenase activities. However, the ScHIDH-R143 mutants (such as R143H and R143K, which are analogous to HsIDH2-R172 mutants) have more robust activity than do the ScHIDH-R114 mutants (analogous to HsIDH2-R140 mutants).

An additional residue that can be mutated is ScHIDH-R124. This residue is one of three Arg residues that contact the homoisocitrate substrate β-carboxyl group, based on structures of the homologous *Schizosaccharomyces pombe* HIDH (i.e., SpHIDH). See Bulfer et al., *Proteins* 80(2): 661-666 (2012). Arg114 and Arg143 are two other Arg residues of ScHIDH that contact the β-carboxyl of the homoisocitrate substrate, based on sequence homology with SpHIDH and an examination of the SpHIDH structure. See Xu et al., *J. Biol. Chem.* 279(32): 33946-33957 (2004). Results described herein show that Arg143 and Arg114, which are the two other ScHIDH Arg residues that contact the β-carboxyl group of the homoisocitrate substrate, result in (R)-2-hydroxyadipate dehydrogenase activity when mutated (FIG. 6). Therefore, the analyses herein suggest that mutations such as ScHIDH-R124H will have (R)-2-hydroxyadipate dehydrogenase activity.

The mutations disclosed herein with the strongest oxidoreductase activity are Arg-to-His mutations, but Arg-to-Lys and Arg-to-Gln, as well as other non-Arg amino acids are likely functional for oxidoreductase activity and are envisioned as alternative aspects of the mutations described herein. For example, Arg could be mutated to His, Lys, Gln, Asn, Leu, Ile, Val, Tyr, Phe, Trp, Cys, Ser, Thr, Met, Glu, Asp, Ala, Gly, or Pro. Further, multiple HIDH active site residues may be simultaneously mutated. For example, the mutations R114H, R115H, R124H, and R143H can be made in a single polypeptide.

Accordingly, described herein are isolated polynucleotides and polypeptides, recombinant methods for producing the polynucleotides and polypeptides, codon-optimized polynucleotides for expressing the polypeptides, vectors containing the polynucleotides, expression systems for producing the polypeptides, and cultured host cells comprising such expression systems.

As noted in one aspect described herein are polynucleotides encoding the polypeptides disclosed herein or a polypeptide having conservative amino acid substitutions thereof. Guidance regarding selection of "conservative" amino acid substitutions is provided in more detail below. In one embodiment, the polynucleotide is DNA.

Another aspect described herein is codon-optimized polynucleotides encoding the polypeptides disclosed herein. A codon optimized polynucleotide encodes a polypeptide, but the native codons are optimized for enhanced expression in the cells of an organism by replacing one or more, or a significant number, of codons of the native sequence with codons that are more frequently or most frequently used in the genes of that particular organism. Various species exhibit biases for particular codons of an amino acid. Species-specific codon tables and programs for codon optimization are available for creating codon optimized coding sequences of the polynucleotides described herein.

Another aspect described herein is isolated polynucleotides encoding the polypeptides disclosed herein. The phrase "isolated polynucleotide" implies that a polynucleotide is removed from its native environment. Thus, a polynucleotide produced and/or contained within a recombinant cultured host cell is considered isolated for purposes described herein. Further, "isolated polynucleotides" are polynucleotides that have been purified, partially or substantially, from a recombinant cultured host. In addition, isolated polynucleotides comprise polynucleotides that are produced by recombinant means, by methods such as PCR, synthetic meas, such as solid-phase synthesis, and any other means know in the art for isolating polynucleotides from their native environment.

Another aspect described herein is a method of making a vector comprising inserting the polynucleotides described herein into a vector. In another aspect, a vector produced by the method is described.

In another aspect, a method of making a cultured host cell comprising introducing the vector into a cultured host cell is described. In another aspect, a cultured host cell is produced by the methods described herein.

In another aspect, isolated polypeptides, produced by a method comprising: (a) introducing a vector comprising a polynucleotide encoding the polypeptide into a cultured host cell; (b) culturing the host cell; (c) expressing the polypeptide; and (d) recovering the polypeptide are described. In another aspect, a method for producing a polypeptide comprising: (a) culturing the host cell described herein under conditions where the vector is expressed; and (b) recovering the polypeptide is described.

In another aspect, cells containing at least one polynucleotide described herein are described. The cells may be prokaryotic or eukaryotic. In one aspect, the cell containing at least one polynucleotide described herein is *Escherichia coli, Sacchromyces cerevisia, Pichia pastoris, Geotrichum candidum, Candida albicans, Rhodotorula rubra,* or *Rhodosporidium* sp.

In one embodiment, the polynucleotide comprises the nucleotide sequence as shown in SEQ ID NOs: 1, 3, 5, 7, 9, 11, 13, 15, 17, 19, 21, 23, 25, 27, 29, 31, 33, 154, 156, 157, 159, 160, 162, 163, 165, 166, 168, 169, 171, or 172 or degenerate, homologous, or codon-optimized variants thereof. In other embodiments, the polypeptide comprises the amino acid sequence as shown in SEQ ID NOs: 2, 4, 6, 8, 10, 12, 14, 16, 18, 20, 22, 24, 26, 28, 30, 32, 34, 35-153, 155, 158, 161, 164, 167, 170, or 173.

In another embodiment, the polynucleotide comprises a polynucleotide capable of hybridizing to the complement of any of the nucleotide sequences as shown in SEQ ID NOs: 1, 3, 5, 7, 9, 11, 13, 15, 17, 19, 21, 23, 25, 27, 29, 31, 33, 154, 156, 157, 159, 160, 162, 163, 165, 166, 168, 169, 171, or 172.

In other aspects, the polynucleotide can comprise (a) a polynucleotide sequence of SEQ ID NOs: 1, 3, 5, 7, 9, 11, 13, 15, 17, 19, 21, 23, 25, 27, 29, 31, 33, 154, 156, 157, 159, 160, 162, 163, 165, 166, 168, 169, 171, or 172, or a fragment thereof, a domain thereof, codon-optimized variants thereof, or degenerate variants thereof; (b) a polynucleotide sequence, fragments thereof, domains thereof, codon-optimized variants thereof, or degenerate variants thereof capable of expressing a functional polypeptide of SEQ ID NOs: 2, 4, 6, 8, 10, 12, 14, 16, 18, 20, 22, 24, 26, 28, 30, 32, 34, 35-153, 155, 158, 161, 164, 167, 170, or 173; (c) a polynucleotide sequence having substantial similarity to (a) or (b); (d) a polynucleotide sequence capable of hybridizing to (a), (b), or (c); (e) a polynucleotide sequence complementary to (a), (b), (c), or (d); or (f) a polynucleotide sequence that is the reverse complement of (a), (b), (c), or (d). Any of the above polynucleotides may be used to enhance, attenuate, repress, or silence the expression of a polynucleotide or polypeptide described herein. In one aspect, the polynucleotide can modulate the expression levels of a polynucleotide in a cell.

The polynucleotides described herein include variants that have substitutions, deletions, and/or additions that can involve one or more nucleotides. The variants can be altered in coding regions, non-coding regions, or both. Alterations in the coding regions can produce conservative or non-conservative amino acid substitutions, deletions, or additions. Especially preferred among these are silent substitutions, additions and deletions, which do not alter the properties and activities of the mutated oxidative decarboxylase proteins or portions thereof, having neomorphic (R)-2-hydroxyadipate dehydrogenase activity. Also especially preferred in this regard are conservative substitutions (see below).

Further embodiments described herein include nucleic acid molecules comprising polynucleotides having nucleotide sequences about 50%, 55%, 60%, 65%, 70%, 75%, 80%, 85%, 90%, 91%, 92%, 93%, 94%, 95%, 96%, 97%, 98%, or 99% identical, and more preferably at least about 90% identical to (a) nucleotide sequences, or degenerate, homologous, or codon-optimized variants thereof, encoding polypeptides having the amino acid sequences in SEQ ID NOs: 2, 4, 6, 8, 10, 12, 14, 16, 18, 20, 22, 24, 26, 28, 30, 32, 34, 35-153, 155, 158, 161, 164, 167, 170, or 173; (b) nucleotide sequences, or degenerate, homologous, or codon-optimized variants thereof, encoding polypeptides having the amino acid sequences in SEQ ID NOs: 2, 4, 6, 8, 10, 12, 14, 16, 18, 20, 22, 24, 26, 28, 30, 32, 34, 35-153, 155, 158, 161, 164, 167, 170, or 173; and (c) nucleotide sequences capable of hybridizing to the complement of any of the nucleotide sequences in (a) or (b) above and capable of expressing functional polypeptides of amino acid sequences in SEQ ID NOs: 2, 4, 6, 8, 10, 12, 14, 16, 18, 20, 22, 24, 26, 28, 30, 32, 34, 35-153, 155, 158, 161, 164, 167, 170, or 173.

In one embodiment, the nucleic acid molecules described herein comprise polynucleotides having a nucleotide sequences that encode polypeptides having the amino acid sequences shown in SEQ ID NOs: 2, 4, 6, 8, 10, 12, 14, 16, 18, 20, 22, 24, 26, 28, 30, 32, 34, 35-153, 155, 158, 161, 164, 167, 170, or 173. In other embodiments, the nucleic acid molecules comprise polynucleotides having the nucleotide sequences shown in SEQ ID NOs: 1, 3, 5, 7, 9, 11, 13, 15, 17, 19, 21, 23, 25, 27, 29, 31, 33, 154, 156, 157, 159, 160, 162, 163, 165, 166, 168, 169, 171, or 172, or degenerate, homologous, or codon-optimized variants thereof.

In one embodiment, the nucleic acid molecules described herein comprise polynucleotides comprising nucleotide sequences encoding polypeptides comprising functional (R)-2-hydroxyacid dehydrogenase useful for converting a 1-carboxy-2-ketoacid to a 1-carboxy-(R)-2-hydroxyacid, or the reverse reaction, comprising a polypeptide, wherein the polynucleotide is at least 90% identical to the polynucleotide sequence shown in SEQ ID NOs: 1, 3, 5, 7, 9, 11, 13, 15, 17, 19, 21, 23, 25, 27, 29, 31, or 33; with the proviso that the encoded polypeptide has at least one or more mutations to the active site at positions V111, R114, R115, R124, R143, or Y150 of SEQ ID NO: 2; wherein the one or more mutations disrupt oxidative decarboxylation but do not disrupt oxidoreductase activity.

In another embodiment, the nucleic acid molecules described herein comprise polynucleotide comprising a nucleotide sequence encoding a polypeptide comprising a functional (R)-2-hydroxyacid dehydrogenase useful for converting a 1-carboxy-2-ketoacid to a 1-carboxy-(R)-2-hydroxyacid, or the reverse reaction, comprising a polypeptide, wherein the polynucleotide is the sequence shown in SEQ ID NOs: 1, 3, 5, 7, 9, 11, 13, 15, 17, 19, 21, 23, 25, 27, 29, 31, or 33, with no more than 120 nucleotide substitutions; with the proviso that the encoded polypeptide has at least one or more mutations to the active site at positions analogous to V111, R114, R115, R124, R143, or Y150 of SEQ ID NO: 2; wherein the one or more mutations disrupt oxidative decarboxylation but do not disrupt oxidoreductase activity.

By a polynucleotide having a nucleotide sequence at least, for example, 90% "identical" to a reference nucleotide sequence encoding a oxidoreductases for enantioselective reactions having neomorphic (R)-2-hydroxyacid dehydrogenase activity is intended that the nucleotide sequence of the polynucleotide be identical to the reference sequence except that the polynucleotide sequence can include up to about ten point mutations per each 100 nucleotides of the reference nucleotide sequence encoding the oxidative decarboxylase polypeptide having neomorphic oxidoreductase or (R)-2-hydroxyacid dehydrogenase activity. In other words, to obtain a polynucleotide having a nucleotide sequence about at least 90% identical to a reference nucleotide sequence, up to 10% of the nucleotides in the reference sequence can be deleted or substituted with another nucleotide, or a number of nucleotides up to 10% of the total nucleotides in the reference sequence can be inserted into the reference sequence. These mutations of the reference sequence can occur at the 5'- or 3'-terminal positions of the reference nucleotide sequence or anywhere between those terminal positions, interspersed either individually among nucleotides in the reference sequence or in one or more contiguous groups within the reference sequence.

As noted above, two or more polynucleotide sequences can be compared by determining their percent identity. Two or more amino acid sequences likewise can be compared by determining their percent identity. The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, *Advances in Applied Mathematics* 2: 4 82-489 (1981). This algorithm can be extended to use with peptide sequences using the scoring matrix developed by Dayhoff, *Atlas of Protein Sequences and Structure*, M. O. Dayhoff ed., 5 suppl. 3: 353-358, National Biomedical Research Foundation, Washington, D.C., USA, and normalized by Gribskov, *Nucl. Acids Res.* 14(6): 6745-6763 (1986). An implementation of this algorithm for nucleic acid and peptide sequences is provided by the Genetics Computer Group (Madison, Wis.) in their BESTFIT utility application. The default parameters for this method are described in the Wisconsin Sequence Analysis Package Program Manual, Version 8 (1995) (available from Genetics Computer Group, Madison, Wis.).

For example, due to the degeneracy of the genetic code, one having ordinary skill in the art will recognize that a large number of the nucleic acid molecules having a sequence at least 50%, 55%, 60%, 65%, 70%, 75%, 80%, 85%, 90%, 91%, 92%, 93%, 94%, 95%, 96%, 97%, 98%, or 99% identical to the nucleic acid sequence shown in SEQ ID NOs: 1, 3, 5, 7, 9, 11, 13, 15, 17, 19, 21, 23, 25, 27, 29, 31, 33, or 154, or degenerate, homologous, or codon-optimized variants thereof, will encode a oxidative decarboxylase polypeptide having neomorphic oxidoreductase activity (e.g., (R)-2-hydroxyadipate dehydrogenase activity).

In fact, because degenerate variants of these nucleotide sequences all encode the same polypeptide, this is clear to the skilled artisan even without performing any functional assays or measurements described herein. It is further recognized in the art that, for such nucleic acid molecules that are not degenerate variants, a reasonable number will also encode an oxidative decarboxylase having neomorphic oxidoreductase activity (e.g., (R)-2-hydroxyadipate dehydrogenase activity). This is because the skilled artisan is fully aware of amino acid substitutions that are either less likely or not likely to significantly affect protein function (e.g., replacing one aliphatic amino acid with a second aliphatic amino acid).

Recently, advances in the synthetic production of longer polynucleotide sequences have enabled the synthetic production of nucleic acids encoding significantly longer polypeptides without the use of traditional cloning techniques. Commercial providers of such services include Blue Heron, Inc., Bothell, Wash. Technology utilized by Blue Heron, Inc. is described in U.S. Pat. Nos. 6,664,112; 6,623,928; 6,613,508; 6,444,422; 6,312,893; 4,652,639; U.S. Published Patent Application Nos. 2002/0119456A1; 2002/0077471A1; and Published International Patent Applications (Publications Nos) WO 03054232A3; WO 0194366A1; WO 9727331A2; and WO 9905322A1, all incorporated herein by reference.

Traditional techniques of molecular biology, microbiology, and recombinant nucleic acid can also be used to produce the polynucleotides described herein. These techniques are well known and are explained in, for example, *Current Protocols in Molecular Biology*, F. M. Ausebel, ed., Vols. I, II, and III (1997); Sambrook et al., *Molecular Cloning: A Laboratory Manual*, 2nd Edition, Cold Spring Harbor Laboratory Press, Cold Spring Harbor, N.Y. (1989); *DNA Cloning: A Practical Approach*, D. N. Glover, ed., Vols. I and II (1985); *Oligonucleotide Synthesis*, M. L. Gait, ed. (1984); *Nucleic Acid Hybridization*, Hames and Higgins, eds. (1985); *Transcription and Translation*, Hames and Higgins, eds. (1984); *Animal Cell Culture*, R. I. Freshney, ed. (1986); Immobilized Cells and Enzymes, IRL Press (1986); Perbal, "*A Practical Guide to Molecular Cloning*"; the series, *Methods in Enzymology*, Academic Press, Inc. (1984); *Gene Transfer Vectors for Mammalian Cells*, J. H. Miller and M. P. Calos, eds., Cold Spring Harbor Laboratory (1987); and *Methods in Enzymology*, Wu and Grossman and Wu, eds., respectively, Vols. 154 and 155, all incorporated herein by reference.

Vectors that include the polynucleotide or nucleic acid molecules described herein, cultured host cells that are genetically engineered with the recombinant vectors, and the production of the oxidative decarboxylase polypeptides having neomorphic (R)-2-hydroxyadipate dehydrogenase activity by recombinant techniques are embodiments of the compositions described herein.

Recombinant constructs can be introduced into cultured host cells using well-known techniques such as infection, transduction, transfection, transvection, electroporation, and transformation.

The vector can be, for example, a phage, plasmid, viral or retroviral vector. Retroviral vectors can be replication competent or replication defective. In the latter case, viral propagation generally will occur only in complementing cultured host cells.

The polynucleotides can be joined to a vector containing a selectable marker for propagation in a cultured host. Generally, a plasmid vector is introduced in a precipitate, such as a calcium phosphate precipitate, or in a complex with a charged lipid. If the vector is a virus, it can be packaged in vitro using an appropriate packaging cell line and then transduced into cultured host cells.

Preferred are vectors comprising cis-acting control regions to the polynucleotide of interest. Appropriate trans-acting factors can be supplied by the cultured host, supplied by a complementing vector, or supplied by the vector itself upon introduction into the cultured host.

In certain embodiments in this regard, the vectors provide for specific expression, which can be inducible and/or cell type-specific. Particularly preferred among such vectors are those inducible by environmental factors that are easy to manipulate, such as temperature and nutrient additives.

Expression vectors useful for the aspects described herein include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

DNA inserts should be operatively linked to an appropriate promoter, such as the phage lambda PL promoter, the *E. coli* lac, trp and tac promoters, the SV40 early and late promoters and promoters of retroviral LTRs, to name a few. Other suitable promoters are known to the skilled artisan. The expression constructs will further contain sites for transcription initiation, termination and, in the transcribed region, a ribosome-binding site for translation. The coding portion of the mature transcripts expressed by the constructs can include a translation initiating at the beginning and a termination codon (UAA, UGA, or UAG) appropriately positioned at the end of the polynucleotide to be transcribed and/or translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate cultured hosts include, but are not limited to, bacterial cells, such as *E. coli, Streptomyces* and *Salmonella typhimurium* cells; fungal cells, such as yeast including *Escherichia coli, Sacchromyces cerevisia, Pichia pastoris, Geotrichum candidum, Candida albicans, Rhodotorula rubra*, or *Rhodosporidium* sp.; insect cells such as *Drosophila* S2 and *Spodoptera* Sf9 cells; animal cells such as CHO, COS and Bowes melanoma cells; and plant cells. Appropriate culture mediums and conditions for the above-described cultured host cells are known in the art.

Among vectors preferred for use in bacteria include e.g., pET24b or pET22b available from Novagen, Madison, Wis. pET-24b(+) and pET-22b(+); pET Expression System 24b (Cat. No. 69750) and 22b (Cat. No. 70765), respectively, EMD Biosciences, Inc., Novagen Brand, Madison, Wis.; see product information section regarding pET-24b and pET-22b for details regarding vector), pQE70, pQE60 and pQE-9, available from Qiagen Inc., Valencia, Calif.; pBS vectors, PHAGESCRIPT vectors, BLUESCRIPT vectors, pNH8A, pNH16a, pNH18A, pNH46A, available from Stratagene, La Jolla, Calif.; and ptrc99a, pKK223-3, pKK233-3, pDR540, pRIT5 available from Pharmacia (now Pfizer, Inc., New York, N.Y.). Among preferred eukaryotic vectors are pWLNEO, pSV2CAT, pOG44, pXT1, and pSG available from Stratagene; and pSVK3, pBPV, pMSG, and pSVL available from Pharmacia. Other suitable vectors are readily apparent to the skilled artisan.

Bacterial promoters suitable for use as described herein include the *E. coli* lacI and lacZ promoters, the T3 and T7 promoters, the gpt promoter, the lambda PR and PL promoters, and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of a vector construct into the cultured host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., *Basic Methods In Molecular Biology*, 2nd Edition (1995).

Transcription of the DNA encoding the polypeptides described herein by higher eukaryotes can be increased by inserting an enhancer sequence into the vector. Enhancers are cis-acting elements of DNA, usually about from 10 to 300 bp that act to increase transcriptional activity of a promoter in a given cultured host cell-type. Examples of enhancers include the SV40 enhancer, which is located on the late side of the replication origin at by 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals can be incorporated into the expressed polypeptide. The signals can be endogenous to the polypeptide or they can be heterologous signals.

The polypeptide can be expressed in a modified form, such as a fusion protein, and can include not only secretion signals, but also additional heterologous functional regions. For instance, a region of additional amino acids, particularly charged amino acids, can be added to the N-terminus, for example, the polypeptide to improve stability and persistence in the cultured host cell, during purification, or during subsequent handling and storage. In addition, peptide moieties can be added to the polypeptide to facilitate purification. Such regions can be removed prior to final preparation of the polypeptide. The additions of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP0464533 (Canadian counterpart, 2,045,869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties. On the other hand, for some uses it would be desirable to be able to delete the Fc part after the fusion protein has been expressed, detected, and purified in the advantageous manner described. This is the case when Fc portion proves to be a hindrance to use in therapy and diagnosis, for example, when the fusion protein is to be used as antigen for immunizations. In drug discovery for example, human proteins have been fused with Fc portions for the purpose of high-throughput screening assays (such as hIL5-receptor, to identify antagonists of hIL-5). See, Bennett, D., et al., *J. Molecular Recognition*, 8: 52-58 (1995) and Johanson, K. et al., *J. Biol. Chem.* 270(16): 9459-9471 (1995).

Polypeptides

The polynucleotides described herein include those encoding mutations, variations, substitutions, and particular examples of the polypeptides described herein. For example, guidance concerning how to make phenotypically silent amino acid substitutions is provided in Bowie, J. U. et al., "Deciphering the Message in Protein Sequences: Tolerance to Amino Acid Substitutions," *Science* 247: 1306-1310 (1990), wherein the authors indicate that proteins are surprisingly tolerant of amino acid substitutions. Although any number of amino acid substitutions can be obtained by the application of such general principles, for specific guidance regarding substitutions, the references cited herein regarding structure and function of oxidative decarboxylase domains can be consulted by one of skill in the art.

It will further be appreciated that, depending on the criteria used, the exact "position" or sequence of the oxidative decarboxylase active site of the polypeptides described herein can differ slightly in particular variations within the scope of the embodiments described herein. For example, the exact location of the active site can vary slightly and/or the amino acid residues surrounding the active site can vary. Thus, variations of the oxidative decarboxylase polypeptides that exhibit neomorphic oxidoreductase activity (e.g., (R)-2-hydroxyadipate dehydrogenase activity) as disclosed herein are envisioned. Such variants include deletions, insertions, inversions, repeats, and substitutions. As indicated above, guidance concerning which amino acid changes are likely to be phenotypically silent can be found in Bowie, J. U., et al., "Deciphering the Message in Protein Sequences: Tolerance to Amino Acid Substitutions," Science 247: 1306-1310 (1990).

Thus, fragments, derivatives, or analogs of the polypeptides of SEQ ID NOs: 2, 4, 6, 8, 10, 12, 14, 16, 18, 20, 22, 24, 26, 28, 30, 32, 34, 35-153, 155, 158, 161, 164, 167, 170, or 173 can be (i) ones in which one or more of the amino acid residues (e.g., 1, 2, 3, 4, 5, 7, 8, 9, 10, 11, 12, 13, 14, 15, 16, 17, 18, 19, 20, 25, 30, 35, 40, 45, or 50 residues, or even more) are substituted with a conserved or non-conserved amino acid residue (preferably a conserved amino acid residue). Such substituted amino acid residues may or may not be one encoded by the genetic code, or (ii) ones in which one or more of the amino acid residues includes a substituent group (e.g., 1, 2, 3, 4, 5, 7, 8, 9, 10, 15, 20, 25, 30, 35, 40, 45, or 50 residues or even more), or (iii) ones in which the mature polypeptide is fused with another compound, such as a compound to increase the half-life of the polypeptide (for example, polyethylene glycol), or (iv) ones in which the additional amino acids are fused to the mature polypeptide, such as an IgG Fc fusion region peptide or leader or secretory sequence or a sequence which is employed for purification of the mature polypeptide or a proprotein sequence. Such fragments, derivatives, and analogs are deemed to be within the scope of those skilled in the art from the teachings herein.

In addition, fragments, derivatives, or analogs of the polypeptides of SEQ ID NOs: 2, 4, 6, 8, 10, 12, 14, 16, 18, 20, 22, 24, 26, 28, 30, 32, 34, 35-153 155, 158, 161, 164, 167, 170, or 173 can be substituted with one or more conserved or non-conserved amino acid residue (preferably a conserved amino acid residue). In some cases these polypeptides, fragments, derivatives, or analogs thereof will have a polypeptide sequence at least 50%, 55%, 60%, 65%, 70%, 75%, 80%, 85%, 90%, 91%, 92%, 93%, 94%, 95%, 96%, 97%, 98%, or 99% identical to the polypeptide sequence shown in SEQ ID NOs: 2, 4, 6, 8, 10, 12, 14, 16, 18, 20, 22, 24, 26, 28, 30, 32, 34, 35-153 155, 158, 161, 164, 167, 170, or 173 and will comprise functional or non-functional proteins or enzymes.

As described herein, in many cases the amino acid substitutions or mutations are preferably of a minor nature, such as conservative amino acid substitutions that do not significantly affect the folding or activity of the protein. Of course, the number of amino acid substitutions a skilled artisan would make depends on many factors, including those described herein. Generally, the number of substitutions for any given polypeptide will not be more than about 100, 90, 80, 70, 60, 50, 40, 30, 25, 20, 19, 18, 17, 16, 15, 14, 13, 12, 11, 10, 9, 8, 7, 5, 6, 4, 3, 2, or 1.

Sequence alignments such as those shown in FIGS. 2B, 3 and 13 can be used to determine where substitutions or mutations can be made in the active site of the enzymes described herein to alter enzymatic activity or generate neomorphic activity. Further, substitutions or mutations can be made in order to modify the primary, secondary, or tertiary structure based on evolutionarily conserved residues as described herein. Such modifications can reduce or enhance enzymatic activity, alter the substrate or co-factor preference, or generate neomorphic enzymatic activity.

Amino acids in the oxidative decarboxylases having neomorphic oxidoreductase activity (e.g., (R)-2-hydroxyadipate dehydrogenase activity) that are essential for function can be identified by methods known in the art, such as site-directed mutagenesis or alanine-scanning mutagenesis. Cunningham and Wells, Science 244: 1081-1085 (1989). The latter procedure introduces single alanine mutations at every residue in the molecule. The resulting mutant molecules are then tested for biological activity, e.g., as shown in the examples provided herein. Sites that are critical for ligand binding can also be determined by structural analysis such as crystallization, nuclear magnetic resonance, or photoaffinity labeling. Smith, et al., J. Mol. Biol. 224: 899-904 (1992) and de Vos, et al. Science 255: 306-312 (1992). Even if deletion of one or more amino acids from the N-terminus of a protein results in modification or loss of one or more biological functions of the protein, other biological activities can be retained.

It is also contemplated that polypeptides useful in production of the "isolated polypeptides" described herein can produced by solid phase synthetic methods. See Houghten, R. A., Proc. Natl. Acad. Sci. USA 82: 5131-5135 (1985); and U.S. Pat. No. 4,631,211 to Houghten et al. (1986).

The polypeptides described herein can be provided in an isolated form. The term "polypeptide" encompasses "isolated polypeptide." The phrase "isolated polypeptide" implies that a polypeptide is removed from its native environment. Thus, a polypeptide produced and/or contained within a recombinant cultured host cell is considered isolated for purposes described herein. Further, "isolated polypeptides" are polypeptides that have been purified, partially or substantially, from a recombinant cultured host.

Polypeptides having an amino acid sequence of an indicated percent identity to a reference amino acid sequence of an oxidative decarboxylase polypeptide having neomorphic oxidoreductase activity e.g., (R)-2-hydroxyadipate dehydrogenase activity) can be determined using the methods, including computer-assisted methods, indicated above regarding polynucleotides. Polypeptide amino acid sequences are examined and compared just as are the nucleotide sequences in the foregoing discussion. One of skill in the art will recognize that such concepts as the molecular endpoints discussed for polynucleotides will have direct analogs when considering the corresponding use of such methods and programs for polypeptide analysis. For example, the manual corrections discussed regarding polynucleotides refer to 5'- and 3'-endpoints of nucleic acids, but the same discussion is applicable to N-termini and C-termini of polypeptides.

The oxidative decarboxylase polypeptides having neomorphic oxidoreductase activity (e.g., (R)-2-hydroxyadipate dehydrogenase activity) which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications can be carried out by known techniques, including but not limited, to specific chemical cleavage by cyanogen bromide, trypsin, chymotrypsin, papain, S.

aureus V8 protease, NaBH$_4$; acetylation, formylation, oxidation, reduction; metabolic synthesis in the presence of tunicamycin, etc.

Additional post-translational modifications can include, for example, e.g., N-linked or O-linked carbohydrate chains, processing of N-terminal or C-terminal ends, attachment of chemical moieties to the amino acid backbone, chemical modifications of N-linked or O-linked carbohydrate chains, and addition of an N-terminal methionine residue as a result of vectors and constructs adapted for expression of oxidative decarboxylase polypeptides having neomorphic oxidoreductase activity in prokaryotic cultured host cells. The polypeptides can also be modified with a detectable label, such as an enzymatic, fluorescent, isotopic, or affinity label to allow for detection and isolation of the protein.

The scope of the compositions or methods described herein includes all actual or potential combinations of aspects, embodiments, examples, and preferences herein described. All enzymatic reactions described herein include the forward and reverse reactions and include the application of the principles of mass action to drive the equilibrium of reactions in one direction or the other by altering the relative concentrations of enzymes, reactants, products, cofactors, intermediate metabolites, feedback inhibitors, or enhancers described herein. Further, physicochemical factors such as pH, temperature, pressure, or solvent can be adjusted to modulate the reactions described herein.

EXAMPLES

Example 1

Preparation of HIDH Constructs

A blunt-ended 1002 base pair (bp) fragment encoding *T. thermophilus* HIDH (TTC1012) lacking the 3'-stop codon was amplified from a *T. thermophilus* HB27 gDNA library (ATCC). A blunt-ended 1110 bp fragment encoding LYS12 lacking the 3'-stop codon was amplified from an *S. cerevisiae* gDNA library using KAPA Taq DNA polymerase (KAPA Biosystems, Woford, Mass.). These fragments were cloned into pTrcHis2-TOPO (Invitrogen, Carlsbad, Calif.) using the manufacturer's instructions. Mutagenesis was performed using the QuikChange Site Directed mutagenesis kit (Agilent). All constructs were sequence verified using pTrcHis2-for and pTrcHis2-rev primers. Constructs are listed in Table 1, SEQ ID NOs: 1-22.

Example 2

Purification of HIDH Mutants

Procedures for expression and purification of homoisocitrate dehydrogenases were adapted from published methods. Lin et al., *Biochemistry* 46: 890-898 (2007). Expression constructs were transformed into BL21-DE3 *E. coli* (Stratagene). A single colony was inoculated into 5 mL of LB-Amp media starter cultures and grown by shaking (225 rpm at 37° C.) for 6 h. Starter cultures (5 mL) were added to 45 mL of LB-Amp, shaken for 2 h, and shaken for an additional 2 h after induction with 1 mM IPTG. Pellets were harvested by centrifugation at 4,500×g at 4° C. and resuspended in 2 mL of Buffer B (500 mM NaCl, 10 mM MgCl$_2$, 20 mM imidazole, 2 mM β-mercaptoethanol, 10 mM Tris, pH 7.5 supplemented with 1×EDTA-free cOmplete Mini™ protease inhibitor from Roche) on ice and sonicated for 6 cycles of 15 seconds each on ice on a Sonifer 250 (Branson). This lysate was cleared by centrifugation at 13,000×g at 4° C. Lysates were loaded on a Ni-NTA Spin Column (Qiagen) that was preequilibrated with Buffer B by spinning for 10 min at 300×g at 4° C. This was then washed with 10-column volumes of Buffer B that contained 75 mM imidazole, 5% glycerol, and 0.1% Triton-X 100 by spinning for 1 min at 900×g. Eluates were obtained using buffer B that was modified to contain 500 mM imidazole. Eluates were normalized to 400 ng/μL, brought to 10% glycerol, and stored at −80° C. as aliquots. Purity was assessed by SDS-PAGE stained with Coomassie Blue G dye (Sigma) or SilverQuest Silver Staining Kit (Life Technologies) (FIG. 7).

Example 3

Preparation of Crude Lysates of HIDH Mutants

To obtain crude lysates, 0.5 mL of starter cultures generated as described above were added to 4.5 mL LB-Amp, shaken for 2 h, and shaken for an additional 2 h after induction with 1 mM IPTG. Pellets from these cultures were harvested by centrifugation at 4500×g at 4° C. These pellets were resuspended into 500 μL of Buffer A (0.2% Triton-X 100, 1 mM PMSF, 0.5 mM EDTA, 10 mM Tris, pH 7.5) on ice and sonicated for 6-cycles of 15 seconds each on ice on a Sonifer 250 (Branson). This was then spun down at 13,000×g at 4° C. for 15 min and the cleared lysates were normalized with additional lysis buffer to 700 ng/4 and stored at −80° C. as aliquots. Protein concentrations were determined using the BioRad Protein Assay reagent according to the manufacturer's instructions.

Example 4

Activity Measurements

NADH, 2-oxoadipate, 2-oxoglutarate, 2-heptandioate, and MgCl$_2$ were from Sigma. Standard reaction mixes contained 15 mM 2-oxoadipate, 100 μM NADH, and a reaction buffer with final concentrations of 20 mM MgCl$_2$ and 500 mM HEPES, pH 7.3. NADH oxidation was monitored by the decrease in fluorescence with excitation of 340 nm and emission of 450 nm on a PolarSTAR Optima plate reader (BMG Labtech). Fluorescence monitored reactions were carried out in 10-μL volumes in a 384-well black microplate (Greiner 788076) covered with clear optical film. The levels of fluorescence were converted to NADH concentrations based on standards of NADH in reaction buffer containing BSA. Reactions with high amounts of NADH were monitored by the UV absorbance of NADH at 340 nm in 40-μL reaction volumes in clear 96-well plates.

Example 5

Reaction Rate Calculations

Reaction rates are NADH oxidation per unit time per unit of purified enzyme or crude lysate and 1 Unit (U) is 1 $\mu mol_{NADH} min^{-1} mg_{enzyme}^{-1}$. Rates are initial rates calculated by least squares linear regression on the first 10 minutes of the reaction. For $K_M$ determination, concentrations of substrate/cofactors at least 5×-higher than the $K_M$ were used, while the species of interest was varied in concentration; substrate/cofactor concentrations: 500 μM NADH; 15 mM 2-oxoadipate; 20 mM $MgCl_2$. Reported α-hydroxyadipate (2-hydroxy adpic acid) $V_{max}$ values were obtained from 2-oxoadipate $K_M$ determination experiments. Michaelis-Menten $K_M$ and $V_{max}$ parameters were estimated by fitting data to a curve using nonlinear regression in GraphPad Prism 5.0 (GraphPad Software, La Jolla, Calif.). Student's t-tests were used to determine whether mean (n=4) rates of reactions in the presence of dicarboxylic acid substrates other than 2-oxoadipate were significantly increased above a nonsubstrate control.

Example 6

Synthesis of Reactants

A racemic mixture of (R)- and (S)-2-hydroxyadipate was generated by reacting 1 mg 2-oxoadipic acid with 1 mg $NaBH_4$ in 200 μL of anhydrous methanol at 60° C. for 30 min and confirmed by direct infusion mass spectrometry. [3,3,4,4-$^2H_4$]-(R/S)-2-hydroxyglutarate (2-hydroxyglutartate; 2HG-d4) was synthesized as described previously. Jin et al., PLoS one 6, e16812: 1-8 (2011).

Example 7

Quantification of (R) and (S)-2-hydroxyadipate by LC-MS/MS

Quantitative, enantiospecific LC-MS/MS was performed based on the procedure described for 2-hydroxyglutarate. Jin et al., PLoS one 6, e16812: 1-8 (2011); Struys, et al., Clin. Chem. 50: 1391-1395 (2004). To 20 μL of reaction mix, 2 μL of 130 μg/mL of a racemic mixture of [3,3,4,4-$^2H4$]-2-hydroxyglutarate (internal standard) in water was added and the mixture dried by vacuum centrifuge (50° C., 15 min). The dry residue was treated with 50 mg/mL freshly prepared diacetyl-L-tartaric anhydride (Sigma) in dichloromethane/glacial acetic acid (4:1 by volume) and heated (75° C., 30 min). After drying (50° C., 15 min) the residue was dissolved in 100 μL of LC mobile phase A (see below) for analysis. An Agilent 1200 series HPLC (Santa Clara, Calif.) was used for liquid chromatography (LC) and a Sciex/Applied Biosystems API 3200 QTrap (Carlsbad, Calif.) was used for triple quadrupole mass spectrometry (MS/MS). Mobile phase A: water, 3% acetonitrile, 280 μL ammonium hydroxide (~25%), pH adjusted to 3.6 with formic acid (~98%). Mobile phase B: methanol. Analytical column: Kinetex C-18, 150×4.6 mm, 2.6 μm, and SafeGuard C-18 4×3 mm guard-column from Phenomenex (Torrance, Calif.). Column temperature: 45° C. Elution gradient at 1 mL/min flow rate: 0-1 min 0% B, 1-2 min 0-100% B, 2-3.5 min 100% B, 3.5-4 min 100-0% B, 4-10 min 0% B. Injection volume: 10 μL. Q1/Q3 (m/z) transitions were monitored: 377/161, 2-hydroxyadipate (2HA) and 367/151, [3,3,4,4-$^2H4$]-2-hydroxyglutarate (2HG-d4). To calibrate, 0, 0.16, 0.54, 1.8, 6, and 20 μg/mL 2-hydroxyadipate (Sigma), synthesized as described above, was analyzed in reaction buffer. (R)- and (S)-enantiomers were discriminated based on time of elution from the HPLC column, using the relative elution time for (R)-2-hydroxyglutarate compared to the racemic mixture of 2-hydroxyglutarate described previously to identify the (R)-2-hydroxyadipate enantiomer. Jin et al., PLoS one 6, e16812: 1-8 (2011). Standards were analyzed alongside experimental samples. Accuracy acceptance criteria were 85% for all but the lowest level (0.16 μg/mL, 80%).

Example 8

TtHIDH-R118H is a (R)-2-hydroxyglutarate Dehydrogenase

The experiments described herein show that the Thermus thermophilus HIDH R188H mutant, TtHIDH-R118H, consumes 2-oxoadipate in the presence of NADH (FIG. 4A). Further experiments confirmed that TtHIDH-R118H produces (R)-2-hydroxyadipate as a product of this reaction (FIG. 4C). TtHIDH-R118H can also use 2-oxoglutarate as a substrate, and the activity is more rapid than that observed with 2-oxoadipate. "Glutarate" refers to a 5-carbon backbone; whereas "adipate" refers to a 6-carbon backbone. Thus, the reaction catalyzed by TtHIDH-R118H that was observed and monitored by the oxidation of NADH is "(R)-2-hydroxyglutarate dehydrogenase" activity (FIG. 4C). The TtHIDH-R118H enzyme therefore acts as an (R)-2-hydroxyglutarate dehydrogenase that performs the following reversible interconversion:

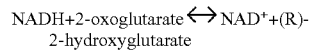

NADH+2-oxoglutarate ⇌ $NAD^+$+(R)-2-hydroxyglutarate

FAD-linked (R)-2-hydroxyglutarate dehydrogenases are abundant in nature. In some human cancers, mutations to HsIDH1 and HsIDH2 effectively convert these enzymes into NADPH-linked 2-hydroxyglutarate dehydrogenases. See Dang et al., Nature 462: 739-744 (2009). Nevertheless, this is the first demonstration of a novel NADH-linked 2-hydroxyglutarate dehydrogenase produced in vitro using site directed mutagenesis. Accordingly, the analagous HIDH mutants described herein are thought to also possess 2-hydroxyglutarate activity. See Tables 1 and 2.

Example 9

Activity Conversion of Isopropylmalate Dehydrogenases and Tartrate Dehydrogenases Polynucleotide and polypeptide sequences for wild type and mutant isopropylmalate dehydrogenases and tartarate dehydrogenase with predicted 2-hydroxyacid dehydrogenase activity based on methods described herein are disclosed. See Table 1, SEQ ID NOs: 23-34. The mutations are analogous to those made in the ScHIDH1-R114H-R115H, or -R143H mutants described herein. See FIG. 2B. Sacchromyces cerevisiae isopropylmalate dehydrogenase (ScIPMDH), Thermus thermophilus isopropylmalate dehydrogenase (TtIPMDH), and E. coli tartarate dehydrogenase (EcTDH) sequences are shown. The mutations disclosed in the sequence listing are Arg-to-His mutations, but Arg-to-Lys and Arg-to-Gln, as well as other non-Arg amino acids are likely functional for neomorphic (R)-2-hydroxyadipate dehydrogenase activity and are envisioned as alternative embodiments of the polypeptides described herein. For example, Arg could be mutated to His, Lys, Gln, Asn, Leu, Ile, Val, Tyr, Phe, Trp, Cys, Ser, Thr, Met, Glu, Asp, Ala, Gly, or Pro. Further, multiple IPMDH or TDH active site residues may be simultaneously mutated. Residues in analagous positions to those of the HsIDH1 or ScHIDH active sites are useful targets for mutagenesis as described herein. For example, residues in positions analagous to V111, R114, R115, R124, R143, Y150, among others, of the ScHIDH polypeptide (i.e., SEQ ID NO: 2) are candidates for mutagenesis as described herein to produce oxidoreductases with neomorphic (R)-2-hydroxyadipate dehydrogenase activity.

TABLE 1

Polynucleotide and Polypeptide Sequences

| Polynucleotides | | Polypeptides | |
|---|---|---|---|
| Construct | SEQ ID NO | Construct | SEQ ID NO |
| Homoisocitrate Dehydrogenases | | | |
| ScHIDH wild type | SEQ ID NO: 1 | ScHIDH wild type | SEQ ID NO: 2 |
| ScHIDH V111D | SEQ ID NO: 3 | ScHIDH V111D | SEQ ID NO: 4 |
| ScHIDH R114Q | SEQ ID NO: 5 | ScHIDH R114Q | SEQ ID NO: 6 |
| ScHIDH R115Q | SEQ ID NO: 7 | ScHIDH R115Q | SEQ ID NO: 8 |
| ScHIDH R143C | SEQ ID NO: 9 | ScHIDH R143C | SEQ ID NO: 10 |
| ScHIDH R143H | SEQ ID NO: 11 | ScHIDH R143H | SEQ ID NO: 12 |
| ScHIDH R143K | SEQ ID NO: 13 | ScHIDH R143K | SEQ ID NO: 14 |
| ScHIDH Y150D | SEQ ID NO: 15 | ScHIDH Y150D | SEQ ID NO: 16 |
| ScHIDH R114Q R143C | SEQ ID NO: 17 | ScHIDH R114Q R143C | SEQ ID NO: 18 |
| TtHIDH wild type | SEQ ID NO: 19 | TtHIDH wild type | SEQ ID NO: 20 |
| TtHIDH-R118H | SEQ ID NO: 21 | TtHIDH-R118H | SEQ ID NO: 22 |
| Isopropylmalate and Tartarate Dehydrogenases | | | |
| ScIPMDH wild type | SEQ ID NO: 23 | ScIPMDH wild type | SEQ ID NO: 24 |
| ScIPMDH R136H | SEQ ID NO: 25 | ScIPMDH R136H | SEQ ID NO: 26 |
| TtIPMDH wild type | SEQ ID NO: 27 | TtIPMDH wild type | SEQ ID NO: 28 |
| TtIPMDH R132H | SEQ ID NO: 29 | TtIPMDH R132H | SEQ ID NO: 30 |
| EcTDH wild type | SEQ ID NO: 31 | EcTDH wild type | SEQ ID NO: 32 |
| EcTDH R133H | SEQ ID NO: 33 | EcTDH R133H | SEQ ID NO: 34 |

Abbreviations:
Sc, *Sacchromyces cerevisiae*;
HIDH, homoisocitrate dehydrogenase;
Tt, *Thermus thermophilus*;
IPMDH, isopropylmalate dehydrogenase;
Ec, *Eschericia coli*;
TDH, tartarate dehydrogenase.

Example 10

Conversion of Homoisocitrate Dehydrogenases to (R)-2-Hydroxyadipate Dehydrogenases Polypeptide sequences for mutant homoisocitrate dehydrogenases available from the NCBI Protein database are listed in Table 2. Genes, comprising nucleotide sequences encoding the respective polypeptides listed in Table 2 are known and available in public databases. Table 2 lists the GI Number for the wild type polypeptide and the encoding polynucleotide can likewise be obtained from the database or by reverse translation, for example. Each polypeptide sequence listed in Table 2 has two Arg-to-His mutations indicated by residue and position number that are expected to convert the wild type enzyme from an oxidative decarboxylase to an oxidoreductase (dehydrogenase) based on the experimental data disclosed herein.

In exemplary, non-limiting embodiments, mutations disclosed in Table 2 and in SEQ ID NOs: 35-138 contain Arg-to-His mutations at positions analogous to R114 and R132 of ScHIDH (i.e., SEQ ID NO: 2), which corresponds to positions R100 and R132, respectively, of HsIDH1 (SEQ ID NO: 140). See FIGS. 2 and 3. For example, SEQ ID NO: 35 comprises the polypeptide sequence of the *Ajellomyces capsulate* HIDH with the mutations R96H and R126H, which correspond to the R114 and R132 mutations of ScHIDH.

The Arg-to-His mutations in Table 2 and in SEQ ID NOs: 35-138 are exemplary because Arg-to-Lys, Arg-to-Gln, as well as other non-Arg amino acids are likely functional for oxidoreductase activity and are envisioned as alternative embodiments of the mutant polypeptides described herein.

For example, the indicated Arg residues can be mutated to His, Lys, Gln, Asn, Leu, Ile, Val, Tyr, Phe, Trp, Cys, Ser, Thr, Met, Glu, Asp, Ala, Gly, or Pro. In addition, multiple HIDH active site residues may be simultaneously mutated in a single polypeptide. For example, mutations to residues in analogous positions of ScHIDH, such as V111, R114, R115, R124, R143, Y150, are envisioned within the scope of the polypeptides described herein. Mutations may be made to polynucleotides encoding the polypeptides described herein or in solid phase syntheses of the polypeptides described herein. Mutations may be made to 1, 2, 3, 4, 5, 6, 7, 8, 9, 10, 15, 20, 30, 40, or 50 or even more amino acid residues in a particular polypeptide. Mutations may be conservative or to change the physicochemical characteristics of a particular residue or position. In some aspects, the polypeptide may have one or more mutations or conservative amino acid substitutions with the proviso that polypeptide has one or more mutations to the active site at positions analogous to V111, R114, R115, R124, R143, or Y150 of the *Saccharomyces cerevisiae* homoisocitrate dehydrogenase (ScHIDH), i.e., SEQ ID NO: 2.

Such mutations may also be incorporated into polynucleotides encoding the mutant polypeptide, for example, by reverse transcribing the polypeptide sequence to generate a codon-optimized nucleotide sequence encoding the polypeptide for expression in a specific organism. Alternatively, the wild-type nucleotide sequence may be cloned from cDNA obtained from the organism, or made synthetically, based on the sequences available from various databases (e.g., NCBI) and mutations incorporated using standard methods known in the art.

TABLE 2

Polypeptide Sequences for Neomorphic (R)-2-hydroxyadipate Dehydrogenases

| SEQ ID NO | Construct Name | Organism | Wild Type Polypeptide NCBI GI No. | Mutations |
|---|---|---|---|---|
| SEQ ID NO: 35 | *Ajellomyces capsulatus* NAm1 HIDH R96H, R126H polypeptide | *Ajellomyces capsulatus* NAm1 | 150415988 | R96H, R126H |
| SEQ ID NO: 36 | *Ajellomyces capsulatus* NAm1 HIDH R96H, R126H polypeptide 2 | *Ajellomyces capsulatus* NAm1 | 154273248 | R96H, R126H |
| SEQ ID NO: 37 | *Ajellomyces dermatitidis* ATCC 18188 HIDH R96H, R126H polypeptide | *Ajellomyces dermatitidis* ATCC 18188 | 327353516 | R96H, R126H |
| SEQ ID NO: 38 | *Ajellomyces dermatitidis* ER-3 HIDH R96H, R126H polypeptide 2 | *Ajellomyces dermatitidis* ER-3 | 239608490 | R96H, R126H |
| SEQ ID NO: 39 | *Ajellomyces dermatitidis* SLH14081 HIDH R96H, R126H polypeptide | *Ajellomyces dermatitidis* SLH14081 | 261187705 | R96H, R126H |
| SEQ ID NO: 40 | *Ajellomyces dermatitidis* SLH14081 HIDH R96H, R126H polypeptide 2 | *Ajellomyces dermatitidis* SLH14081 | 239594078 | R96H, R126H |
| SEQ ID NO: 41 | *Arthroderma gypseum* CBS 118893 HIDH R96H, R127H polypeptide | *Arthroderma gypseum* CBS 118893 | 315041683 | R96H, R127H |
| SEQ ID NO: 42 | *Arthroderma gypseum* CBS 118893 HIDH R96H, R127H polypeptide 2 | *Arthroderma gypseum* CBS 118893 | 311345252 | R96H, R127H |
| SEQ ID NO: 43 | *Arthroderma otae* CBS 113480 HIDH R96H, R127H polypeptide | *Arthroderma otae* CBS 113480 | 238839988 | R96H, R127H |
| SEQ ID NO: 44 | *Arthroderma otae* CBS 113480 HIDH R96H, R127H polypeptide 2 | *Arthroderma otae* CBS 113480 | 296818397 | R96H, R127H |
| SEQ ID NO: 45 | *Aspergillus kawachii* IFO 4308 HIDH R98H, R128H polypeptide | *Aspergillus kawachii* IFO 4308 | 358373946 | R98H, R128H |
| SEQ ID NO: 46 | *Aspergillus niger* CBS 513.88 HIDH R98H, R128H polypeptide | *Aspergillus niger* CBS 513.88 | 145250547 | R98H, R128H |
| SEQ ID NO: 47 | *Aspergillus oryzae* RIB40 HIDH R97H, R126H polypeptide | *Aspergillus oryzae* RIB40 | 169768000 | R97H, R126H |
| SEQ ID NO: 48 | *Aspergillus terreus* NIH2624 HIDH R140H, R170H polypeptide | *Aspergillus terreus* NIH2624 | 114193793 | R140H, R170H |
| SEQ ID NO: 49 | *Aspergillus terreus* NIH2624 HIDH R140H, R170H polypeptide 2 | *Aspergillus terreus* NIH2624 | 115390729 | R140H, R170H |
| SEQ ID NO: 50 | *Candida albicans* SC5314 HIDH R112H, R140H polypeptide | *Candida albicans* SC5314 | 46440053 | R112H, R140H |
| SEQ ID NO: 51 | *Candida albicans* SC5314 HIDH R112H, R140H polypeptide 2 | *Candida albicans* SC5314 | 46439950 | R112H, R140H |
| SEQ ID NO: 52 | *Candida albicans* SC5314 HIDH R112H, R140H polypeptide 3 | *Candida albicans* SC5314 | 68475341 | R112H, R140H |
| SEQ ID NO: 53 | *Candida albicans* SC5314 HIDH R112H, R140H polypeptide 4 | *Candida albicans* SC5314 | 68475148 | R112H, R140H |
| SEQ ID NO: 54 | *Candida albicans* WO-1 HIDH R112H, R140H polypeptide | *Candida albicans* WO-1 | 238879624 | R112H, R140H |
| SEQ ID NO: 55 | *Candida dubliniensis* CD36 HIDH R112H, R140H polypeptide | *Candida dubliniensis* CD36 | 223645080 | R112H, R140H |
| SEQ ID NO: 56 | *Candida dubliniensis* CD36 HIDH R112H, R140H polypeptide 2 | *Candida dubliniensis* CD36 | 241958032 | R112H, R140H |
| SEQ ID NO: 57 | *Candida parapsilosis* HIDH R104H, R132H polypeptide | *Candida parapsilosis* | 354545019 | R104H, R132H |
| SEQ ID NO: 58 | *Candida tropicalis* MYA-3404 HIDH R113H, R141H polypeptide | *Candida tropicalis* MYA-3404 | 255722457 | R113H, R141H |
| SEQ ID NO: 59 | *Candida tropicalis* MYA-3404 HIDH R113H, R141H polypeptide 2 | *Candida tropicalis* MYA-3404 | 240136652 | R113H, R141H |
| SEQ ID NO: 60 | *Chaetomium thermophilum* DSM 1495 HIDH R97H, R125H polypeptide | *Chaetomium thermophilum* DSM 1495 | 340923999 | R97H, R125H |
| SEQ ID NO: 61 | *Coprinopsis cinerea* okayama7#130 HIDH R107H, R138H polypeptide | *Coprinopsis cinerea* okayama7#130 | 169860569 | R107H, R138H |

TABLE 2-continued

Polypeptide Sequences for Neomorphic (R)-2-hydroxyadipate Dehydrogenases

| SEQ ID NO | Construct Name | Organism | Wild Type Polypeptide NCBI GI No. | Mutations |
|---|---|---|---|---|
| SEQ ID NO: 62 | *Coprinopsis cinerea* okayama7#130 HIDH R107H, R138H polypeptide 2 | *Coprinopsis cinerea* okayama7#130 | 116501641 | R107H, R138H |
| SEQ ID NO: 63 | *Cordyceps militaris* CM01 HIDH R96H, R124H polypeptide | *Cordyceps militaris* CM01 | 346322262 | R96H, R124H |
| SEQ ID NO: 64 | *Deinococcus radiodurans* HIDH R90H, R120H polypeptide | *Deinococcus radiodurans* | 40645339 | R9OH, R120H |
| SEQ ID NO: 65 | *Glarea lozoyensis* 74030 HIDH R96H, R124H polypeptide | *Glarea lozoyensis* 74030 | 361123851 | R96H, R124H |
| SEQ ID NO: 66 | *Komagataella pastoris* CBS 7435 HIDH R109H, R137H polypeptide | *Komagataella pastoris* CBS 7435 | 328351473 | R109H, R137H |
| SEQ ID NO: 67 | *Lodderomyces elongisporus* NRRL YB-4239 HIDH R112H, R140H polypeptide | *Lodderomyces elongisporus* NRRL YB-4239 | 146447623 | R112H, R140H |
| SEQ ID NO: 68 | *Lodderomyces elongisporus* NRRL YB-4239 HIDH R112H, R140H polypeptide 2 | *Lodderomyces elongisporus* NRRL YB-4239 | 149246399 | R112H, R140H |
| SEQ ID NO: 69 | *Magnaporthe oryzae* 70-15 HIDH R97H, R125H polypeptide | *Magnaporthe oryzae* 70-15 | 351646875 | R97H, R125H |
| SEQ ID NO: 70 | *Marinithermus hydrothermalis* DSM 14884 HIDH R90H, R120H polypeptide | *Marinithermus hydrothermalis* DSM 14884 | 328451367 | R90H, R120H |
| SEQ ID NO: 71 | *Marinithermus hydrothermalis* DSM 14884 HIDH R90H, R120H polypeptide 2 | *Marinithermus hydrothermalis* DSM 14884 | 328951043 | R90H, R120H |
| SEQ ID NO: 72 | *Meiothermus silvanus* DSM 9946 HIDH R90H, R120H polypeptide | *Meiothermus silvanus* DSM 9946 | 297565766 | R90H, R120H |
| SEQ ID NO: 73 | *Meiothermus silvanus* DSM 9946 HIDH R90H, R120H polypeptide 2 | *Meiothermus silvanus* DSM 9946 | 296850215 | R90H, R120H |
| SEQ ID NO: 74 | *Metarhizium acridum* CQMa 102 HIDH R96H, R124H polypeptide | *Metarhizium acridum* CQMa 102 | 322700171 | R96H, R124H |
| SEQ ID NO: 75 | *Metarhizium anisopliae* ARSEF 23 HIDH R96H, R124H polypeptide | *Metarhizium anisopliae* ARSEF 23 | 322711926 | R96H, R124H |
| SEQ ID NO: 76 | *Methanocaldococcus jannaschii* HIDH R87H, R128H polypeptide | *Methanocaldococcus jannaschii* | 229504888 | R87H, R128H |
| SEQ ID NO: 77 | *Methanocaldococcus jannaschii* DSM 2661 HIDH | *Methanocaldococcus jannaschii* DSM 2661 | 168805636 | R87H, R128H |
| SEQ ID NO: 78 | *Methanohalophilus mahii* DSM 5219 HIDH R84H, R117H polypeptide | *Methanohalophilus mahii* DSM 5219 | 292665816 | R84H, R117H |
| SEQ ID NO: 79 | *Methanohalophilus mahii* DSM 5219 HIDH R84H, R117H polypeptide 2 | *Methanohalophilus mahii* DSM 5219 | 294494817 | R84H, R117H |
| SEQ ID NO: 80 | *Methanosaeta concilii* GP6 HIDH R80H, R103H polypeptide | *Methanosoeta concilii* GP6 | 328928696 | R80H, R103H |
| SEQ ID NO: 81 | *Methanosaeta concilii* GP6 HIDH R80H, R103H polypeptide 2 | *Methanosoeta concilii* GP6 | 330507888 | R80H, R103H |
| SEQ ID NO: 82 | *Neurospora crassa* OR74A HIDH R96H, R125H polypeptide | *Neurospora crass* OR74A | 85117930 | R96H, R125H |
| SEQ ID NO: 83 | *Neurospora crassa* OR74A HIDH R96H, R125H polypeptide 2 | *Neurospora crass* OR74A | 28927149 | R96H, R125H |
| SEQ ID NO: 84 | *Neurospora tetrasperma* FGSC 2509 HIDH R96H, R125H polypeptide | *Neurospora tetrasperma* FGSC 2509 | 350295426 | R96H, R125H |
| SEQ ID NO: 85 | *Oceanithermus profundus* DSM 14977 HIDH R91H, R121H polypeptide | *Oceanithermus profundus* DSM 14977 | 313152992 | R91H, R121H |
| SEQ ID NO: 86 | *Oceanithermus profundus* DSM 14977 HIDH R91H, R121H polypeptide 2 | *Oceanithermus profundus* DSM 14977 | 313680277 | R91H, R121H |

TABLE 2-continued

Polypeptide Sequences for Neomorphic (R)-2-hydroxyadipate Dehydrogenases

| SEQ ID NO | Construct Name | Organism | Wild Type Polypeptide NCBI GI No. | Mutations |
|---|---|---|---|---|
| SEQ ID NO: 87 | *Ogataea parapolymorpha* DL-1 HIDH R95H, R123H polypeptide | *Ogataea parapolymorpho* DL-1 | 320583008 | R95H, R123H |
| SEQ ID NO: 88 | *Paracoccidioides brasiliensis* Pb01 HIDH R96H, R125H polypeptide | *Paracoccidioides brasiliensis* Pb01 | 226279774 | R96H, R125H |
| SEQ ID NO: 89 | *Paracoccidioides brasiliensis* Pb01 HIDH R96H, R125H polypeptide 2 | *Paracoccidioides brasiliensis* Pb01 | 295662188 | R96H, R125H |
| SEQ ID NO: 90 | *Paracoccidioides brasiliensis* Pb18 HIDH R96H, R125H polypeptide | *Paracoccidioides brasiliensis* Pb18 | 226289652 | R96H, R125H |
| SEQ ID NO: 91 | *Pyrococcus horikoshii* HIDH R86H, R111H polypeptide | *Pyrococcus horikoshii* | 62909981 | R86H, R111H |
| SEQ ID NO: 92 | *Roseiflexus* sp. RS-1 HIDH R91H, R125H polypeptide | *Roseiflexus* sp. RS-1 | 148567321 | R91H, R125H |
| SEQ ID NO: 93 | *Sacchromyces cerevisiae* HIDH R114H, R143H polypeptide | *Sacchromyces cerevisiae* | 731845 | R114H, R143H |
| SEQ ID NO: 94 | *Schizosaccharomyces japonicus* yFS275 HIDH R97H, R126H polypeptide | *Schizosaccharomyces japonicus* yFS275 | 213402013 | R97H, R126H |
| SEQ ID NO: 95 | *Schizosaccharomyces japonicus* yFS275 HIDH R97H, R126H polypeptide 2 | *Schizosaccharomyces japonicus* yFS275 | 211999826 | R97H, R126H |
| SEQ ID NO: 96 | *Schizosaccharomyces pombe* HIDH R97H, R126H polypeptide | *Schizosaccharomyces pombe* | 2388955 | R97H, R126H |
| SEQ ID NO: 97 | *Schizosaccharomyces pombe* HIDH R97H, R126H polypeptide 2 | *Schizosaccharomyces pombe* | 74626630 | R97H, R126H |
| SEQ ID NO: 98 | *Schizosaccharomyces pombe* HIDH R101H, R130H polypeptide | *Schizosaccharomyces pombe* | 356624656 | R101H, R130H |
| SEQ ID NO: 99 | *Schizosaccharomyces pombe* HIDH R101H, R130H polypeptide 2 | *Schizosaccharomyces pombe* | 356624655 | R101H, R130H |
| SEQ ID NO: 100 | *Schizosaccharomyces pombe* HIDH R101H, R130H polypeptide 3 | *Schizosaccharomyces pombe* | 356624654 | R101H, R130H |
| SEQ ID NO: 101 | *Schizosaccharomyces pombe* HIDH R101H, R130H polypeptide 4 | *Schizosaccharomyces pombe* | 356624653 | R101H, R130H |
| SEQ ID NO: 102 | *Schizosaccharomyces pombe* 972h-HIDH R97H, R126H polypeptide | *Schizosaccharomyces pombe* 972h- | 19114916 | R97H, R126H |
| SEQ ID NO: 103 | *Starkeya novella* DSM 506 HIDH R92H, R123H polypeptide | *Starkeya novella* DSM 506 | 298294272 | R92H, R123H |
| SEQ ID NO: 104 | *Starkeya novella* DSM 506 HIDH R92H, R123H polypeptide 2 | *Starkeya novella* DSM 506 | 296930783 | R92H, R123H |
| SEQ ID NO: 105 | *Streptococcus vestibularis* F0396 HIDH R99H, R126H polypeptide | *Streptococcus vestibularis* F0396 | 312863177 | R99H, R126H |
| SEQ ID NO: 106 | *Streptococcus vestibularis* F0396 HIDH R99H, R126H polypeptide 2 | *Streptococcus vestibularis* F0396 | 311100713 | R99H, R126H |
| SEQ ID NO: 107 | *Thermococcus kodakarensis* KOD1 HIDH R86H, R111H polypeptide | *Thermococcus kodakarensis* KOD1 | 57158539 | R86H, R111H |
| SEQ ID NO: 108 | *Thermus aquaticus* HIDH R88H, R118H polypeptide | *Thermus aquaticus* | 207367111 | R88H, R118H |
| SEQ ID NO: 109 | *Thermus aquaticus* Y51MC23 HIDH R88H, R118H polypeptide | *Thermus aquaticus* Y51MC23 | 218294940 | R88H, R118H |
| SEQ ID NO: 110 | *Thermus aquaticus* Y51MC23 HIDH R88H, R118H polypeptide 2 | *Thermus aquaticus* Y51MC23 | 218244848 | R88H, R118H |
| SEQ ID NO: 111 | *Thermus* sp. CCB US3 UF1 HIDH R88H, R118H polypeptide | *Thermus* sp. CCB_US3_UF1 | 359290168 | R88H, R118H |
| SEQ ID NO: 112 | *Thermus thermophilus* HIDH R88H, R118H polypeptide | *Thermus thermophilus* | 20086367 | R88H, R118H |

TABLE 2-continued

Polypeptide Sequences for Neomorphic (R)-2-hydroxyadipate Dehydrogenases

| SEQ ID NO | Construct Name | Organism | Wild Type Polypeptide NCBI GI No. | Mutations |
|---|---|---|---|---|
| SEQ ID NO: 113 | *Thermus thermophilus* HIDH R88H, R118H polypeptide 2 | *Thermus thermophilus* | 347447275 | R88H, R118H |
| SEQ ID NO: 114 | *Thermus thermophilus* HIDH R88H, R118H polypeptide 3 | *Thermus thermophilus* | 347447274 | R88H, R118H |
| SEQ ID NO: 115 | *Thermus thermophilus* HIDH R88H, R118H polypeptide 4 | *Thermus thermophilus* | 347447273 | R88H, R118H |
| SEQ ID NO: 116 | *Thermus thermophilus* HIDH R88H, R118H polypeptide 5 | *Thermus thermophilus* | 347447272 | R88H, R118H |
| SEQ ID NO: 117 | *Thermus thermophilus* HIDH R87H, R117H polypeptide | *Thermus thermophilus* | 78100866 | R87H, R117H |
| SEQ ID NO: 118 | *Thermus thermophilus* HIDH R87H, R117H polypeptide 2 | *Thermus thermophilus* | 78100865 | R87H, R117H |
| SEQ ID NO: 119 | *Thermus thermophilus* HB27 HIDH R88H, R118H polypeptide | *Thermus thermophilus* HB27 | 46199314 | R87H, R118H |
| SEQ ID NO: 120 | *Thermus thermophilus* HB27 HIDH R88H, R118H polypeptide 2 | *Thermus thermophilus* HB27 | 46196939 | R88H, R118H |
| SEQ ID NO: 121 | *Thermus thermophilus* HB27 HIDH R94H, R132H polypeptide | *Thermus thermophilus* HB27 | 21262177 | R94H, R132H |
| SEQ ID NO: 122 | *Thermus thermophilus* HB27 HIDH R104H, R137H polypeptide | *Thermus thermophilus* HB27 | 21262175 | R104H, R137H |
| SEQ ID NO: 123 | *Thermus thermophilus* HB8 HIDH R88H, R118H polypeptide | *Thermus thermophilus* HB8 | 40645343 | R88H, R118H |
| SEQ ID NO: 124 | *Thermus thermophilus* HB8 HIDH R88H, R118H polypeptide 2 | *Thermus thermophilus* HB8 | 55981347 | R88H, R118H |
| SEQ ID NO: 125 | *Thermus thermophilus* HB8 HIDH R88H, R118H polypeptide3 | *Thermus thermophilus* HB8 | 55772760 | R88H, R118H |
| SEQ ID NO: 126 | *Thermus thermophilus* SG0.5JP17-16 HIDH R88H, R118H polypeptide | *Thermus thermophilus* SG0.5JP17-16 | 333967025 | R88H, R118H |
| SEQ ID NO: 127 | *Thermus thermophilus* with Directed Evolution HIDH R88H, R118H polypeptide | *Thermus thermophilus* with Directed Evolution | 321159634 | R88H, R118H |
| SEQ ID NO: 128 | *Thermus thermophilus* with Directed Evolution HIDH R88H, R118H polypeptide 2 | *Thermus thermophilus* with Directed Evolution | 321159633 | R88H, R118H |
| SEQ ID NO: 129 | *Thermus thermophilus* with Directed Evolution HIDH R88H, R118H polypeptide 3 | *Thermus thermophilus* with Directed Evolution | 321159632 | R88H, R118H |
| SEQ ID NO: 130 | *Thermus thermophilus* with Directed Evolution HIDH R88H, R118H polypeptide 4 | *Thermus thermophilus* with Directed Evolution | 321159631 | R88H, R118H |
| SEQ ID NO: 131 | *Trichophyton equinum* CBS 127.97 HIDH R96H, R127H polypeptide | *Trichophyton equinum* CBS 127.97 | 326482838 | R96H, R127H |
| SEQ ID NO: 132 | *Truepera radiovictrix* DSM 17093 HIDH R93H, R123H polypeptide | *Truepera radiovictrix* DSM 17093 | 297625050 | R93H, R123H |
| SEQ ID NO: 133 | *Truepera radiovictrix* DSM 17093 HIDH R93H, R123H polypeptide 2 | *Truepera radiovictrix* DSM 17093 | 297166230 | R93H, R123H |
| SEQ ID NO: 134 | *Uncinocarpus reesii* 1704 HIDH R97H, R127H polypeptide | *Uncinocarpus reesii* 1704 | 258577237 | R97H, R127H |
| SEQ ID NO: 135 | *Uncinocarpus reesii* 1704 HIDH R97H, R127H polypeptide 2 | *Uncinocarpus reesii* 1704 | 237903066 | R97H, R127H |
| SEQ ID NO: 136 | *Verticillium albo-atrum* VaMs.102 HIDH R96H, R124H polypeptide | *Verticillium albo-atrum* VaMs.102 | 302416209 | R96H, R124H |
| SEQ ID NO: 137 | *Verticillium albo-atrum* VaMs.102 HIDH R96H, R124H polypeptide 2 | *Verticillium albo-atrum* VaMs.102 | 261355352 | R96H, R124H |
| SEQ ID NO: 138 | *Verticillium dahliae* VdLs.17 HIDH R96H, R124H polypeptide | *Verticillium dahliae* VdLs.17 | 346973982 | R96H, R124H |

Example 11

Kinetic Characterization of ScHIDH R143 Mutants

Assays were performed with 40 ng/μL enzyme, 15 mM 2-oxoadipate, 100 μM NADH, 20 mM $MgCl_2$ and 100 mM HEPES, pH 7.3 in 10 or 20 μL volumes in 384-well black microplates. NADH concentration was monitored by the decrease in fluorescence (excitation wavelength: 340 nm; emission wavelength: 450 nm) on a fluorescent plate reader. The fluorescence intensities were converted to NADH concentrations based on NADH standards. Reactions with high amounts of NADH (>300 μM) were monitored by the UV absorbance of NADH at 340 nm in a 40 μL reaction volume in a clear 96-well plate on the same plate reader. Reactions with ScHIDH were carried out at 25° C. and reactions with TtHIDH were carried out at 45° C. Reported rates are initial rates from the first 10 minutes of reaction. For $K_M$ determination, concentrations of substrate at least 5×-higher than the $K_M$ were used (for NADH, 500 μM; for 2-oxoadipate, 15 mM) while the substrate of interest was varied in concentration. $K_M$ and $V_{max}$ were estimated by fitting data to equation (1) using nonlinear regression, where x is substrate concentration and y is the rate.

$$y = V_{max} \cdot x / K_M + x \quad (1)$$

Rate data for ScHIDH-R143C, -R143H, and -R143K are summarized in Table 3.

TABLE 3

Summary of kinetic parameters for ScHIDH Arg143 mutants

| Mutant | $K_M$ 2-oxoadipate (mM) | $K_M$ NADH (μM) | $K_M$ MgCl2 (mM) | $V_{max}$ (μmol min$^{-1}$ mg$^{-1}$)* | pH optimum | Enantiomeric Excess | $V_{max}$ 2-oxoglutarate (μmol min$^{-1}$ mg$^{-1}$) |
|---|---|---|---|---|---|---|---|
| R143C | 11 | 320 | | 0.065 | | >99.2 | |
| R143H | 2.0 | 88 | 1.2 | 0.036 | 7.4 | >99.1 | n.d. |
| R143K | 9.4 | 1100 | | 0.011 | | >92.0 | |

*Turnover, $k_{cat}(sec^{-1})$ is equal to 0.75 × $V_{max}$;
n.d.: not determined

Example 12 pH-Dependence of ScHIDH-R143H

ScHIDH-R143H activity was assayed in HEPES buffer at various pH under the standard reaction conditions described in Example 11, above. The rate is relative to the rate at pH 7.4. The pH optimum was estimated to be 7.4, similar to the wild type enzyme. The results are shown in FIG. 11. This pH is compatible with the cytosol of most organisms for use in bio-based chemical production.

Example 13

Magnesium Dependence of ScHIDH-R143H

ScHIDH-R143H activity was assayed at various $MgCl_2$ concentrations under the standard reaction conditions described in Example 11. The rate is relative to the rate at 20 mM $MgCl_2$. The $K_M$ for $MgCl_2$ was estimated to be 1.1 mM, similar to the wild type ScHIDH enzyme. The results are shown in FIG. 12.

Example 14

Alignment and Activity of ScHIDH-R115Q

The activity for purified ScHIDH-R115Q mutant was also determined. This mutant behaved essentially the same as wild type when assayed under standard reaction conditions, as described above (40 ng enzyme, 10 mM 2-oxoadipate, 100 μM NADH, 0.5 M HEPES, pH 7.4, 20 mM $MgCl_2$). The data for ScHIDH R115Q provide additional evidence regarding the mutants that were active and those that were not, which was not obvious based on alignments or even structural data. See FIG. 13. Notably, it was not clear whether R114 or R115 was functionally analogous to HsIDH1-R100 because both residues aligned very closely with HsIDH1-R100 in terms of both the primary sequence and the three-dimensional structure of the enzyme.

In contrast to ScHIDH-R143H, the ScHIDH-R115Q mutant did not oxidize NADH in the presence of 2-oxoadipate or NADH alone when assayed under standard reaction conditions (see FIGS. 14A and B). However, like wild-type ScHIDH, the R115Q mutant did oxidize NADH when $CO_2$ was provided as a substrate in the form of $NaHCO_3$ (see FIG. 14C). Taken together, these results show that the ScHIDH-R115Q mutant has similar reactivity as the wild type ScHIDH. Thus, even though it was unclear whether Arg114 or Arg115 was analogous to the cancer-associated Arg100 mutation that produces functional alterations in human IDH1, these data show that ScHIDH Arg114 is the functional analog of human IDH1 Arg100.

Example 15

Generation of an Expression System for Biosynthesis of Adipic Acid and Other Metabolites Plasmids were created for expressing a ScHIDH mutant and enzymes in the biosynthetic pathway in a microorganism. *Saccharomyces cerevisiae* was selected as a host organism. In contrast to most organisms, thermophilic bacteria and fungi, including *S. cerevisiae*, produce 2-oxoadipate as an intermediate in an alternate lysine biosynthesis pathway (see FIG. 15). Thus, yeast provides 2-oxoadipate as starting material for biosynthetic adipic acid synthesis via a metabolic pathway. Furthermore, *S. cerevisiae* is an established host for biomolecule synthesis, many mutant strains are available, and numerous genetic tools are available to manipulate this organism.

*S. cerevisiae* ura3-52 lys2-801amber ade2-101ochre trp1-Δ63 his3-Δ200 leu2-Δ1 (YPH499, described in pESC Yeast Epitope Tagging Vectors Clontech manual 217451-12) was used as the host strain genotype to facilitate 2-oxoadipate as a reactant for adipic acid biosynthesis. This strain has a deletion of the Lys2 (lys2-801amber) gene encoding alpha aminoadipate reductase (AAR) which normally functions in lysine biosynthesis. See Chattoo et al., Genetics 93(1): 51-65 (1979). AAR (EC 1.2.1.31) catalyzes the reduction of 2-aminoadipate (species 3 in FIG. 15) at C6 to the semialdehyde (species 4 in FIG. 15). In this system, Lys2 deficiency leads to buildup of 2-aminoadipate. Alpha aminoadipate aminotransferase (AAT, EC 2.6.1.39) catalyzes the conversion of 2-oxoadipate (species 2 in FIG. 15) to 2-aminoadipate proximal to Lys2/AAR in the fungal lysine biosynthesis pathway. AAT is feedback inhibited by 2-aminoadipate, leading to 2-oxoadipate accumulation which can be driven into an exogenous adipic acid pathway.

Six genes encoding four enzymes in an exogenous, ScHIDH-mutant-initiated, adipic acid biosynthesis pathway in yeast were cloned and expressed. The pathway is shown in FIG. 16. Mutant ScHIDH initiates adipic acid biosynthesis by specifically acting on 2-oxoadipate to divert it into an exogenous adipic acid biosynthetic pathway. The remaining exogenous biosynthetic pathway is carried out by glutaconate CoA-transferase; hydroxyglutaryl-CoA dehydratase; and a non-decarboxylating glutaryl-coenzyme A dehydrogenase. All genes were synthesized with codon-optimization for yeast expression using de novo gene synthesis. The original genes, codon-optimized sequences, and polypeptides are listed in Table 4. Note that the ScHIDH mutant (LYS12 mutant) is not codon-optimized because the gene is from *S. cerevisiae*.

The ScHIDH-R143c mutant was selected and generated because in vitro data showed the R143C mutant to have the highest maximal turnover of any ScHIDH mutant assayed. The mitochondrial localization sequence consisting of ScHIDH residues 2-21 was deleted to target ScHIDH-R143C to the cytosol. This localization was chosen because the remaining exogenous adipic acid biosynthesis enzymes are also produced in the cytosol, and because 2-oxoadipate substrate is shuttled into the cytosol for the next step in its normal biosynthesis into lysine.

The gctA and gctB genes from *A. fermentans* encoding glutaconate CoA-transferase were generated to catalyze the second and fourth steps in the biocatalytic route to adipic acid following diversion from the general metabolism by ScHIDH mutant. The second step was activation of (R)-2-hyroxyadipate (species 2 in FIG. 16) with a CoA thioester to generate (R)-2-hydroxyadipoyl-CoA (species 3 in FIG. 16) for the second step of exogenous adipate biosynthesis pathway (FIG. 16). The fourth step was liberation of the CoA thioester from (E)-2-hexenedioyl-CoA (species 4 in FIG. 16) to generate (E)-2-hexenedioate (species 5 in FIG. 16), recycling the CoA thioester. Alternatively, the double bond could be reduced before liberation of the thioester, in which case glutaconate CoA-transferase would liberate the CoA thioester from adipoyl-CoA (species 7 in FIG. 16) to form adipic acid (species 6 in FIG. 16). hgdA and hgdB genes from C. symbiosum and hgdC from *A. fermentans* encoding 2-hydroxyglutaryl-CoA dehydratase subunits (hgdA and hgdB) and co-activator (hgdC) were generated to oxidize the 2-hydroxyl group of (R)-2-hydroxyadipoyl-CoA (species 3 in FIG. 16) to a double bond in (E)-2-hexenedioyl-CoA (species 4 in FIG. 16). Activity of enzymes encoded by gctA, gctB, hgdA, hgdB, hgdC towards 6-carbon substrates was confirmed previously. See Parthasarathy et al., *Biochemistry* 50(17): 3540-3550 (2011).

TABLE 4

Polynucleotide and Polypeptide Sequences for Enzymes in an Adipate Biosynthetic Pathway

| SEQ ID NO | Construct Name | WT Organism | NCBI/Genbank No. |
|---|---|---|---|
| SEQ ID NO: 154 | Lys12 homoisocitrate dehydrogenase polynucleotide | S. cerevisiae | NM_001179442.1 |
| SEQ ID NO: 155 | Lys12 isocitrate dehydrogenase polypeptide | S. cerevisiae | NP_012172.1 |
| SEQ ID NO: 156 | gctA, glutaconate CoA-transferase subunit A polynucleotide | Acidaminococcus fermentans | X81440.1 |
| SEQ ID NO: 157 | Codon optimized gctA polynucleotide* | Artificial | — |
| SEQ ID NO: 158 | gctA, glutaconate CoA-transferase subunit A polypeptide | A. fermentans | YP_003399488.1 |
| SEQ ID NO: 159 | gctB, glutaconate CoA-transferase subunit B polynucleotide | A. fermentans | X81440.1 |
| SEQ ID NO: 160 | Codon optimized gctB polynucleotide | Artificial | — |
| SEQ ID NO: 161 | gctB, glutaconate CoA-transferase subunit B polypeptide | A. fermentans | YP_003399487.1 |
| SEQ ID NO: 162 | hgdA, (R)-2-hydroxyglutaryl-CoA dehydratase subunit A polynucleotide | Clostridium symbiosum | AF123384.1 |
| SEQ ID NO: 163 | Codon optimized hgdA, subunit A polynucleotide | Artificial | — |
| SEQ ID NO: 164 | hgdA, (R)-2-hydroxyglutaryl-CoA dehydratase subunit A polypeptide | C. symbiosum | ZP_08091114.1 |
| SEQ ID NO: 165 | hgdB, (R)-2-hydroxyglutaryl-CoA dehydratase subunit B polynucleotide | C. symbiosum | AF123384.1 |
| SEQ ID NO: 166 | Codon optimized hgdB polynucleotide | Artificial | — |
| SEQ ID NO: 167 | hgdB, (R)-2-hydroxyglutaryl-CoA dehydratase subunit B polypeptide | C. symbiosum | ZP_06344556.1 |
| SEQ ID NO: 168 | hgdC, (R)-2-hydroxyglutaryl-CoA dehydratase subunit C polynucleotide | A. fermentans | X59645.1 |
| SEQ ID NO: 169 | Codon optimized hgdC polynucleotide | Artificial | — |
| SEQ ID NO: 170 | hgdC, (R)-2-hydroxyglutaryl-CoA dehydratase subunit C polypeptide | A. fermentans | YP_003399485.1 |
| SEQ ID NO: 171 | gdh, glutaryl-CoA dehydrogenase polynucleotide | Desulfococcus multivorans | FJ688103.1 |

TABLE 4-continued

Polynucleotide and Polypeptide Sequences for Enzymes in an Adipate Biosynthetic Pathway

| SEQ ID NO | Construct Name | WT Organism | NCBI/Genbank No. |
| --- | --- | --- | --- |
| SEQ ID NO: 172 | Codon optimized gdh polynucleotide | Artificial | — |
| SEQ ID NO: 173 | gdh, glutaryl-CoA dehydrogenase polypeptide | D. multivorans | ACP50614.1 |

*Codon optimized polynucleotides are optimized for expression in S. cerevisiae; however, the polynucleotides can be optimized for expression in various other host organisms including Escherichia coli, Pichia pastoris, Geotrichum candidum, Candida albicans, Rhodotorula rubra, or Rhodosporidium sp., inter alia.

The pESC-leu2d-gctA/gctB/lys12* vector is shown in FIG. 17. This plasmid was constructed from pESC-leu2d to provide high plasmid copy number under control of leucine selection for yeast expression of epitope-tagged inserted genes. See Ro et al., BMC biotechnol. 8(83) 1-14 (2008). 5' BamHI and 3' SalI sites were added to gctA to clone this gene into MCS2 in frame with a C-terminal MYC tag to generate pESC-leu2d-gctA as a construction intermediate. 5' SpeI and 3' SacI sites were added to gctB and this gene was cloned into MCS1 of pESC-leu2d-gctA in frame with a C-terminal Flag tag, generating pESC-leu2d-gctA/gctB. 5' BamHIH and 3' SalI sites were added to lys12, with the mitochondrial localization signal removed and R143C mutation introduced as described above, to clone this gene into pESC-His MCS2 in frame with a C-terminal MYC tag to generate pESC-His-lys12* as a construction intermediate. Then, a PGAL1-lys12*-tCYC1 fragment with 5' HpaI and 3' KasI sites was liberated from pESC-His-lys12* and cloned into HpaI and KasI sites in the backbone of pESC-Leu2d-gctB/gctA to generate pESC-leu2d-gctA/gctB/lys12*.

The pESC-His-hgdA/hgdB/hgdC plasmid is shown in FIG. 18. This plasmid was constructed from pESC-His (described in pESC Yeast Epitope Tagging Vectors Clontech manual 217451-12), which can be selected by removing histidine from growth media, for yeast expression of epitope-tagged inserted genes. 5' BamHI and 3' SalI sites were added to hgdC to clone this gene into MCS2 in frame with a C-terminal MYC tag to generate pESC-His-hgdC as a construction intermediate. 5' EcoRI and 3' NotI sites were added to hgdA and this gene was cloned into MCS1 of pESC-His-hgdC in frame with a C-terminal Flag tag, generating pESC-leu2d-hgdA/hgdC. Restriction sites 5' BamHI and 3' SalI sites were added to hgdB to clone this gene into pESC-leu2d MCS2 in frame with a C-terminal MYC tag to generate pESC-leu2d-hgdB as a construction intermediate. Then, a PGAL1-hgdB-tCYC1 fragment with 5' HpaI and 3' KasI sites was liberated from pESC-leu2d-hgdB* and cloned into HpaI and KasI sites in the backbone of pESC-His-hgdA/hgdC to generate pESC-His-hgdA/hgdB/hgdC.

The ScHIDH biosynthetic pathway for adipic acid combines expression of the genes from pESC-leu2d-gctA/gctB/lys12* and pESC-His-hgdA/hgdB/hgdC with an enzyme system to saturate the double bond on (E)-2-hexenedioate or (E)-2-hexenedioyl-CoA. One approach is to express the yeast-optimized coding sequence for non-decarboxylating glutaryl-CoA dehydrogenase encoded by the gdh gene from Desulfococcus multivorans (otherwise known as acd gene, NCBI: FJ688103.1) to saturate (E)-2-hexenedioyl-CoA (species 4 in FIG. 16) to adipoyl-CoA (species 7 in FIG. 16). See Wischgoll et al., J. Bacteriol. 191(13): 4401-4409 (2009); Wischgoll et al., Biochemistry 49(25): 5350-5357 (2010); Parthasarathy et al., Biochemistry 50(17): 3540-3550 (2011). The pESC-Trp-gdh is presented in FIG. 19. pESC-Trp-gdh is generated by cloning gcd with 5' BamHI and 3' SalI sites into MCS2 in frame with a C-terminal MYC tag.

This pathway or segments of this pathway are used to generate intermediates in the adipic acid biosynthesis pathway, including (R)-2-hydroxyadipoyl-CoA (species 3 in FIG. 16) or (E)-2-hexenedioate (species 5 in FIG. 16), by adjusting the combination of downstream enzymes included in the expression system (see FIG. 15). pESC-leu2d-gctA/gctB/lys12* can be used to generate (R)-2-hydroxyadipoyl-CoA. pESC-leu2d-gctA/gctB/lys12* and pESC-His-hgdA/hgdB/hgdC can be used to generate (E)-2-hexenedioate. The utility of biocatalytic production of (E)-2-hexenedioate is that it provides a biosynthetic route for a non-commercially available fine chemical that could be catalytically reduced to adipic acid, potentially at a cost savings compared to non-biological catalytic adipic acid synthesis methods.

(E)-2-hexenedioate was synthesized as described by Tanaka. See Tanaka et al., Intl. J. Systematic Evol. Microbiol. 50: 639-644 (2000). Adipic acid was obtained for use as standards for analytical methods to assess production of (E)-2-hexenedioate and adipic acid by the biosynthetic pathway using LC-MS, LC-UV, or other analytical methods.

The biosynthetic pathway is optimized by quantifying adipic acid, (E)-2-hexenedioic acid, or other intermediates produced. LC-MS or other available analytical methods are used. Tanaka et al., Intl. J. Systematic Evol. Microbiol. 50: 639-644 (2000). Optimization includes varying the host strain to other yeasts, including Sacchromyces cerevisia, Pichia pastoris, Geotrichum candidum, Candida albicans, Rhodotorula rubra, or Rhodosporidium sp. Optimization may also include varying the host strain to non-fungal hosts including bacteria, algae, and other organisms such as Escherichia coli, Bacillus subtilis, Streptomyces fradiae, Paracoccus haeundaensis, and Dictyostelium discoideum, Optimization may include altering the growth temperature at different points during organism growth, altering media composition, altering feedstock composition, altering concentrations of lysine, etc., for of the growing conditions. Optimization may include using different combinations of genes on different plasmids, using different expression plasmids, changing the location (N- or C-terminal) and type of epitope tags on genes, and removing epitope tags from genes. Optimization may include using different species of origin for gctA, gctB, hgdA, hgdB, hgdC, and lys12 and other genes. Optimization may include creating organisms with stable insertion of the expression cassettes into the organism genome for stable expression (as opposed to transient plasmid expression). The biosynthetic pathway is scaled-up by iteratively using larger growing containers (ranging from 1 mL to multi-liter-scale to kiloliter-scale to process-scale vessels (e.g., >1000 L).

What is claimed is:

1. A polynucleotide comprising a nucleotide sequence encoding a polypeptide comprising a functional (R)-2-hydroxyacid dehydrogenase useful for catalyzing the enantioselective conversion of a 1-carboxy-2-ketoacid to a 1-carboxy-(R)-2-hydroxyacid, or the reverse reaction,
   wherein the encoded polypeptide is at least 90% identical to the amino acid sequence of SEQ ID NO: 2, with the proviso that the encoded polypeptide comprises arginine 143 substituted with histidine or cysteine; and
   wherein the R143H or R143C substitution disrupts oxidative decarboxylation activity but does not disrupt oxidoreductase activity.

2. The polynucleotide of claim 1, wherein the encoded polypeptide comprises the amino acid sequence of any one of SEQ ID NOs: 10, 12, 18, or 93.

3. A vector comprising the polynucleotide of claim 2.

4. A cultured cell comprising the vector of claim 3.

5. The polynucleotide of claim 1, wherein the encoded polypeptide comprises the amino acid sequence of any one of SEQ ID NOs: 10, 12, 18, or 93 with no more than 16 amino acid substitutions.

6. A vector comprising the polynucleotide of claim 5.

7. A cultured cell comprising the vector of claim 6.

8. A vector comprising the polynucleotide of claim 1.

9. A cultured cell comprising the vector of claim 8.

10. The polynucleotide of claim 1, wherein the encoded polypeptide is at least 98% identical to the amino acid sequence of any one of SEQ ID NOs: 10, 12, 18, or 93.

11. The polynucleotide of claim 1, wherein the encoded polypeptide further comprises one or more amino acid substitutions selected from the group consisting of V111D, R114Q, R115Q, R124H, and Y150D.

12. The polynucleotide of claim 1, wherein the encoded polypeptide comprises the amino acid sequence of SEQ ID NO:12.

13. The polynucleotide of claim 1, wherein the nucleotide sequence comprises any one of SEQ ID NOs: 9, 11, or 17, or a degenerate or codon-optimized variant thereof.

14. A composition useful for catalyzing the conversion of a 1-carboxy-2-ketoacid to a 1-carboxy-(R)-2-hydroxyacid, or the reverse reaction, comprising:
   (a) a polynucleotide comprising a nucleotide sequence encoding a polypeptide comprising a functional (R)-2-hydroxyacid dehydrogenase;
   (b) a polynucleotide comprising a nucleotide sequence, capable of hybridizing to the complement of (a) under hybridization conditions comprising 7% sodium dodecyl sulfate, 0.5 M $Na_2HPO_4$, 1 mM EDTA at 60° C. with washing in 1×SSC, 0.1% SDS at 60° C., encoding a polypeptide comprising a functional (R)-2-hydroxyacid dehydrogenase;
   (c) a vector comprising (a) or (b); or
   (d) an organism transformed with (c); and
   wherein the encoded (R)-2-hydroxyacid dehydrogenase polypeptide is at least 90% identical to the amino acid sequence of SEQ ID NO: 2, with the proviso that the (R)-2-hydroxyacid dehydrogenase polypeptide comprises arginine 143 substituted with histidine or cysteine;
   wherein the R143H or R143C substitution disrupts oxidative decarboxylation activity but does not disrupt oxidoreductase activity; and
   wherein the (R)-2-hydroxyacid dehydrogenase catalyzes the conversion of 1-carboxy-2-ketoacid to a 1-carboxy-(R)-2-hydroxyacid, in the presence of NADH.

15. The composition of claim 14, wherein the 1-carboxy-2-ketoacid is 2-oxoadipate or 2-oxoglutarate and the 1-carboxy-(R)-2-hydroxyacid is adipate, (E)-2-hexenedioate, or glutarate.

16. The composition of claim 14, wherein the encoded (R)-2-hydroxyacid dehydrogenase polypeptide further comprises one or more amino acid substitutions selected from the group consisting of V111D, R114Q, R115Q, R124H, and Y150D.

17. The composition of claim 14, wherein the encoded (R)-2-hydroxyacid dehydrogenase polypeptide comprises the amino acid sequence of any one of SEQ ID NOs: 10, 12, 18, or 93.

18. The composition of claim 14, wherein the encoded (R)-2-hydroxyacid dehydrogenase polypeptide comprises the amino acid sequence of SEQ ID NO:12.

19. The composition of claim 14, wherein the polynucleotide comprises the nucleotide sequence of any one of SEQ ID NOs: 9, 11, or 17, or a degenerate or codon-optimized variant thereof.

20. The composition of claim 14, wherein the organism is *Escherichia coli, Sacchromyces cerevisiae, Pichia pastoris, Geotrichum candidum, Candida albicans, Rhodotorula rubra,* or *Rhodosporidium* sp.

* * * * *

SEQUENCE LISTING

<160> NUMBER OF SEQ ID NOS: 173

<210> SEQ ID NO 1
<211> LENGTH: 1113
<212> TYPE: DNA
<213> ORGANISM: Saccharomyces cerevisiae

<400> SEQUENCE: 1

```
atgtttagat ctgttgctac tagattatct gcctgccgtg ggttagcatc taacgctgct      60
cgcaaatcac tcactattgg tcttatcccc ggtgacggta tcggtaagga agtcattcct     120
gctggtaagc aagttttgga aaaccttaac tccaagcacg gcctaagctt caactttatt     180
gatctctacg ccggtttcca aacattccaa gaaacaggaa aggcgttgcc tgatgagact     240
gttaaagtgt tgaaggaaca atgtcaaggt gctcttttcg gtgcagttca gtctccaact     300
actaaggtgg aaggttactc ctcaccaatt gttgctctaa ggagggaaat gggcctttc     360
gctaatgttc gtcctgttaa gtctgtagag ggagaaaagg gtaaaccaat tgacatggtt     420
atcgtcagag aaaatactga ggacctgtac attaaaattg aaaaaacata cattgacaag     480
gccacaggta caagagttgc tgatgccaca agagaatat  ccgaaattgc aacaagaaga     540
attgcaacca ttgcattaga tattgccttg aaaagattac aaacaagagg ccaagccact     600
ttgacagtga ctcataaatc aaatgttcta tctcaaagtg atggtctatt cagagaaatc     660
tgtaaggaag tctacgaatc taacaaggac aagtacggtc aaatcaaata taacgaacaa     720
attgtggatt ccatggttta taggctgttc agagaaccac aatgttttga tgtgatagtg     780
gcaccaaacc tatacgggga tatattatct gacggtgctg ctgctttagt cggttcatta     840
ggtgttgttc aagcgccaa cgtaggtcca gaaattgtca ttggtgaacc atgccatggt     900
tctgcaccag atattgctgg taaaggtatt gctaacccaa tcgccactat aagatctact     960
gctttgatgt tggaattctt gggccacaac gaagctgccc aagatatcta caaggctgtt    1020
gatgctaact aagagagggg ttctatcaag acaccagatt taggtggtaa ggcttctact    1080
caacaagtcg ttgacgacgt tttgtcgaga tta                                 1113
```

<210> SEQ ID NO 2
<211> LENGTH: 371
<212> TYPE: PRT
<213> ORGANISM: Saccharomyces cerevisiae

<400> SEQUENCE: 2

```
Met Phe Arg Ser Val Ala Thr Arg Leu Ser Ala Cys Arg Gly Leu Ala
1               5                   10                  15

Ser Asn Ala Ala Arg Lys Ser Leu Thr Ile Gly Leu Ile Pro Gly Asp
            20                  25                  30

Gly Ile Gly Lys Glu Val Ile Pro Ala Gly Lys Gln Val Leu Glu Asn
        35                  40                  45

Leu Asn Ser Lys His Gly Leu Ser Phe Asn Phe Ile Asp Leu Tyr Ala
    50                  55                  60

Gly Phe Gln Thr Phe Gln Glu Thr Gly Lys Ala Leu Pro Asp Glu Thr
65                  70                  75                  80

Val Lys Val Leu Lys Glu Gln Cys Gln Gly Ala Leu Phe Gly Ala Val
                85                  90                  95

Gln Ser Pro Thr Thr Lys Val Glu Gly Tyr Ser Ser Pro Ile Val Ala
            100                 105                 110

Leu Arg Arg Glu Met Gly Leu Phe Ala Asn Val Arg Pro Val Lys Ser
```

```
                   115                 120                 125
Val Glu Gly Glu Lys Gly Lys Pro Ile Asp Met Val Ile Val Arg Glu
    130                 135                 140

Asn Thr Glu Asp Leu Tyr Ile Lys Ile Glu Lys Thr Tyr Ile Asp Lys
145                 150                 155                 160

Ala Thr Gly Thr Arg Val Ala Asp Ala Thr Lys Arg Ile Ser Glu Ile
                165                 170                 175

Ala Thr Arg Arg Ile Ala Thr Ile Ala Leu Asp Ile Ala Leu Lys Arg
            180                 185                 190

Leu Gln Thr Arg Gly Gln Ala Thr Leu Thr Val Thr His Lys Ser Asn
        195                 200                 205

Val Leu Ser Gln Ser Asp Gly Leu Phe Arg Glu Ile Cys Lys Glu Val
    210                 215                 220

Tyr Glu Ser Asn Lys Asp Lys Tyr Gly Gln Ile Lys Tyr Asn Glu Gln
225                 230                 235                 240

Ile Val Asp Ser Met Val Tyr Arg Leu Phe Arg Glu Pro Gln Cys Phe
                245                 250                 255

Asp Val Ile Val Ala Pro Asn Leu Tyr Gly Asp Ile Leu Ser Asp Gly
            260                 265                 270

Ala Ala Ala Leu Val Gly Ser Leu Gly Val Val Pro Ser Ala Asn Val
        275                 280                 285

Gly Pro Glu Ile Val Ile Gly Glu Pro Cys His Gly Ser Ala Pro Asp
    290                 295                 300

Ile Ala Gly Lys Gly Ile Ala Asn Pro Ile Ala Thr Ile Arg Ser Thr
305                 310                 315                 320

Ala Leu Met Leu Glu Phe Leu Gly His Asn Glu Ala Ala Gln Asp Ile
                325                 330                 335

Tyr Lys Ala Val Asp Ala Asn Leu Arg Glu Gly Ser Ile Lys Thr Pro
            340                 345                 350

Asp Leu Gly Gly Lys Ala Ser Thr Gln Gln Val Val Asp Asp Val Leu
        355                 360                 365

Ser Arg Leu
    370

<210> SEQ ID NO 3
<211> LENGTH: 1113
<212> TYPE: DNA
<213> ORGANISM: Artificial Sequence
<220> FEATURE:
<223> OTHER INFORMATION: ScHIDH V111D polynucleotide

<400> SEQUENCE: 3
atgtttagat ctgttgctac tagattatct gcctgccgtg ggttagcatc taacgctgct      60
cgcaaatcac tcactattgg tcttatcccc ggtgacggta tcggtaagga agtcattcct     120
gctggtaagc aagttttgga aaaccttaac tccaagcacg gcctaagctt caactttatt     180
gatctctacg ccggtttcca acattccaa gaaacaggaa aggcgttgcc tgatgagact     240
gttaaagtgt tgaaggaaca atgtcaaggt gctctttttcg gtgcagttca gtctccaact     300
actaaggtgg aaggttactc ctcaccaatt gatgctctaa ggagggaaat gggcctttc     360 gctaatgttc gtcctgttaa gtctgtagag ggagaaaagg gtaaaccaat tgacatggtt     420
atcgtcagag aaaatactga ggacctgtac attaaaattg aaaaaacata cattgacaag     480
gccacaggta caagagttgc tgatgccaca aagagaaatat ccgaaattgc aacaagaaga     540
attgcaacca ttgcattaga tattgccttg aaaagattac aaacaagagg ccaagccact     600
```

```
ttgacagtga ctcataaatc aaatgttcta tctcaaagtg atggtctatt cagagaaatc    660
tgtaaggaag tctacgaatc taacaaggac aagtacggtc aaatcaaata taacgaacaa    720
attgtggatt ccatggttta taggctgttc agagaaccac aatgttttga tgtgatagtg    780
gcaccaaacc tatacgggga tatattatct gacggtgctg ctgctttagt cggttcatta    840
ggtgttgttc caagcgccaa cgtaggtcca gaaattgtca ttggtgaacc atgccatggt    900
tctgcaccag atattgctgg taaggtatt gctaacccaa tcgccactat aagatctact     960
gctttgatgt ggaattcttt gggccacaac gaagctgccc aagatatcta caaggctgtt   1020
gatgctaact aagagaggg ttctatcaag acaccagatt taggtggtaa ggcttctact    1080
caacaagtcg ttgacgacgt tttgtcgaga tta                                1113
```

<210> SEQ ID NO 4
<211> LENGTH: 371
<212> TYPE: PRT
<213> ORGANISM: Artificial Sequence
<220> FEATURE:
<223> OTHER INFORMATION: ScHIDH V111D polypeptide

<400> SEQUENCE: 4

```
Met Phe Arg Ser Val Ala Thr Arg Leu Ser Ala Cys Arg Gly Leu Ala
1               5                   10                  15

Ser Asn Ala Ala Arg Lys Ser Leu Thr Ile Gly Leu Ile Pro Gly Asp
            20                  25                  30

Gly Ile Gly Lys Glu Val Ile Pro Ala Gly Lys Gln Val Leu Glu Asn
        35                  40                  45

Leu Asn Ser Lys His Gly Leu Ser Phe Asn Phe Ile Asp Leu Tyr Ala
    50                  55                  60

Gly Phe Gln Thr Phe Gln Glu Thr Gly Lys Ala Leu Pro Asp Glu Thr
65                  70                  75                  80

Val Lys Val Leu Lys Glu Gln Cys Gln Gly Ala Leu Phe Gly Ala Val
                85                  90                  95

Gln Ser Pro Thr Thr Lys Val Glu Gly Tyr Ser Ser Pro Ile Asp Ala
            100                 105                 110

Leu Arg Arg Glu Met Gly Leu Phe Ala Asn Val Arg Pro Val Lys Ser
        115                 120                 125

Val Glu Gly Glu Lys Gly Lys Pro Ile Asp Met Val Ile Val Arg Glu
    130                 135                 140

Asn Thr Glu Asp Leu Tyr Ile Lys Ile Glu Lys Thr Tyr Ile Asp Lys
145                 150                 155                 160

Ala Thr Gly Thr Arg Val Ala Asp Ala Thr Lys Arg Ile Ser Glu Ile
                165                 170                 175

Ala Thr Arg Arg Ile Ala Thr Ile Ala Leu Asp Ile Ala Leu Lys Arg
            180                 185                 190

Leu Gln Thr Arg Gly Gln Ala Thr Leu Thr Val Thr His Lys Ser Asn
        195                 200                 205

Val Leu Ser Gln Ser Asp Gly Leu Phe Arg Glu Ile Cys Lys Glu Val
    210                 215                 220

Tyr Glu Ser Asn Lys Asp Lys Tyr Gly Gln Ile Lys Tyr Asn Glu Gln
225                 230                 235                 240

Ile Val Asp Ser Met Val Tyr Arg Leu Phe Arg Glu Pro Gln Cys Phe
                245                 250                 255

Asp Val Ile Val Ala Pro Asn Leu Tyr Gly Asp Ile Leu Ser Asp Gly
            260                 265                 270

Ala Ala Ala Leu Val Gly Ser Leu Gly Val Val Pro Ser Ala Asn Val
```

```
                275                 280                 285
Gly Pro Glu Ile Val Ile Gly Glu Pro Cys His Gly Ser Ala Pro Asp
        290                 295                 300
Ile Ala Gly Lys Gly Ile Ala Asn Pro Ile Ala Thr Ile Arg Ser Thr
305                 310                 315                 320
Ala Leu Met Leu Glu Phe Leu Gly His Asn Glu Ala Ala Gln Asp Ile
                325                 330                 335
Tyr Lys Ala Val Asp Ala Asn Leu Arg Glu Gly Ser Ile Lys Thr Pro
            340                 345                 350
Asp Leu Gly Gly Lys Ala Ser Thr Gln Gln Val Val Asp Asp Val Leu
        355                 360                 365
Ser Arg Leu
    370

<210> SEQ ID NO 5
<211> LENGTH: 1113
<212> TYPE: DNA
<213> ORGANISM: Artificial Sequence
<220> FEATURE:
<223> OTHER INFORMATION: ScHIDH R114Q polynucleotide

<400> SEQUENCE: 5
atgtttagat ctgttgctac tagattatct gcctgccgtg ggttagcatc taacgctgct      60
cgcaaatcac tcactattgg tcttatcccc ggtgacggta tcggtaagga agtcattcct     120
gctggtaagc aagttttgga aaaccttaac tccaagcacg gcctaagctt caactttatt     180
gatctctacg ccggtttcca acattccaa gaaacaggaa aggcgttgcc tgatgagact      240
gttaaagtgt tgaaggaaca atgtcaaggt gctcttttcg gtgcagttca gtctccaact     300
actaaggtgg aaggttactc ctcaccaatt gttgctctac agagggaaat gggccttttc     360
gctaatgttc gtcctgttaa gtctgtagag ggagaaaagg gtaaaccaat gacacatggt     420
atcgtcagag aaaatactga ggacctgtac attaaaattg aaaaaacata cattgacaag     480
gccacaggta caagagttgc tgatgccaca aagagaatat ccgaaattgc aacaagaaga     540
attgcaacca ttgcattaga tattgccttg aaaagattac aaacaagagg ccaagccact     600
ttgacagtga ctcataaatc aaatgttcta tctcaaagtg atggtctatt cagagaaatc     660
tgtaaggaag tctacgaatc taacaaggac aagtacggtc aaatcaaata taacgaacaa     720
attgtggatt ccatggttta taggctgttc agagaaccac aatgttttga tgtgatagtg     780
gcaccaaacc tatacgggga tatattatct gacggtgctg ctgctttagt cggttcatta     840
ggtgttgttc aagcgccaa cgtaggtcca gaaattgtca ttggtgaacc atgccatggt     900
tctgcaccag atattgctgg taaaggtatt gctaacccaa tcgccactat aagatctact     960
gctttgatgt tggaattctt gggccacaac gaagctgccc aagatatcta caaggctgtt    1020
gatgctaact aagagagggg ttctatcaag acaccagatt taggtggtaa ggcttctact    1080
caacaagtcg ttgacgacgt tttgtcgaga tta                                 1113

<210> SEQ ID NO 6
<211> LENGTH: 371
<212> TYPE: PRT
<213> ORGANISM: Artificial Sequence
<220> FEATURE:
<223> OTHER INFORMATION: ScHIDH R114Q polypeptide

<400> SEQUENCE: 6

Met Phe Arg Ser Val Ala Thr Arg Leu Ser Ala Cys Arg Gly Leu Ala
1               5                   10                  15
```

Ser Asn Ala Ala Arg Lys Ser Leu Thr Ile Gly Leu Ile Pro Gly Asp
            20                  25                  30

Gly Ile Gly Lys Glu Val Ile Pro Ala Gly Lys Gln Val Leu Glu Asn
        35                  40                  45

Leu Asn Ser Lys His Gly Leu Ser Phe Asn Phe Ile Asp Leu Tyr Ala
 50                  55                  60

Gly Phe Gln Thr Phe Gln Glu Thr Gly Lys Ala Leu Pro Asp Glu Thr
 65                  70                  75                  80

Val Lys Val Leu Lys Glu Gln Cys Gln Gly Ala Leu Phe Gly Ala Val
                85                  90                  95

Gln Ser Pro Thr Thr Lys Val Glu Gly Tyr Ser Ser Pro Ile Val Ala
            100                 105                 110

Leu Gln Arg Glu Met Gly Leu Phe Ala Asn Val Arg Pro Val Lys Ser
            115                 120                 125

Val Glu Gly Glu Lys Gly Lys Pro Ile Asp Met Val Ile Val Arg Glu
        130                 135                 140

Asn Thr Glu Asp Leu Tyr Ile Lys Ile Glu Lys Thr Tyr Ile Asp Lys
145                 150                 155                 160

Ala Thr Gly Thr Arg Val Ala Asp Ala Thr Lys Arg Ile Ser Glu Ile
                165                 170                 175

Ala Thr Arg Arg Ile Ala Thr Ile Ala Leu Asp Ile Ala Leu Lys Arg
            180                 185                 190

Leu Gln Thr Arg Gly Gln Ala Thr Leu Thr Val Thr His Lys Ser Asn
        195                 200                 205

Val Leu Ser Gln Ser Asp Gly Leu Phe Arg Glu Ile Cys Lys Glu Val
210                 215                 220

Tyr Glu Ser Asn Lys Asp Lys Tyr Gly Gln Ile Lys Tyr Asn Glu Gln
225                 230                 235                 240

Ile Val Asp Ser Met Val Tyr Arg Leu Phe Arg Glu Pro Gln Cys Phe
                245                 250                 255

Asp Val Ile Val Ala Pro Asn Leu Tyr Gly Asp Ile Leu Ser Asp Gly
            260                 265                 270

Ala Ala Ala Leu Val Gly Ser Leu Gly Val Val Pro Ser Ala Asn Val
        275                 280                 285

Gly Pro Glu Ile Val Ile Gly Glu Pro Cys His Gly Ser Ala Pro Asp
290                 295                 300

Ile Ala Gly Lys Gly Ile Ala Asn Pro Ile Ala Thr Ile Arg Ser Thr
305                 310                 315                 320

Ala Leu Met Leu Glu Phe Leu Gly His Asn Glu Ala Ala Gln Asp Ile
                325                 330                 335

Tyr Lys Ala Val Asp Ala Asn Leu Arg Glu Gly Ser Ile Lys Thr Pro
            340                 345                 350

Asp Leu Gly Gly Lys Ala Ser Thr Gln Gln Val Asp Asp Val Leu
        355                 360                 365

Ser Arg Leu
    370

<210> SEQ ID NO 7
<211> LENGTH: 1113
<212> TYPE: DNA
<213> ORGANISM: Artificial Sequence
<220> FEATURE:
<223> OTHER INFORMATION: ScHIDH R115Q polynucleotide

<400> SEQUENCE: 7

```
atgtttagat ctgttgctac tagattatct gcctgccgtg ggttagcatc taacgctgct    60
cgcaaatcac tcactattgg tcttatcccc ggtgacggta tcggtaagga agtcattcct   120
gctggtaagc aagttttgga aaaccttaac tccaagcacg gcctaagctt caactttatt   180
gatctctacg ccggttttcca aacattccaa gaaacaggaa aggcgttgcc tgatgagact   240
gttaaagtgt tgaaggaaca aatgtcaaggt gctcttttcg gtgcagttca gtctccaact   300
actaaggtgg aaggttactc ctcaccaatt gttgctctaa ggcaggaaat gggccttttc   360
gctaatgttc gtcctgttaa gtctgtagag ggagaaaagg gtaaaccaat tgacatggtt   420
atcgtcagag aaaatactga ggacctgtac attaaaattg aaaaaacata cattgacaag   480
gccacaggta caagagttgc tgatgccaca agagaatat ccgaaattgc aacaagaaga   540
attgcaacca ttgcattaga tattgccttg aaaagattac aaacaagagg ccaagccact   600
ttgacagtga ctcataaatc aaatgttcta tctcaaagtg atggtctatt cagagaaatc   660
tgtaaggaag tctacgaatc taacaaggac aagtacggtc aaatcaaata taacgaacaa   720
attgtggatt ccatggttta taggctgttc agagaaccac aatgttttga tgtgatagtg   780
gcaccaaacc tatacgggga tatattatct gacggtgctg ctgctttagt cggttcatta   840
ggtgttgttc caagcgccaa cgtaggtcca gaaattgtca ttggtgaacc atgccatggt   900
tctgcaccag atattgctgg taaaggtatt gctaacccaa tcgccactat aagatctact   960
gctttgatgt tggaattctt gggccacaac gaagctgccc aagatatcta caaggctgtt  1020
gatgctaact aagagaggg ttctatcaag acaccagatt taggtggtaa ggcttctact  1080
caacaagtcg ttgacgacgt tttgtcgaga tta                                1113
```

<210> SEQ ID NO 8
<211> LENGTH: 371
<212> TYPE: PRT
<213> ORGANISM: Artificial Sequence
<220> FEATURE:
<223> OTHER INFORMATION: ScHIDH R115Q polypeptide

<400> SEQUENCE: 8

```
Met Phe Arg Ser Val Ala Thr Arg Leu Ser Ala Cys Arg Gly Leu Ala
1               5                   10                  15

Ser Asn Ala Ala Arg Lys Ser Leu Thr Ile Gly Leu Ile Pro Gly Asp
            20                  25                  30

Gly Ile Gly Lys Glu Val Ile Pro Ala Gly Lys Gln Val Leu Glu Asn
        35                  40                  45

Leu Asn Ser Lys His Gly Leu Ser Phe Asn Phe Ile Asp Leu Tyr Ala
    50                  55                  60

Gly Phe Gln Thr Phe Gln Glu Thr Gly Lys Ala Leu Pro Asp Glu Thr
65                  70                  75                  80

Val Lys Val Leu Lys Glu Gln Cys Gln Gly Ala Leu Phe Gly Ala Val
                85                  90                  95

Gln Ser Pro Thr Thr Lys Val Glu Gly Tyr Ser Ser Pro Ile Val Ala
            100                 105                 110

Leu Arg Gln Glu Met Gly Leu Phe Ala Asn Val Arg Pro Val Lys Ser
        115                 120                 125

Val Glu Gly Glu Lys Gly Lys Pro Ile Asp Met Val Ile Val Arg Glu
    130                 135                 140

Asn Thr Glu Asp Leu Tyr Ile Lys Ile Glu Lys Thr Tyr Ile Asp Lys
145                 150                 155                 160

Ala Thr Gly Thr Arg Val Ala Asp Ala Thr Lys Arg Ile Ser Glu Ile
                165                 170                 175
```

```
Ala Thr Arg Arg Ile Ala Thr Ile Ala Leu Asp Ile Ala Leu Lys Arg
            180                 185                 190

Leu Gln Thr Arg Gly Gln Ala Thr Leu Thr Val Thr His Lys Ser Asn
        195                 200                 205

Val Leu Ser Gln Ser Asp Gly Leu Phe Arg Glu Ile Cys Lys Glu Val
    210                 215                 220

Tyr Glu Ser Asn Lys Asp Lys Tyr Gly Gln Ile Lys Tyr Asn Glu Gln
225                 230                 235                 240

Ile Val Asp Ser Met Val Tyr Arg Leu Phe Arg Glu Pro Gln Cys Phe
                245                 250                 255

Asp Val Ile Val Ala Pro Asn Leu Tyr Gly Asp Ile Leu Ser Asp Gly
            260                 265                 270

Ala Ala Ala Leu Val Gly Ser Leu Gly Val Val Pro Ser Ala Asn Val
        275                 280                 285

Gly Pro Glu Ile Val Ile Gly Glu Pro Cys His Gly Ser Ala Pro Asp
    290                 295                 300

Ile Ala Gly Lys Gly Ile Ala Asn Pro Ile Ala Thr Ile Arg Ser Thr
305                 310                 315                 320

Ala Leu Met Leu Glu Phe Leu Gly His Asn Glu Ala Ala Gln Asp Ile
                325                 330                 335

Tyr Lys Ala Val Asp Ala Asn Leu Arg Glu Gly Ser Ile Lys Thr Pro
            340                 345                 350

Asp Leu Gly Gly Lys Ala Ser Thr Gln Gln Val Val Asp Asp Val Leu
        355                 360                 365

Ser Arg Leu
    370

<210> SEQ ID NO 9
<211> LENGTH: 1113
<212> TYPE: DNA
<213> ORGANISM: Artificial Sequence
<220> FEATURE:
<223> OTHER INFORMATION: ScHIDH R143C polynucleotide

<400> SEQUENCE: 9
atgtttagat ctgttgctac tagattatct gcctgccgtg ggttagcatc taacgctgct      60
cgcaaatcac tcactattgg tcttatcccc ggtgacggta tcggtaagga agtcattcct     120
gctggtaagc aagttttgga aaaccttaac tccaagcacg gcctaagctt caactttatt     180
gatctctacg ccggtttcca acattccaa gaaacaggaa aggcgttgcc tgatgagact      240
gttaaagtgt tgaaggaaca atgtcaaggt gctctttttcg gtgcagttca gtctccaact     300
actaaggtgg aaggttactc ctcaccaatt gttgctctaa ggagggaaat gggccttttc     360
gctaatgttc gtcctgttaa gtctgtagag ggagaaaagg gtaaaccaat gacatggtt      420
atcgtctgcg aaaatactga ggacctgtac attaaaattg aaaaaacata cattgacaag     480
gccacaggta caagagttgc tgatgccaca agagaatat ccgaaattgc aacaagaaga      540
attgcaacca ttgcattaga tattgccttg aaaagattac aaacaagagg ccaagccact     600
ttgacagtga ctcataaatc aaatgttcta tctcaaagtg atggtctatt cagagaaatc     660
tgtaaggaag tctacgaatc taacaaggac aagtacggtc aaatcaaata taacgaacaa     720
attgtggatt ccatggttta taggctgttc agagaaccac aatgttttga tgtgatagtg     780
gcaccaaacc tatacgggga tatattatct gacggtgctg ctgctttagt cggttcatta     840
ggtgttgttc caagcgccaa cgtaggtcca gaaattgtca ttggtgaacc atgccatggt     900
```

```
tctgcaccag atattgctgg taaaggtatt gctaacccaa tcgccactat aagatctact    960
gctttgatgt tggaattctt gggccacaac gaagctgccc aagatatcta caaggctgtt   1020
gatgctaact taagagaggg ttctatcaag acaccagatt taggtggtaa ggcttctact   1080
caacaagtcg ttgacgacgt tttgtcgaga tta                                1113
```

<210> SEQ ID NO 10
<211> LENGTH: 371
<212> TYPE: PRT
<213> ORGANISM: Artificial Sequence
<220> FEATURE:
<223> OTHER INFORMATION: ScHIDH R143C polypeptide

<400> SEQUENCE: 10

```
Met Phe Arg Ser Val Ala Thr Arg Leu Ser Ala Cys Arg Gly Leu Ala
1               5                   10                  15

Ser Asn Ala Ala Arg Lys Ser Leu Thr Ile Gly Leu Ile Pro Gly Asp
            20                  25                  30

Gly Ile Gly Lys Glu Val Ile Pro Ala Gly Lys Gln Val Leu Glu Asn
        35                  40                  45

Leu Asn Ser Lys His Gly Leu Ser Phe Asn Phe Ile Asp Leu Tyr Ala
50                  55                  60

Gly Phe Gln Thr Phe Gln Glu Thr Gly Lys Ala Leu Pro Asp Glu Thr
65                  70                  75                  80

Val Lys Val Leu Lys Glu Gln Cys Gln Gly Ala Leu Phe Gly Ala Val
                85                  90                  95

Gln Ser Pro Thr Thr Lys Val Glu Gly Tyr Ser Ser Pro Ile Val Ala
            100                 105                 110

Leu Arg Arg Glu Met Gly Leu Phe Ala Asn Val Arg Pro Val Lys Ser
        115                 120                 125

Val Glu Gly Glu Lys Gly Lys Pro Ile Asp Met Val Ile Val Cys Glu
130                 135                 140

Asn Thr Glu Asp Leu Tyr Ile Lys Ile Glu Lys Thr Tyr Ile Asp Lys
145                 150                 155                 160

Ala Thr Gly Thr Arg Val Ala Asp Ala Thr Lys Arg Ile Ser Glu Ile
                165                 170                 175

Ala Thr Arg Arg Ile Ala Thr Ile Ala Leu Asp Ile Ala Leu Lys Arg
            180                 185                 190

Leu Gln Thr Arg Gly Gln Ala Thr Leu Thr Val Thr His Lys Ser Asn
        195                 200                 205

Val Leu Ser Gln Ser Asp Gly Leu Phe Arg Glu Ile Cys Lys Glu Val
210                 215                 220

Tyr Glu Ser Asn Lys Asp Lys Tyr Gly Gln Ile Lys Tyr Asn Glu Gln
225                 230                 235                 240

Ile Val Asp Ser Met Val Tyr Arg Leu Phe Arg Glu Pro Gln Cys Phe
                245                 250                 255

Asp Val Ile Val Ala Pro Asn Leu Tyr Gly Asp Ile Leu Ser Asp Gly
            260                 265                 270

Ala Ala Ala Leu Val Gly Ser Leu Gly Val Val Pro Ser Ala Asn Val
        275                 280                 285

Gly Pro Glu Ile Val Ile Gly Glu Pro Cys His Gly Ser Ala Pro Asp
290                 295                 300

Ile Ala Gly Lys Gly Ile Ala Asn Pro Ile Ala Thr Ile Arg Ser Thr
305                 310                 315                 320

Ala Leu Met Leu Glu Phe Leu Gly His Asn Glu Ala Ala Gln Asp Ile
                325                 330                 335
```

```
Tyr Lys Ala Val Asp Ala Asn Leu Arg Glu Gly Ser Ile Lys Thr Pro
            340                 345                 350

Asp Leu Gly Gly Lys Ala Ser Thr Gln Gln Val Val Asp Asp Val Leu
        355                 360                 365

Ser Arg Leu
    370

<210> SEQ ID NO 11
<211> LENGTH: 1113
<212> TYPE: DNA
<213> ORGANISM: Artificial Sequence
<220> FEATURE:
<223> OTHER INFORMATION: ScHIDH R143H polynucleotide

<400> SEQUENCE: 11
atgtttagat ctgttgctac tagattatct gcctgccgtg ggttagcatc taacgctgct      60
cgcaaatcac tcactattgg tcttatcccc ggtgacggta tcggtaagga agtcattcct     120
gctggtaagc aagttttgga aaaccttaac tccaagcacg gcctaagctt caactttatt     180
gatctctacg ccggtttcca acattccaa gaaacaggaa aggcgttgcc tgatgagact      240
gttaaagtgt tgaaggaaca atgtcaaggt gctcttttcg gtgcagttca gtctccaact     300
actaaggtgg aaggttactc ctcaccaatt gttgctctaa ggagggaaat gggccttttc     360
gctaatgttc gtcctgttaa gtctgtagag ggagaaaagg gtaaaccaat tgacatggtt     420
atcgtccatg aaaatactga ggacctgtac attaaaattg aaaaaacata cattgacaag     480
gccacaggta caagagttgc tgatgccaca aagagaatat ccgaaattgc aacaagaaga     540
attgcaacca ttgcattaga tattgccttg aaaagattac aaacaagagg ccaagccact     600
ttgacagtga ctcataaatc aaatgttcta tctcaaagtg atggtctatt cagagaaatc     660
tgtaaggaag tctacgaatc taacaaggac aagtacggtc aaatcaaata taacgaacaa     720
attgtggatt ccatggttta taggctgttc agagaaccac aatgttttga tgtgatagtg     780
gcaccaaacc tatacgggga tatattatct gacggtgctg ctgctttagt cggttcatta     840
ggtgttgttc aagcgccaa cgtaggtcca gaaattgtca ttggtgaacc atgccatggt     900
tctgcaccag atattgctgg taaaggtatt gctaacccaa tcgccactat aagatctact     960
gctttgatgt tggaattctt gggccacaac gaagctgccc aagatatcta caaggctgtt    1020
gatgctaact aagagaggg ttctatcaag acaccagatt taggtggtaa ggcttctact    1080
caacaagtcg ttgacgacgt tttgtcgaga tta                                 1113

<210> SEQ ID NO 12
<211> LENGTH: 371
<212> TYPE: PRT
<213> ORGANISM: Artificial Sequence
<220> FEATURE:
<223> OTHER INFORMATION: ScHIDH R143H polypeptide

<400> SEQUENCE: 12

Met Phe Arg Ser Val Ala Thr Arg Leu Ser Ala Cys Arg Gly Leu Ala
1               5                   10                  15

Ser Asn Ala Ala Arg Lys Ser Leu Thr Ile Gly Leu Ile Pro Gly Asp
            20                  25                  30

Gly Ile Gly Lys Glu Val Ile Pro Ala Gly Lys Gln Val Leu Glu Asn
        35                  40                  45

Leu Asn Ser Lys His Gly Leu Ser Phe Asn Phe Ile Asp Leu Tyr Ala
    50                  55                  60
```

```
Gly Phe Gln Thr Phe Gln Glu Thr Gly Lys Ala Leu Pro Asp Glu Thr
 65                  70                  75                  80

Val Lys Val Leu Lys Glu Gln Cys Gln Gly Ala Leu Phe Gly Ala Val
                 85                  90                  95

Gln Ser Pro Thr Thr Lys Val Glu Gly Tyr Ser Ser Pro Ile Val Ala
            100                 105                 110

Leu Arg Arg Glu Met Gly Leu Phe Ala Asn Val Arg Pro Val Lys Ser
        115                 120                 125

Val Glu Gly Glu Lys Gly Lys Pro Ile Asp Met Val Ile Val His Glu
130                 135                 140

Asn Thr Glu Asp Leu Tyr Ile Lys Ile Glu Lys Thr Tyr Ile Asp Lys
145                 150                 155                 160

Ala Thr Gly Thr Arg Val Ala Asp Ala Thr Lys Arg Ile Ser Glu Ile
                165                 170                 175

Ala Thr Arg Arg Ile Ala Thr Ile Ala Leu Asp Ile Ala Leu Lys Arg
            180                 185                 190

Leu Gln Thr Arg Gly Gln Ala Thr Leu Thr Val Thr His Lys Ser Asn
        195                 200                 205

Val Leu Ser Gln Ser Asp Gly Leu Phe Arg Glu Ile Cys Lys Glu Val
210                 215                 220

Tyr Glu Ser Asn Lys Asp Lys Tyr Gly Gln Ile Lys Tyr Asn Glu Gln
225                 230                 235                 240

Ile Val Asp Ser Met Val Tyr Arg Leu Phe Arg Glu Pro Gln Cys Phe
                245                 250                 255

Asp Val Ile Val Ala Pro Asn Leu Tyr Gly Asp Ile Leu Ser Asp Gly
            260                 265                 270

Ala Ala Ala Leu Val Gly Ser Leu Gly Val Val Pro Ser Ala Asn Val
        275                 280                 285

Gly Pro Glu Ile Val Ile Gly Glu Pro Cys His Gly Ser Ala Pro Asp
290                 295                 300

Ile Ala Gly Lys Gly Ile Ala Asn Pro Ile Ala Thr Ile Arg Ser Thr
305                 310                 315                 320

Ala Leu Met Leu Glu Phe Leu Gly His Asn Glu Ala Ala Gln Asp Ile
                325                 330                 335

Tyr Lys Ala Val Asp Ala Asn Leu Arg Glu Gly Ser Ile Lys Thr Pro
            340                 345                 350

Asp Leu Gly Gly Lys Ala Ser Thr Gln Gln Val Val Asp Asp Val Leu
        355                 360                 365

Ser Arg Leu
    370

<210> SEQ ID NO 13
<211> LENGTH: 1113
<212> TYPE: DNA
<213> ORGANISM: Artificial Sequence
<220> FEATURE:
<223> OTHER INFORMATION: ScHIDH R143K polynucleotide

<400> SEQUENCE: 13
atgtttagat ctgttgctac tagattatct gcctgccgtg ggttagcatc taacgctgct      60
cgcaaatcac tcactattgg tcttatcccc ggtgacggta tcggtaagga agtcattcct     120
gctggtaagc aagttttgga aaaccttaac tccaagcacg gcctaagctt caactttatt     180
gatctctacg ccggtttcca acattccaa gaaacaggaa aggcgttgcc tgatgagact     240
gttaaagtgt tgaaggaaca atgtcaaggt gctctttcg gtgcagttca gtctccaact     300
```

```
actaaggtgg aaggttactc ctcaccaatt gttgctctaa ggagggaaat gggccttttc    360
gctaatgttc gtcctgttaa gtctgtagag ggagaaaagg gtaaaccaat tgacatggtt    420
atcgtcaaag aaaatactga ggacctgtac attaaaattg aaaaaacata cattgacaag    480
gccacaggta caagagttgc tgatgccaca aagagaatat ccgaaattgc aacaagaaga    540
attgcaacca ttgcattaga tattgccttg aaaagattac aaacaagagg ccaagccact    600
ttgacagtga ctcataaatc aaatgttcta tctcaaagtg atggtctatt cagagaaatc    660
tgtaaggaag tctacgaatc taacaaggac aagtacggtc aaatcaaata taacgaacaa    720
attgtggatt ccatggttta taggctgttc agagaaccac aatgttttga tgtgatagtg    780
gcaccaaacc tatacgggga tatattatct gacggtgctg ctgctttagt cggttcatta    840
ggtgttgttc aagcgccaa cgtaggtcca gaaattgtca ttggtgaacc atgccatggt    900
tctgcaccag atattgctgg taaaggtatt gctaacccaa tcgccactat aagatctact    960
gctttgatgt tggaattctt gggccacaac gaagctgccc aagatatcta caaggctgtt   1020
gatgctaact taagagaggg ttctatcaag acaccagatt taggtggtaa ggcttctact   1080
caacaagtcg ttgacgacgt tttgtcgaga tta                               1113
```

<210> SEQ ID NO 14
<211> LENGTH: 371
<212> TYPE: PRT
<213> ORGANISM: Artificial Sequence
<220> FEATURE:
<223> OTHER INFORMATION: ScHIDH R143K polypeptide

<400> SEQUENCE: 14

```
Met Phe Arg Ser Val Ala Thr Arg Leu Ser Ala Cys Arg Gly Leu Ala
1               5                   10                  15

Ser Asn Ala Ala Arg Lys Ser Leu Thr Ile Gly Leu Ile Pro Gly Asp
            20                  25                  30

Gly Ile Gly Lys Glu Val Ile Pro Ala Gly Lys Gln Val Leu Glu Asn
        35                  40                  45

Leu Asn Ser Lys His Gly Leu Ser Phe Asn Phe Ile Asp Leu Tyr Ala
    50                  55                  60

Gly Phe Gln Thr Phe Gln Glu Thr Gly Lys Ala Leu Pro Asp Glu Thr
65                  70                  75                  80

Val Lys Val Leu Lys Glu Gln Cys Gln Gly Ala Leu Phe Gly Ala Val
                85                  90                  95

Gln Ser Pro Thr Thr Lys Val Glu Gly Tyr Ser Ser Pro Ile Val Ala
            100                 105                 110

Leu Arg Arg Glu Met Gly Leu Phe Ala Asn Val Arg Pro Val Lys Ser
        115                 120                 125

Val Glu Gly Glu Lys Gly Lys Pro Ile Asp Met Val Ile Val Lys Glu
    130                 135                 140

Asn Thr Glu Asp Leu Tyr Ile Lys Ile Glu Lys Thr Tyr Ile Asp Lys
145                 150                 155                 160

Ala Thr Gly Thr Arg Val Ala Asp Ala Thr Lys Arg Ile Ser Glu Ile
                165                 170                 175

Ala Thr Arg Arg Ile Ala Thr Ile Ala Leu Asp Ile Ala Leu Lys Arg
            180                 185                 190

Leu Gln Thr Arg Gly Gln Ala Thr Leu Thr Val Thr His Lys Ser Asn
        195                 200                 205

Val Leu Ser Gln Ser Asp Gly Leu Phe Arg Glu Ile Cys Lys Glu Val
    210                 215                 220
```

Tyr Glu Ser Asn Lys Asp Lys Tyr Gly Gln Ile Lys Tyr Asn Glu Gln
225                 230                 235                 240

Ile Val Asp Ser Met Val Tyr Arg Leu Phe Arg Glu Pro Gln Cys Phe
            245                 250                 255

Asp Val Ile Val Ala Pro Asn Leu Tyr Gly Asp Ile Leu Ser Asp Gly
        260                 265                 270

Ala Ala Ala Leu Val Gly Ser Leu Gly Val Val Pro Ser Ala Asn Val
    275                 280                 285

Gly Pro Glu Ile Val Ile Gly Glu Pro Cys His Gly Ser Ala Pro Asp
    290                 295                 300

Ile Ala Gly Lys Gly Ile Ala Asn Pro Ile Ala Thr Ile Arg Ser Thr
305                 310                 315                 320

Ala Leu Met Leu Glu Phe Leu Gly His Asn Glu Ala Ala Gln Asp Ile
            325                 330                 335

Tyr Lys Ala Val Asp Ala Asn Leu Arg Glu Gly Ser Ile Lys Thr Pro
        340                 345                 350

Asp Leu Gly Gly Lys Ala Ser Thr Gln Gln Val Val Asp Asp Val Leu
    355                 360                 365

Ser Arg Leu
    370

<210> SEQ ID NO 15
<211> LENGTH: 1113
<212> TYPE: DNA
<213> ORGANISM: Artificial Sequence
<220> FEATURE:
<223> OTHER INFORMATION: ScHIDH Y150D polynucleotide

<400> SEQUENCE: 15
atgtttagat ctgttgctac tagattatct gcctgccgtg ggttagcatc taacgctgct      60
cgcaaatcac tcactattgg tcttatcccc ggtgacggta tcggtaagga agtcattcct     120
gctggtaagc aagttttgga aaaccttaac tccaagcacg cctaagcttc aactttatt     180
gatctctacg ccggtttcca acattccaa gaaacaggaa aggcgttgcc tgatgagact     240
gttaaagtgt tgaaggaaca atgtcaaggt gctcttttcg gtgcagttca gtctccaact     300
actaaggtgg aaggttactc ctcaccaatt gttgctctaa ggagggaaat gggccttttc     360
gctaatgttc gtcctgttaa gtctgtagag ggagaaaagg gtaaaccaat tgacatggtt     420
atcgtcagag aaaatactga ggacctggac attaaaattg aaaaaacata cattgacaag     480
gccacaggta caagagttgc tgatgccaca agagaaaat ccgaaattgc aacaagaaga     540
attgcaacca ttgcattaga tattgccttg aaaagattac aaacaagagg ccaagccact     600
ttgacagtga ctcataaatc aaatgttcta tctcaaagtg atggtctatt cagagaaatc     660
tgtaaggaag tctacgaatc taacaaggac aagtacggtc aaatcaaata taacgaacaa     720
attgtggatt ccatggttta taggctgttc agagaaccac aatgttttga tgtgatagtg     780
gcaccaaacc tatacgggga tatattatct gacggtgctg ctgctttagt cggttcatta     840
ggtgttgttc caagcgccaa cgtaggtcca gaaattgtca ttggtgaacc atgccatggt     900
tctgcaccag atattgctgg taaaggtatt gctaacccaa tcgccactat aagatctact     960
gctttgatgt tggaattctt gggccacaac gaagctgccc aagatatcta caaggctgtt    1020
gatgctaact taagagaggg ttctatcaag acaccagatt taggtggtaa ggcttctact    1080
caacaagtcg ttgacgacgt tttgtcgaga tta                                 1113

<210> SEQ ID NO 16

<211> LENGTH: 371
<212> TYPE: PRT
<213> ORGANISM: Artificial Sequence
<220> FEATURE:
<223> OTHER INFORMATION: ScHIDH Y150D polypeptide

<400> SEQUENCE: 16

| | | | | | | | | | | | | | | |
|---|---|---|---|---|---|---|---|---|---|---|---|---|---|---|
| Met | Phe | Arg | Ser | Val | Ala | Thr | Arg | Leu | Ser | Ala | Cys | Arg | Gly | Leu | Ala |
| 1 | | | | 5 | | | | | 10 | | | | | 15 | |

| Ser | Asn | Ala | Ala | Arg | Lys | Ser | Leu | Thr | Ile | Gly | Leu | Ile | Pro | Gly | Asp |
| | | | 20 | | | | | 25 | | | | | 30 | | |

| Gly | Ile | Gly | Lys | Glu | Val | Ile | Pro | Ala | Gly | Lys | Gln | Val | Leu | Glu | Asn |
| | | 35 | | | | | 40 | | | | | 45 | | | |

| Leu | Asn | Ser | Lys | His | Gly | Leu | Ser | Phe | Asn | Phe | Ile | Asp | Leu | Tyr | Ala |
| | 50 | | | | | 55 | | | | | 60 | | | | |

| Gly | Phe | Gln | Thr | Phe | Gln | Glu | Thr | Gly | Lys | Ala | Leu | Pro | Asp | Glu | Thr |
| 65 | | | | | 70 | | | | | 75 | | | | | 80 |

| Val | Lys | Val | Leu | Lys | Glu | Gln | Cys | Gln | Gly | Ala | Leu | Phe | Gly | Ala | Val |
| | | | | 85 | | | | | 90 | | | | | 95 | |

| Gln | Ser | Pro | Thr | Thr | Lys | Val | Glu | Gly | Tyr | Ser | Ser | Pro | Ile | Val | Ala |
| | | | 100 | | | | | 105 | | | | | 110 | | |

| Leu | Arg | Arg | Glu | Met | Gly | Leu | Phe | Ala | Asn | Val | Arg | Pro | Val | Lys | Ser |
| | | 115 | | | | | 120 | | | | | 125 | | | |

| Val | Glu | Gly | Glu | Lys | Gly | Lys | Pro | Ile | Asp | Met | Val | Ile | Val | Arg | Glu |
| | 130 | | | | | 135 | | | | | 140 | | | | |

| Asn | Thr | Glu | Asp | Leu | Asp | Ile | Lys | Ile | Glu | Lys | Thr | Tyr | Ile | Asp | Lys |
| 145 | | | | | 150 | | | | | 155 | | | | | 160 |

| Ala | Thr | Gly | Thr | Arg | Val | Ala | Asp | Ala | Thr | Lys | Arg | Ile | Ser | Glu | Ile |
| | | | | 165 | | | | | 170 | | | | | 175 | |

| Ala | Thr | Arg | Arg | Ile | Ala | Thr | Ile | Ala | Leu | Asp | Ile | Ala | Leu | Lys | Arg |
| | | | 180 | | | | | 185 | | | | | 190 | | |

| Leu | Gln | Thr | Arg | Gly | Gln | Ala | Thr | Leu | Thr | Val | Thr | His | Lys | Ser | Asn |
| | | 195 | | | | | 200 | | | | | 205 | | | |

| Val | Leu | Ser | Gln | Ser | Asp | Gly | Leu | Phe | Arg | Glu | Ile | Cys | Lys | Glu | Val |
| | 210 | | | | | 215 | | | | | 220 | | | | |

| Tyr | Glu | Ser | Asn | Lys | Asp | Lys | Tyr | Gly | Gln | Ile | Lys | Tyr | Asn | Glu | Gln |
| 225 | | | | | 230 | | | | | 235 | | | | | 240 |

| Ile | Val | Asp | Ser | Met | Val | Tyr | Arg | Leu | Phe | Arg | Glu | Pro | Gln | Cys | Phe |
| | | | | 245 | | | | | 250 | | | | | 255 | |

| Asp | Val | Ile | Val | Ala | Pro | Asn | Leu | Tyr | Gly | Asp | Ile | Leu | Ser | Asp | Gly |
| | | | 260 | | | | | 265 | | | | | 270 | | |

| Ala | Ala | Ala | Leu | Val | Gly | Ser | Leu | Gly | Val | Val | Pro | Ser | Ala | Asn | Val |
| | | 275 | | | | | 280 | | | | | 285 | | | |

| Gly | Pro | Glu | Ile | Val | Ile | Gly | Glu | Pro | Cys | His | Gly | Ser | Ala | Pro | Asp |
| | 290 | | | | | 295 | | | | | 300 | | | | |

| Ile | Ala | Gly | Lys | Gly | Ile | Ala | Asn | Pro | Ile | Ala | Thr | Ile | Arg | Ser | Thr |
| 305 | | | | | 310 | | | | | 315 | | | | | 320 |

| Ala | Leu | Met | Leu | Glu | Phe | Leu | Gly | His | Asn | Glu | Ala | Ala | Gln | Asp | Ile |
| | | | | 325 | | | | | 330 | | | | | 335 | |

| Tyr | Lys | Ala | Val | Asp | Ala | Asn | Leu | Arg | Glu | Gly | Ser | Ile | Lys | Thr | Pro |
| | | | 340 | | | | | 345 | | | | | 350 | | |

| Asp | Leu | Gly | Gly | Lys | Ala | Ser | Thr | Gln | Gln | Val | Val | Asp | Val | Leu |
| | | 355 | | | | | 360 | | | | | 365 | | |

| Ser | Arg | Leu |
| | | 370 |

<210> SEQ ID NO 17
<211> LENGTH: 1113
<212> TYPE: DNA
<213> ORGANISM: Artificial Sequence
<220> FEATURE:
<223> OTHER INFORMATION: ScHIDH R114Q R143C polynucleotide

<400> SEQUENCE: 17

```
atgtttagat ctgttgctac tagattatct gcctgccgtg ggttagcatc taacgctgct     60
cgcaaatcac tcactattgg tcttatcccc ggtgacggta tcggtaagga agtcattcct    120
gctggtaagc aagttttgga aaaccttaac tccaagcacg gcctaagctt caactttatt    180
gatctctacg ccggtttcca acattccaa gaaacaggaa aggcgttgcc tgatgagact    240
gttaaagtgt tgaaggaaca atgtcaaggt gctcttttcg gtgcagttca gtctccaact    300
actaaggtgg aaggttactc ctcaccaatt gttgctctac agagggaaat gggcctttc    360
gctaatgttc gtcctgttaa gtctgtagag ggagaaaagg gtaaaccaat tgacatggtt    420
atcgtctgcg aaaatactga ggacctgtac attaaaattg aaaaaacata cattgacaag    480
gccacaggta caagagttgc tgatgccaca aagagaatat ccgaaattgc aacaagaaga    540
attgcaacca ttgcattaga tattgccttg aaaagattac aaacaagagg ccaagccact    600
ttgacagtga ctcataaatc aaatgttcta tctcaaagtg atggtctatt cagagaaatc    660
tgtaaggaag tctacgaatc taacaaggac aagtacggtc aaatcaaata taacgaacaa    720
attgtggatt ccatggttta taggctgttc agagaaccac aatgttttga tgtgatagtg    780
gcaccaaacc tatacgggga tatattatct gacggtgctg ctgctttagt cggttcatta    840
ggtgttgttc aagcgccaa cgtaggtcca gaaattgtca ttggtgaacc atgccatggt    900
tctgcaccag atattgctgg taaggtatt gctaacccaa tcgccactat aagatctact    960
gctttgatgt tggaattctt gggccacaac gaagctgccc aagatatcta caaggctgtt   1020
gatgctaact aagagaggg ttctatcaag acaccagatt taggtggtaa ggcttctact   1080
caacaagtcg ttgacgacgt tttgtcgaga tta                                 1113
```

<210> SEQ ID NO 18
<211> LENGTH: 371
<212> TYPE: PRT
<213> ORGANISM: Artificial Sequence
<220> FEATURE:
<223> OTHER INFORMATION: ScHIDH R114Q R143C polypeptide

<400> SEQUENCE: 18

```
Met Phe Arg Ser Val Ala Thr Arg Leu Ser Ala Cys Arg Gly Leu Ala
1               5                   10                  15

Ser Asn Ala Ala Arg Lys Ser Leu Thr Ile Gly Leu Ile Pro Gly Asp
            20                  25                  30

Gly Ile Gly Lys Glu Val Ile Pro Ala Gly Lys Gln Val Leu Glu Asn
        35                  40                  45

Leu Asn Ser Lys His Gly Leu Ser Phe Asn Phe Ile Asp Leu Tyr Ala
    50                  55                  60

Gly Phe Gln Thr Phe Gln Glu Thr Gly Lys Ala Leu Pro Asp Glu Thr
65                  70                  75                  80

Val Lys Val Leu Lys Glu Gln Cys Gln Gly Ala Leu Phe Gly Ala Val
                85                  90                  95

Gln Ser Pro Thr Thr Lys Val Glu Gly Tyr Ser Ser Pro Ile Val Ala
            100                 105                 110

Leu Gln Arg Glu Met Gly Leu Phe Ala Asn Val Arg Pro Val Lys Ser
```

115                 120                 125
Val Glu Gly Glu Lys Gly Lys Pro Ile Asp Met Val Ile Val Cys Glu
130                 135                 140

Asn Thr Glu Asp Leu Tyr Ile Lys Ile Glu Lys Thr Tyr Ile Asp Lys
145                 150                 155                 160

Ala Thr Gly Thr Arg Val Ala Asp Ala Thr Lys Arg Ile Ser Glu Ile
                165                 170                 175

Ala Thr Arg Arg Ile Ala Thr Ile Ala Leu Asp Ile Ala Leu Lys Arg
            180                 185                 190

Leu Gln Thr Arg Gly Gln Ala Thr Leu Thr Val Thr His Lys Ser Asn
        195                 200                 205

Val Leu Ser Gln Ser Asp Gly Leu Phe Arg Glu Ile Cys Lys Glu Val
    210                 215                 220

Tyr Glu Ser Asn Lys Asp Lys Tyr Gly Gln Ile Lys Tyr Asn Glu Gln
225                 230                 235                 240

Ile Val Asp Ser Met Val Tyr Arg Leu Phe Arg Glu Pro Gln Cys Phe
                245                 250                 255

Asp Val Ile Val Ala Pro Asn Leu Tyr Gly Asp Ile Leu Ser Asp Gly
            260                 265                 270

Ala Ala Ala Leu Val Gly Ser Leu Gly Val Val Pro Ser Ala Asn Val
        275                 280                 285

Gly Pro Glu Ile Val Ile Gly Glu Pro Cys His Gly Ser Ala Pro Asp
    290                 295                 300

Ile Ala Gly Lys Gly Ile Ala Asn Pro Ile Ala Thr Ile Arg Ser Thr
305                 310                 315                 320

Ala Leu Met Leu Glu Phe Leu Gly His Asn Glu Ala Ala Gln Asp Ile
                325                 330                 335

Tyr Lys Ala Val Asp Ala Asn Leu Arg Glu Gly Ser Ile Lys Thr Pro
            340                 345                 350

Asp Leu Gly Gly Lys Ala Ser Thr Gln Gln Val Val Asp Asp Val Leu
        355                 360                 365

Ser Arg Leu
    370

<210> SEQ ID NO 19
<211> LENGTH: 1005
<212> TYPE: DNA
<213> ORGANISM: Thermus thermophilus

<400> SEQUENCE: 19
atggcgtacc ggatctgctt gattgagggc gacggcatcg gcacgaggt catccccgcg      60 gcgcggaggg tgctggaggc caccggcctc ccctggagt cgtggaggc ggaggcgggc     120 tgggagacct tgagagaag agggacctcc gtccccgagg agacggtgga agatcctg      180 tcctgccacg ccaccctctt cggggccgcc accagcccca ccgtaaagt gccgggcttc     240 ttcggggcga tccgctacct caggcgcagg ctggacctct acgccaacgt ccgccccgcc    300
aagagccgcc ccgtcccggg aagccgcccc ggcgtggacc tggtcatcgt ccgggagaac    360 accgaaggc tttacgtgga gcaggaaagg cgctacctgg acgtggccat cgccgacgcc    420
gtcatctcca agaaggccag cgagcgcatc ggccggccg ccttaaggat cgccgagggc    480
cggccccgca aaacccttca catcgcccac aaggccaacg tcctcccct cacccagggg    540 ctcttcctgg acacggtcaa ggaggtggcc aaggacttcc ccctggtgaa cgtgcaggac    600
atcatcgtgg acaactgcgc catgcagctc gtcatgcgtc ccgagcgctt tgacgtcatc    660

-continued

```
gtcaccacca acctcctggg ggacatcctc tccgacctcg ccgcggggct cgtggggggc    720
ctgggcctcg cccccctcggg caacatcggg gacaccaccg cggtctttga gcccgtccac    780
ggctccgccc ccgacatcgc cggcaagggc atcgccaacc ccacggcggc catcctctcc    840
gcggccatga tgctggacta cctgggggag aaggaggcgg ccaagcgggt ggagaaggcg    900
gtggacctgg tgctggagcg ggggcccagg acccctgacc tgggcgggga cgccaccacg    960
gaagccttca ccgaggccgt ggtggaggcg ctcaagagcc tgtag                   1005
```

<210> SEQ ID NO 20
<211> LENGTH: 334
<212> TYPE: PRT
<213> ORGANISM: Thermus thermophilus

<400> SEQUENCE: 20

```
Met Ala Tyr Arg Ile Cys Leu Ile Glu Gly Asp Gly Ile Gly His Glu
1               5                   10                  15

Val Ile Pro Ala Ala Arg Arg Val Leu Glu Ala Thr Gly Leu Pro Leu
            20                  25                  30

Glu Phe Val Glu Ala Glu Ala Gly Trp Glu Thr Phe Glu Arg Arg Gly
        35                  40                  45

Thr Ser Val Pro Glu Glu Thr Val Glu Lys Ile Leu Ser Cys His Ala
    50                  55                  60

Thr Leu Phe Gly Ala Ala Thr Ser Pro Thr Arg Lys Val Pro Gly Phe
65                  70                  75                  80

Phe Gly Ala Ile Arg Tyr Leu Arg Arg Leu Asp Leu Tyr Ala Asn
            85                  90                  95

Val Arg Pro Ala Lys Ser Arg Pro Val Pro Gly Ser Arg Pro Gly Val
            100                 105                 110

Asp Leu Val Ile Val Arg Glu Asn Thr Glu Gly Leu Tyr Val Glu Gln
            115                 120                 125

Glu Arg Arg Tyr Leu Asp Val Ala Ile Ala Asp Ala Val Ile Ser Lys
    130                 135                 140

Lys Ala Ser Glu Arg Ile Gly Arg Ala Ala Leu Arg Ile Ala Glu Gly
145                 150                 155                 160

Arg Pro Arg Lys Thr Leu His Ile Ala His Lys Ala Asn Val Leu Pro
                165                 170                 175

Leu Thr Gln Gly Leu Phe Leu Asp Thr Val Lys Glu Val Ala Lys Asp
            180                 185                 190

Phe Pro Leu Val Asn Val Gln Asp Ile Ile Val Asp Asn Cys Ala Met
        195                 200                 205

Gln Leu Val Met Arg Pro Glu Arg Phe Asp Val Ile Val Thr Thr Asn
    210                 215                 220

Leu Leu Gly Asp Ile Leu Ser Asp Leu Ala Ala Gly Leu Val Gly Gly
225                 230                 235                 240

Leu Gly Leu Ala Pro Ser Gly Asn Ile Gly Asp Thr Thr Ala Val Phe
                245                 250                 255

Glu Pro Val His Gly Ser Ala Pro Asp Ile Ala Gly Lys Gly Ile Ala
            260                 265                 270

Asn Pro Thr Ala Ala Ile Leu Ser Ala Ala Met Met Leu Asp Tyr Leu
        275                 280                 285

Gly Glu Lys Glu Ala Ala Lys Arg Val Glu Lys Ala Val Asp Leu Val
    290                 295                 300

Leu Glu Arg Gly Pro Arg Thr Pro Asp Leu Gly Gly Asp Ala Thr Thr
305                 310                 315                 320
```

```
Glu Ala Phe Thr Glu Ala Val Val Glu Ala Leu Lys Ser Leu
            325                 330
```

<210> SEQ ID NO 21
<211> LENGTH: 1002
<212> TYPE: DNA
<213> ORGANISM: Artificial Sequence
<220> FEATURE:
<223> OTHER INFORMATION: TtHIDH R118H polynucleotide

<400> SEQUENCE: 21

```
atggcgtacc ggatctgctt gattgagggc gacggcatcg gcacgaggt catccccgcg      60
gcgcggaggg tgctggaggc caccggcctc ccctggagt cgtggaggc ggaggcgggc     120
tgggagacct ttgagagaag agggacctcc gtccccgagg agacggtgga aagatcctg     180
tcctgccacg ccaccctctt cggggccgcc accagcccca ccgtaaagt gccgggcttc     240
ttcggggcga tccgctacct caggcgcagg ctggacctct acgccaacgt ccgccccgcc     300
aagagccgcc ccgtcccggg aagccgcccc ggcgtgacc tggtcatcgt ccatgagaac     360
accgaagggc tttacgtgga gcaggaaagg cgctacctgg acgtggccat cgccgacgcc     420
gtcatctcca gaaggccag cgagcgcatc ggccgggccg ccttaaggat cgccgagggc     480
cggccccgca aaacccttca catcgcccac aaggccaacg tcctcccct cacccagggg     540
ctcttcctgg acacggtcaa ggaggtggcc aaggacttcc cctggtgaa cgtgcaggac     600
atcatcgtgg acaactgcgc catgcagctc gtcatgcgtc ccgagcgctt tgacgtcatc     660
gtcaccacca acctcctggg ggacatcctc tccgacctcg ccgcggggct cgtggggggc     720
ctgggcctcg cccctcggg caacatcggg gacaccaccg cggtctttga gcccgtccac     780
ggctccgccc ccgacatcgc cggcaagggc atcgccaacc ccacggcggc catcctctcc     840
gcggccatga tgctggacta cctgggggag aaggaggcgg ccaagcgggt ggagaaggcg     900
gtggacctgg tgctggagcg ggggcccagg accctgacc tgggcgggga cgccaccacg     960
gaagccttca ccgaggccgt ggtggaggcg ctcaagagcc tg                     1002
```

<210> SEQ ID NO 22
<211> LENGTH: 334
<212> TYPE: PRT
<213> ORGANISM: Artificial Sequence
<220> FEATURE:
<223> OTHER INFORMATION: TtHIDH R118H polypeptide

<400> SEQUENCE: 22

```
Met Ala Tyr Arg Ile Cys Leu Ile Glu Gly Asp Gly Ile Gly His Glu
1               5                   10                  15

Val Ile Pro Ala Ala Arg Arg Val Leu Glu Ala Thr Gly Leu Pro Leu
            20                  25                  30

Glu Phe Val Glu Ala Glu Ala Gly Trp Glu Thr Phe Glu Arg Arg Gly
        35                  40                  45

Thr Ser Val Pro Glu Glu Thr Val Glu Lys Ile Leu Ser Cys His Ala
    50                  55                  60

Thr Leu Phe Gly Ala Ala Thr Ser Pro Thr Arg Lys Val Pro Gly Phe
65                  70                  75                  80

Phe Gly Ala Ile Arg Tyr Leu Arg Arg Leu Asp Leu Tyr Ala Asn
                85                  90                  95

Val Arg Pro Ala Lys Ser Arg Pro Val Pro Gly Ser Arg Pro Gly Val
            100                 105                 110

Asp Leu Val Ile Val His Glu Asn Thr Glu Gly Leu Tyr Val Glu Gln
        115                 120                 125
```

```
Glu Arg Arg Tyr Leu Asp Val Ala Ile Ala Asp Ala Val Ile Ser Lys
            130                 135                 140
Lys Ala Ser Glu Arg Ile Gly Arg Ala Ala Leu Arg Ile Ala Glu Gly
145                 150                 155                 160
Arg Pro Arg Lys Thr Leu His Ile Ala His Lys Ala Asn Val Leu Pro
                165                 170                 175
Leu Thr Gln Gly Leu Phe Leu Asp Thr Val Lys Glu Val Ala Lys Asp
            180                 185                 190
Phe Pro Leu Val Asn Val Gln Asp Ile Ile Val Asp Asn Cys Ala Met
            195                 200                 205
Gln Leu Val Met Arg Pro Glu Arg Phe Asp Val Ile Val Thr Thr Asn
            210                 215                 220
Leu Leu Gly Asp Ile Leu Ser Asp Leu Ala Ala Gly Leu Val Gly Gly
225                 230                 235                 240
Leu Gly Leu Ala Pro Ser Gly Asn Ile Gly Asp Thr Thr Ala Val Phe
                245                 250                 255
Glu Pro Val His Gly Ser Ala Pro Asp Ile Ala Gly Lys Gly Ile Ala
            260                 265                 270
Asn Pro Thr Ala Ala Ile Leu Ser Ala Ala Met Met Leu Asp Tyr Leu
            275                 280                 285
Gly Glu Lys Glu Ala Ala Lys Arg Val Glu Lys Ala Val Asp Leu Val
290                 295                 300
Leu Glu Arg Gly Pro Arg Thr Pro Asp Leu Gly Gly Asp Ala Thr Thr
305                 310                 315                 320
Glu Ala Phe Thr Glu Ala Val Val Glu Ala Leu Lys Ser Leu
                325                 330

<210> SEQ ID NO 23
<211> LENGTH: 1095
<212> TYPE: DNA
<213> ORGANISM: Saccharomyces cerevisiae

<400> SEQUENCE: 23
atgtctgccc taagaagat cgtcgttttg ccaggtgacc acgttggtca agaaatcaca      60
gccgaagcca ttaaggttct taaagctatt tctgatgttc gttccaatgt caagttcgat     120
ttcgaaaatc atttaattgg tggtgctgct atcgatgcta aggtgttcc acttccagat     180
gaggcgctgg aagcctccaa gaaggctgat gccgttttgt aggtgctgt gggtggtcct     240
aaatggggta ccggtagtgt tagacctgaa caaggtttac taaaaatccg taagaacctt     300
caattgtacg ccaacttaag accatgtaac tttgcatccg actctctttt agacttatct     360
ccaatcaagc acaatttgc taaaggtact gacttcgttg ttgtcagaga attagtggga     420
ggtatttact ttggtaagag aaaggaagac gatggtgatg gtgtcgcttg ggatagtgaa     480
caatacaccg ttccagaagt gcaaagaatc acaagaatgg ccgctttcat ggccctacaa     540
catgagccac cattgcctat ttggtccttg gataaagcta atgttttggc ctcttcaaga     600
ttatggagaa aaactgtgga ggaaaccatc aagaacgaat ccctacatt gaaggttcaa     660
catcaattga ttgattctgc cgccatgatc ctagttaaga acccaaccca cctaaatggt     720
attataatca ccagcaacat gtttggtgat atcatctccg atgaagcctc cgttatccca     780
ggttccttgg gtttgttgcc atctgcgtcc ttggcctctt gccagacaa gaacaccgca     840
tttggttttgt acgaaccatg ccacggttct gctccagatt tgccaaagaa taaggtcaac     900
cctatcgcca ctatcttgtc tgctgcaatg atgttgaaat tgtcattgaa cttgcctgaa     960
```

```
gaaggtaagg ccattgaaga tgcagttaaa aaggttttgg atgcaggtat cagaactggt   1020
gatttaggtg gttccaacag taccaccgaa gtcggtgatg ctgtcgccga agaagttaag   1080
aaaatccttg cttaa                                                    1095
```

<210> SEQ ID NO 24
<211> LENGTH: 364
<212> TYPE: PRT
<213> ORGANISM: Saccharomyces cerevisiae

<400> SEQUENCE: 24

```
Met Ser Ala Pro Lys Lys Ile Val Val Leu Pro Gly Asp His Val Gly
1               5                   10                  15

Gln Glu Ile Thr Ala Glu Ala Ile Lys Val Leu Lys Ala Ile Ser Asp
            20                  25                  30

Val Arg Ser Asn Val Lys Phe Asp Phe Glu Asn His Leu Ile Gly Gly
        35                  40                  45

Ala Ala Ile Asp Ala Thr Gly Val Pro Leu Pro Asp Glu Ala Leu Glu
    50                  55                  60

Ala Ser Lys Lys Ala Asp Ala Val Leu Leu Gly Ala Val Gly Gly Pro
65                  70                  75                  80

Lys Trp Gly Thr Gly Ser Val Arg Pro Glu Gln Gly Leu Leu Lys Ile
                85                  90                  95

Arg Lys Glu Leu Gln Leu Tyr Ala Asn Leu Arg Pro Cys Asn Phe Ala
            100                 105                 110

Ser Asp Ser Leu Leu Asp Leu Ser Pro Ile Lys Pro Gln Phe Ala Lys
        115                 120                 125

Gly Thr Asp Phe Val Val Val Arg Glu Leu Val Gly Gly Ile Tyr Phe
    130                 135                 140

Gly Lys Arg Lys Glu Asp Asp Gly Asp Gly Val Ala Trp Asp Ser Glu
145                 150                 155                 160

Gln Tyr Thr Val Pro Glu Val Gln Arg Ile Thr Arg Met Ala Ala Phe
                165                 170                 175

Met Ala Leu Gln His Glu Pro Pro Leu Pro Ile Trp Ser Leu Asp Lys
            180                 185                 190

Ala Asn Val Leu Ala Ser Ser Arg Leu Trp Arg Lys Thr Val Glu Glu
        195                 200                 205

Thr Ile Lys Asn Glu Phe Pro Thr Leu Lys Val Gln His Gln Leu Ile
    210                 215                 220

Asp Ser Ala Ala Met Ile Leu Val Lys Asn Pro Thr His Leu Asn Gly
225                 230                 235                 240

Ile Ile Ile Thr Ser Asn Met Phe Gly Asp Ile Ile Ser Asp Glu Ala
                245                 250                 255

Ser Val Ile Pro Gly Ser Leu Gly Leu Leu Pro Ser Ala Ser Leu Ala
            260                 265                 270

Ser Leu Pro Asp Lys Asn Thr Ala Phe Gly Leu Tyr Glu Pro Cys His
        275                 280                 285

Gly Ser Ala Pro Asp Leu Pro Lys Asn Lys Val Asn Pro Ile Ala Thr
    290                 295                 300

Ile Leu Ser Ala Ala Met Met Leu Lys Leu Ser Leu Asn Leu Pro Glu
305                 310                 315                 320

Glu Gly Lys Ala Ile Glu Asp Ala Val Lys Lys Val Leu Asp Ala Gly
                325                 330                 335

Ile Arg Thr Gly Asp Leu Gly Gly Ser Asn Ser Thr Thr Glu Val Gly
            340                 345                 350
```

```
Asp Ala Val Ala Glu Glu Val Lys Lys Ile Leu Ala
        355                 360
```

<210> SEQ ID NO 25
<211> LENGTH: 1095
<212> TYPE: DNA
<213> ORGANISM: Artificial Sequence
<220> FEATURE:
<223> OTHER INFORMATION: ScIPMDH R136H polynucleotide

<400> SEQUENCE: 25

```
atgtctgccc ctaagaagat cgtcgttttg ccaggtgacc acgttggtca agaaatcaca      60
gccgaagcca ttaaggttct taaagctatt tctgatgttc gttccaatgt caagttcgat     120
ttcgaaaatc atttaattgg tggtgctgct atcgatgcta caggtgttcc acttccagat     180
gaggcgctgg aagcctccaa gaaggctgat gccgttttgt taggtgctgt gggtggtcct     240
aaatggggta ccggtagtgt tagacctgaa caaggtttac taaaaatccg taagaacctt     300
caattgtacg ccaacttaag accatgtaac tttgcatccg actctctttt agacttatct     360
ccaatcaagc cacaatttgc taaaggtact gacttcgttg ttgtccatga attagtggga     420
ggtatttact ttggtaagag aaaggaagac gatggtgatg gtgtcgcttg ggatagtgaa     480
caatacaccg ttccagaagt gcaaagaatc acaagaatgg ccgctttcat ggccctacaa     540
catgagccac cattgcctat tggtccttga dataaagcta atgttttggc ctcttcaaga     600
ttatggagaa aaactgtgga ggaaaccatc aagaacgaat ccctacatt gaaggttcaa     660
catcaattga ttgattctgc cgccatgatc ctagttaaga acccaaccca cctaaatggt     720
attataatca ccagcaacat gtttggtgat atcatctccg atgaagcctc cgttatccca     780
ggttccttgg gtttgttgcc atctgcgtcc ttggcctctt tgccagacaa gaacaccgca     840
tttggtttgt acgaaccatg ccacggttct gctccagatt tgccaaagaa taaggtcaac     900
cctatcgcca ctatcttgtc tgctgcaatg atgttgaaat tgtcattgaa cttgcctgaa     960
gaaggtaagg ccattgaaga tgcagttaaa aaggttttgg atgcaggtat cagaactggt     1020
gatttaggtg gttccaacag taccaccgaa gtcggtgatg ctgtcgccga agaagttaag     1080
aaaatccttg cttaa                                                     1095
```

<210> SEQ ID NO 26
<211> LENGTH: 364
<212> TYPE: PRT
<213> ORGANISM: Artificial Sequence
<220> FEATURE:
<223> OTHER INFORMATION: ScIPMDH R136H polypeptide

<400> SEQUENCE: 26

```
Met Ser Ala Pro Lys Lys Ile Val Val Leu Pro Gly Asp His Val Gly
1               5                   10                  15

Gln Glu Ile Thr Ala Glu Ala Ile Lys Val Leu Lys Ala Ile Ser Asp
            20                  25                  30

Val Arg Ser Asn Val Lys Phe Asp Phe Glu Asn His Leu Ile Gly Gly
        35                  40                  45

Ala Ala Ile Asp Ala Thr Gly Val Pro Leu Pro Asp Glu Ala Leu Glu
    50                  55                  60

Ala Ser Lys Lys Ala Asp Ala Val Leu Leu Gly Ala Val Gly Gly Pro
65                  70                  75                  80

Lys Trp Gly Thr Gly Ser Val Arg Pro Glu Gln Gly Leu Leu Lys Ile
                85                  90                  95

Arg Lys Glu Leu Gln Leu Tyr Ala Asn Leu Arg Pro Cys Asn Phe Ala
```

|  |  |  |  | 100 |  |  |  |  | 105 |  |  |  |  | 110 |  |  |  |
|---|---|---|---|---|---|---|---|---|---|---|---|---|---|---|---|---|---|
| Ser | Asp | Ser | Leu | Leu | Asp | Leu | Ser | Pro | Ile | Lys | Pro | Gln | Phe | Ala | Lys |  |  |
|  |  |  |  | 115 |  |  |  |  | 120 |  |  |  |  | 125 |  |  |  |
| Gly | Thr | Asp | Phe | Val | Val | Val | His | Glu | Leu | Val | Gly | Gly | Ile | Tyr | Phe |  |  |
|  |  |  |  | 130 |  |  |  |  | 135 |  |  |  |  | 140 |  |  |  |
| Gly | Lys | Arg | Lys | Glu | Asp | Asp | Gly | Asp | Gly | Val | Ala | Trp | Asp | Ser | Glu |  |  |
| 145 |  |  |  |  | 150 |  |  |  |  | 155 |  |  |  |  | 160 |  |  |
| Gln | Tyr | Thr | Val | Pro | Glu | Val | Gln | Arg | Ile | Thr | Arg | Met | Ala | Ala | Phe |  |  |
|  |  |  |  | 165 |  |  |  |  | 170 |  |  |  |  | 175 |  |  |  |
| Met | Ala | Leu | Gln | His | Glu | Pro | Pro | Leu | Pro | Ile | Trp | Ser | Leu | Asp | Lys |  |  |
|  |  |  |  | 180 |  |  |  |  | 185 |  |  |  |  | 190 |  |  |  |
| Ala | Asn | Val | Leu | Ala | Ser | Ser | Arg | Leu | Trp | Arg | Lys | Thr | Val | Glu | Glu |  |  |
|  |  |  |  | 195 |  |  |  |  | 200 |  |  |  |  | 205 |  |  |  |
| Thr | Ile | Lys | Asn | Glu | Phe | Pro | Thr | Leu | Lys | Val | Gln | His | Gln | Leu | Ile |  |  |
|  |  |  |  | 210 |  |  |  |  | 215 |  |  |  |  | 220 |  |  |  |
| Asp | Ser | Ala | Ala | Met | Ile | Leu | Val | Lys | Asn | Pro | Thr | His | Leu | Asn | Gly |  |  |
| 225 |  |  |  |  | 230 |  |  |  |  | 235 |  |  |  |  | 240 |  |  |
| Ile | Ile | Ile | Thr | Ser | Asn | Met | Phe | Gly | Asp | Ile | Ile | Ser | Asp | Glu | Ala |  |  |
|  |  |  |  | 245 |  |  |  |  | 250 |  |  |  |  | 255 |  |  |  |
| Ser | Val | Ile | Pro | Gly | Ser | Leu | Gly | Leu | Leu | Pro | Ser | Ala | Ser | Leu | Ala |  |  |
|  |  |  |  | 260 |  |  |  |  | 265 |  |  |  |  | 270 |  |  |  |
| Ser | Leu | Pro | Asp | Lys | Asn | Thr | Ala | Phe | Gly | Leu | Tyr | Glu | Pro | Cys | His |  |  |
|  |  |  |  | 275 |  |  |  |  | 280 |  |  |  |  | 285 |  |  |  |
| Gly | Ser | Ala | Pro | Asp | Leu | Pro | Lys | Asn | Lys | Val | Asn | Pro | Ile | Ala | Thr |  |  |
|  |  |  |  | 290 |  |  |  |  | 295 |  |  |  |  | 300 |  |  |  |
| Ile | Leu | Ser | Ala | Ala | Met | Met | Leu | Lys | Leu | Ser | Leu | Asn | Leu | Pro | Glu |  |  |
| 305 |  |  |  |  | 310 |  |  |  |  | 315 |  |  |  |  | 320 |  |  |
| Glu | Gly | Lys | Ala | Ile | Glu | Asp | Ala | Val | Lys | Lys | Val | Leu | Asp | Ala | Gly |  |  |
|  |  |  |  | 325 |  |  |  |  | 330 |  |  |  |  | 335 |  |  |  |
| Ile | Arg | Thr | Gly | Asp | Leu | Gly | Ser | Asn | Ser | Thr | Thr | Glu | Val | Gly |  |  |  |
|  |  |  |  | 340 |  |  |  |  | 345 |  |  |  |  | 350 |  |  |  |
| Asp | Ala | Val | Ala | Glu | Glu | Val | Lys | Lys | Ile | Leu | Ala |  |  |  |  |  |  |
|  |  |  |  | 355 |  |  |  |  | 360 |  |  |  |  |  |  |  |  |

<210> SEQ ID NO 27
<211> LENGTH: 1038
<212> TYPE: DNA
<213> ORGANISM: Thermus thermophilus

<400> SEQUENCE: 27

```
atgaaggtgg ccgtgctccc cggggacggg atcggccccg aggtcaccga ggccgccctg      60
aaggtcctaa gggccctgga cgaggccgag ggcctgggcc tcgcctacga ggtcttcccc     120
ttcggcgggg cggccataga cgccttcggc gagcccttcc ccgagcccac gcgaaagggc     180
gtggaggagg cggaggcggt gcttctggga agcgtggggg ggcccaagtg ggacggcctt     240
ccccgcaaga tccgcccgga cgggggcttc ttttccttaa ggaaaagcca ggacctcttc     300
gccaacctcc gccggccaa ggtcttcccc gggctggaaa gcttttcccc cctgaaggag     360
gagatcgccc gggggggtgga cgtcctcatc gtccgggagc tcaccggggg gatctacttc     420
ggggagcccc gggggatgtc ggaggccgag gcctggaaca cggagcgcta cagcaagccc     480
gaggtggagc gggtggcccg ggtggccttt gaggcggcga ggaagcgcag gaagcacgtg     540
gtgagcgtgg acaaggcgaa cgtcctcgag gtggggagt  ctggcgcaa gaccgtggag     600
gaggtggggc ggggctaccc cgacgtcgcc ctggagcacc agtacgtgga cgccatggcc     660
```

```
atgcacctgg tccgctcccc tgcccgcttt gacgtggtgg tcacggggaa catcttcggg    720
gacatcctct cggacctggc gagcgtcctc ccaggctctc taggcctcct ccctccgcc     780 tccttgggaa ggggcacccc ggtctttgag cccgtgcacg gctccgcccc ggacatcgcc    840
ggcaaaggcc tcgccaaccc cacggccgcc atcctctccg cggccatgat gctggagcac    900
gccttcggcc tggtggagct ggcgcggaag gtggaagacg cggtggccaa ggccctcctg    960
gaggccccac cccccgacct cggggggaagc gcgggcacgg aggccttcac ggccacggtc   1020
ctccgccacc tcgcctaa                                                  1038
```

<210> SEQ ID NO 28
<211> LENGTH: 345
<212> TYPE: PRT
<213> ORGANISM: Thermus thermophilus
<400> SEQUENCE: 28

```
Met Lys Val Ala Val Leu Pro Gly Asp Gly Ile Gly Pro Glu Val Thr
1               5                   10                  15

Glu Ala Ala Leu Lys Val Leu Arg Ala Leu Asp Glu Ala Glu Gly Leu
            20                  25                  30

Gly Leu Ala Tyr Glu Val Phe Pro Phe Gly Gly Ala Ala Ile Asp Ala
        35                  40                  45

Phe Gly Glu Pro Phe Pro Glu Pro Thr Arg Lys Gly Val Glu Ala
    50                  55                  60

Glu Ala Val Leu Leu Gly Ser Val Gly Gly Pro Lys Trp Asp Gly Leu
65                  70                  75                  80

Pro Arg Lys Ile Arg Pro Glu Thr Gly Leu Leu Ser Leu Arg Lys Ser
                85                  90                  95

Gln Asp Leu Phe Ala Asn Leu Arg Pro Ala Lys Val Phe Pro Gly Leu
            100                 105                 110

Glu Arg Leu Ser Pro Leu Lys Glu Glu Ile Ala Arg Gly Val Asp Val
        115                 120                 125

Leu Ile Val Arg Glu Leu Thr Gly Gly Ile Tyr Phe Gly Glu Pro Arg
    130                 135                 140

Gly Met Ser Glu Ala Glu Ala Trp Asn Thr Glu Arg Tyr Ser Lys Pro
145                 150                 155                 160

Glu Val Glu Arg Val Ala Arg Val Ala Phe Glu Ala Ala Arg Lys Arg
                165                 170                 175

Arg Lys His Val Val Ser Val Asp Lys Ala Asn Val Leu Glu Val Gly
            180                 185                 190

Glu Phe Trp Arg Lys Thr Val Glu Glu Val Gly Arg Gly Tyr Pro Asp
        195                 200                 205

Val Ala Leu Glu His Gln Tyr Val Asp Ala Met Ala Met His Leu Val
    210                 215                 220

Arg Ser Pro Ala Arg Phe Asp Val Val Thr Gly Asn Ile Phe Gly
225                 230                 235                 240

Asp Ile Leu Ser Asp Leu Ala Ser Val Leu Pro Gly Ser Leu Gly Leu
                245                 250                 255

Leu Pro Ser Ala Ser Leu Gly Arg Gly Thr Pro Val Phe Glu Pro Val
            260                 265                 270

His Gly Ser Ala Pro Asp Ile Ala Gly Lys Gly Leu Ala Asn Pro Thr
        275                 280                 285

Ala Ala Ile Leu Ser Ala Ala Met Met Leu Glu His Ala Phe Gly Leu
    290                 295                 300

Val Glu Leu Ala Arg Lys Val Glu Asp Ala Val Ala Lys Ala Leu Leu
```

```
                305                 310                 315                 320
Glu Ala Pro Pro Pro Asp Leu Gly Gly Ser Ala Gly Thr Glu Ala Phe
                325                 330                 335
Thr Ala Thr Val Leu Arg His Leu Ala
                340             345

<210> SEQ ID NO 29
<211> LENGTH: 1038
<212> TYPE: DNA
<213> ORGANISM: Artificial Sequence
<220> FEATURE:
<223> OTHER INFORMATION: TtIPMDH R132H polynucleotide

<400> SEQUENCE: 29
atgaaggtgg ccgtgctccc cggggacggg atcggccccg aggtcaccga ggccgccctg      60
aaggtcctaa gggccctgga cgaggccgag ggcctgggcc tcgcctacga ggtcttcccc     120
ttcggcgggg cggccataga cgccttcggc gagcccttcc ccgagcccac gcgaaagggc     180
gtggaggagg cggaggcggt gcttctggga agcgtggggg ggcccaagtg ggacggcctt     240
ccccgcaaga tccgcccgga gacggggctt ctttccttaa ggaaaagcca ggacctcttc     300
gccaacctcc gcccggccaa ggtcttcccc gggctggaaa ggctttcccc cctgaaggag     360
gagatcgccc gggggtgga cgtcctcatc gtccatgagc tcaccggggg gatctacttc     420
ggggagcccc gggggatgtc ggaggccgag gcctggaaca cggagcgcta cagcaagccc     480
gaggtggagc gggtggcccg ggtggccttt gaggcggcga ggaagcgcag gaagcacgtg     540
gtgagcgtgg acaaggcgaa cgtcctcgag gtggggagt tctggcgcaa gaccgtggag     600
gaggtggggc ggggctaccc cgacgtcgcc ctggagcacc agtacgtgga cgccatggcc     660
atgcacctgg tccgctcccc tgcccgcttt gacgtggtgg tcacggggaa catcttcggg     720
gacatcctct cggacctggc gagcgtcctc ccaggctctc taggcctcct ccctccgcc     780
tccttgggaa ggggcacccc ggtctttgag cccgtgcacg gctccgcccc ggacatcgcc     840
ggcaaaggcc tcgccaaccc cacggccgcc atcctctccg cggccatgat gctggagcac     900
gccttcggcc tggtggagct ggcgcggaag gtggaagacg cggtggccaa ggcccttctg     960
gaggccccac cccccgacct cggggaagc gcgggcacgg aggccttcac ggccacggtc    1020
ctccgccacc tcgcctaa                                                   1038

<210> SEQ ID NO 30
<211> LENGTH: 345
<212> TYPE: PRT
<213> ORGANISM: Artificial Sequence
<220> FEATURE:
<223> OTHER INFORMATION: TtIPMDH R132H polypeptide

<400> SEQUENCE: 30

Met Lys Val Ala Val Leu Pro Gly Asp Gly Ile Gly Pro Glu Val Thr
1               5                   10                  15
Glu Ala Ala Leu Lys Val Leu Arg Ala Leu Asp Glu Ala Glu Gly Leu
            20                  25                  30
Gly Leu Ala Tyr Glu Val Phe Pro Phe Gly Gly Ala Ala Ile Asp Ala
        35                  40                  45
Phe Gly Glu Pro Phe Pro Glu Pro Thr Arg Lys Gly Val Glu Glu Ala
    50                  55                  60
Glu Ala Val Leu Leu Gly Ser Val Gly Gly Pro Lys Trp Asp Gly Leu
65                  70                  75                  80
Pro Arg Lys Ile Arg Pro Glu Thr Gly Leu Leu Ser Leu Arg Lys Ser
```

|  |  |  |  | 85 |  |  |  |  | 90 |  |  |  |  | 95 |  |

Gln Asp Leu Phe Ala Asn Leu Arg Pro Ala Lys Val Phe Pro Gly Leu
                100                 105                 110

Glu Arg Leu Ser Pro Leu Lys Glu Glu Ile Ala Arg Gly Val Asp Val
            115                 120                 125

Leu Ile Val His Glu Leu Thr Gly Gly Ile Tyr Phe Gly Glu Pro Arg
        130                 135                 140

Gly Met Ser Glu Ala Glu Ala Trp Asn Thr Glu Arg Tyr Ser Lys Pro
145                 150                 155                 160

Glu Val Glu Arg Val Ala Arg Val Ala Phe Glu Ala Ala Arg Lys Arg
                165                 170                 175

Arg Lys His Val Val Ser Val Asp Lys Ala Asn Val Leu Glu Val Gly
            180                 185                 190

Glu Phe Trp Arg Lys Thr Val Glu Glu Val Gly Arg Gly Tyr Pro Asp
        195                 200                 205

Val Ala Leu Glu His Gln Tyr Val Asp Ala Met Ala Met His Leu Val
210                 215                 220

Arg Ser Pro Ala Arg Phe Asp Val Val Thr Gly Asn Ile Phe Gly
225                 230                 235                 240

Asp Ile Leu Ser Asp Leu Ala Ser Val Leu Pro Gly Ser Leu Gly Leu
                245                 250                 255

Leu Pro Ser Ala Ser Leu Gly Arg Gly Thr Pro Val Phe Glu Pro Val
            260                 265                 270

His Gly Ser Ala Pro Asp Ile Ala Gly Lys Gly Leu Ala Asn Pro Thr
        275                 280                 285

Ala Ala Ile Leu Ser Ala Ala Met Met Leu Glu His Ala Phe Gly Leu
        290                 295                 300

Val Glu Leu Ala Arg Lys Val Glu Asp Ala Val Ala Lys Ala Leu Leu
305                 310                 315                 320

Glu Ala Pro Pro Pro Asp Leu Gly Gly Ser Ala Gly Thr Glu Ala Phe
                325                 330                 335

Thr Ala Thr Val Leu Arg His Leu Ala
            340                 345

<210> SEQ ID NO 31
<211> LENGTH: 1086
<212> TYPE: DNA
<213> ORGANISM: Escherichia coli

<400> SEQUENCE: 31
atgatgaaaa cgatgcgtat tgctgcgatc ccgggagacg ggattggcaa agaagtcctt      60
cctgaaggga ttcgcgtgtt acaggctgcc gctgagcgct ggggcttcgc cttgagtttt     120
gagcaaatgg agtgggcgag ctgcgagtat tacagccatc acggtaaaat gatgccggac     180
gactggcatg agcaacttag ccgtttcgac gccatctatt ttggtgccgt cggctggccg     240
gacaccgttc cggaccatat ttcgttgtgg ggttcgctgc tgaaatttcg tcgtgaattc     300
gaccagtacg tcaacctgcg cccggttcgt ctctttcctg cgttccctg cccgctggcg     360 ggaaaacagc ctggcgacat cgattttta gtggtcaggg aaaacaccga aggcgaatat     420
tcctcgctcg gcggtagagt gaatgaaggt acagagcatg aagtcgtcat tcaggaatcg     480
gtatttacgc gtcgtggtgt cgatcgcatt ttgcgttatg ccttcgaact tgcgcaaagc     540
cgcccacgta agacgctaac ttctgccact aaatcaaacg gtttagccat cagcatgccg     600
tactgggatg agcgagtgga agcaatggcc gagaattacc cggagatccg ctgggacaag     660

-continued

```
cagcatattg atattctctg cgcgcgtttt gtgatgcagc cggaacgctt cgatgtggtg    720
gtggcgtcca atttgtttgg cgatatcctt tccgatcttg gcccggcctg caccggcacc    780
attggcattg ccccatccgc caacctgaat ccggaacgca ctttcccctc gctcttcgag    840
cctgtccacg gttccgcgcc ggatatctac gggaaaaata ttgctaaccc tatcgccaca    900
atttgggccg gggcaatgat gctcgatttt ctcggcaatg gcgatgagcg tttccagcaa    960
gcgcataacg gtattctggc agcgattgaa gaagtgattg ctcacgggcc gaaaacaccg   1020
gatatgaaag gcagtgccac cacgccacag gttgccgacg cgatttgcaa aattattttg   1080
cgttaa                                                              1086
```

<210> SEQ ID NO 32
<211> LENGTH: 361
<212> TYPE: PRT
<213> ORGANISM: Escherichia coli

<400> SEQUENCE: 32

```
Met Met Lys Thr Met Arg Ile Ala Ala Ile Pro Gly Asp Gly Ile Gly
1               5                   10                  15

Lys Glu Val Leu Pro Glu Gly Ile Arg Val Leu Gln Ala Ala Ala Glu
            20                  25                  30

Arg Trp Gly Phe Ala Leu Ser Phe Glu Gln Met Glu Trp Ala Ser Cys
        35                  40                  45

Glu Tyr Tyr Ser His His Gly Lys Met Met Pro Asp Asp Trp His Glu
    50                  55                  60

Gln Leu Ser Arg Phe Asp Ala Ile Tyr Phe Gly Ala Val Gly Trp Pro
65                  70                  75                  80

Asp Thr Val Pro Asp His Ile Ser Leu Trp Gly Ser Leu Leu Lys Phe
                85                  90                  95

Arg Arg Glu Phe Asp Gln Tyr Val Asn Leu Arg Pro Val Arg Leu Phe
            100                 105                 110

Pro Gly Val Pro Cys Pro Leu Ala Gly Lys Gln Pro Gly Asp Ile Asp
        115                 120                 125

Phe Tyr Val Val Arg Glu Asn Thr Glu Gly Glu Tyr Ser Ser Leu Gly
    130                 135                 140

Gly Arg Val Asn Glu Gly Thr Glu His Glu Val Val Ile Gln Glu Ser
145                 150                 155                 160

Val Phe Thr Arg Arg Gly Val Asp Arg Ile Leu Arg Tyr Ala Phe Glu
                165                 170                 175

Leu Ala Gln Ser Arg Pro Arg Lys Thr Leu Thr Ser Ala Thr Lys Ser
            180                 185                 190

Asn Gly Leu Ala Ile Ser Met Pro Tyr Trp Asp Glu Arg Val Glu Ala
        195                 200                 205

Met Ala Glu Asn Tyr Pro Glu Ile Arg Trp Asp Lys Gln His Ile Asp
    210                 215                 220

Ile Leu Cys Ala Arg Phe Val Met Gln Pro Glu Arg Phe Asp Val Val
225                 230                 235                 240

Val Ala Ser Asn Leu Phe Gly Asp Ile Leu Ser Asp Leu Gly Pro Ala
                245                 250                 255

Cys Thr Gly Thr Ile Gly Ile Ala Pro Ser Ala Asn Leu Asn Pro Glu
            260                 265                 270

Arg Thr Phe Pro Ser Leu Phe Glu Pro Val His Gly Ser Ala Pro Asp
        275                 280                 285

Ile Tyr Gly Lys Asn Ile Ala Asn Pro Ile Ala Thr Ile Trp Ala Gly
    290                 295                 300
```

Ala Met Met Leu Asp Phe Leu Gly Asn Gly Asp Glu Arg Phe Gln Gln
305                 310                 315                 320

Ala His Asn Gly Ile Leu Ala Ala Ile Glu Glu Val Ile Ala His Gly
                325                 330                 335

Pro Lys Thr Pro Asp Met Lys Gly Ser Ala Thr Thr Pro Gln Val Ala
            340                 345                 350

Asp Ala Ile Cys Lys Ile Ile Leu Arg
        355                 360

<210> SEQ ID NO 33
<211> LENGTH: 1086
<212> TYPE: DNA
<213> ORGANISM: Artificial Sequence
<220> FEATURE:
<223> OTHER INFORMATION: EcTDH R133H polynucleotide

<400> SEQUENCE: 33

```
atgatgaaaa cgatgcgtat tgctgcgatc ccgggagacg ggattggcaa agaagtcctt    60
cctgaaggga ttcgcgtgtt acaggctgcc gctgagcgct ggggcttcgc cttgagtttt   120
gagcaaatgg agtgggcgag ctgcgagtat tacagccatc acggtaaaat gatgccggac   180
gactggcatg agcaacttag ccgtttcgac gccatctatt ttggtgccgt cggctggccg   240
gacaccgttc cggaccatat ttcgttgtgg ggttcgctgc tgaaatttcg tcgtgaattc   300
gaccagtacg tcaacctgcg cccggttcgt ctctttcctg gcgttccctg cccgctggcg   360
ggaaaacagc ctggcgacat cgattttac gtggtccatg aaaacaccga aggcgaatat   420
tcctcgctcg gcggtagagt gaatgaaggt acagagcatg aagtcgtcat tcaggaatcg   480
gtatttacgc gtcgtggtgt cgatcgcatt ttgcgttatg ccttcgaact tgcgcaaagc   540
cgcccacgta agacgctaac ttctgccact aaatcaaacg gtttagccat cagcatgccg   600
tactgggatg agcgagtgga agcaatggcc gagaattacc cggagatccg ctgggacaag   660
cagcatattg atattctctg cgcgcgtttt tgtgatgcag cggaacgctt cgatgtggtg   720
gtggcgtcca atttgtttgg cgatatcctt tccgatcttg gcccggcctg caccggcacc   780
attggcattg ccccatccgc caacctgaat ccggaacgca cttttcccctc gctcttcgag   840
cctgtccacg gttccgcgcc ggatatctac gggaaaaata ttgctaaccc tatcgccaca   900
atttgggccg gggcaatgat gctcgatttt ctcggcaatg gcgatgagcg tttccagcaa   960
gcgcataacg gtattctggc agcgattgaa gaagtgattg ctcacgggcc gaaaacaccg  1020
gatatgaaag gcagtgccac cacgccacag gttgccgacg cgatttgcaa aattattttg  1080
cgttaa                                                             1086
```

<210> SEQ ID NO 34
<211> LENGTH: 361
<212> TYPE: PRT
<213> ORGANISM: Artificial Sequence
<220> FEATURE:
<223> OTHER INFORMATION: EcTDH R133H polypeptide

<400> SEQUENCE: 34

Met Met Lys Thr Met Arg Ile Ala Ala Ile Pro Gly Asp Gly Ile Gly
1               5                   10                  15

Lys Glu Val Leu Pro Glu Gly Ile Arg Val Leu Gln Ala Ala Ala Glu
            20                  25                  30

Arg Trp Gly Phe Ala Leu Ser Phe Glu Gln Met Glu Trp Ala Ser Cys
        35                  40                  45

```
Glu Tyr Tyr Ser His His Gly Lys Met Met Pro Asp Asp Trp His Glu
 50                  55                  60

Gln Leu Ser Arg Phe Asp Ala Ile Tyr Phe Gly Ala Val Gly Trp Pro
 65                  70                  75                  80

Asp Thr Val Pro Asp His Ile Ser Leu Trp Gly Ser Leu Leu Lys Phe
                 85                  90                  95

Arg Arg Glu Phe Asp Gln Tyr Val Asn Leu Arg Pro Val Arg Leu Phe
            100                 105                 110

Pro Gly Val Pro Cys Pro Leu Ala Gly Lys Gln Pro Gly Asp Ile Asp
        115                 120                 125

Phe Tyr Val Val His Glu Asn Thr Glu Gly Glu Tyr Ser Ser Leu Gly
    130                 135                 140

Gly Arg Val Asn Glu Gly Thr Glu His Glu Val Val Ile Gln Glu Ser
145                 150                 155                 160

Val Phe Thr Arg Arg Gly Val Asp Arg Ile Leu Arg Tyr Ala Phe Glu
                165                 170                 175

Leu Ala Gln Ser Arg Pro Arg Lys Thr Leu Thr Ser Ala Thr Lys Ser
            180                 185                 190

Asn Gly Leu Ala Ile Ser Met Pro Tyr Trp Asp Glu Arg Val Glu Ala
        195                 200                 205

Met Ala Glu Asn Tyr Pro Glu Ile Arg Trp Asp Lys Gln His Ile Asp
    210                 215                 220

Ile Leu Cys Ala Arg Phe Val Met Gln Pro Glu Arg Phe Asp Val Val
225                 230                 235                 240

Val Ala Ser Asn Leu Phe Gly Asp Ile Leu Ser Asp Leu Gly Pro Ala
                245                 250                 255

Cys Thr Gly Thr Ile Gly Ile Ala Pro Ser Ala Asn Leu Asn Pro Glu
            260                 265                 270

Arg Thr Phe Pro Ser Leu Phe Glu Pro Val His Gly Ser Ala Pro Asp
        275                 280                 285

Ile Tyr Gly Lys Asn Ile Ala Asn Pro Ile Ala Thr Ile Trp Ala Gly
    290                 295                 300

Ala Met Met Leu Asp Phe Leu Gly Asn Gly Asp Glu Arg Phe Gln Gln
305                 310                 315                 320

Ala His Asn Gly Ile Leu Ala Ala Ile Glu Glu Val Ile Ala His Gly
                325                 330                 335

Pro Lys Thr Pro Asp Met Lys Gly Ser Ala Thr Thr Pro Gln Val Ala
            340                 345                 350

Asp Ala Ile Cys Lys Ile Ile Leu Arg
        355                 360

<210> SEQ ID NO 35
<211> LENGTH: 363
<212> TYPE: PRT
<213> ORGANISM: Ajellomyces capsulatus

<400> SEQUENCE: 35

Met Ala Ala Arg Thr Leu Arg Ile Gly Leu Ile Pro Gly Asp Gly Ile
1

```
Ile Leu Lys Lys Glu Cys Asp Gly Ala Leu Phe Gly Ala Val Ser Ser
 65                  70                  75                  80

Pro Ser Thr Lys Val Thr Gly Tyr Ser Ser Pro Ile Val Ala Leu His
             85                  90                  95

Lys Arg Leu Asp Leu Tyr Ala Asn Val Arg Pro Val Arg Thr Thr Ile
            100                 105                 110

Gly Ser Ser Gly Ser Asn Pro Ile Asp Leu Val Ile Val His Glu Asn
            115                 120                 125

Thr Glu Asp Leu Tyr Val Lys Asp Glu Lys Thr Phe Asp Ser Pro Asn
        130                 135                 140

Gly Lys Val Ala Glu Ala Ile Lys Arg Ile Ser Glu His Ala Ser Phe
145                 150                 155                 160

Arg Ile Ala Thr Met Ala Gly Asp Ile Ala Leu Arg Arg Gln Lys Ile
                165                 170                 175

Arg Asp Gly Ala Ala Ala Ser Thr Lys Ser Asn Thr Arg Ser Lys Pro
            180                 185                 190

Met Val Thr Ile Thr His Lys Ser Asn Val Leu Ser Gln Thr Asp Gly
        195                 200                 205

Leu Phe Arg Glu Thr Ala Arg Arg Ala Leu Ala Gln Pro Cys Phe Ala
210                 215                 220

Asp Thr Val Ala Val Glu Glu Gln Ile Val Asp Ser Met Val Tyr Lys
225                 230                 235                 240

Leu Phe Arg Gln Pro Ser Tyr Tyr Asp Val Ile Val Ala Pro Asn Leu
                245                 250                 255

Tyr Gly Asp Ile Leu Ser Asp Gly Ala Ala Leu Val Gly Ser Leu
            260                 265                 270

Gly Leu Val Pro Ser Ala Asn Val Ser Glu Lys Phe Ala Ile Gly Glu
        275                 280                 285

Pro Cys His Gly Ser Ala Pro Asp Ile Glu Gly Lys Gly Ile Ala Asn
290                 295                 300

Pro Ile Ala Thr Leu Arg Ser Val Ala Leu Met Leu Glu Phe Leu Gly
305                 310                 315                 320

Glu Glu Lys Ala Ala Ser Ile Tyr Lys Ala Val Asp Ala Asn Leu
                325                 330                 335

Asp Glu Gly Lys Phe Leu Ser Pro Asp Leu Gly Gly Lys Ala Lys Ala
            340                 345                 350

Glu Glu Val Val Ala Asp Val Leu Arg Arg Leu
        355                 360

<210> SEQ ID NO 36
<211> LENGTH: 363
<212> TYPE: PRT
<213> ORGANISM: Ajellomyces capsulatus

<400> SEQUENCE: 36

```
Pro Ser Thr Lys Val Thr Gly Tyr Ser Ser Pro Ile Val Ala Leu His
            85                  90                  95

Lys Arg Leu Asp Leu Tyr Ala Asn Val Arg Pro Val Arg Thr Thr Ile
            100                 105                 110

Gly Ser Ser Gly Ser Asn Pro Ile Asp Leu Val Ile Val His Glu Asn
            115                 120                 125

Thr Glu Asp Leu Tyr Val Lys Asp Glu Lys Thr Phe Asp Ser Pro Asn
            130                 135                 140

Gly Lys Val Ala Glu Ala Ile Lys Arg Ile Ser Glu His Ala Ser Phe
145                 150                 155                 160

Arg Ile Ala Thr Met Ala Gly Asp Ile Ala Leu Arg Arg Gln Lys Ile
            165                 170                 175

Arg Asp Gly Ala Ala Ala Ser Thr Lys Ser Asn Thr Arg Ser Lys Pro
            180                 185                 190

Met Val Thr Ile Thr His Lys Ser Asn Val Leu Ser Gln Thr Asp Gly
            195                 200                 205

Leu Phe Arg Glu Thr Ala Arg Arg Ala Leu Ala Gln Pro Cys Phe Ala
            210                 215                 220

Asp Thr Val Ala Val Glu Glu Gln Ile Val Asp Ser Met Val Tyr Lys
225                 230                 235                 240

Leu Phe Arg Gln Pro Ser Tyr Tyr Asp Val Ile Val Ala Pro Asn Leu
            245                 250                 255

Tyr Gly Asp Ile Leu Ser Asp Gly Ala Ala Ala Leu Val Gly Ser Leu
            260                 265                 270

Gly Leu Val Pro Ser Ala Asn Val Ser Glu Lys Phe Ala Ile Gly Glu
            275                 280                 285

Pro Cys His Gly Ser Ala Pro Asp Ile Glu Gly Lys Gly Ile Ala Asn
            290                 295                 300

Pro Ile Ala Thr Leu Arg Ser Val Ala Leu Met Leu Glu Phe Leu Gly
305                 310                 315                 320

Glu Glu Lys Ala Ala Ala Ser Ile Tyr Lys Ala Val Asp Ala Asn Leu
            325                 330                 335

Asp Glu Gly Lys Phe Leu Ser Pro Asp Leu Gly Gly Lys Ala Lys Ala
            340                 345                 350

Glu Glu Val Val Ala Asp Val Leu Arg Arg Leu
            355                 360

<210> SEQ ID NO 37
<211> LENGTH: 363
<212> TYPE: PRT
<213> ORGANISM: Ajellomyces dermatitidis

<400> SEQUENCE: 37

Met Ala Ala Arg Thr Leu Arg Ile Gly Leu Ile Pro Gly Asp Gly Ile
1               5                   10                  15

Gly Arg Glu Val Ile Pro Ala Gly Arg Lys Leu Leu Glu Ser Leu Pro
            20                  25                  30

Ala Ser Le

```
Lys Lys Leu Asp Leu Tyr Ala Asn Val Arg Pro Val Arg Thr Thr Thr
            100                 105                 110

Gly Ser Ser Gly Ser Asn Pro Ile Asp Leu Val Ile Val His Glu Asn
            115                 120                 125

Thr Glu Asp Leu Tyr Val Lys Asp Glu Lys Thr Tyr Asp Ser Pro Asn
        130                 135                 140

Gly Lys Val Ala Glu Ala Ile Lys Arg Ile Ser Glu His Ala Ser Phe
145                 150                 155                 160

Arg Ile Ala Thr Met Ala Gly Asn Ile Ala Leu Arg Arg Gln Lys Ile
                165                 170                 175

Arg Asp Thr Ala Ala Ala Ser Asp Asn Val Asn Thr Arg Ser Lys Pro
            180                 185                 190

Met Val Thr Ile Thr His Lys Ser Asn Val Leu Ser Gln Thr Asp Gly
            195                 200                 205

Leu Phe Arg Glu Thr Ala Arg Arg Ala Leu Ala Gln Pro Leu Phe Ile
        210                 215                 220

Asp Thr Val Ala Val Glu Glu Gln Ile Val Asp Ser Met Val Tyr Lys
225                 230                 235                 240

Leu Phe Arg Gln Pro Ser Tyr Tyr Asp Val Ile Val Ala Pro Asn Leu
                245                 250                 255

Tyr Gly Asp Ile Leu Ser Asp Gly Ala Ala Ala Leu Val Gly Ser Leu
            260                 265                 270

Gly Leu Val Pro Ser Ala Asn Val Ser Asp Asn Phe Ala Ile Gly Glu
        275                 280                 285

Pro Cys His Gly Ser Ala Pro Asp Ile Glu Gly Lys Gly Ile Ala Asn
        290                 295                 300

Pro Ile Ala Thr Leu Arg Ser Val Ala Leu Met Leu Glu Phe Leu Gly
305                 310                 315                 320

Glu Glu Lys Ala Ala Ala Ile Ile Tyr Lys Ala Val Asp Ala Asn Leu
                325                 330                 335

Asp Glu Gly Lys Phe Leu Ser Pro Leu Gly Gly Lys Ala Lys Thr
            340                 345                 350

Asp Glu Val Val Ala Asp Val Leu Arg Arg Leu
            355                 360

<210> SEQ ID NO 38
<211> LENGTH: 363
<212> TYPE: PRT
<213> ORGANISM: Ajellomyces dermatitidis

<400> SEQUENCE: 38

Met Ala Ala Arg Thr Leu Arg Ile Gly Leu Ile Pro Gly Asp Gly Ile
1               5                   10                  15

Gly Arg Glu Val Ile Pro Ala Gly Arg Lys Leu Leu Glu Ser Leu Pro
            20                  25                  30

Ala Ser Leu Gly Leu Asn Phe Ser Phe Val Asp Leu Glu Ala Gly Tyr
        35                  40                  45

Asn Thr Phe Lys Lys Thr Gly Thr Ala Leu Pro Asp Lys Thr Val Glu
    50                  55                  60

Ile Leu Lys Lys Glu Cys Asp Gly Ala Leu Phe Gly Ala Val Ser Ser
65                  70                  75                  80

Pro Ser Thr Lys Val Ala Gly Tyr Ser Ser Pro Ile Val Ala Leu His
                85                  90                  95

Lys Lys Leu Asp Leu Tyr Ala Asn Val Arg Pro Val Arg Thr Thr Thr
            100                 105                 110
```

```
Gly Ser Ser Gly Ser Asn Pro Ile Asp Leu Val Ile Val His Glu Asn
            115                 120                 125

Thr Glu Asp Leu Tyr Val Lys Asp Glu Lys Thr Tyr Asp Ser Pro Asn
        130                 135                 140

Gly Lys Val Ala Glu Ala Ile Lys Arg Ile Ser Glu His Ala Ser Phe
145                 150                 155                 160

Arg Ile Ala Thr Met Ala Gly Asn Ile Ala Leu Arg Arg Gln Lys Ile
                165                 170                 175

Arg Asp Thr Ala Ala Ala Ser Asp Asn Val Asn Thr Arg Ser Lys Pro
            180                 185                 190

Met Val Thr Ile Thr His Lys Ser Asn Val Leu Ser Gln Thr Asp Gly
        195                 200                 205

Leu Phe Arg Glu Thr Ala Arg Arg Ala Leu Ala Gln Pro Leu Phe Ile
    210                 215                 220

Asp Thr Val Ala Val Glu Glu Gln Ile Val Asp Ser Met Val Tyr Lys
225                 230                 235                 240

Leu Phe Arg Gln Pro Ser Tyr Tyr Asp Val Ile Val Ala Pro Asn Leu
                245                 250                 255

Tyr Gly Asp Ile Leu Ser Asp Gly Ala Ala Leu Val Gly Ser Leu
            260                 265                 270

Gly Leu Val Pro Ser Ala Asn Val Ser Asp Asn Phe Ala Ile Gly Glu
        275                 280                 285

Pro Cys His Gly Ser Ala Pro Asp Ile Glu Gly Lys Gly Ile Ala Asn
    290                 295                 300

Pro Ile Ala Thr Leu Arg Ser Val Ala Leu Met Leu Glu Phe Leu Gly
305                 310                 315                 320

Glu Glu Lys Ala Ala Ile Ile Tyr Lys Ala Val Asp Ala Asn Leu
                325                 330                 335

Asp Glu Gly Lys Phe Leu Ser Pro Leu Gly Gly Lys Ala Lys Thr
            340                 345                 350

Asp Glu Val Val Ala Asp Val Leu Arg Arg Leu
            355                 360

<210> SEQ ID NO 39
<211> LENGTH: 363
<212> TYPE: PRT
<213> ORGANISM: Ajellomyces dermatitidis

<400> SEQUENCE: 39

Met Ala Ala Arg Thr Leu Arg Ile Gly Leu Ile Pro Gly Asp Gly Ile
1               5                   10                  15

Gly Arg Glu Val Ile Pro Ala Gly Arg Lys Leu Leu Glu Ser Leu Pro
            20                  25                  30

Ala Ser Leu Gly Leu Asn Phe Ser Phe Val Asp Leu Glu Ala Gly Tyr
        35                  40                  45

Asn Thr Phe Lys Lys Thr Gly Thr Ala Leu Pro Asp Lys Thr Val Glu
    50                  55                  60

Ile Leu Lys Lys Glu Cys Asp Gly Ala Leu Phe Gly Ala Val Ser Ser
65                  70                  75                  80

Pro Ser Thr Lys Val Ala Gly Tyr Ser Ser Pro Ile Val Ala Leu His
                85                  90                  95

Lys Lys Leu Asp Leu Tyr Ala Asn Val Arg Pro Val Arg Thr Thr Thr
            100                 105                 110

Gly Ser Ser Gly Ser Asn Pro Ile Asp Leu Val Ile Val His Glu Asn
            115                 120                 125
```

```
Thr Glu Asp Leu Tyr Val Lys Asp Glu Lys Thr Tyr Asp Ser Pro Asn
    130                 135                 140

Gly Lys Val Ala Glu Ala Ile Lys Arg Ile Ser Glu His Ala Ser Phe
145                 150                 155                 160

Arg Ile Ala Thr Met Ala Gly Asn Ile Ala Leu Arg Arg Gln Lys Ile
                165                 170                 175

Arg Asp Thr Ala Ala Ala Ser Asp Asn Val Asn Thr Arg Ser Lys Pro
            180                 185                 190

Met Val Thr Ile Thr His Lys Ser Asn Val Leu Ser Gln Thr Asp Gly
        195                 200                 205

Leu Phe Arg Glu Thr Ala Arg Arg Ala Leu Ala Gln Pro Leu Phe Ile
    210                 215                 220

Asp Thr Val Ala Val Glu Glu Gln Ile Val Asp Ser Met Val Tyr Lys
225                 230                 235                 240

Leu Phe Arg Gln Pro Ser Tyr Tyr Asp Val Ile Val Ala Pro Asn Leu
                245                 250                 255

Tyr Gly Asp Ile Leu Ser Asp Gly Ala Ala Leu Val Gly Ser Leu
            260                 265                 270

Gly Leu Val Pro Ser Ala Asn Val Ser Asp Asn Phe Ala Ile Gly Glu
        275                 280                 285

Pro Cys His Gly Ser Ala Pro Asp Ile Glu Gly Lys Gly Ile Ala Asn
    290                 295                 300

Pro Ile Ala Thr Leu Arg Ser Val Ala Leu Met Leu Glu Phe Leu Gly
305                 310                 315                 320

Glu Glu Lys Ala Ala Ala Ile Ile Tyr Lys Ala Val Asp Ala Asn Leu
                325                 330                 335

Asp Glu Gly Lys Phe Leu Ser Pro Asp Leu Gly Gly Lys Ala Lys Thr
            340                 345                 350

Asp Glu Val Val Ala Asp Val Leu Arg Arg Leu
        355                 360

<210> SEQ ID NO 40
<211> LENGTH: 363
<212> TYPE: PRT
<213> ORGANISM: Ajellomyces dermatitidis

<400> SEQUENCE: 40

Met Ala Ala Arg Thr Leu Arg Ile Gly Leu Ile Pro Gly Asp Gly Ile
1               5                   10                  15

Gly Arg Glu Val Ile Pro Ala Gly Arg Lys Leu Leu Gly Ser Leu Pro
            20                  25                  30

Ala Ser Leu Gly Leu Asn Phe Ser Phe Val Asp Leu Glu Ala Gly Tyr
        35                  40                  45

Asn Thr Phe Lys Lys Thr Gly Thr Ala Leu Pro Asp Lys Thr Val Glu
    50                  55                  60

Ile Leu Lys Lys Glu Cys Asp Gly Ala Leu Phe Gly Ala Val Ser Ser
65                  70                  75                  80

Pro Ser Thr Lys Val Ala Gly Tyr Ser Ser Pro Ile Val Ala Leu His
                85                  90                  95

Lys Lys Leu Asp Leu Tyr Ala Asn Val Arg Pro Val Arg Thr Thr Thr
            100                 105                 110

Gly Ser Ser Gly Ser Asn Pro Ile Asp Leu Val Ile Val His Glu Asn
        115                 120                 125

Thr Glu Asp Leu Tyr Val Lys Asp Glu Lys Thr Tyr Asp Ser Pro Asn
    130                 135                 140
```

```
Gly Lys Val Ala Glu Ala Ile Lys Arg Ile Ser Glu His Ala Ser Phe
145                 150                 155                 160

Arg Ile Ala Thr Met Ala Gly Asn Ile Ala Leu Arg Arg Gln Lys Ile
                165                 170                 175

Arg Asp Thr Ala Ala Ser Asp Asn Val Asn Thr Arg Ser Lys Pro
            180                 185                 190

Met Val Thr Ile Thr His Lys Ser Asn Val Leu Ser Gln Thr Asp Gly
            195                 200                 205

Leu Phe Arg Glu Thr Ala Arg Arg Ala Leu Ala Gln Pro Leu Phe Ile
        210                 215                 220

Asp Thr Val Ala Val Glu Glu Gln Ile Val Asp Ser Met Val Tyr Lys
225                 230                 235                 240

Leu Phe Arg Gln Pro Ser Tyr Tyr Asp Val Ile Val Ala Pro Asn Leu
                245                 250                 255

Tyr Gly Asp Ile Leu Ser Asp Gly Ala Ala Leu Val Gly Ser Leu
            260                 265                 270

Gly Leu Val Pro Ser Ala Asn Val Ser Asp Asn Phe Ala Ile Gly Glu
            275                 280                 285

Pro Cys His Gly Ser Ala Pro Asp Ile Glu Gly Lys Gly Ile Ala Asn
290                 295                 300

Pro Ile Ala Thr Leu Arg Ser Val Ala Leu Met Leu Glu Phe Leu Gly
305                 310                 315                 320

Glu Glu Lys Ala Ala Ala Ile Ile Tyr Lys Ala Val Asp Ala Asn Leu
                325                 330                 335

Asp Glu Gly Lys Phe Leu Ser Pro Asp Leu Gly Gly Lys Ala Lys Thr
            340                 345                 350

Asp Glu Val Val Ala Asp Val Leu Arg Arg Leu
            355                 360

<210> SEQ ID NO 41
<211> LENGTH: 360
<212> TYPE: PRT
<213> ORGANISM: Arthroderma gypseum

<400> SEQUENCE: 41

Met Ala Ala Arg Thr Leu Arg Ile Gly Leu Ile Pro Gly Asp Gly Ile
1               5                   10                  15

Gly Arg Glu Val Ile Pro Ala Gly Arg Arg Ile Leu Glu Ala Leu Pro
                20                  25                  30

Ala Ser Leu Gly Leu Lys Phe Thr Phe Val Asp Leu Glu Ala Gly Tyr
            35                  40                  45

Asp Thr Phe Leu Arg Thr Lys Thr Ala Leu Pro Asp Lys Thr Val Glu
        50                  55                  60

Thr Leu Lys Lys Glu Cys Asp Gly Ala Leu Phe Gly Ala Val Ser Ser
65                  70                  75                  80

Pro Ser Thr Lys Val Ala Gly Tyr Ser Ser Pro Ile Val Ala Leu His
                85                  90                  95

Lys Lys Leu Asp Leu Tyr Ala Asn Val Arg Pro Val Lys Thr Thr Ala
            100                 105                 110

Gly Ala Asn Ala Ser Val Arg Pro Ile Asp Leu Val Ile Val His Glu
        115                 120                 125

Asn Thr Glu Asp Leu Tyr Val Lys Glu Lys Thr Tyr Asp Thr Pro
    130                 135                 140

Asp Gly Lys Val Ala Glu Ala Ile Lys Arg Ile Ser Glu Arg Ala Ser
145                 150                 155                 160
```

```
Phe Arg Ile Gly Ala Met Ala Gly Glu Ile Ala Leu Arg Arg Gln Lys
                165                 170                 175

Ile Arg Gln Ala Gln Ser Ala Asn Thr Thr Thr Glu Pro Met Val
            180                 185                 190

Thr Ile Thr His Lys Ser Asn Val Leu Ser Gln Ser Asp Gly Leu Phe
        195                 200                 205

Arg Glu Thr Cys Arg Lys Ala Leu Ala Asn Asp Lys Phe Ser Ser Ile
    210                 215                 220

Asn Val Glu Glu Gln Ile Val Asp Ser Met Val Tyr Lys Leu Phe Arg
225                 230                 235                 240

Gln Pro Ser Tyr Tyr Asp Val Ile Val Ala Pro Asn Leu Tyr Gly Asp
                245                 250                 255

Ile Leu Ser Asp Gly Ala Ala Leu Val Gly Ser Leu Gly Leu Val
            260                 265                 270

Pro Ser Ala Asn Val Gly Asp Gly Phe Ala Ile Gly Glu Pro Cys His
            275                 280                 285

Gly Ser Ala Pro Asp Ile Glu Gly Lys Gly Ile Ala Asn Pro Ile Ala
            290                 295                 300

Thr Ile Arg Ser Thr Ala Leu Met Leu Glu Phe Leu Gly Glu Gly Glu
305                 310                 315                 320

Ala Ala Ala Arg Ile Tyr Ala Ala Val Asp Ala Asn Leu Asp Glu Gly
                325                 330                 335

Arg Leu Leu Ser Pro Asp Leu Gly Gly Lys Ala Thr Thr Thr Glu Val
                340                 345                 350

Leu Glu Asp Val Leu Lys Lys Leu
                355                 360

<210> SEQ ID NO 42
<211> LENGTH: 360
<212> TYPE: PRT
<213> ORGANISM: Arthroderma gypseum

<400> SEQUENCE: 42

Met Ala Ala Arg Thr Leu Arg Ile Gly Leu Ile Pro Gly Asp Gly Ile
1               5                   10                  15

Gly Arg Glu Val Ile Pro Ala Gly Arg Arg Ile Leu Glu Ala Leu Pro
            20                  25                  30

Ala Ser Leu Gly Leu Lys Phe Thr Phe Val Asp Leu Glu Ala Gly Tyr
        35                  40                  45

Asp Thr Phe Leu Arg Thr Lys Thr Ala Leu Pro Asp Lys Thr Val Glu
    50                  55                  60

Thr Leu Lys Lys Glu Cys Asp Gly Ala Leu Phe Gly Ala Val Ser Ser
65                  70                  75                  80

Pro Ser Thr Lys Val Ala Gly Tyr Ser Ser Pro Ile Val Ala Leu His
                85                  90                  95

Lys Lys Leu Asp Leu Tyr Ala Asn Val Arg Pro Val Lys Thr Thr Ala
                100                 105                 110

Gly Ala Asn Ala Ser Val Arg Pro Ile Asp Leu Val Ile Val His Glu
            115                 120                 125

Asn Thr Glu Asp Leu Tyr Val Lys Glu Lys Thr Tyr Asp Thr Pro
    130                 135                 140

Asp Gly Lys Val Ala Glu Ala Ile Lys Arg Ile Ser Glu Arg Ala Ser
145                 150                 155                 160

Phe Arg Ile Gly Ala Met Ala Gly Glu Ile Ala Leu Arg Arg Gln Lys
                165                 170                 175
```

```
Ile Arg Gln Ala Gln Ser Ala Asn Thr Thr Thr Glu Pro Met Val
            180                 185                 190

Thr Ile Thr His Lys Ser Asn Val Leu Ser Gln Ser Asp Gly Leu Phe
        195                 200                 205

Arg Glu Thr Cys Arg Lys Ala Leu Ala Asn Asp Lys Phe Ser Ser Ile
210                 215                 220

Asn Val Glu Glu Gln Ile Val Asp Ser Met Val Tyr Lys Leu Phe Arg
225                 230                 235                 240

Gln Pro Ser Tyr Tyr Asp Val Ile Val Ala Pro Asn Leu Tyr Gly Asp
                245                 250                 255

Ile Leu Ser Asp Gly Ala Ala Leu Val Gly Ser Leu Gly Leu Val
            260                 265                 270

Pro Ser Ala Asn Val Gly Asp Gly Phe Ala Ile Gly Glu Pro Cys His
            275                 280                 285

Gly Ser Ala Pro Asp Ile Glu Gly Lys Gly Ile Ala Asn Pro Ile Ala
290                 295                 300

Thr Ile Arg Ser Thr Ala Leu Met Leu Glu Phe Leu Gly Glu Gly Glu
305                 310                 315                 320

Ala Ala Ala Arg Ile Tyr Ala Val Asp Ala Asn Leu Asp Glu Gly
                325                 330                 335

Arg Leu Leu Ser Pro Asp Leu Gly Gly Lys Ala Thr Thr Thr Glu Val
            340                 345                 350

Leu Glu Asp Val Leu Lys Lys Leu
            355                 360

<210> SEQ ID NO 43
<211> LENGTH: 361
<212> TYPE: PRT
<213> ORGANISM: Arthroderma otae

<400> SEQUENCE: 43

Met Ala Ala Arg Thr Leu Arg Ile Gly Leu Ile Pro Gly Asp Gly Ile
1               5                   10                  15

Gly Arg Glu Val Ile Pro Ala Gly Arg Arg Ile Leu Glu Ala Leu Pro
            20                  25                  30

Ala Ser Leu Gly Leu Lys Phe Ser Phe Val Asp Leu Glu Ala Gly Tyr
        35                  40                  45

Asp Thr Phe Leu Arg Thr Lys Thr Ala Leu Pro Asp Lys Thr Val Glu
    50                  55                  60

Thr Leu Lys Lys Glu Cys Asp Gly Ala Leu Phe Gly Ala Val Ser Ser
65                  70                  75                  80

Pro Ser Thr Lys Val Ala Gly Tyr Ser Ser Pro Ile Val Ala Leu His
                85                  90                  95

Lys Lys Leu Asp Leu Tyr Ala Asn Val Arg Pro Val Lys Thr Thr Ala
            100                 105                 110

Gly Ala Asn Ala Ser Ala Arg Pro Ile Asp Leu Val Ile Val His Glu
        115                 120                 125

Asn Thr Glu Asp Leu Tyr Val Lys Glu Lys Thr Tyr Asp Thr Pro
    130                 135                 140

Asn Gly Lys Val Ala Glu Ala Ile Lys Arg Ile Ser Glu Arg Ala Ser
145                 150                 155                 160

Phe Arg Ile Gly Thr Met Ala Gly Asp Ile Ala Leu Arg Arg Gln Lys
                165                 170                 175

Val Arg Asp Ser Gln Gln Ser Thr Ala Thr Ala Thr Ser Pro Met
            180                 185                 190
```

-continued

```
Val Thr Ile Thr His Lys Ser Asn Val Leu Ser Gln Ser Asp Gly Leu
            195                 200                 205

Phe Arg Glu Thr Cys Arg Lys Ala Leu Ala Asp Asp Arg Phe Asp Lys
        210                 215                 220

Val His Val Glu Glu Gln Ile Val Asp Ser Met Val Tyr Lys Leu Phe
225                 230                 235                 240

Arg Gln Pro Ser Tyr Tyr Asp Val Ile Val Ala Pro Asn Leu Tyr Gly
                245                 250                 255

Asp Ile Leu Ser Asp Gly Ala Ala Leu Val Gly Ser Leu Gly Leu
            260                 265                 270

Val Pro Ser Ala Asn Val Gly Asp Gly Phe Ala Ile Gly Glu Pro Cys
        275                 280                 285

His Gly Ser Ala Pro Asp Ile Glu Gly Gln Gly Ile Ala Asn Pro Ile
    290                 295                 300

Ala Thr Ile Arg Ser Thr Ala Leu Met Leu Glu Phe Leu Gly Glu Gly
305                 310                 315                 320

Glu Ala Ala Ala Lys Ile Tyr Ala Ala Val Asp Ala Asn Leu Asp Glu
                325                 330                 335

Gly Arg Phe Leu Ser Pro Asp Leu Gly Gly Lys Ala Thr Thr Ala Glu
            340                 345                 350

Val Leu Glu Asp Val Leu Gly Lys Leu
            355                 360
```

<210> SEQ ID NO 44
<211> LENGTH: 361
<212> TYPE: PRT
<213> ORGANISM: Arthroderma otae

<400> SEQUENCE: 44

```
Met Ala Ala Arg Thr Leu Arg Ile Gly Leu Ile Pro Gly Asp Gly Ile
1               5                   10                  15

Gly Arg Glu Val Ile Pro Ala Gly Arg Arg Ile Leu Glu Ala Leu Pro
            20                  25                  30

Ala Ser Leu Gly Leu Lys Phe Ser Phe Val Asp Leu Glu Ala Gly Tyr
        35                  40                  45

Asp Thr Phe Leu Arg Thr Lys Thr Ala Leu Pro Asp Lys Thr Val Glu
    50                  55                  60

Thr Leu Lys Lys Glu Cys Asp Gly Ala Leu Phe Gly Ala Val Ser Ser
65                  70                  75                  80

Pro Ser Thr Lys Val Ala Gly Tyr Ser Ser Pro Ile Val Ala Leu His
                85                  90                  95

Lys Lys Leu Asp Leu Tyr Ala Asn Val Arg Pro Val Lys Thr Thr Ala
            100                 105                 110

Gly Ala Asn Ala Ser Ala Arg Pro Ile Asp Leu Val Ile Val His Glu
        115                 120                 125

Asn Thr Glu Asp Leu Tyr Val Lys Glu Glu Lys Thr Tyr Asp Thr Pro
    130                 135                 140

Asn Gly Lys Val Ala Glu Ala Ile Lys Arg Ile Ser Glu Arg Ala Ser
145                 150                 155                 160

Phe Arg Ile Gly Thr Met Ala Gly Asp Ile Ala Leu Arg Arg Gln Lys
                165                 170                 175

Val Arg Asp Ser Gln Gln Ser Thr Ala Thr Ala Thr Ser Pro Met
            180                 185                 190

Val Thr Ile Thr His Lys Ser Asn Val Leu Ser Gln Ser Asp Gly Leu
        195                 200                 205
```

```
Phe Arg Glu Thr Cys Arg Lys Ala Leu Ala Asp Asp Arg Phe Asp Lys
    210                 215                 220

Val His Val Glu Glu Gln Ile Val Asp Ser Met Val Tyr Lys Leu Phe
225                 230                 235                 240

Arg Gln Pro Ser Tyr Tyr Asp Val Ile Val Ala Pro Asn Leu Tyr Gly
                245                 250                 255

Asp Ile Leu Ser Asp Gly Ala Ala Leu Val Gly Ser Leu Gly Leu
            260                 265                 270

Val Pro Ser Ala Asn Val Gly Asp Gly Phe Ala Ile Gly Glu Pro Cys
        275                 280                 285

His Gly Ser Ala Pro Asp Ile Glu Gly Gln Gly Ile Ala Asn Pro Ile
    290                 295                 300

Ala Thr Ile Arg Ser Thr Ala Leu Met Leu Glu Phe Leu Gly Glu Gly
305                 310                 315                 320

Glu Ala Ala Ala Lys Ile Tyr Ala Ala Val Asp Ala Asn Leu Asp Glu
                325                 330                 335

Gly Arg Phe Leu Ser Pro Asp Leu Gly Gly Lys Ala Thr Thr Ala Glu
            340                 345                 350

Val Leu Glu Asp Val Leu Gly Lys Leu
            355                 360
```

<210> SEQ ID NO 45
<211> LENGTH: 361
<212> TYPE: PRT
<213> ORGANISM: Aspergillus kawachii

<400> SEQUENCE: 45

```
Met Ala Ala Ala Ala Arg Thr Leu Arg Ile Gly Leu Ile Pro Gly Asp
1               5                   10                  15

Gly Ile Gly Arg Glu Val Ile Pro Ala Gly Arg Lys Val Leu Glu Ser
            20                  25                  30

Leu Pro Ser Ser Leu Asn Leu Lys Phe Ser Phe Val Asp Leu Asp Ala
        35                  40                  45

Gly Phe Asp Thr Phe Lys Arg Thr Gly Ser Ala Leu Pro Asp Lys Thr
    50                  55                  60

Val Glu Ile Leu Lys Lys Glu Cys Asp Gly Ala Leu Phe Gly Ala Val
65                  70                  75                  80

Ser Ser Pro Ser Thr Lys Val Ala Gly Tyr Ser Ser Pro Ile Val Ala
                85                  90                  95

Leu His Lys Lys Leu Asp Leu Tyr Ala Asn Val Arg Pro Val Lys Thr
            100                 105                 110

Thr Ala Gly Ser Thr Asp Gly Lys Pro Ile Asp Leu Val Ile Val His
        115                 120                 125

Glu Asn Thr Glu Asp Leu Tyr Val Lys Glu Glu Gln Thr Lys Glu Thr
    130                 135                 140

Pro Asn Gly Lys Val Ala Glu Ala Ile Lys Arg Ile Ser Glu Asn Ala
145                 150                 155                 160

Ser Ser Arg Ile Ser Thr Ile Ala Gly Glu Ile Ala Leu Arg Arg Gln
                165                 170                 175

Lys Ile Arg Ser Val Ala Gly Ile Ala Gly Leu Arg Thr Glu Pro Met
            180                 185                 190

Val Thr Ile Thr His Lys Ser Asn Val Leu Ser Gln Thr Asp Gly Leu
        195                 200                 205

Phe Arg Glu Thr Ala Arg Lys Ala Leu Ser Ala Asp Arg Phe Ser Ser
    210                 215                 220
```

```
Val Gln Val Glu Glu Gln Ile Val Asp Ser Met Val Tyr Lys Leu Phe
225                 230                 235                 240

Arg Gln Pro Glu Tyr Tyr Asp Val Ile Val Ala Pro Asn Leu Tyr Gly
            245                 250                 255

Asp Ile Leu Ser Asp Gly Ala Ala Leu Val Gly Ser Leu Gly Leu
        260                 265                 270

Val Pro Ser Ala Asn Val Gly Asp Gly Phe Ala Ile Gly Glu Pro Cys
        275                 280                 285

His Gly Ser Ala Pro Asp Ile Glu Gly Lys Gly Ile Ala Asn Pro Ile
        290                 295                 300

Ala Thr Leu Arg Ser Val Ala Leu Met Leu Glu Phe Leu Gly Glu Glu
305                 310                 315                 320

Thr Ala Ala Lys Ile Tyr Thr Ala Val Asp Ala Asn Leu Asp Glu
            325                 330                 335

Ala Lys Phe Leu Ser Pro Asp Met Gly Gly Lys Ala Thr Thr Gln Glu
            340                 345                 350

Val Leu Asp Asp Val Leu Lys Arg Leu
            355                 360

<210> SEQ ID NO 46
<211> LENGTH: 361
<212> TYPE: PRT
<213> ORGANISM: Aspergillus niger

<400> SEQUENCE: 46

Met Ala Ala Ala Ala Arg Thr Leu Arg Ile Gly Leu Ile Pro Gly Asp
1               5                   10                  15

Gly Ile Gly Arg Glu Val Ile Pro Ala Gly Arg Lys Val Leu Glu Ser
            20                  25                  30

Leu Pro Ser Ser Leu Asn Leu Lys Phe Ser Phe Val Asp Leu Asp Ala
        35                  40                  45

Gly Phe Asp Thr Phe Lys Arg Thr Gly Ser Ala Leu Pro Asp Lys Thr
    50                  55                  60

Val Glu Ile Leu Lys Lys Glu Cys Asp Gly Ala Leu Phe Gly Ala Val
65                  70                  75                  80

Ser Ser Pro Ser Thr Lys Val Ala Gly Tyr Ser Ser Pro Ile Val Ala
                85                  90                  95

Leu His Lys Lys Leu Asp Leu Tyr Ala Asn Val Arg Pro Val Lys Thr
            100                 105                 110

Thr Ala Gly Ser Thr Asp Gly Lys Pro Ile Asp Leu Val Ile Val His
        115                 120                 125

Glu Asn Thr Glu Asp Leu Tyr Val Lys Glu Gln Thr Lys Glu Thr
130                 135                 140

Pro Asn Gly Lys Val Ala Glu Ala Ile Lys Arg Ile Ser Glu Asn Ala
145                 150                 155                 160

Ser Ser Arg Ile Ser Thr Ile Ala Gly Glu Ile Ala Leu Arg Arg Gln
            165                 170                 175

Lys Ile Arg Ser Val Ala Gly Ile Ala Gly Leu Arg Thr Glu Pro Met
            180                 185                 190

Val Thr Ile Thr His Lys Ser Asn Val Leu Ser Gln Thr Asp Gly Leu
            195                 200                 205

Phe Arg Glu Thr Ala Arg Lys Ala Leu Ser Ala Asp Arg Phe Ser Ser
    210                 215                 220

Val Gln Val Glu Glu Gln Ile Val Asp Ser Met Val Tyr Lys Leu Phe
225                 230                 235                 240
```

```
Arg Gln Pro Glu Tyr Tyr Asp Val Ile Val Ala Pro Asn Leu Tyr Gly
                245                 250                 255

Asp Ile Leu Ser Asp Gly Ala Ala Leu Val Gly Ser Leu Gly Leu
            260                 265                 270

Val Pro Ser Ala Asn Val Gly Asp Gly Phe Ala Ile Gly Glu Pro Cys
            275                 280                 285

His Gly Ser Ala Pro Asp Ile Glu Gly Lys Gly Ile Ala Asn Pro Ile
            290                 295                 300

Ala Thr Leu Arg Ser Val Ala Leu Met Leu Glu Phe Leu Gly Glu Glu
305                 310                 315                 320

Thr Ala Ala Lys Ile Tyr Thr Ala Val Asp Ala Asn Leu Asp Glu
                325                 330                 335

Ala Lys Phe Leu Ser Pro Asp Met Gly Gly Lys Ala Thr Thr Gln Glu
                340                 345                 350

Val Leu Asp Asp Val Leu Lys Arg Leu
                355                 360

<210> SEQ ID NO 47
<211> LENGTH: 359
<212> TYPE: PRT
<213> ORGANISM: Aspergillus oryzae

<400> SEQUENCE: 47

Met Ala Ala Ala Arg Thr Leu Arg Ile Gly Leu Ile Pro Gly Asp Gly
1               5                   10                  15

Ile Gly Arg Glu Val Ile Pro Ala Gly Arg Lys Val Leu Glu Ser Leu
                20                  25                  30

Pro Ala Ser Leu Asn Leu Asn Phe Ser Phe Val Asn Leu Asp Ala Gly
            35                  40                  45

Phe Asp Thr Phe Lys Gln Thr Gly Thr Ala Leu Pro Asp Lys Thr Val
    50                  55                  60

Glu Thr Leu Lys Lys Glu Cys Asp Gly Ala Leu Phe Gly Ala Val Ser
65                  70                  75                  80

Ser Pro Ser Thr Lys Val Ala Gly Tyr Ser Ser Pro Ile Val Ala Leu
                85                  90                  95

His Lys Lys Leu Asp Leu Tyr Ala Asn Val Arg Pro Val Lys Ser Thr
            100                 105                 110

Ile Gly Gly Gly Arg Asn Pro Val Asp Leu Val Ile Val His Glu Asn
            115                 120                 125

Thr Glu Asp Leu Tyr Val Lys Glu Gln Thr Lys Asp Thr Pro Asn
    130                 135                 140

Gly Lys Val Ala Glu Ala Ile Lys Arg Ile Ser Glu Asn Ala Ser Phe
145                 150                 155                 160

Arg Ile Ser Ser Ile Ala Gly Glu Ile Ala Leu Arg Arg Gln Lys Ile
                165                 170                 175

Arg Asp Ala Ala Ser Thr Thr Gly Leu Arg Thr Lys Pro Met Val Thr
            180                 185                 190

Ile Thr His Lys Ser Asn Val Leu Ser Gln Thr Asp Gly Leu Phe Arg
    195                 200                 205

Glu Thr Ala Arg Lys Ala Leu Ala Ala Glu Arg Phe Ser Ser Val Glu
    210                 215                 220

Val Glu Glu Gln Ile Val Asp Ser Met Val Tyr Lys Leu Phe Arg Gln
225                 230                 235                 240

Pro Glu Tyr Tyr Asp Val Ile Val Ala Pro Asn Leu Tyr Gly Asp Ile
                245                 250                 255
```

```
Leu Ser Asp Gly Ala Ala Leu Val Gly Ser Leu Gly Leu Val Pro
            260                 265                 270

Ser Ala Asn Val Gly Asp Gly Phe Ala Ile Gly Glu Pro Cys His Gly
                275                 280                 285

Ser Ala Pro Asp Ile Glu Gly Gln Gly Ile Ala Asn Pro Ile Ala Thr
            290                 295                 300

Leu Arg Ser Ala Ala Leu Met Leu Glu Phe Leu Gly Glu Gly Ala
305                 310                 315                 320

Ala Ala Lys Ile Tyr Thr Ala Val Asp Ala Asn Leu Asp Glu Gly Lys
                325                 330                 335

Tyr Leu Ser Pro Asp Met Gly Gly Lys Ala Ser Thr Gln Glu Val Leu
            340                 345                 350

Asp Asp Val Leu Lys Arg Leu
            355

<210> SEQ ID NO 48
<211> LENGTH: 403
<212> TYPE: PRT
<213> ORGANISM: Aspergillus terreus

<400> SEQUENCE: 48

Met Val Lys Thr His Pro Ala Ile Thr Ala Gly Ala Thr Leu Ile Arg
1               5                   10                  15

Ala Val Gly Phe Pro Leu Ala Pro Ile Val Gly Glu Thr Phe Phe Ser
                20                  25                  30

Val Gln Phe Thr Pro Ser Arg His Tyr Cys Ala Met Ala Ala Ala Arg
            35                  40                  45

Thr Leu Arg Ile Gly Leu Ile Pro Gly Asp Gly Ile Gly Arg Glu Val
        50                  55                  60

Ile Pro Ala Gly Arg Arg Leu Leu Glu Ser Leu Pro Ser Ser Leu Asn
65                  70                  75                  80

Leu Lys Phe Ser Phe Val Asp Leu Asp Ala Gly Phe Asp Thr Phe Lys
                85                  90                  95

Arg Thr Gly Thr Ala Leu Pro Asp Lys Thr Val Glu Ile Leu Lys Lys
                100                 105                 110

Glu Cys Asp Gly Ala Leu Phe Gly Ala Val Ser Ser Pro Ser Thr Lys
            115                 120                 125

Val Ala Gly Tyr Ser Ser Pro Ile Val Ala Leu His Lys Lys Leu Asp
        130                 135                 140

Leu Tyr Ala Asn Val Arg Pro Val Lys Thr Thr Ser Gly Asp Ser Lys
145                 150                 155                 160

Gly Asn Pro Ile Asp Leu Val Ile Val His Glu Asn Thr Glu Asp Leu
                165                 170                 175

Tyr Val Lys Glu Glu Gln Thr Lys Asp Thr Pro Asn Gly Lys Val Ala
            180                 185                 190

Glu Ala Ile Lys Arg Ile Ser Glu Asn Ala Ser Ser Arg Ile Ser Thr
        195                 200                 205

Ile Ala Gly Glu Ile Ala Leu Arg Arg Gln Lys Ile Arg Asp Val Ala
    210                 215                 220

Ala Thr Pro Gly Leu Arg Ser Lys Pro Met Val Thr Ile Thr His Lys
225                 230                 235                 240

Ser Asn Val Leu Ser Gln Thr Asp Gly Leu Phe Arg Glu Thr Ala Arg
                245                 250                 255

Lys Ala Leu Ser Ala Asp Arg Phe Ser Ser Val Glu Val Glu Glu Gln
            260                 265                 270
```

-continued

Ile Val Asp Ser Met Val Tyr Lys Leu Phe Arg Gln Pro Glu Tyr Tyr
       275                 280                 285

Asp Val Ile Val Ala Pro Asn Leu Tyr Gly Asp Ile Leu Ser Asp Gly
290                 295                 300

Ala Ala Ala Leu Val Gly Ser Leu Gly Leu Val Pro Ser Ala Asn Val
305                 310                 315                 320

Gly Asp Gly Phe Ala Ile Gly Glu Pro Cys His Gly Ser Ala Pro Asp
                325                 330                 335

Ile Glu Gly Lys Gly Ile Ala Asn Pro Ile Ala Thr Leu Arg Ser Val
            340                 345                 350

Ala Leu Met Leu Glu Phe Leu Gly Glu Glu Asn Ala Ala Ala Lys Ile
        355                 360                 365

Tyr Thr Ala Val Asp Ala Asn Leu Asp Glu Gly Lys Tyr Leu Ser Pro
370                 375                 380

Asp Met Gly Gly Lys Ala Thr Thr Gln Gln Val Leu Asp Asp Val Leu
385                 390                 395                 400

Lys Arg Leu

<210> SEQ ID NO 49
<211> LENGTH: 403
<212> TYPE: PRT
<213> ORGANISM: Aspergillus terreus

<400> SEQUENCE: 49

Met Val Lys Thr His Pro Ala Ile Thr Ala Gly Ala Thr Leu Ile Arg
1               5                   10                  15

Ala Val Gly Phe Pro Leu Ala Pro Ile Val Gly Glu Thr Phe Phe Ser
            20                  25                  30

Val Gln Phe Thr Pro Ser Arg His Tyr Cys Ala Met Ala Ala Ala Arg
        35                  40                  45

Thr Leu Arg Ile Gly Leu Ile Pro Gly Asp Gly Ile Gly Arg Glu Val
    50                  55                  60

Ile Pro Ala Gly Arg Arg Leu Leu Glu Ser Leu Pro Ser Ser Leu Asn
65                  70                  75                  80

Leu Lys Phe Ser Phe Val Asp Leu Asp Ala Gly Phe Asp Thr Phe Lys
                85                  90                  95

Arg Thr Gly Thr Ala Leu Pro Asp Lys Thr Val Glu Ile Leu Lys Lys
            100                 105                 110

Glu Cys Asp Gly Ala Leu Phe Gly Ala Val Ser Ser Pro Ser Thr Lys
        115                 120                 125

Val Ala Gly Tyr Ser Ser Pro Ile Val Ala Leu His Lys Lys Leu Asp
    130                 135                 140

Leu Tyr Ala Asn Val Arg Pro Val Lys Thr Thr Ser Gly Asp Ser Lys
145                 150                 155                 160

Gly Asn Pro Ile Asp Leu Val Ile Val His Glu Asn Thr Glu Asp Leu
                165                 170                 175

Tyr Val Lys Glu Glu Gln Thr Lys Asp Thr Pro Asn Gly Lys Val Ala
            180                 185                 190

Glu Ala Ile Lys Arg Ile Ser Glu Asn Ala Ser Ser Arg Ile Ser Thr
        195                 200                 205

Ile Ala Gly Glu Ile Ala Leu Arg Arg Gln Lys Ile Arg Asp Val Ala
    210                 215                 220

Ala Thr Pro Gly Leu Arg Ser Lys Pro Met Val Thr Ile Thr His Lys
225                 230                 235                 240

Ser Asn Val Leu Ser Gln Thr Asp Gly Leu Phe Arg Glu Thr Ala Arg

```
                 245                 250                 255
Lys Ala Leu Ser Ala Asp Arg Phe Ser Ser Val Glu Val Glu Glu Gln
                260                 265                 270

Ile Val Asp Ser Met Val Tyr Lys Leu Phe Arg Gln Pro Glu Tyr Tyr
            275                 280                 285

Asp Val Ile Val Ala Pro Asn Leu Tyr Gly Asp Ile Leu Ser Asp Gly
        290                 295                 300

Ala Ala Ala Leu Val Gly Ser Leu Gly Leu Val Pro Ser Ala Asn Val
305                 310                 315                 320

Gly Asp Gly Phe Ala Ile Gly Glu Pro Cys His Gly Ser Ala Pro Asp
                325                 330                 335

Ile Glu Gly Lys Gly Ile Ala Asn Pro Ile Ala Thr Leu Arg Ser Val
            340                 345                 350

Ala Leu Met Leu Glu Phe Leu Gly Glu Glu Asn Ala Ala Ala Lys Ile
        355                 360                 365

Tyr Thr Ala Val Asp Ala Asn Leu Asp Glu Gly Lys Tyr Leu Ser Pro
    370                 375                 380

Asp Met Gly Gly Lys Ala Thr Thr Gln Gln Val Leu Asp Asp Val Leu
385                 390                 395                 400

Lys Arg Leu

<210> SEQ ID NO 50
<211> LENGTH: 376
<212> TYPE: PRT
<213> ORGANISM: Candida albicans

<400> SEQUENCE: 50

Met Leu Ala Ala Arg Ser Ser Ile Arg Arg Cys Phe Ser Thr Ser Ser
1               5                   10                  15

Thr Thr Leu Lys Ser Leu Lys Ile Gly Leu Ile Pro Gly Asp Gly Ile
            20                  25                  30

Gly Arg Glu Val Ile Pro Ala Gly Lys Ala Val Leu Glu Asn Leu Pro
        35                  40                  45

Ala Lys His Asp Leu Gln Phe Glu Phe Val Asn Leu Asp Ala Gly Phe
    50                  55                  60

Glu Leu Phe Lys Lys Thr Gly Thr Ala Leu Pro Asp Glu Thr Val Asp
65                  70                  75                  80

Val Leu Lys Lys Glu Cys Asp Gly Ala Leu Phe Gly Ala Val Ser Ser
                85                  90                  95

Pro Thr Thr Lys Val Ala Gly Tyr Ser Ser Pro Ile Val Ala Leu His
            100                 105                 110

Lys Lys Leu Gly Leu Tyr Ala Asn Val Arg Pro Val Lys Ser Val Glu
        115                 120                 125

Gly Ile Gly Arg Pro Val Asp Met Val Ile Val His Glu Asn Thr Glu
    130                 135                 140

Asp Leu Tyr Ile Lys Glu Glu Arg Val Tyr Lys Lys Glu Asp Gly Thr
145                 150                 155                 160

Lys Val Ala Glu Ala Ile Lys Arg Ile Thr Glu Thr Ala Ser Thr Arg
                165                 170                 175

Ile Ala Lys Met Ala Tyr Glu Ile Ala Leu Gln Arg Glu Ala Val Arg
            180                 185                 190

Lys Gly Thr Ser Gly Lys Gln Leu His Glu Lys Pro Ser Val Thr Val
        195                 200                 205

Thr His Lys Ser Asn Val Leu Ser Gln Ser Asp Gly Leu Phe Arg Glu
    210                 215                 220
```

```
Thr Cys Arg Ala Val Tyr Asp Ala Asn Ala Asn Glu Tyr Gly Gly Ile
225                 230                 235                 240

Glu Tyr Lys Glu Gln Ile Val Asp Ser Met Val Tyr Arg Met Phe Arg
            245                 250                 255

Glu Pro Glu Ile Phe Asp Val Val Ala Pro Asn Leu Tyr Gly Asp
        260                 265                 270

Ile Leu Ser Asp Gly Ala Ala Leu Val Gly Ser Leu Gly Val Val
    275                 280                 285

Pro Ser Ala Asn Val Gly Asp Asn Phe Ala Ile Gly Glu Pro Cys His
    290                 295                 300

Gly Ser Ala Pro Asp Ile Glu Gly Lys Gly Ile Ser Asn Pro Val Ala
305                 310                 315                 320

Thr Ile Arg Ser Thr Ala Leu Met Leu Glu Phe Met Gly Tyr Pro Glu
            325                 330                 335

Ala Ala Ala Thr Ile Tyr Gln Ala Val Asp Ala Asn Leu Ala Glu Asp
            340                 345                 350

Lys Ile Lys Thr Pro Asp Leu Gly Gly Asn Ser Thr Thr Gln Glu Val
            355                 360                 365

Ile Asp Asp Ile Ile Arg Arg Phe
370                 375

<210> SEQ ID NO 51
<211> LENGTH: 376
<212> TYPE: PRT
<213> ORGANISM: Candida albicans

<400> SEQUENCE: 51

Met Leu Ala Ala Arg Ser Ser Ile Arg Arg Cys Phe Ser Thr Ser Ser
1               5                   10                  15

Thr Thr Leu Lys Ser Leu Lys Ile Gly Leu Ile Pro Gly Asp Gly Ile
            20                  25                  30

Gly Arg Glu Val Ile Pro Ala Gly Lys Ala Val Leu Glu Asn Leu Pro
        35                  40                  45

Ala Lys His Asp Leu Gln Phe Glu Phe Val Asn Leu Asp Ala Gly Phe
    50                  55                  60

Glu Leu Phe Lys Lys Thr Gly Thr Ala Leu Pro Asp Glu Thr Val Asp
65                  70                  75                  80

Val Leu Lys Lys Glu Cys Asp Gly Ala Leu Phe Gly Ala Val Ser Ser
                85                  90                  95

Pro Thr Thr Lys Val Ala Gly Tyr Ser Ser Pro Ile Val Ala Leu His
            100                 105                 110

Lys Lys Leu Gly Leu Tyr Ala Asn Val Arg Pro Val Lys Ser Val Glu
        115                 120                 125

Gly Ile Gly Arg Pro Val Asp Met Val Ile Val His Glu Asn Thr Glu
    130                 135                 140

Asp Leu Tyr Ile Lys Glu Arg Val Tyr Lys Lys Glu Asp Gly Thr
145                 150                 155                 160

Lys Val Ala Glu Ala Ile Lys Arg Ile Thr Glu Thr Ala Ser Thr Arg
                165                 170                 175

Ile Ala Lys Met Ala Tyr Glu Ile Ala Leu Gln Arg Glu Ala Val Arg
            180                 185                 190

Lys Gly Thr Ser Gly Lys Gln Leu His Glu Lys Pro Ser Val Thr Val
        195                 200                 205

Thr His Lys Ser Asn Val Leu Ser Gln Ser Asp Gly Leu Phe Arg Glu
    210                 215                 220
```

```
Thr Cys Arg Ala Val Tyr Asp Ala Asn Ala Asn Glu Tyr Gly Gly Ile
225                 230                 235                 240

Glu Tyr Lys Glu Gln Ile Val Asp Ser Met Val Tyr Arg Met Phe Arg
            245                 250                 255

Glu Pro Glu Ile Phe Asp Val Val Ala Pro Asn Leu Tyr Gly Asp
            260                 265                 270

Ile Leu Ser Asp Gly Ala Ala Leu Val Gly Ser Leu Gly Val Val
            275                 280                 285

Pro Ser Ala Asn Val Gly Asp Asn Phe Ala Ile Gly Glu Pro Cys His
            290                 295                 300

Gly Ser Ala Pro Asp Ile Glu Gly Lys Gly Ile Ser Asn Pro Val Ala
305                 310                 315                 320

Thr Ile Arg Ser Thr Ala Leu Met Leu Glu Phe Met Gly Tyr Pro Glu
                325                 330                 335

Ala Ala Ala Thr Ile Tyr Gln Ala Val Asp Ala Asn Leu Ala Glu Asp
                340                 345                 350

Lys Ile Lys Thr Pro Asp Leu Gly Gly Asn Ser Thr Thr Gln Glu Val
                355                 360                 365

Ile Asp Asp Ile Ile Arg Arg Phe
370                 375

<210> SEQ ID NO 52
<211> LENGTH: 376
<212> TYPE: PRT
<213> ORGANISM: Candida albicans

<400> SEQUENCE: 52

Met Leu Ala Ala Arg Ser Ser Ile Arg Arg Cys Phe Ser Thr Ser Ser
1               5                   10                  15

Thr Thr Leu Lys Ser Leu Lys Ile Gly Leu Ile Pro Gly Asp Gly Ile
            20                  25                  30

Gly Arg Glu Val Ile Pro Ala Gly Lys Ala Val Leu Glu Asn Leu Pro
        35                  40                  45

Ala Lys His Asp Leu Gln Phe Glu Phe Val Asn Leu Asp Ala Gly Phe
    50                  55                  60

Glu Leu Phe Lys Lys Thr Gly Thr Ala Leu Pro Asp Glu Thr Val Asp
65                  70                  75                  80

Val Leu Lys Lys Glu Cys Asp Gly Ala Leu Phe Gly Ala Val Ser Ser
                85                  90                  95

Pro Thr Thr Lys Val Ala Gly Tyr Ser Ser Pro Ile Val Ala Leu His
            100                 105                 110

Lys Lys Leu Gly Leu Tyr Ala Asn Val Arg Pro Val Lys Ser Val Glu
        115                 120                 125

Gly Ile Gly Arg Pro Val Asp Met Val Ile Val His Glu Asn Thr Glu
    130                 135                 140

Asp Leu Tyr Ile Lys Glu Glu Arg Val Tyr Lys Lys Glu Asp Gly Thr
145                 150                 155                 160

Lys Val Ala Glu Ala Ile Lys Arg Ile Thr Glu Thr Ala Ser Thr Arg
                165                 170                 175

Ile Ala Lys Met Ala Tyr Glu Ile Ala Leu Gln Arg Glu Ala Val Arg
                180                 185                 190

Lys Gly Thr Ser Gly Lys Gln Leu His Glu Lys Pro Ser Val Thr Val
            195                 200                 205

Thr His Lys Ser Asn Val Leu Ser Gln Ser Asp Gly Leu Phe Arg Glu
        210                 215                 220
```

```
Thr Cys Arg Ala Val Tyr Asp Ala Asn Ala Asn Glu Tyr Gly Gly Ile
225                 230                 235                 240

Glu Tyr Lys Glu Gln Ile Val Asp Ser Met Val Tyr Arg Met Phe Arg
            245                 250                 255

Glu Pro Glu Ile Phe Asp Val Val Ala Pro Asn Leu Tyr Gly Asp
        260                 265                 270

Ile Leu Ser Asp Gly Ala Ala Leu Val Gly Ser Leu Gly Val Val
            275                 280                 285

Pro Ser Ala Asn Val Gly Asp Asn Phe Ala Ile Gly Glu Pro Cys His
        290                 295                 300

Gly Ser Ala Pro Asp Ile Glu Gly Lys Gly Ile Ser Asn Pro Val Ala
305                 310                 315                 320

Thr Ile Arg Ser Thr Ala Leu Met Leu Glu Phe Met Gly Tyr Pro Glu
            325                 330                 335

Ala Ala Ala Thr Ile Tyr Gln Ala Val Asp Ala Asn Leu Ala Glu Asp
            340                 345                 350

Lys Ile Lys Thr Pro Asp Leu Gly Gly Asn Ser Thr Thr Gln Glu Val
            355                 360                 365

Ile Asp Asp Ile Ile Arg Arg Phe
370                 375

<210> SEQ ID NO 53
<211> LENGTH: 376
<212> TYPE: PRT
<213> ORGANISM: Candida albicans

<400> SEQUENCE: 53

Met Leu Ala Ala Arg Ser Ser Ile Arg Arg Cys Phe Ser Thr Ser Ser
1               5                   10                  15

Thr Thr Leu Lys Ser Leu Lys Ile Gly Leu Ile Pro Gly Asp Gly Ile
            20                  25                  30

Gly Arg Glu Val Ile Pro Ala Gly Lys Ala Val Leu Glu Asn Leu Pro
        35                  40                  45

Ala Lys His Asp Leu Gln Phe Glu Phe Val Asn Leu Asp Ala Gly Phe
    50                  55                  60

Glu Leu Phe Lys Lys Thr Gly Thr Ala Leu Pro Asp Glu Thr Val Asp
65                  70                  75                  80

Val Leu Lys Lys Glu Cys Asp Gly Ala Leu Phe Gly Ala Val Ser Ser
                85                  90                  95

Pro Thr Thr Lys Val Ala Gly Tyr Ser Ser Pro Ile Val Ala Leu His
            100                 105                 110

Lys Lys Leu Gly Leu Tyr Ala Asn Val Arg Pro Val Lys Ser Val Glu
        115                 120                 125

Gly Ile Gly Arg Pro Val Asp Met Val Ile Val His Glu Asn Thr Glu
    130                 135                 140

Asp Leu Tyr Ile Lys Glu Arg Val Tyr Lys Lys Glu Asp Gly Thr
145                 150                 155                 160

Lys Val Ala Glu Ala Ile Lys Arg Ile Thr Glu Thr Ala Ser Thr Arg
                165                 170                 175

Ile Ala Lys Met Ala Tyr Glu Ile Ala Leu Gln Arg Glu Ala Val Arg
            180                 185                 190

Lys Gly Thr Ser Gly Lys Gln Leu His Glu Lys Pro Ser Val Thr Val
        195                 200                 205

Thr His Lys Ser Asn Val Leu Ser Gln Ser Asp Gly Leu Phe Arg Glu
    210                 215                 220
```

```
Thr Cys Arg Ala Val Tyr Asp Ala Asn Ala Asn Glu Tyr Gly Gly Ile
225                 230                 235                 240

Glu Tyr Lys Glu Gln Ile Val Asp Ser Met Val Tyr Arg Met Phe Arg
            245                 250                 255

Glu Pro Glu Ile Phe Asp Val Val Ala Pro Asn Leu Tyr Gly Asp
        260                 265                 270

Ile Leu Ser Asp Gly Ala Ala Leu Val Gly Ser Leu Gly Val Val
        275                 280                 285

Pro Ser Ala Asn Val Gly Asp Asn Phe Ala Ile Gly Glu Pro Cys His
        290                 295                 300

Gly Ser Ala Pro Asp Ile Glu Gly Lys Gly Ile Ser Asn Pro Val Ala
305                 310                 315                 320

Thr Ile Arg Ser Thr Ala Leu Met Leu Glu Phe Met Gly Tyr Pro Glu
            325                 330                 335

Ala Ala Ala Thr Ile Tyr Gln Ala Val Asp Ala Asn Leu Ala Glu Asp
            340                 345                 350

Lys Ile Lys Thr Pro Asp Leu Gly Gly Asn Ser Thr Thr Gln Glu Val
            355                 360                 365

Ile Asp Asp Ile Ile Arg Arg Phe
370                 375

<210> SEQ ID NO 54
<211> LENGTH: 376
<212> TYPE: PRT
<213> ORGANISM: Candida albicans

<400> SEQUENCE: 54

Met Leu Ala Ala Arg Ser Ser Ile Arg Arg Cys Phe Ser Thr Ser Ser
1               5                   10                  15

Thr Thr Leu Lys Ser Leu Lys Ile Gly Leu Ile Ser Gly Asp Gly Ile
            20                  25                  30

Gly Arg Glu Val Ile Pro Ala Gly Lys Ala Val Leu Glu Asn Leu Pro
        35                  40                  45

Ser Lys His Asp Leu Gln Phe Glu Phe Val Asn Leu Asp Ala Gly Phe
    50                  55                  60

Glu Leu Phe Lys Lys Thr Gly Thr Ala Leu Pro Asp Glu Thr Val Asp
65                  70                  75                  80

Val Leu Lys Lys Glu Cys Asp Gly Ala Leu Phe Gly Ala Val Ser Ser
                85                  90                  95

Pro Thr Thr Lys Val Ala Gly Tyr Ser Ser Pro Ile Val Ala Leu His
        100                 105                 110

Lys Lys Leu Gly Leu Tyr Ala Asn Val Arg Pro Val Lys Ser Val Glu
    115                 120                 125

Gly Ile Gly Arg Pro Val Asp Met Val Ile Val His Glu Asn Thr Glu
130                 135                 140

Asp Leu Tyr Ile Lys Glu Arg Val Tyr Lys Lys Glu Asp Gly Thr
145                 150                 155                 160

Lys Val Ala Glu Ala Ile Lys Arg Ile Thr Glu Thr Ala Ser Thr Arg
                165                 170                 175

Ile Ala Lys Met Ala Tyr Glu Ile Ala Leu Gln Arg Glu Ala Val Arg
            180                 185                 190

Lys Gly Thr Ser Gly Lys Gln Leu His Glu Lys Pro Ser Val Thr Val
        195                 200                 205

Thr His Lys Ser Asn Val Leu Ser Gln Ser Asp Gly Leu Phe Arg Glu
    210                 215                 220
```

```
Thr Cys Arg Ala Val Tyr Asp Ala Asn Ala Asn Glu Tyr Gly Gly Ile
225                 230                 235                 240

Glu Tyr Lys Glu Gln Ile Val Asp Ser Met Val Tyr Arg Met Phe Arg
            245                 250                 255

Glu Pro Glu Ile Phe Asp Val Val Ala Pro Asn Leu Tyr Gly Asp
                260                 265                 270

Ile Leu Ser Asp Gly Ala Ala Leu Val Gly Ser Leu Gly Val Val
            275                 280                 285

Pro Ser Ala Asn Val Gly Asp Asn Phe Ala Ile Gly Glu Pro Cys His
            290                 295                 300

Gly Ser Ala Pro Asp Ile Glu Gly Lys Gly Ile Ser Asn Pro Val Ala
305                 310                 315                 320

Thr Ile Arg Ser Thr Ala Leu Met Leu Glu Phe Met Gly Tyr Pro Glu
                325                 330                 335

Ala Ala Ala Thr Ile Tyr Gln Ala Val Asp Ala Asn Leu Ala Glu Asp
                340                 345                 350

Lys Ile Lys Thr Pro Asp Leu Gly Gly Asn Ser Thr Thr Gln Glu Val
            355                 360                 365

Ile Asp Asp Ile Ile Arg Arg Phe
370                 375

<210> SEQ ID NO 55
<211> LENGTH: 376
<212> TYPE: PRT
<213> ORGANISM: Candida dubliniensis

<400> SEQUENCE: 55

Met Leu Ala Ala Arg Ser Ser Ile Arg Arg Cys Phe Ser Thr Thr Ser
1               5                   10                  15

Thr Thr Leu Lys Ser Leu Lys Ile Gly Leu Ile Pro Gly Asp Gly Ile
            20                  25                  30

Gly Arg Glu Val Ile Pro Ala Gly Lys Ala Val Leu Glu Asn Leu Pro
        35                  40                  45

Ala Lys His Asp Leu Gln Phe Glu Phe Val Asn Leu Asp Ala Gly Phe
    50                  55                  60

Glu Leu Phe Lys Lys Thr Gly Thr Ala Leu Pro Asp Glu Thr Val Asp
65                  70                  75                  80

Ile Leu Lys Lys Glu Cys Asp Gly Ala Leu Phe Gly Ala Val Ser Ser
                85                  90                  95

Pro Thr Thr Lys Val Ala Gly Tyr Ser Ser Pro Ile Val Ala Leu His
            100                 105                 110

Lys Lys Leu Gly Leu Tyr Ala Asn Val Arg Pro Val Lys Ser Val Glu
        115                 120                 125

Gly Ile Gly Arg Pro Val Asp Met Val Ile Val His Glu Asn Thr Glu
130                 135                 140

Asp Leu Tyr Ile Lys Glu Arg Val Tyr Lys Lys Glu Asp Gly Thr
145                 150                 155                 160

Lys Val Ala Glu Ala Ile Lys Arg Ile Thr Glu Thr Ala Ser Thr Lys
                165                 170                 175

Ile Ala Lys Met Ala Phe Glu Ile Ala Leu Gln Arg Glu Ala Val Arg
            180                 185                 190

Lys Gly Thr Ser Gly Lys Gln Leu His Glu Lys Pro Ser Val Thr Val
        195                 200                 205

Thr His Lys Ser Asn Val Leu Ser Gln Ser Asp Gly Leu Phe Arg Glu
    210                 215                 220
```

```
Thr Cys Arg Ala Val Tyr Asp Ala Asn Ala Asn Glu Tyr Gly Gly Ile
225                 230                 235                 240

Glu Tyr Lys Glu Gln Ile Val Asp Ser Met Val Tyr Arg Met Phe Arg
            245                 250                 255

Glu Pro Glu Ile Phe Asp Val Val Ala Pro Asn Leu Tyr Gly Asp
            260                 265                 270

Ile Leu Ser Asp Gly Ala Ala Leu Val Gly Ser Leu Gly Val Val
        275                 280                 285

Pro Ser Ala Asn Val Gly Asp Ser Phe Ala Ile Gly Glu Pro Cys His
        290                 295                 300

Gly Ser Ala Pro Asp Ile Glu Gly Lys Gly Ile Ser Asn Pro Val Ala
305                 310                 315                 320

Thr Ile Arg Ser Thr Ala Leu Met Leu Glu Phe Met Gly Tyr Pro Glu
            325                 330                 335

Ala Ala Ala Thr Ile Tyr Gln Ala Val Asp Ala Asn Leu Ala Glu Asp
            340                 345                 350

Lys Ile Lys Thr Pro Asp Leu Gly Gly Asn Ser Thr Thr Gln Glu Val
        355                 360                 365

Ile Asp Asp Ile Ile Arg Arg Phe
370                 375

<210> SEQ ID NO 56
<211> LENGTH: 376
<212> TYPE: PRT
<213> ORGANISM: Candida dubliniensis

<400> SEQUENCE: 56

Met Leu Ala Ala Arg Ser Ser Ile Arg Arg Cys Phe Ser Thr Thr Ser
1               5                   10                  15

Thr Thr Leu Lys Ser Leu Lys Ile Gly Leu Ile Pro Gly Asp Gly Ile
            20                  25                  30

Gly Arg Glu Val Ile Pro Ala Gly Lys Ala Val Leu Glu Asn Leu Pro
        35                  40                  45

Ala Lys His Asp Leu Gln Phe Glu Phe Val Asn Leu Asp Ala Gly Phe
    50                  55                  60

Glu Leu Phe Lys Lys Thr Gly Thr Ala Leu Pro Asp Glu Thr Val Asp
65                  70                  75                  80

Ile Leu Lys Lys Glu Cys Asp Gly Ala Leu Phe Gly Ala Val Ser Ser
                85                  90                  95

Pro Thr Thr Lys Val Ala Gly Tyr Ser Ser Pro Ile Val Ala Leu His
            100                 105                 110

Lys Lys Leu Gly Leu Tyr Ala Asn Val Arg Pro Val Lys Ser Val Glu
        115                 120                 125

Gly Ile Gly Arg Pro Val Asp Met Val Ile Val His Glu Asn Thr Glu
130                 135                 140

Asp Leu Tyr Ile Lys Glu Arg Val Tyr Lys Lys Glu Asp Gly Thr
145                 150                 155                 160

Lys Val Ala Glu Ala Ile Lys Arg Ile Thr Glu Thr Ala Ser Thr Lys
                165                 170                 175

Ile Ala Lys Met Ala Phe Glu Ile Ala Leu Gln Arg Glu Ala Val Arg
            180                 185                 190

Lys Gly Thr Ser Gly Lys Gln Leu His Glu Lys Pro Ser Val Thr Val
        195                 200                 205

Thr His Lys Ser Asn Val Leu Ser Gln Ser Asp Gly Leu Phe Arg Glu
    210                 215                 220
```

```
Thr Cys Arg Ala Val Tyr Asp Ala Asn Ala Asn Glu Tyr Gly Gly Ile
225                 230                 235                 240

Glu Tyr Lys Glu Gln Ile Val Asp Ser Met Val Tyr Arg Met Phe Arg
            245                 250                 255

Glu Pro Glu Ile Phe Asp Val Val Ala Pro Asn Leu Tyr Gly Asp
        260                 265                 270

Ile Leu Ser Asp Gly Ala Ala Leu Val Gly Ser Leu Gly Val Val
        275                 280                 285

Pro Ser Ala Asn Val Gly Asp Ser Phe Ala Ile Gly Glu Pro Cys His
290                 295                 300

Gly Ser Ala Pro Asp Ile Glu Gly Lys Gly Ile Ser Asn Pro Val Ala
305                 310                 315                 320

Thr Ile Arg Ser Thr Ala Leu Met Leu Glu Phe Met Gly Tyr Pro Glu
            325                 330                 335

Ala Ala Ala Thr Ile Tyr Gln Ala Val Asp Ala Asn Leu Ala Glu Asp
            340                 345                 350

Lys Ile Lys Thr Pro Asp Leu Gly Gly Asn Ser Thr Thr Gln Glu Val
            355                 360                 365

Ile Asp Asp Ile Ile Arg Arg Phe
370                 375

<210> SEQ ID NO 57
<211> LENGTH: 369
<212> TYPE: PRT
<213> ORGANISM: Candida parapsilosis

<400> SEQUENCE: 57

Met Arg Cys Phe Ser Thr Ser Ala Pro Ala Leu Lys Thr Ile Lys Ile
1               5                   10                  15

Gly Leu Ile Pro Gly Asp Gly Ile Gly Arg Glu Val Ile Pro Ala Gly
            20                  25                  30

Gln Lys Val Leu Glu Ser Leu Pro Ala Lys Tyr Asp Leu Arg Phe Glu
        35                  40                  45

Phe Val Asn Leu Asp Ala Gly Tyr Glu Leu Phe Lys Lys Thr Gly Thr
    50                  55                  60

Ala Leu Pro Asp Lys Thr Val Asp Val Leu Lys Asn Glu Cys Asp Gly
65                  70                  75                  80

Ala Leu Phe Gly Ala Val Ser Ser Pro Thr Thr Lys Val Ala Gly Tyr
                85                  90                  95

Ser Ser Pro Ile Val Ala Leu His Lys Lys Leu Gly Leu Tyr Ala Asn
            100                 105                 110

Val Arg Pro Val Lys Ser Val Lys Gly Ile Gly Arg Pro Val Asp Met
        115                 120                 125

Val Ile Val His Glu Asn Thr Glu Asp Leu Tyr Val Lys Glu Glu Lys
130                 135                 140

Thr Phe Glu Lys Glu Asp Gly Thr Lys Val Ala Glu Ala Ile Lys Arg
145                 150                 155                 160

Ile Thr Glu Thr Ala Ser Lys Arg Ile Ala Lys Met Ala Tyr Asp Ile
                165                 170                 175

Ala Val Gln Arg Gln Gly Ile Arg Asp Ala Ser Ser Ser Glu Gln
            180                 185                 190

Leu His Lys Ser Pro Ser Val Thr Val Thr His Lys Ser Asn Val Leu
        195                 200                 205

Ser Gln Ser Asp Gly Leu Phe Arg Glu Ser Cys Arg Glu Val Tyr Asp
210                 215                 220
```

```
Ala Asn Lys Asp Lys Tyr Lys Asp Val Glu Tyr Lys Glu Gln Ile Val
225                 230                 235                 240

Asp Ser Met Val Tyr Lys Met Phe Arg Asp Pro Glu Val Phe Asp Val
            245                 250                 255

Val Val Ala Pro Asn Leu Tyr Gly Asp Ile Leu Ser Asp Gly Ala Ala
            260                 265                 270

Ala Leu Val Gly Ser Leu Gly Val Val Pro Ser Ala Asn Val Gly Asp
            275                 280                 285

Ser Phe Ala Ile Gly Glu Pro Cys His Gly Ser Ala Pro Asp Ile Glu
            290                 295                 300

Gly Lys Gly Ile Ser Asn Pro Ile Ala Thr Ile Arg Ser Thr Ala Leu
305                 310                 315                 320

Met Leu Glu Phe Met Gly Tyr Pro Glu Ala Ala Ala Lys Ile Tyr Glu
            325                 330                 335

Ala Val Asp Ala Asn Leu Ala Glu Asp Lys Ile Lys Thr Pro Asp Leu
            340                 345                 350

Gly Gly Gln Ser Ser Thr Asn Glu Val Val Glu Asp Ile Ile Lys Arg
            355                 360                 365

Phe

<210> SEQ ID NO 58
<211> LENGTH: 377
<212> TYPE: PRT
<213> ORGANISM: Candida tropicalis

<400> SEQUENCE: 58

Met Leu Ala Ala Ser Arg Ser Ser Ile Arg Arg Cys Phe Ser Thr Ser
1               5                   10                  15

Ala Thr Ala Leu Lys Thr Leu Lys Ile Gly Leu Ile Pro Gly Asp Gly
            20                  25                  30

Ile Gly Arg Glu Val Ile Pro Ala Gly Gln Ala Val Leu Glu Asn Leu
            35                  40                  45

Pro Ala Lys His Asp Leu Gln Phe Glu Phe Val Asn Leu Asp Ala Gly
        50                  55                  60

Phe Glu Leu Phe Lys Lys Thr Gly Thr Ala Leu Pro Asp Glu Thr Val
65                  70                  75                  80

Asp Val Leu Lys Lys Glu Cys Asp Gly Ala Leu Phe Gly Ala Val Ser
                85                  90                  95

Ser Pro Thr Thr Lys Val Ala Gly Tyr Ser Ser Pro Ile Val Ala Leu
            100                 105                 110

His Lys Lys Met Gly Leu Tyr Ala Asn Val Arg Pro Val Lys Ser Val
            115                 120                 125

Glu Gly Ile Gly Arg Pro Val Asp Met Val Ile Val His Glu Asn Thr
130                 135                 140

Glu Asp Leu Tyr Ile Lys Glu Arg Val Tyr Lys Lys Glu Asp Gly
145                 150                 155                 160

Thr Lys Val Ala Glu Ala Ile Lys Arg Ile Thr Glu Thr Ala Ser Thr
                165                 170                 175

Arg Ile Ala Lys Met Ala Tyr Asp Ile Ala Leu Gln Arg Glu Ala Val
            180                 185                 190

Arg Lys Gly Ser Ser Ala Lys Gln Leu His Asp Lys Pro Ser Val Thr
            195                 200                 205

Val Thr His Lys Ser Asn Val Leu Ser Gln Ser Asp Gly Leu Phe Arg
            210                 215                 220
```

```
Glu Thr Cys Arg Ala Val Tyr Asp Ala Asn Ile Asn Glu Tyr Gly Gly
225                 230                 235                 240

Ile Glu Tyr Lys Glu Gln Ile Val Asp Ser Met Val Tyr Arg Met Phe
            245                 250                 255

Arg Glu Pro Glu Ile Phe Asp Val Val Ala Pro Asn Leu Tyr Gly
        260                 265                 270

Asp Ile Leu Ser Asp Gly Ala Ala Leu Val Gly Ser Leu Gly Val
        275                 280                 285

Val Pro Ser Ala Asn Val Gly Asp Asn Phe Ala Ile Gly Glu Pro Cys
    290                 295                 300

His Gly Ser Ala Pro Asp Ile Glu Gly Lys Gly Ile Ser Asn Pro Ile
305                 310                 315                 320

Ala Thr Ile Arg Ser Thr Ala Leu Met Leu Glu Phe Met Gly Tyr Pro
                325                 330                 335

Glu Ala Ala Ala Thr Ile Tyr Glu Ala Val Asp Ala Asn Leu Ala Glu
                340                 345                 350

Asp Lys Ile Lys Thr Pro Asp Leu Gly Gly Asn Ser Thr Thr Gln Asp
            355                 360                 365

Val Ile Asn Asp Val Ile Arg Arg Phe
    370                 375

<210> SEQ ID NO 59
<211> LENGTH: 377
<212> TYPE: PRT
<213> ORGANISM: Candida tropicalis

<400> SEQUENCE: 59

Met Leu Ala Ala Ser Arg Ser Ser Ile Arg Arg Cys Phe Ser Thr Ser
1               5                   10                  15

Ala Thr Ala Leu Lys Thr Leu Lys Ile Gly Leu Ile Pro Gly Asp Gly
            20                  25                  30

Ile Gly Arg Glu Val Ile Pro Ala Gly Gln Ala Val Leu Glu Asn Leu
        35                  40                  45

Pro Ala Lys His Asp Leu Gln Phe Glu Phe Val Asn Leu Asp Ala Gly
50                  55                  60

Phe Glu Leu Phe Lys Lys Thr Gly Thr Ala Leu Pro Asp Glu Thr Val
65                  70                  75                  80

Asp Val Leu Lys Lys Glu Cys Asp Gly Ala Leu Phe Gly Ala Val Ser
                85                  90                  95

Ser Pro Thr Thr Lys Val Ala Gly Tyr Ser Ser Pro Ile Val Ala Leu
            100                 105                 110

His Lys Lys Met Gly Leu Tyr Ala Asn Val Arg Pro Val Lys Ser Val
        115                 120                 125

Glu Gly Ile Gly Arg Pro Val Asp Met Val Ile Val His Glu Asn Thr
130                 135                 140

Glu Asp Leu Tyr Ile Lys Glu Arg Val Tyr Lys Lys Glu Asp Gly
145                 150                 155                 160

Thr Lys Val Ala Glu Ala Ile Lys Arg Ile Thr Glu Thr Ala Ser Thr
                165                 170                 175

Arg Ile Ala Lys Met Ala Tyr Asp Ile Ala Leu Gln Arg Glu Ala Val
            180                 185                 190

Arg Lys Gly Ser Ser Ala Lys Gln Leu His Asp Lys Pro Ser Val Thr
        195                 200                 205

Val Thr His Lys Ser Asn Val Leu Ser Gln Ser Asp Gly Leu Phe Arg
    210                 215                 220
```

```
Glu Thr Cys Arg Ala Val Tyr Asp Ala Asn Ile Asn Glu Tyr Gly Gly
225                 230                 235                 240

Ile Glu Tyr Lys Glu Gln Ile Val Asp Ser Met Val Tyr Arg Met Phe
            245                 250                 255

Arg Glu Pro Glu Ile Phe Asp Val Val Ala Pro Asn Leu Tyr Gly
        260                 265                 270

Asp Ile Leu Ser Asp Gly Ala Ala Leu Val Gly Ser Leu Gly Val
            275                 280                 285

Val Pro Ser Ala Asn Val Gly Asp Asn Phe Ala Ile Gly Glu Pro Cys
        290                 295                 300

His Gly Ser Ala Pro Asp Ile Glu Gly Lys Gly Ile Ser Asn Pro Ile
305                 310                 315                 320

Ala Thr Ile Arg Ser Thr Ala Leu Met Leu Glu Phe Met Gly Tyr Pro
                325                 330                 335

Glu Ala Ala Ala Thr Ile Tyr Glu Ala Val Asp Ala Asn Leu Ala Glu
                340                 345                 350

Asp Lys Ile Lys Thr Pro Asp Leu Gly Gly Asn Ser Thr Thr Gln Asp
            355                 360                 365

Val Ile Asn Asp Val Ile Arg Arg Phe
    370                 375

<210> SEQ ID NO 60
<211> LENGTH: 359
<212> TYPE: PRT
<213> ORGANISM: Chaetomium thermophilum

<400> SEQUENCE: 60

Met Ala Ala Arg Arg Thr Leu Arg Ile Gly Leu Ile Pro Gly Asp Gly
1               5                   10                  15

Ile Gly Lys Glu Val Ile Pro Ala Gly Arg Arg Ile Leu Glu Ala Leu
            20                  25                  30

Pro Ala Ser Leu Gly Leu Lys Phe Glu Phe Ile Asp Leu Lys Ala Gly
        35                  40                  45

Trp Glu Thr Phe Gln Gln Thr Gly Val Ala Leu Pro Glu Glu Thr Val
50                  55                  60

Ser Val Leu Lys Ser Asp Cys Asp Gly Ala Leu Phe Gly Ala Val Ser
65                  70                  75                  80

Ser Pro Thr Ser Ala Val Lys Gly Tyr Ser Ser Pro Ile Val Ala Leu
                85                  90                  95

His Lys Leu Leu Asp Leu Tyr Ala Asn Val Arg Pro Val Lys Thr Val
            100                 105                 110

Val Ser Ala Pro Lys Pro Ile Asp Met Val Ile Val His Glu Asn Thr
        115                 120                 125

Glu Asp Leu Tyr Val Lys Glu Lys Thr Phe Asp Thr Pro Asn Gly
    130                 135                 140

Lys Val Ala Glu Ala Val Lys Arg Ile Ser Gln Arg Ala Ser Ser Arg
145                 150                 155                 160

Ile Ala Thr Met Ala Gly Glu Ile Ala Leu Arg Arg Gln Lys Ile Arg
                165                 170                 175

Ala Ala Gly Ser Pro Ser Ile His Lys Gly Pro Leu Val Thr Ile Thr
            180                 185                 190

His Lys Ser Asn Val Leu Ser Gln Thr Asp Gly Leu Phe Arg Ser Thr
        195                 200                 205

Ala Arg Glu Ala Leu Ala Ala Pro Arg Phe Lys Asp Ala Gly Val Ala
    210                 215                 220
```

```
Val Glu Glu Gln Ile Val Asp Ser Met Val Tyr Lys Leu Phe Arg Gln
225                 230                 235                 240

Pro Glu Ala Tyr Asp Val Ile Val Ala Pro Asn Leu Tyr Gly Asp Ile
            245                 250                 255

Leu Ser Asp Gly Ala Ala Leu Val Gly Ser Leu Gly Leu Val Pro
        260                 265                 270

Ser Ala Asn Val Gly Glu Gly Phe Ala Ile Gly Glu Pro Cys His Gly
    275                 280                 285

Ser Ala Pro Asp Ile Gln Gly Lys Gly Ile Ala Asn Pro Ile Ala Thr
    290                 295                 300

Leu Arg Ser Ala Ala Leu Met Leu Glu Phe Leu Asn Glu Glu Ala
305                 310                 315                 320

Ala Ala Lys Ile Tyr Glu Ala Val Asp Ala Asn Leu Thr Glu Gly Lys
                325                 330                 335

Leu Leu Ser Pro Asp Leu Gly Gly Thr Ala Thr Thr Glu Glu Val Val
                340                 345                 350

Gln Asp Ile Leu Lys Arg Leu
                355
```

<210> SEQ ID NO 61
<211> LENGTH: 362
<212> TYPE: PRT
<213> ORGANISM: Coprinopsis cinerea

<400> SEQUENCE: 61

```
Met Phe Arg Ala Pro Ile Arg Lys Leu Thr Thr Ala Ala Thr Arg Gln
1               5                   10                  15

Ser Leu Lys Ile Gly Leu Ile Pro Ala Asp Gly Ile Gly Lys Glu Val
            20                  25                  30

Ile Pro Ala Ala Arg Ala Ala Ile Val Ala Leu Gly Asn Asp Ile Pro
        35                  40                  45

Lys Pro Glu Phe Ile Asp Leu Asn Ala Gly Trp Glu Thr Phe Thr Arg
    50                  55                  60

Thr Gly Val Ala Leu Pro Glu Glu Thr Val Arg Val Leu His Glu Glu
65                  70                  75                  80

Cys Asp Cys Ala Leu Phe Gly Ser Val Ser Ser Pro Ser Arg Lys Val
                85                  90                  95

Thr Gly Tyr Ser Ser Pro Ile Val Ala Leu His Lys Glu Leu Asp Leu
            100                 105                 110

Tyr Ala Asn Ile Arg Pro Val Thr Ser Val Ala Pro Glu Ala Gly Gln
        115                 120                 125

Gln Pro Ala Val Asp Leu Ile Val Val Arg Glu Asn Thr Glu Cys Leu
    130                 135                 140

Tyr Val Lys Gln Glu Gln Gln Thr Ile Gly Glu Asn Gly Lys Glu Ala
145                 150                 155                 160

Arg Ala Thr Arg Leu Ile Thr Glu Arg Ala Ser Arg Ile Gly Gln
                165                 170                 175

Met Ala Phe Glu Leu Ala Ala Arg Pro Arg Lys His Leu Thr Val
                180                 185                 190

Ile His Lys Ser Asn Val Leu Ser Ile Thr Asp Gly Leu Phe Arg Glu
        195                 200                 205

Thr Val Arg Ala Val Pro Arg Leu Pro Glu Val Asn Gly Lys Tyr Asp
    210                 215                 220

Asp Val Thr Ile Met Glu Gln Leu Val Asp Ser Ala Val Tyr Arg Leu
225                 230                 235                 240
```

-continued

Phe Arg Glu Pro Glu Val Phe Asp Val Met Val Ala Pro Asn Leu Tyr
            245                 250                 255

Gly Asp Ile Ile Ser Asp Ala Ala Ala Leu Val Gly Ser Leu Gly
        260                 265                 270

Leu Ile Pro Ser Val Asn Ala Gly Asp Asn Phe Val Met Gly Glu Pro
        275                 280                 285

Val His Gly Ser Ala Pro Asp Ile Glu Gly Lys Gly Ile Ala Asn Pro
    290                 295                 300

Ile Ala Ser Ile Arg Ser Ala Ala Leu Met Leu Arg His Leu Gly Tyr
305                 310                 315                 320

Thr Lys Gly Ala Asp Arg Leu Asp Leu Ala Val Asp Gln Val Ile Arg
                325                 330                 335

Glu Gly Lys Tyr Leu Thr Pro Asp Leu Lys Gly Lys Ser Thr Thr Arg
            340                 345                 350

Glu Val Leu Asp Ala Val Leu Ala Lys Ile
            355                 360

<210> SEQ ID NO 62
<211> LENGTH: 362
<212> TYPE: PRT
<213> ORGANISM: Coprinopsis cinerea

<400> SEQUENCE: 62

Met Phe Arg Ala Pro Ile Arg Lys Leu Thr Thr Ala Ala Thr Arg Gln
1               5                   10                  15

Ser Leu Lys Ile Gly Leu Ile Pro Ala Asp Gly Ile Gly Lys Glu Val
            20                  25                  30

Ile Pro Ala Ala Arg Ala Ala Ile Val Ala Leu Gly Asn Asp Ile Pro
        35                  40                  45

Lys Pro Glu Phe Ile Asp Leu Asn Ala Gly Trp Glu Thr Phe Thr Arg
    50                  55                  60

Thr Gly Val Ala Leu Pro Glu Glu Thr Val Arg Val Leu Arg Glu Glu
65                  70                  75                  80

Cys Asp Cys Ala Leu Phe Gly Ser Val Ser Pro Ser Arg Lys Val
                85                  90                  95

Thr Gly Tyr Ser Ser Pro Ile Val Ala Leu His Lys Glu Leu Asp Leu
            100                 105                 110

Tyr Ala Asn Ile Arg Pro Val Thr Ser Val Ala Pro Glu Ala Gly Gln
        115                 120                 125

Gln Pro Ala Val Asp Leu Ile Val Val His Glu Asn Thr Glu Cys Leu
    130                 135                 140

Tyr Val Lys Gln Glu Gln Gln Thr Ile Gly Glu Asn Gly Lys Glu Ala
145                 150                 155                 160

Arg Ala Thr Arg Leu Ile Thr Glu Arg Ala Ser Arg Ile Gly Gln
                165                 170                 175

Met Ala Phe Glu Leu Ala Ala Ala Arg Pro Arg Lys His Leu Thr Val
            180                 185                 190

Ile His Lys Ser Asn Val Leu Ser Ile Thr Asp Gly Leu Phe Arg Glu
        195                 200                 205

Thr Val Arg Ala Val Pro Arg Leu Pro Glu Val Asn Gly Lys Tyr Asp
    210                 215                 220

Asp Val Thr Ile Met Glu Gln Leu Val Asp Ser Ala Val Tyr Arg Leu
225                 230                 235                 240

Phe Arg Glu Pro Glu Val Phe Asp Val Met Val Ala Pro Asn Leu Tyr
            245                 250                 255

```
Gly Asp Ile Ile Ser Asp Ala Ala Ala Leu Val Gly Ser Leu Gly
            260                 265                 270

Leu Ile Pro Ser Val Asn Ala Gly Asp Asn Phe Val Met Gly Glu Pro
        275                 280                 285

Val His Gly Ser Ala Pro Asp Ile Glu Gly Lys Gly Ile Ala Asn Pro
    290                 295                 300

Ile Ala Ser Ile Arg Ser Ala Ala Leu Met Leu Arg His Leu Gly Tyr
305                 310                 315                 320

Thr Lys Gly Ala Asp Arg Leu Asp Leu Ala Val Asp Gln Val Ile Arg
                325                 330                 335

Glu Gly Lys Tyr Leu Thr Pro Asp Leu Lys Gly Lys Ser Thr Thr Arg
            340                 345                 350

Glu Val Leu Asp Ala Val Leu Ala Lys Ile
            355                 360

<210> SEQ ID NO 63
<211> LENGTH: 356
<212> TYPE: PRT
<213> ORGANISM: Cordyceps militaris

<400> SEQUENCE: 63

Met Ser Leu Arg Thr Leu Arg Ile Gly Leu Ile Pro Gly Asp Gly Ile
1               5                   10                  15

Gly Lys Glu Val Ile Pro Ala Gly Arg Arg Val Leu Glu Ala Leu Pro
            20                  25                  30

Ala Ala Leu Lys Leu Lys Phe Asp Phe Val Asn Leu His Ala Gly Phe
        35                  40                  45

Glu Thr Phe Glu Lys Thr Gly Thr Ala Leu Pro Asp Ala Thr Val Asp
    50                  55                  60

Thr Leu Arg Ser Glu Cys Gln Gly Ala Leu Phe Gly Ala Val Ser Ser
65                  70                  75                  80

Pro Thr His Ala Val Ala Gly Tyr Ser Ser Pro Ile Val Ala Leu His
                85                  90                  95

Lys Arg Leu Asp Leu Tyr Ala Asn Val Arg Pro Val Lys Thr Val Leu
            100                 105                 110

Thr Ala Pro Lys Pro Ile Asp Met Val Ile Val His Glu Asn Thr Glu
        115                 120                 125

Asp Leu Tyr Val Lys Glu Glu Thr Thr Arg Gln Thr Pro Glu Gly Arg
    130                 135                 140

Val Ala Glu Ala Ile Lys Arg Ile Ser Glu Arg Ala Thr Phe Arg Ile
145                 150                 155                 160

Ala Thr Met Ala Gly Asp Ile Ala Val Arg Arg Gln Lys Leu Arg Glu
                165                 170                 175

Ala Gly Ala Ala Ser Ile His Lys Ser Pro Val Val Thr Ile Thr His
            180                 185                 190

Lys Ser Asn Val Leu Ser Gln Thr Asp Gly Leu Phe Arg Glu Val Ser
        195                 200                 205

Lys Thr Ala Leu Ala Asp Pro Arg Phe Ala Ser Val Ala Val Glu Glu
    210                 215                 220

Gln Ile Val Asp Ser Met Val Tyr Lys Leu Phe Arg Gln Pro Glu Asp
225                 230                 235                 240

Tyr Asp Val Ile Val Ala Pro Asn Leu Tyr Gly Asp Ile Leu Ser Asp
                245                 250                 255

Gly Ala Ala Ala Leu Val Gly Ser Leu Gly Leu Val Pro Ser Ala Asn
            260                 265                 270
```

```
Val Gly Glu Gly Phe Ala Ile Gly Glu Pro Cys His Gly Ser Ala Pro
            275                 280                 285

Asp Ile Met Gly Arg Gly Val Ala Asn Pro Ile Ala Thr Ile Arg Ser
        290                 295                 300

Ala Ala Leu Met Leu Glu Phe Leu Glu Pro Ala Ala Ala Ala
305                 310                 315                 320

Ile Tyr Ala Ala Val Asp Ala Asn Leu Glu Glu Gly Lys Leu Leu Ser
                325                 330                 335

Pro Asp Leu Gly Gly Thr Ala Thr Thr Glu Gln Val Val Glu Asp Ile
            340                 345                 350

Leu Arg Arg Leu
        355

<210> SEQ ID NO 64
<211> LENGTH: 333
<212> TYPE: PRT
<213> ORGANISM: Deinococcus radiodurans
<220> FEATURE:
<221> NAME/KEY: misc_feature
<222> LOCATION: (309)..(309)
<223> OTHER INFORMATION: Xaa can be any naturally occurring amino acid

<400> SEQUENCE: 64

Met Ala Lys Tyr Arg Ile Cys Leu Ile Glu Gly Asp Gly Ile Gly His
1               5                   10                  15

Glu Val Ile Pro Ala Ala Lys Arg Val Leu Glu Ala Ala Gly Phe Asp
            20                  25                  30

Ala Glu Tyr Val His Ala Glu Ala Gly Tyr Glu Tyr Phe Leu Asp His
        35                  40                  45

Gly Thr Ser Val Pro Glu Ala Thr Tyr Asp Ala Val Glu Asn Thr Asp
    50                  55                  60

Ala Thr Leu Phe Gly Ala Thr Ser Pro Ser Gly Glu Lys Pro Ala
65                  70                  75                  80

Gly Phe Phe Gly Ala Ile Arg His Leu His Gln Lys Tyr Asn Leu Tyr
                85                  90                  95

Ala Asn Val Arg Pro Thr Lys Thr Arg Pro Val Pro His Ser Tyr Glu
            100                 105                 110

Asn Val Asp Leu Val Ile Val His Glu Asn Thr Gln Gly Leu Tyr Val
        115                 120                 125

Glu Gln Glu Arg Arg Tyr Gly Asp Thr Ala Ile Ala Asp Thr Val Ile
    130                 135                 140

Thr Arg Glu Ala Ser Asp Arg Ile Gly Lys Phe Ala Ala Asp Leu Ala
145                 150                 155                 160

Met Lys Arg Ser Lys Arg Leu Thr Val Val His Lys Ser Asn Val Leu
                165                 170                 175

Pro Val Thr Gln Gly Leu Phe Met Asn Thr Ile Leu Asp His Thr Lys
            180                 185                 190

Thr Val Glu Gly Leu Ser Thr Ser Thr Met Ile Val Asp Asn Ala Ala
        195                 200                 205

Met Gln Leu Val Arg Asn Pro Gln Gln Phe Asp Val Met Val Met Thr
    210                 215                 220

Asn Met Phe Gly Asp Ile Leu Ser Asp Leu Ala Ala Gly Leu Val Gly
225                 230                 235                 240

Gly Leu Gly Ile Ala Ala Ser Gly Asn Val Gly Asp Gln Phe Gly Ile
                245                 250                 255

Phe Glu Ser Val His Gly Ser Ala Pro Asp Ile Ala Gly Gln Gly Ile
            260                 265                 270
```

```
Ser Asn Pro Thr Ala Thr Ile Leu Ala Ala Val Ile Met Leu Asp His
        275                 280                 285

Leu Gly Asp His Glu Thr Ala Arg Arg Leu Asp Asn Ala Ile Asn Lys
290                 295                 300

Val Leu Ala Glu Xaa Pro Arg Thr Arg Asp Leu Gly Gly Thr Ala Gly
305                 310                 315                 320

Thr Gln Glu Phe Thr Glu Ala Val Ile Lys Ala Leu Ala
                325                 330

<210> SEQ ID NO 65
<211> LENGTH: 357
<212> TYPE: PRT
<213> ORGANISM: Glarea lozoyensis

<400> SEQUENCE: 65

Met Ala Ala Arg Thr Leu Arg Ile Gly Leu Ile Pro Gly Asp Gly Ile
1               5                   10                  15

Gly Lys Glu Val Ile Pro Ala Gly Arg Lys Ile Leu Glu Ala Leu Pro
            20                  25                  30

Ala Ser Leu Lys Leu Lys Phe Glu Phe Val Asp Leu Lys Ala Gly Phe
        35                  40                  45

Glu Ala Phe Glu Gln Thr Gly Ala Ala Leu Pro Glu Lys Thr Val Glu
    50                  55                  60

Ile Leu Lys Asn Glu Cys Asp Gly Ala Leu Phe Gly Ala Val Ser Ser
65                  70                  75                  80

Pro Ser Lys Ala Val Lys Gly Tyr Ser Ser Pro Ile Val Ala Leu His
                85                  90                  95

Lys Arg Leu Asp Leu Tyr Ala Asn Val Arg Pro Val Lys Ser Val Met
            100                 105                 110

Thr Ala Lys Asn Pro Ile Asp Met Val Ile Val His Glu Asn Thr Glu
        115                 120                 125

Asp Val Tyr Val Lys Glu Glu Lys Thr Tyr Asp Thr Pro Glu Gly Lys
    130                 135                 140

Val Ala Glu Ala Ile Lys Arg Ile Ser Glu Lys Ala Ser Phe Arg Ile
145                 150                 155                 160

Ala Thr Met Ala Gly Glu Ile Ala Leu Arg Arg Gln Lys Ile Arg Asp
                165                 170                 175

Ser Gly Val Pro Ser Ile His Lys Ser Pro Met Val Thr Ile Thr His
            180                 185                 190

Lys Ser Asn Val Leu Ser Gln Thr Asp Gly Leu Phe Arg Ser Thr Ala
        195                 200                 205

Arg Glu Ala Leu Ala Ala His Lys Phe Ala Ser Ser Val Gly Val Glu
    210                 215                 220

Glu Gln Ile Val Asp Ser Met Val Tyr Lys Leu Phe Arg Gln Pro Glu
225                 230                 235                 240

Thr Tyr Asp Val Ile Val Ala Pro Asn Phe Tyr Gly Asp Ile Leu Ser
                245                 250                 255

Asp Gly Ala Ala Ala Leu Val Gly Ser Leu Gly Leu Val Pro Ser Ala
            260                 265                 270

Asn Val Gly Glu Gly Phe Ala Ile Gly Glu Pro Cys His Gly Ser Ala
        275                 280                 285

Pro Asp Ile Met Gly Gln Asp Ile Ala Asn Pro Ile Ala Thr Leu Arg
    290                 295                 300

Ser Val Ala Leu Met Leu Glu Phe Leu Asp Glu Glu Val Ala Ala Ala
305                 310                 315                 320
```

Lys Ile Tyr Ser Ala Val Asp Ala Asn Leu Glu Glu Gly Arg Leu Leu
            325                 330                 335

Ser Pro Asp Leu Gly Gly Thr Ala Ser Thr Thr Gln Val Val Glu Asp
            340                 345                 350

Ile Leu Arg Arg Leu
            355

<210> SEQ ID NO 66
<211> LENGTH: 370
<212> TYPE: PRT
<213> ORGANISM: Komagataella pastoris

<400> SEQUENCE: 66

Met Leu Ser Ala Val Arg Asn Asn Val Arg Ser Tyr Ser Thr Ala Val
1               5                   10                  15

Lys Thr Leu Lys Ile Gly Leu Ile Pro Gly Asp Gly Ile Gly Arg Glu
            20                  25                  30

Val Ile Pro Ala Gly Lys Gln Ile Leu Glu Ala Leu Pro Ala Glu His
        35                  40                  45

Gly Leu Lys Phe Glu Phe Gln Asn Leu Asp Ala Gly Phe Glu Leu Phe
    50                  55                  60

Lys Lys Thr Gly Val Ala Leu Pro Asp Ala Thr Val Glu Ala Leu Lys
65                  70                  75                  80

Gln Asn Cys Asp Gly Ala Leu Phe Gly Ala Val Ser Ser Pro Thr Thr
                85                  90                  95

Lys Val Glu Gly Tyr Ser Ser Pro Ile Val Ala Leu His Lys Lys Met
            100                 105                 110

Gly Leu Tyr Ala Asn Val Arg Pro Val Lys Ser Val Glu Gly Ile Gly
        115                 120                 125

Arg Pro Val Asp Met Val Ile Val His Glu Asn Thr Glu Asp Leu Tyr
    130                 135                 140

Ile Lys Glu Glu Arg Val Tyr Glu Lys Asp Gly Gln Lys Ile Ala Glu
145                 150                 155                 160

Ala Ile Lys Arg Ile Ser Glu Asn Ala Thr Asn Lys Ile Gly Lys Met
                165                 170                 175

Ala Leu Glu Ile Ala Leu Gln Arg Gln Ala Val Arg Glu Leu Gly Gly
            180                 185                 190

Thr Ser Leu His Ser Lys Pro Ser Leu Thr Val Thr His Lys Ser Asn
        195                 200                 205

Val Leu Ala Leu Ser Asp Gly Leu Phe Arg Glu Thr Ile Lys Lys Leu
    210                 215                 220

Tyr Asp Ser Asn Ser Lys Tyr Ala Ser Ile Glu Tyr Lys Glu Gln Ile
225                 230                 235                 240

Val Asp Ser Met Val Tyr Arg Met Phe Arg Glu Pro Glu Ile Phe Asp
                245                 250                 255

Val Val Val Ala Pro Asn Leu Tyr Gly Asp Ile Leu Ser Asp Gly Ala
            260                 265                 270

Ala Ala Leu Val Gly Ser Leu Gly Val Val Pro Ser Ala Asn Val Gly
        275                 280                 285

Asp Asp Phe Ala Ile Gly Glu Pro Cys His Gly Ser Ala Pro Asp Ile
    290                 295                 300

Glu Gly Lys Gly Ile Ser Asn Pro Val Ala Thr Ile Arg Ser Thr Ala
305                 310                 315                 320

Leu Met Leu Glu Phe Met Gly Tyr Pro Lys Ala Ala Gln Ile Tyr
                325                 330                 335

```
Ala Ala Val Asp Ser Asn Leu Ala Glu Asp Lys Ile Lys Thr Pro Asp
            340                 345                 350

Leu Asn Gly Lys Ser Thr Thr Gln Glu Val Val Asp Asp Ile Ile Arg
            355                 360                 365

Arg Phe
    370

<210> SEQ ID NO 67
<211> LENGTH: 377
<212> TYPE: PRT
<213> ORGANISM: Lodderomyces elongisporus

<400> SEQUENCE: 67

Met Leu Ser Thr Ser His Ser Ile Lys Arg Cys Phe Ser Thr Ser Ser
1               5                   10                  15

Pro Leu Leu Lys Thr Leu Lys Ile Gly Leu Ile Pro Gly Asp Gly Ile
            20                  25                  30

Gly Arg Glu Val Ile Pro Ala Gly Gln Lys Val Leu Glu Ser Leu Pro
        35                  40                  45

Ser Lys Phe Asp Leu Gln Phe Glu Phe Val Asn Leu Asp Ala Gly Phe
    50                  55                  60

Glu Leu Phe Lys Lys Thr Gly Thr Ala Leu Pro Asp Gln Thr Val Glu
65                  70                  75                  80

Thr Leu Lys Asn Glu Cys Asp Gly Ala Leu Phe Gly Ala Val Ser Ser
                85                  90                  95

Pro Thr Thr Lys Val Gly Tyr Ser Ser Pro Ile Val Ala Leu His
            100                 105                 110

Lys Lys Leu Gly Leu Tyr Ala Asn Val Arg Pro Val Lys Ser Val Lys
        115                 120                 125

Gly Val Gly Arg Pro Val Asp Met Val Ile Val His Glu Asn Thr Glu
130                 135                 140

Asp Leu Tyr Val Lys Glu Glu Lys Thr Tyr Gln Lys Glu Asp Gly Thr
145                 150                 155                 160

Lys Val Ala Glu Ala Ile Lys Arg Ile Ser Glu Thr Ala Ser Lys Arg
                165                 170                 175

Ile Ala Lys Met Ala Tyr Asp Ile Ala Leu Gln Arg Gln Ala Ile Arg
            180                 185                 190

Asp Ala Ser Pro Gly Ser Glu Gln Leu His Ser Lys Pro Ser Val Thr
        195                 200                 205

Val Thr His Lys Ser Asn Val Leu Ser Gln Ser Asp Gly Leu Phe Arg
    210                 215                 220

Glu Ser Cys Arg Ser Val Tyr Asp Ala Asn Lys Asp Lys Tyr Ser Gly
225                 230                 235                 240

Val Asp His Lys Glu Gln Ile Val Asp Ser Met Val Tyr Arg Met Phe
                245                 250                 255

Arg Glu Pro Glu Ile Phe Asp Val Val Val Ala Pro Asn Leu Tyr Gly
            260                 265                 270

Asp Ile Leu Ser Asp Gly Ala Ala Ala Leu Val Gly Ser Leu Gly Val
        275                 280                 285

Val Pro Ser Ala Asn Val Gly Glu Asn Phe Ala Ile Gly Glu Pro Cys
    290                 295                 300

His Gly Ser Ala Pro Asp Ile Glu Gly Lys Gly Ile Ser Asn Pro Ile
305                 310                 315                 320

Ala Thr Ile Arg Ser Thr Ala Leu Met Leu Glu Phe Met Gly Tyr Pro
                325                 330                 335
```

Glu Ala Ala Ala Lys Ile Tyr Glu Ala Val Asp Ala Asn Leu Ser Glu
            340                 345                 350

Asp Lys Ile Lys Thr Pro Asp Leu Gly Gly Asn Ser Thr Thr Gln Glu
            355                 360                 365

Val Ile Glu Asp Ile Val Arg Arg Phe
            370                 375

<210> SEQ ID NO 68
<211> LENGTH: 377
<212> TYPE: PRT
<213> ORGANISM: Lodderomyces elongisporus

<400> SEQUENCE: 68

Met Leu Ser Thr Ser His Ser Ile Lys Arg Cys Phe Ser Thr Ser Ser
1               5                   10                  15

Pro Leu Leu Lys Thr Leu Lys Ile Gly Leu Ile Pro Gly Asp Gly Ile
            20                  25                  30

Gly Arg Glu Val Ile Pro Ala Gly Gln Lys Val Leu Glu Ser Leu Pro
        35                  40                  45

Ser Lys Phe Asp Leu Gln Phe Glu Phe Val Asn Leu Asp Ala Gly Phe
    50                  55                  60

Glu Leu Phe Lys Lys Thr Gly Thr Ala Leu Pro Asp Gln Thr Val Glu
65                  70                  75                  80

Thr Leu Lys Asn Glu Cys Asp Gly Ala Leu Phe Gly Ala Val Ser Ser
                85                  90                  95

Pro Thr Thr Lys Val Glu Gly Tyr Ser Ser Pro Ile Val Ala Leu His
            100                 105                 110

Lys Lys Leu Gly Leu Tyr Ala Asn Val Arg Pro Val Lys Ser Val Lys
        115                 120                 125

Gly Val Gly Arg Pro Val Asp Met Val Ile Val His Glu Asn Thr Glu
130                 135                 140

Asp Leu Tyr Val Lys Glu Glu Lys Thr Tyr Gln Lys Glu Asp Gly Thr
145                 150                 155                 160

Lys Val Ala Glu Ala Ile Lys Arg Ile Ser Glu Thr Ala Ser Lys Arg
                165                 170                 175

Ile Ala Lys Met Ala Tyr Asp Ile Ala Leu Gln Arg Gln Ala Ile Arg
            180                 185                 190

Asp Ala Ser Pro Gly Ser Glu Gln Leu His Ser Lys Pro Ser Val Thr
        195                 200                 205

Val Thr His Lys Ser Asn Val Leu Ser Gln Ser Asp Gly Leu Phe Arg
    210                 215                 220

Glu Ser Cys Arg Ser Val Tyr Asp Ala Asn Lys Asp Lys Tyr Ser Gly
225                 230                 235                 240

Val Asp His Lys Glu Gln Ile Val Asp Ser Met Val Tyr Arg Met Phe
                245                 250                 255

Arg Glu Pro Glu Ile Phe Asp Val Val Val Ala Pro Asn Leu Tyr Gly
            260                 265                 270

Asp Ile Leu Ser Asp Gly Ala Ala Ala Leu Val Gly Ser Leu Gly Val
        275                 280                 285

Val Pro Ser Ala Asn Val Gly Glu Asn Phe Ala Ile Gly Glu Pro Cys
    290                 295                 300

His Gly Ser Ala Pro Asp Ile Glu Gly Lys Gly Ile Ser Asn Pro Ile
305                 310                 315                 320

Ala Thr Ile Arg Ser Thr Ala Leu Met Leu Glu Phe Met Gly Tyr Pro
                325                 330                 335

```
Glu Ala Ala Ala Lys Ile Tyr Glu Ala Val Asp Ala Asn Leu Ser Glu
            340                 345                 350

Asp Lys Ile Lys Thr Pro Asp Leu Gly Gly Asn Ser Thr Thr Gln Glu
        355                 360                 365

Val Ile Glu Asp Ile Val Arg Arg Phe
    370                 375

<210> SEQ ID NO 69
<211> LENGTH: 360
<212> TYPE: PRT
<213> ORGANISM: Magnaporthe oryzae

<400> SEQUENCE: 69

Met Ala Thr Ala Arg Ala Leu Arg Ile Gly Leu Ile Ala Gly Asp Gly
1               5                   10                  15

Ile Gly Lys Asp Val Val Pro Ala Gly Arg Arg Val Leu Glu Ala Leu
            20                  25                  30

Pro Ala Ser Leu Gly Leu Arg Phe Ser Phe Val Asp Leu Gln Ala Gly
        35                  40                  45

Phe Gln Thr Phe Glu Glu Thr Gly Ser Ala Leu Pro Asp Arg Thr Val
    50                  55                  60

Glu Thr Leu Lys Gly Glu Cys Asp Gly Ala Leu Phe Gly Ala Val Ser
65                  70                  75                  80

Ser Pro Thr Lys Pro Val Lys Gly Tyr Ser Ser Pro Ile Val Gly Leu
                85                  90                  95

His Lys Lys Leu Asp Leu Tyr Ala Asn Val Arg Pro Val Lys Thr Val
            100                 105                 110

Val Ser Ala Pro Arg Pro Ile Asp Met Val Ile Val His Glu Asn Thr
        115                 120                 125

Glu Asp Leu Tyr Val Lys Asp Glu Arg Thr Phe Asp Ala Pro Asp Gly
    130                 135                 140

Ser Gly Pro Val Ala Glu Ala Ile Lys Arg Ile Ser Tyr Arg Ala Ser
145                 150                 155                 160

His Arg Ile Ala Ser Met Ala Gly Glu Ile Ala Leu Arg Arg Gln Lys
                165                 170                 175

Ile Arg Ala Ala Gly Ala Pro Ser Ile His Ser Ser Pro Leu Val Thr
            180                 185                 190

Ile Thr His Lys Ser Asn Val Leu Ser Gln Thr Asp Gly Leu Phe Arg
        195                 200                 205

Ser Thr Ala Lys Glu Ala Leu Ala Asp Pro Lys Tyr Ala Gly Ser Val
    210                 215                 220

Ala Val Glu Glu Gln Ile Val Asp Ser Met Val Tyr Lys Leu Phe Arg
225                 230                 235                 240

Gln Pro Glu Asp Tyr Asp Val Ile Val Ala Pro Asn Leu Tyr Gly Asp
                245                 250                 255

Ile Leu Ser Asp Gly Ala Ala Ala Leu Val Gly Ser Leu Gly Leu Val
            260                 265                 270

Pro Ser Ala Asn Val Gly Asp Gly Phe Val Met Gly Glu Pro Cys His
        275                 280                 285

Gly Ser Ala Pro Asp Ile Met Gly Lys Asn Ile Ala Asn Pro Ile Ala
    290                 295                 300

Thr Leu Arg Ser Ala Ala Leu Met Leu Glu Phe Leu Asn Glu Glu Glu
305                 310                 315                 320

Ala Ala Ala Lys Ile Tyr Ala Ala Val Asp Ala Asn Leu Val Glu Gly
                325                 330                 335
```

```
Lys Val Leu Ser Pro Asp Leu Gly Gly Lys Ala Thr Thr Asp Gln Val
            340                 345                 350

Leu Glu Asp Ile Leu Arg Arg Leu
            355                 360

<210> SEQ ID NO 70
<211> LENGTH: 335
<212> TYPE: PRT
<213> ORGANISM: Marinithermus hydrothermalis

<400> SEQUENCE: 70

Met Gly Gln Thr Tyr Arg Ile Cys Leu Ile Glu Gly Asp Gly Ile Gly
1               5                   10                  15

His Glu Val Val Pro Ala Ala Arg Arg Val Leu Glu Ala Thr Gly Leu
            20                  25                  30

Lys Phe Glu Phe Thr Glu Ala Glu Ala Gly Trp Glu Thr Phe Glu Lys
        35                  40                  45

Tyr Gly Thr Ser Val Pro Glu Glu Thr Val Glu Lys Ile Arg Ala Ala
    50                  55                  60

Asp Ala Thr Leu Phe Gly Ala Ala Thr Ser Pro Thr Arg Lys Val Glu
65                  70                  75                  80

Gly Phe Phe Gly Ala Ile Arg Tyr Leu His Lys Arg Leu Asp Leu Phe
                85                  90                  95

Ala Asn Val Arg Pro Ala Lys Tyr His Pro Val Pro Gly Ala Ile Gln
            100                 105                 110

Gly Thr Asp Leu Val Val His Glu Asn Thr Glu Gly Leu Tyr Val
            115                 120                 125

Glu Gln Glu Arg Arg Tyr Ala Arg Gly Arg Ile Ala Ile Ala Asp Arg
130                 135                 140

Val Ile Thr Tyr Asp Ala Ser Tyr Arg Ile Ala Glu Tyr Ala Leu Lys
145                 150                 155                 160

Leu Ala Gln Arg Arg Gly Lys Leu Ala Leu Val His Lys Ala Asn
                165                 170                 175

Val Leu Pro Leu Ser Asp Gly Leu Phe Leu Glu Ala Ala Tyr Asp Ala
            180                 185                 190

Ala Lys His Tyr Pro Asp Val Glu Ile Ser Glu Val Ile Val Asp Ala
        195                 200                 205

Cys Ala Met Arg Leu Val Arg Arg Pro Gln Asp Phe Asp Val Leu Val
210                 215                 220

Met Glu Asn Leu Phe Gly Asp Ile Ile Ser Asp Leu Thr Ala Gly Leu
225                 230                 235                 240

Val Gly Gly Leu Gly Ile Ala Pro Ser Gly Asn Ile Gly Glu Glu Ala
                245                 250                 255

Ala Ile Phe Glu Pro Val His Gly Ser Ala Pro Asp Ile Ala Gly Lys
            260                 265                 270

Gly Ile Ala Asn Pro Thr Ala Thr Ile Leu Ser Ala Ala Met Met Leu
        275                 280                 285

Glu His Leu Gly Glu Lys Glu Ala Ala Glu Arg Ile Glu Arg Ala Val
    290                 295                 300

Asp Arg Val Leu Ala Glu Gly Pro Arg Thr Pro Asp Leu Gly Gly Asp
305                 310                 315                 320

Ala Thr Thr Glu Ala Phe Thr Asp Ala Val Ile Arg Ala Leu Gly
                325                 330                 335

<210> SEQ ID NO 71
```

```
<211> LENGTH: 335
<212> TYPE: PRT
<213> ORGANISM: Marinithermus hydrothermalis

<400> SEQUENCE: 71
```

Met Gly Gln Thr Tyr Arg Ile Cys Leu Ile Glu Gly Asp Gly Ile Gly
1               5                   10                  15

His Glu Val Val Pro Ala Ala Arg Arg Val Leu Glu Ala Thr Gly Leu
            20                  25                  30

Lys Phe Glu Phe Thr Glu Ala Glu Ala Gly Trp Glu Thr Phe Glu Lys
        35                  40                  45

Tyr Gly Thr Ser Val Pro Glu Glu Thr Val Glu Lys Ile Arg Ala Ala
    50                  55                  60

Asp Ala Thr Leu Phe Gly Ala Ala Thr Ser Pro Thr Arg Lys Val Glu
65                  70                  75                  80

Gly Phe Phe Gly Ala Ile Arg Tyr Leu His Lys Arg Leu Asp Leu Phe
                85                  90                  95

Ala Asn Val Arg Pro Ala Lys Tyr His Pro Val Pro Gly Ala Ile Gln
            100                 105                 110

Gly Thr Asp Leu Val Val His Glu Asn Thr Glu Gly Leu Tyr Val
        115                 120                 125

Glu Gln Glu Arg Arg Tyr Ala Arg Gly Arg Ile Ala Ile Ala Asp Arg
    130                 135                 140

Val Ile Thr Tyr Asp Ala Ser Tyr Arg Ile Ala Glu Tyr Ala Leu Lys
145                 150                 155                 160

Leu Ala Gln Arg Arg Gly Lys Leu Ala Leu Val His Lys Ala Asn
                165                 170                 175

Val Leu Pro Leu Ser Asp Gly Leu Phe Leu Glu Ala Ala Tyr Asp Ala
            180                 185                 190

Ala Lys His Tyr Pro Asp Val Glu Ile Ser Glu Val Ile Val Asp Ala
        195                 200                 205

Cys Ala Met Arg Leu Val Arg Arg Pro Gln Asp Phe Asp Val Leu Val
    210                 215                 220

Met Glu Asn Leu Phe Gly Asp Ile Ile Ser Asp Leu Thr Ala Gly Leu
225                 230                 235                 240

Val Gly Gly Leu Gly Ile Ala Pro Ser Gly Asn Ile Gly Glu Ala
                245                 250                 255

Ala Ile Phe Glu Pro Val His Gly Ser Ala Pro Asp Ile Ala Gly Lys
            260                 265                 270

Gly Ile Ala Asn Pro Thr Ala Thr Ile Leu Ser Ala Ala Met Met Leu
        275                 280                 285

Glu His Leu Gly Glu Lys Glu Ala Ala Glu Arg Ile Glu Arg Ala Val
    290                 295                 300

Asp Arg Val Leu Ala Glu Gly Pro Arg Thr Pro Asp Leu Gly Gly Asp
305                 310                 315                 320

Ala Thr Thr Glu Ala Phe Thr Asp Ala Val Ile Arg Ala Leu Gly
                325                 330                 335

```
<210> SEQ ID NO 72
<211> LENGTH: 334
<212> TYPE: PRT
<213> ORGANISM: Meiothermus silvanus

<400> SEQUENCE: 72
```

Met Ser Arg Val Tyr Arg Ile Cys Leu Ile Glu Gly Asp Gly Ile Gly
1               5                   10                  15

-continued

His Glu Val Val Pro Ala Ala Arg His Val Leu Glu Ala Thr Gly Leu
             20                  25                  30

Lys Cys Glu Phe Val Glu Ala Glu Ala Gly Trp Glu Thr Phe Glu Arg
         35                  40                  45

Arg Gly Thr Ser Val Pro Glu Glu Thr Val Glu Ile Val Lys Ser Ala
     50                  55                  60

Asp Ala Thr Leu Phe Gly Ala Ala Thr Ser Pro Thr Lys Lys Val Glu
 65                  70                  75                  80

Gly Phe Phe Gly Ala Ile Arg Tyr Leu His Arg Arg Leu Asp Leu Phe
                 85                  90                  95

Ala Asn Val Arg Pro Ala Lys His His Pro Val Lys Gly Ser Thr Pro
            100                 105                 110

Gly Thr Asp Leu Val Val His Glu Asn Thr Glu Gly Leu Tyr Val
        115                 120                 125

Glu Gln Glu Arg Arg Tyr Ala Lys Gly Lys Val Ala Ile Ala Asp Arg
    130                 135                 140

Val Ile Thr Tyr Asp Ala Ser Tyr Arg Ile Val Glu Tyr Ala Leu Lys
145                 150                 155                 160

Leu Ala Arg Thr Arg Arg Lys Gln Leu Ala Leu Val His Lys Ala Asn
                165                 170                 175

Val Leu Pro Leu Ser Asp Gly Leu Phe Leu Glu Ala Ala Tyr Asp Ala
            180                 185                 190

Ala Lys His Tyr Pro Asp Ile Gln Val Ser Glu Val Ile Val Asp Ala
        195                 200                 205

Cys Ala Met Arg Leu Val Arg Asn Pro Gln Ser Phe Asp Val Leu Val
    210                 215                 220

Met Glu Asn Leu Phe Gly Asp Ile Leu Ser Asp Leu Thr Ala Gly Leu
225                 230                 235                 240

Val Gly Gly Leu Gly Ile Ala Pro Ser Gly Asn Ile Gly Glu Gln Ala
                245                 250                 255

Ala Ile Phe Glu Pro Val His Gly Ser Ala Pro Asp Ile Ala Gly Lys
            260                 265                 270

Gly Val Ala Asn Pro Thr Ala Ala Ile Leu Ser Ala Ala Ile Met Leu
        275                 280                 285

Asp Tyr Leu Gly Glu His Glu Thr Ala Arg Arg Ile Glu Lys Ala Val
    290                 295                 300

Asp Ile Thr Leu Glu Gln Gly Pro Leu Thr Pro Asp Leu Gly Gly Lys
305                 310                 315                 320

Ala Gly Thr Leu Glu Phe Ala Lys Ala Val Ala Ala Ala Leu
                325                 330

<210> SEQ ID NO 73
<211> LENGTH: 334
<212> TYPE: PRT
<213> ORGANISM: Meiothermus silvanus

<400> SEQUENCE: 73

Met Ser Arg Val Tyr Arg Ile Cys Leu Ile Glu Gly Asp Gly Ile Gly
1               5                   10                  15

His Glu Val Val Pro Ala Ala Arg His Val Leu Glu Ala Thr Gly Leu
             20                  25                  30

Lys Cys Glu Phe Val Glu Ala Glu Ala Gly Trp Glu Thr Phe Glu Arg
         35                  40                  45

Arg Gly Thr Ser Val Pro Glu Glu Thr Val Glu Ile Val Lys Ser Ala
     50                  55                  60

```
Asp Ala Thr Leu Phe Gly Ala Ala Thr Ser Pro Thr Lys Lys Val Glu
 65                  70                  75                  80

Gly Phe Phe Gly Ala Ile Arg Tyr Leu His Arg Arg Leu Asp Leu Phe
                 85                  90                  95

Ala Asn Val Arg Pro Ala Lys His His Pro Val Lys Gly Ser Thr Pro
            100                 105                 110

Gly Thr Asp Leu Val Val Val His Glu Asn Thr Glu Gly Leu Tyr Val
        115                 120                 125

Glu Gln Glu Arg Arg Tyr Ala Lys Gly Lys Val Ala Ile Ala Asp Arg
130                 135                 140

Val Ile Thr Tyr Asp Ala Ser Tyr Arg Ile Val Glu Tyr Ala Leu Lys
145                 150                 155                 160

Leu Ala Arg Thr Arg Arg Lys Gln Leu Ala Leu Val His Lys Ala Asn
                165                 170                 175

Val Leu Pro Leu Ser Asp Gly Leu Phe Leu Glu Ala Ala Tyr Asp Ala
            180                 185                 190

Ala Lys His Tyr Pro Asp Ile Gln Val Ser Glu Val Ile Val Asp Ala
        195                 200                 205

Cys Ala Met Arg Leu Val Arg Asn Pro Gln Ser Phe Asp Val Leu Val
    210                 215                 220

Met Glu Asn Leu Phe Gly Asp Ile Leu Ser Asp Leu Thr Ala Gly Leu
225                 230                 235                 240

Val Gly Gly Leu Gly Ile Ala Pro Ser Gly Asn Ile Gly Glu Gln Ala
                245                 250                 255

Ala Ile Phe Glu Pro Val His Gly Ser Ala Pro Asp Ile Ala Gly Lys
            260                 265                 270

Gly Val Ala Asn Pro Thr Ala Ala Ile Leu Ser Ala Ala Ile Met Leu
        275                 280                 285

Asp Tyr Leu Gly Glu His Glu Thr Ala Arg Arg Ile Glu Lys Ala Val
    290                 295                 300

Asp Ile Thr Leu Glu Gln Gly Pro Leu Thr Pro Asp Leu Gly Gly Lys
305                 310                 315                 320

Ala Gly Thr Leu Glu Phe Ala Lys Ala Val Ala Ala Leu
                325                 330

<210> SEQ ID NO 74
<211> LENGTH: 356
<212> TYPE: PRT
<213> ORGANISM: Metarhizium acridum

<400> SEQUENCE: 74

Met Ser Phe Arg Thr Leu Arg Ile Gly Leu Ile Pro Gly Asp Gly Ile
 1               5                  10                  15

Gly Lys Glu Val Ile Pro Ala Gly Arg Arg Val Leu Glu Ala Leu Pro
            20                  25                  30

Ser Tyr Leu Asn Leu Lys Ph

```
Thr Ala Pro Lys Pro Ile Asp Met Val Ile Val His Glu Asn Thr Glu
        115                 120                 125

Asp Leu Tyr Val Lys Gln Glu Lys Thr Phe Asp Gly Pro Asp Gly Lys
    130                 135                 140

Val Ala Glu Ala Ile Lys Arg Ile Ser Glu Lys Ala Ser Leu Arg Ile
145                 150                 155                 160

Ala Ala Met Ala Gly Asp Ile Ala Ile Arg Arg Asp Arg Ile Arg Gln
                165                 170                 175

Ser Gly Ala Ala Ser Ile His Lys Lys Pro Leu Val Thr Ile Thr His
                180                 185                 190

Lys Ser Asn Val Leu Ser Gln Thr Asp Gly Leu Phe Arg Glu Ala Ser
                195                 200                 205

Lys Arg Ala Leu Ala Asp Pro Arg Phe Ala Thr Val Lys Val Glu Glu
    210                 215                 220

Gln Ile Val Asp Ser Met Val Tyr Lys Leu Phe Arg Gln Pro Glu Asp
225                 230                 235                 240

Tyr Asp Val Ile Val Ala Pro Asn Leu Tyr Gly Asp Ile Leu Ser Asp
                245                 250                 255

Gly Ala Ala Leu Val Gly Ser Leu Gly Leu Val Pro Ser Ala Asn
                260                 265                 270

Val Gly Glu Gly Phe Ala Ile Gly Glu Pro Cys His Gly Ser Ala Pro
                275                 280                 285

Asp Ile Met Gly Lys Gly Val Ala Asn Pro Ile Ala Thr Val Arg Ser
    290                 295                 300

Ala Ala Leu Met Leu Glu Phe Leu Asp Glu Pro Ala Ala Ala Ala Lys
305                 310                 315                 320

Ile Tyr Ala Ala Val Asp Ala Asn Leu Glu Glu Gly Glu Leu Leu Ser
                325                 330                 335

Pro Asp Leu Gly Gly Ser Ala Thr Thr Glu Gln Val Val Glu Asp Ile
                340                 345                 350

Leu Lys Lys Leu
        355

<210> SEQ ID NO 75
<211> LENGTH: 356
<212> TYPE: PRT
<213> ORGANISM: Metarhizium anisopliae

<400> SEQUENCE: 75

Met Ser Val Arg Thr Leu Arg Ile Gly Leu Ile Pro Gly Asp Gly Ile
1               5                   10                  15

Gly Lys Glu Val Ile Pro Ala Gly Arg Arg Val Leu Glu Ala Leu Pro
                20                  25                  30

Ser Tyr Leu Asn Leu Asn Phe Glu Phe Val Asn Leu Lys Ala Gly Phe
            35                  40                  45

Glu Ala Phe Glu Gln Thr Gly Thr Ala Leu Pro Glu Ala Thr Val Asp
        50                  55                  60

Val Leu Arg Asn Glu Cys Asp Gly Ala Leu Phe Gly Ala Val Ser Ser
65                  70                  75                  80

Pro Thr His Ala Val Lys Gly Tyr Ser Ser Pro Ile Val Ala Leu His
                85                  90                  95

Lys Arg Leu Asp Leu Tyr Ala Asn Val Arg Pro Val Lys Thr Val Met
                100                 105                 110

Thr Ala Pro Lys Pro Ile Asp Met Val Ile Val His Glu Asn Thr Glu
        115                 120                 125
```

```
Asp Leu Tyr Val Lys Gln Glu Lys Thr Phe Asp Gly Pro Asp Gly Lys
    130                 135                 140

Val Ala Glu Ala Ile Lys Arg Ile Ser Glu Lys Ala Ser Leu Arg Ile
145                 150                 155                 160

Ala Ala Met Ala Gly Glu Ile Ala Val Arg Arg Asp Arg Ile Arg Gln
                165                 170                 175

Ser Gly Ala Ala Ser Ile His Lys Lys Pro Leu Val Thr Ile Thr His
                180                 185                 190

Lys Ser Asn Val Leu Ser Gln Thr Asp Gly Leu Phe Arg Glu Ala Ser
            195                 200                 205

Lys Arg Ala Leu Ala Asp Pro Lys Phe Ala Thr Val Lys Val Glu Glu
    210                 215                 220

Gln Ile Val Asp Ser Met Val Tyr Lys Leu Phe Arg Gln Pro Glu Asp
225                 230                 235                 240

Tyr Asp Val Ile Val Ala Pro Asn Leu Tyr Gly Asp Ile Leu Ser Asp
                245                 250                 255

Gly Ala Ala Leu Val Gly Ser Leu Gly Leu Val Pro Ser Ala Asn
                260                 265                 270

Val Gly Glu Gly Phe Ala Ile Gly Glu Pro Cys His Gly Ser Ala Pro
            275                 280                 285

Asp Ile Met Gly Lys Gly Val Ala Asn Pro Ile Ala Thr Leu Arg Ser
    290                 295                 300

Ala Ala Leu Met Leu Glu Phe Leu Asp Glu Pro Ala Ala Ala Ala Lys
305                 310                 315                 320

Ile Tyr Ala Ala Val Asp Ala Asn Leu Glu Gly Glu Leu Leu Ser
                325                 330                 335

Pro Asp Leu Gly Gly Ser Ala Thr Thr Glu Gln Val Val Glu Asp Ile
            340                 345                 350

Leu Lys Lys Leu
            355

<210> SEQ ID NO 76
<211> LENGTH: 347
<212> TYPE: PRT
<213> ORGANISM: Methanocaldococcus jannaschii

<400> SEQUENCE: 76

Met Met Lys Val Cys Val Ile Glu Gly Asp Gly Ile Gly Lys Glu Val
1               5                   10                  15

Ile Pro Glu Ala Ile Lys Ile Leu Asn Glu Leu Gly Glu Phe Glu Ile
                20                  25                  30

Ile Lys Gly Glu Ala Gly Leu Glu Cys Leu Lys Lys Tyr Gly Asn Ala
            35                  40                  45

Leu Pro Glu Asp Thr Ile Glu Lys Ala Lys Glu Ala Asp Ile Ile Leu
    50                  55                  60

Phe Gly Ala Ile Thr Ser Pro Pro Gly Glu Val Lys Asn Tyr Lys
65                  70                  75                  80

Ser Pro Ile Ile Thr Leu His Lys Met Phe His Leu Tyr Ala Asn Val
                85                  90                  95

Arg Pro Ile Asn Asn Phe Gly Ile Gly Gln Leu Ile Gly Lys Ile Ala
            100                 105                 110

Asp Tyr Glu Phe Leu Asn Ala Lys Asn Ile Asp Ile Val Ile Ile His
            115                 120                 125

Glu Asn Thr Glu Asp Leu Tyr Val Gly Arg Glu Arg Leu Glu Asn Asp
    130                 135                 140
```

```
Thr Ala Ile Ala Glu Arg Val Ile Thr Arg Lys Gly Ser Glu Arg Ile
145                 150                 155                 160

Ile Arg Phe Ala Phe Glu Tyr Ala Ile Lys Asn Asn Arg Lys Lys Val
                165                 170                 175

Ser Cys Ile His Lys Ala Asn Val Leu Arg Ile Thr Asp Gly Leu Phe
            180                 185                 190

Leu Glu Val Phe Asn Glu Ile Lys Lys His Tyr Asn Ile Glu Ala Asp
        195                 200                 205

Asp Tyr Leu Val Asp Ser Thr Ala Met Asn Leu Ile Lys His Pro Glu
    210                 215                 220

Lys Phe Asp Val Ile Val Thr Thr Asn Met Phe Gly Asp Ile Leu Ser
225                 230                 235                 240

Asp Glu Ala Ser Ala Leu Ile Gly Gly Leu Gly Leu Ala Pro Ser Ala
                245                 250                 255

Asn Ile Gly Asp Asp Lys Ala Leu Phe Glu Pro Val His Gly Ser Ala
            260                 265                 270

Pro Asp Ile Ala Gly Lys Gly Ile Ala Asn Pro Met Ala Ser Ile Leu
        275                 280                 285

Ser Ile Ala Met Leu Phe Asp Tyr Ile Gly Lys Glu Lys Gly Asp
290                 295                 300

Leu Ile Arg Glu Ala Val Lys Tyr Cys Leu Ile Asn Lys Lys Val Thr
305                 310                 315                 320

Pro Asp Leu Gly Gly Asp Leu Lys Thr Lys Asp Val Gly Asp Glu Ile
                325                 330                 335

Leu Asn Tyr Ile Arg Lys Lys Leu Lys Gly Tyr
            340                 345

<210> SEQ ID NO 77
<211> LENGTH: 347
<212> TYPE: PRT
<213> ORGANISM: Methanocaldococcus jannaschii

<400> SEQUENCE: 77

Met Met Lys Val Cys Val Ile Glu Gly Asp Gly Ile Gly Lys Glu Val
1               5                   10                  15

Ile Pro Glu Ala Ile Lys Ile Leu Asn Glu Leu Gly Glu Phe Glu Ile
                20                  25                  30

Ile Lys Gly Glu Ala Gly Leu Glu Cys Leu Lys Lys Tyr Gly Asn Ala
            35                  40                  45

Leu Pro Glu Asp Thr Ile Glu Lys Ala Lys Glu Ala Asp Ile Ile Leu
        50                  55                  60

Phe Gly Ala Ile Thr Ser Pro Lys Pro Gly Glu Val Lys Asn Tyr Lys
65                  70                  75                  80

Ser Pro Ile Ile Thr Leu His Lys Met Phe His Leu Tyr Ala Asn Val
                85                  90                  95

Arg Pro Ile Asn Asn Phe Gly Ile Gly Gln Leu Ile Gly Lys Ile Ala
            100                 105                 110

Asp Tyr Glu Phe Leu Asn Ala Lys Asn Ile Asp Ile Val Ile His
        115                 120                 125

Glu Asn Thr Glu Asp Leu Tyr Val Gly Arg Glu Arg Leu Glu Asn Asp
    130                 135                 140

Thr Ala Ile Ala Glu Arg Val Ile Thr Arg Lys Gly Ser Glu Arg Ile
145                 150                 155                 160

Ile Arg Phe Ala Phe Glu Tyr Ala Ile Lys Asn Asn Arg Lys Lys Val
                165                 170                 175
```

```
Ser Cys Ile His Lys Ala Asn Val Leu Arg Ile Thr Asp Gly Leu Phe
            180                 185                 190

Leu Glu Val Phe Asn Glu Ile Lys His Tyr Asn Ile Glu Ala Asp
        195                 200                 205

Asp Tyr Leu Val Asp Ser Thr Ala Met Asn Leu Ile Lys His Pro Glu
    210                 215                 220

Lys Phe Asp Val Ile Val Thr Thr Asn Met Phe Gly Asp Ile Leu Ser
225                 230                 235                 240

Asp Glu Ala Ser Ala Leu Ile Gly Gly Leu Gly Leu Ala Pro Ser Ala
                245                 250                 255

Asn Ile Gly Asp Asp Lys Ala Leu Phe Glu Pro Val His Gly Ser Ala
                260                 265                 270

Pro Asp Ile Ala Gly Lys Gly Ile Ala Asn Pro Met Ala Ser Ile Leu
        275                 280                 285

Ser Ile Ala Met Leu Phe Asp Tyr Ile Gly Glu Lys Glu Lys Gly Asp
    290                 295                 300

Leu Ile Arg Glu Ala Val Lys Tyr Cys Leu Ile Asn Lys Lys Val Thr
305                 310                 315                 320

Pro Asp Leu Gly Gly Asp Leu Lys Thr Lys Asp Val Gly Asp Glu Ile
                325                 330                 335

Leu Asn Tyr Ile Arg Lys Lys Leu Lys Gly Tyr
                340                 345

<210> SEQ ID NO 78
<211> LENGTH: 331
<212> TYPE: PRT
<213> ORGANISM: Methanohalophilus mahii

<400> SEQUENCE: 78

Met Lys Leu Ala Val Ile Glu Gly Asp Gly Val Gly Lys Glu Val Ile
1               5                   10                  15

Pro Ala Ala Leu Arg Val Leu Asp Cys Phe Asp Leu Pro Leu Glu Ile
                20                  25                  30

Ile Pro Leu Glu Leu Gly Tyr Gly Lys Trp Glu Lys Thr Gly Gln Ala
            35                  40                  45

Ile Thr Asp Ala Asp Leu Glu Ile Leu Lys Asn Cys Asp Cys Ile Leu
    50                  55                  60

Phe Gly Ala Val Thr Thr Pro Ala Asp Pro Asn Tyr Lys Ser Val Leu
65                  70                  75                  80

Leu Thr Ile His Arg Glu Leu Asp Leu Tyr Ala Asn Ile Arg Pro Leu
                85                  90                  95

Lys Pro Ile Lys Gly Ile Glu Gly Ala Thr Gly Asn Thr Asp Phe Asp
            100                 105                 110

Ile Leu Val Val His Glu Asn Thr Glu Gly Leu Tyr Ser Ser Ile Glu
    115                 120                 125

Glu Val Gly Glu Asn Glu Ala Trp Ser Lys Arg Ile Ile Thr Arg Arg
130                 135                 140

Ala Ser Glu Arg Ile Ala Gln Ile Ala Cys Glu Tyr Ala Ala Lys Arg
145                 150                 155                 160

His Asn His Leu Thr Ile Val His Lys Ser Asn Val Ile Lys Ala Asp
                165                 170                 175

Ser Leu Phe Leu Asn Thr Cys Arg Asn Val Ala Gln Ala His Asn Val
            180                 185                 190

Ile His Asp Thr Met Leu Val Asp Ala Met Ala Tyr Asp Met Val Arg
    195                 200                 205
```

```
Ser Pro Glu Lys Tyr Asp Val Val Ala Pro Asn Leu Tyr Gly Asp
    210                 215                 220

Ile Leu Ser Asp Leu Gly Gly Ala Leu Val Gly Ser Leu Gly Leu Leu
225                 230                 235                 240

Pro Ser Ala Asn Ile Gly Glu Lys Gln Ala Phe Phe Glu Pro Val His
            245                 250                 255

Gly Ser Ala Pro Asp Ile Ala Gly Lys Gly Ile Ala Asn Pro Ile Ala
            260                 265                 270

Ala Val Leu Ser Val Ala Met Leu Leu Asp Trp Leu Asp Arg Pro Glu
        275                 280                 285

Gln Ala Arg Ile Val Arg Glu Ala Val Glu Ala Ser Ile Asn Glu Asp
        290                 295                 300

Ile Lys Thr Ala Asp Leu Gly Gly Asn Phe Thr Thr Glu Gln Val Thr
305                 310                 315                 320

Gly Phe Leu Val Arg Tyr Val Gln Ser His Ser
            325                 330

<210> SEQ ID NO 79
<211> LENGTH: 331
<212> TYPE: PRT
<213> ORGANISM: Methanohalophilus mahii

<400> SEQUENCE: 79

Met Lys Leu Ala Val Ile Glu Gly Asp Gly Val Gly Lys Glu Val Ile
1               5                   10                  15

Pro Ala Ala Leu Arg Val Leu Asp Cys Phe Asp Leu Pro Leu Glu Ile
            20                  25                  30

Ile Pro Leu Glu Leu Gly Tyr Gly Lys Trp Glu Lys Thr Gly Gln Ala
        35                  40                  45

Ile Thr Asp Ala Asp Leu Glu Ile Leu Lys Asn Cys Asp Cys Ile Leu
    50                  55                  60

Phe Gly Ala Val Thr Thr Pro Ala Asp Pro Asn Tyr Lys Ser Val Leu
65                  70                  75                  80

Leu Thr Ile His Arg Glu Leu Asp Leu Tyr Ala Asn Ile Arg Pro Leu
                85                  90                  95

Lys Pro Ile Lys Gly Ile Glu Gly Ala Thr Gly Asn Thr Asp Phe Asp
            100                 105                 110

Ile Leu Val Val His Glu Asn Thr Glu Gly Leu Tyr Ser Ser Ile Glu
        115                 120                 125

Glu Val Gly Glu Asn Glu Ala Trp Ser Lys Arg Ile Ile Thr Arg Arg
    130                 135                 140

Ala Ser Glu Arg Ile Ala Gln Ile Ala Cys Glu Tyr Ala Ala Lys Arg
145                 150                 155                 160

His Asn His Leu Thr Ile Val His Lys Ser Asn Val Ile Lys Ala Asp
                165                 170                 175

Ser Leu Phe Leu Asn Thr Cys Arg Asn Val Ala Gln Ala His Asn Val
            180                 185                 190

Ile His Asp Thr Met Leu Val Asp Ala Met Ala Tyr Asp Met Val Arg
        195                 200                 205

Ser Pro Glu Lys Tyr Asp Val Val Ala Pro Asn Leu Tyr Gly Asp
    210                 215                 220

Ile Leu Ser Asp Leu Gly Gly Ala Leu Val Gly Ser Leu Gly Leu Leu
225                 230                 235                 240

Pro Ser Ala Asn Ile Gly Glu Lys Gln Ala Phe Phe Glu Pro Val His
            245                 250                 255
```

```
Gly Ser Ala Pro Asp Ile Ala Gly Lys Gly Ile Ala Asn Pro Ile Ala
            260                 265                 270

Ala Val Leu Ser Val Ala Met Leu Asp Trp Leu Asp Arg Pro Glu
        275                 280                 285

Gln Ala Arg Ile Val Arg Glu Ala Val Glu Ala Ser Ile Asn Glu Asp
    290                 295                 300

Ile Lys Thr Ala Asp Leu Gly Gly Asn Phe Thr Glu Gln Val Thr
305                 310                 315                 320

Gly Phe Leu Val Arg Tyr Val Gln Ser His Ser
                325                 330

<210> SEQ ID NO 80
<211> LENGTH: 317
<212> TYPE: PRT
<213> ORGANISM: Methanosaeta concilii

<400> SEQUENCE: 80

Met Ile Ala Gly Asp Gly Ile Gly Pro Glu Val Val Glu Ser Ala Leu
1               5                   10                  15

Glu Val Leu Arg Ala Ala Gly Ala Ser Leu Asp Leu Val His Phe Glu
            20                  25                  30

Ile Gly Leu Gly Arg Trp Lys Arg Thr Gly Glu Ala Met Asp Glu Asp
        35                  40                  45

Asp Leu Glu Glu Ile Ser Gly Cys Asp Cys Ile Leu Leu Gly Ala Ile
    50                  55                  60

Thr Thr Pro Pro Asp Pro Asn Tyr Arg Ser Val Leu Leu Arg Leu His
65                  70                  75                  80

Arg Ala Leu Asp Leu Tyr Ala Asn Ile Arg Pro Phe Gln Ser His Asp
                85                  90                  95

Leu Asp Phe Ile Ile Val His Glu Asn Thr Glu Gly Leu Tyr Ser Gly
            100                 105                 110

Val Glu Glu Val Gly Val Glu Ser Arg Thr Leu Arg Val Ile Thr
        115                 120                 125

Arg Arg Gly Ser Glu Arg Ile Ala Glu Ala Ala Cys Asp Leu Ala Ala
130                 135                 140

Arg Arg Arg Arg Leu Thr Ile Ile His Lys Ser Asn Val Leu Arg Ser
145                 150                 155                 160

Asp Arg Leu Phe Leu Gln Thr Cys Arg Glu Val Ala Glu Arg Arg Gly
                165                 170                 175

Ile Leu Tyr Glu Asp Met Leu Val Asp Ala Ala Ala Tyr Asn Leu Val
            180                 185                 190

Thr Asn Pro Gln Arg Phe Asp Val Leu Val Thr Thr Asn Leu Phe Gly
        195                 200                 205

Asp Ile Leu Ser Asp Glu Ala Ala Gly Val Ile Gly Ser Leu Gly Leu
    210                 215                 220

Cys Ala Ser Ala Asn Leu Gly Lys Ser Arg Ala Leu Phe Glu Pro Ile
225                 230                 235                 240

His Gly Ser Ala Pro Asp Ile Ala Gly Lys Gly Ile Ala Asn Pro Val
                245                 250                 255

Gly Ala Ile Arg Ser Ala Ala Met Met Met Arg Trp Leu Gly Glu Leu
            260                 265                 270

Glu Ala Ala Gly Arg Met Glu Glu Ala Val Lys Lys Ala Leu Ser Ala
        275                 280                 285

Gly Val Arg Thr Pro Asp Leu Gly Gly Arg Cys Ser Thr Ser Glu Val
    290                 295                 300
```

```
Thr Gly Ala Val Thr Gly Tyr Leu Met Ala Glu Glu Ser
305                 310                 315
```

<210> SEQ ID NO 81
<211> LENGTH: 317
<212> TYPE: PRT
<213> ORGANISM: Methanosaeta concilii

<400> SEQUENCE: 81

```
Met Ile Ala Gly Asp Gly Ile Gly Pro Glu Val Val Glu Ser Ala Leu
1               5                   10                  15

Glu Val Leu Arg Ala Ala Gly Ala Ser Leu Asp Leu Val His Phe Glu
            20                  25                  30

Ile Gly Leu Gly Arg Trp Lys Arg Thr Gly Glu Ala Met Asp Glu Asp
        35                  40                  45

Asp Leu Glu Glu Ile Ser Gly Cys Asp Cys Ile Leu Leu Gly Ala Ile
    50                  55                  60

Thr Thr Pro Pro Asp Pro Asn Tyr Arg Ser Val Leu Leu Arg Leu His
65                  70                  75                  80

Arg Ala Leu Asp Leu Tyr Ala Asn Ile Arg Pro Phe Gln Ser His Asp
                85                  90                  95

Leu Asp Phe Ile Ile Val His Glu Asn Thr Glu Gly Leu Tyr Ser Gly
            100                 105                 110

Val Glu Val Gly Val Glu Ser Arg Thr Leu Arg Val Ile Thr
        115                 120                 125

Arg Gly Ser Glu Arg Ile Ala Glu Ala Ala Cys Asp Leu Ala Ala
    130                 135                 140

Arg Arg Arg Leu Thr Ile Ile His Lys Ser Asn Val Leu Arg Ser
145                 150                 155                 160

Asp Arg Leu Phe Leu Gln Thr Cys Arg Glu Val Ala Glu Arg Gly
                165                 170                 175

Ile Leu Tyr Glu Asp Met Leu Val Asp Ala Ala Ala Tyr Asn Leu Val
            180                 185                 190

Thr Asn Pro Gln Arg Phe Asp Val Leu Val Thr Thr Asn Leu Phe Gly
            195                 200                 205

Asp Ile Leu Ser Asp Glu Ala Ala Gly Val Ile Gly Ser Leu Gly Leu
    210                 215                 220

Cys Ala Ser Ala Asn Leu Gly Lys Ser Arg Ala Leu Phe Glu Pro Ile
225                 230                 235                 240

His Gly Ser Ala Pro Asp Ile Ala Gly Lys Gly Ile Ala Asn Pro Val
                245                 250                 255

Gly Ala Ile Arg Ser Ala Ala Met Met Met Arg Trp Leu Gly Glu Leu
            260                 265                 270

Glu Ala Ala Gly Arg Met Glu Glu Ala Val Lys Lys Ala Leu Ser Ala
        275                 280                 285

Gly Val Arg Thr Pro Asp Leu Gly Arg Cys Ser Thr Ser Glu Val
    290                 295                 300

Thr Gly Ala Val Thr Gly Tyr Leu Met Ala Glu Glu Ser
305                 310                 315
```

<210> SEQ ID NO 82
<211> LENGTH: 357
<212> TYPE: PRT
<213> ORGANISM: Neurospora crassa

<400> SEQUENCE: 82

```
Met Ala Ala Arg Thr Leu Lys Ile Gly Leu Ile Pro Gly Asp Gly Ile
```

```
                1               5                   10                  15
Gly Lys Glu Val Ile Pro Ala Gly Arg Arg Ile Leu Glu Ala Leu Pro
                20                  25                  30

Ala Ser Leu Gly Leu Lys Phe Glu Phe Ile Asp Leu Lys Ala Gly Trp
            35                  40                  45

Glu Thr Phe Glu Gln Thr Gly Asn Ala Leu Pro Glu Thr Val Ser
    50                  55                  60

Ile Leu Lys Ser Glu Cys Asp Gly Ala Leu Phe Gly Ala Val Ser Ser
65                  70                  75                  80

Pro Thr Lys Ala Val Lys Gly Tyr Ser Ser Pro Ile Val Ala Leu His
                85                  90                  95

Lys Lys Leu Asp Leu Tyr Ala Asn Val Arg Pro Val Lys Ser Val Arg
                100                 105                 110

Gly Pro Gly Val Lys Pro Ile Asp Met Val Ile Val His Glu Asn Thr
            115                 120                 125

Glu Asp Leu Tyr Val Lys Glu Lys Thr Tyr Asp Thr Pro Glu Gly
    130                 135                 140

Lys Val Ala Glu Ala Ile Lys Arg Ile Ser Gln Arg Ala Ser Ser Arg
145                 150                 155                 160

Ile Ala Thr Ile Ala Gly Glu Ile Ala Leu Arg Arg Gln Lys Ile Arg
                165                 170                 175

Glu Gly Gly Ser Pro Ser Ile His Lys Gly Pro Leu Val Thr Val Thr
            180                 185                 190

His Lys Ser Asn Val Leu Ser Gln Thr Asp Gly Leu Phe Arg Ser Thr
            195                 200                 205

Ala Arg Glu Ala Leu Ala Ala Gly Arg Phe Thr Ser Val Ala Val Glu
    210                 215                 220

Glu Gln Ile Val Asp Ser Met Val Tyr Lys Leu Phe Arg Gln Pro Glu
225                 230                 235                 240

Ala Tyr Asp Val Ile Val Ala Pro Asn Leu Tyr Gly Asp Ile Leu Ser
                245                 250                 255

Asp Gly Ala Ala Ala Leu Val Gly Ser Leu Gly Leu Val Pro Ser Ala
            260                 265                 270

Asn Val Gly Glu Gly Phe Ala Ile Gly Glu Pro Cys His Gly Ser Ala
            275                 280                 285

Pro Asp Ile Gln Gly Gln Asn Ile Ala Asn Pro Ile Ala Thr Leu Arg
            290                 295                 300

Ser Ala Ala Leu Met Leu Glu Phe Leu Asn Glu Glu Ala Ala Ala
305                 310                 315                 320

Lys Ile Tyr Ala Ala Val Asp Ala Asn Leu Glu Glu Gly Lys Leu Leu
                325                 330                 335

Ser Pro Asp Leu Gly Gly Lys Ala Lys Thr Glu Glu Val Val Gln Asp
            340                 345                 350

Ile Leu Arg Arg Leu
            355

<210> SEQ ID NO 83
<211> LENGTH: 357
<212> TYPE: PRT
<213> ORGANISM: Neurospora crassa

<400> SEQUENCE: 83

Met Ala Ala Arg Thr Leu Lys Ile Gly Leu Ile Pro Gly Asp Gly Ile
1               5                   10                  15

Gly Lys Glu Val Ile Pro Ala Gly Arg Arg Ile Leu Glu Ala Leu Pro
```

```
                    20                  25                  30
Ala Ser Leu Gly Leu Lys Phe Glu Phe Ile Asp Leu Lys Ala Gly Trp
         35                  40                  45

Glu Thr Phe Glu Gln Thr Gly Asn Ala Leu Pro Glu Glu Thr Val Ser
     50                  55                  60

Ile Leu Lys Ser Glu Cys Asp Gly Ala Leu Phe Gly Ala Val Ser Ser
 65                  70                  75                  80

Pro Thr Lys Ala Val Lys Gly Tyr Ser Ser Pro Ile Val Ala Leu His
                 85                  90                  95

Lys Lys Leu Asp Leu Tyr Ala Asn Val Arg Pro Val Lys Ser Val Arg
            100                 105                 110

Gly Pro Gly Val Lys Pro Ile Asp Met Val Ile Val His Glu Asn Thr
        115                 120                 125

Glu Asp Leu Tyr Val Lys Glu Glu Lys Thr Tyr Asp Thr Pro Glu Gly
    130                 135                 140

Lys Val Ala Glu Ala Ile Lys Arg Ile Ser Gln Arg Ala Ser Ser Arg
145                 150                 155                 160

Ile Ala Thr Ile Ala Gly Glu Ile Ala Leu Arg Arg Gln Lys Ile Arg
                165                 170                 175

Glu Gly Gly Ser Pro Ser Ile His Lys Gly Pro Leu Val Thr Val Thr
            180                 185                 190

His Lys Ser Asn Val Leu Ser Gln Thr Asp Gly Leu Phe Arg Ser Thr
        195                 200                 205

Ala Arg Glu Ala Leu Ala Ala Gly Arg Phe Thr Ser Val Ala Val Glu
    210                 215                 220

Glu Gln Ile Val Asp Ser Met Val Tyr Lys Leu Phe Arg Gln Pro Glu
225                 230                 235                 240

Ala Tyr Asp Val Ile Val Ala Pro Asn Leu Tyr Gly Asp Ile Leu Ser
                245                 250                 255

Asp Gly Ala Ala Ala Leu Val Gly Ser Leu Gly Leu Val Pro Ser Ala
            260                 265                 270

Asn Val Gly Glu Gly Phe Ala Ile Gly Glu Pro Cys His Gly Ser Ala
        275                 280                 285

Pro Asp Ile Gln Gly Gln Asn Ile Ala Asn Pro Ile Ala Thr Leu Arg
    290                 295                 300

Ser Ala Ala Leu Met Leu Glu Phe Leu Asn Glu Glu Ala Ala Ala
305                 310                 315                 320

Lys Ile Tyr Ala Ala Val Asp Ala Asn Leu Glu Glu Gly Lys Leu Leu
                325                 330                 335

Ser Pro Asp Leu Gly Gly Lys Ala Lys Thr Glu Glu Val Val Gln Asp
            340                 345                 350

Ile Leu Arg Arg Leu
        355

<210> SEQ ID NO 84
<211> LENGTH: 357
<212> TYPE: PRT
<213> ORGANISM: Neurospora tetrasperma

<400> SEQUENCE: 84

Met Ala Ala Arg Thr Leu Lys Ile Gly Leu Ile Pro Gly Asp Gly Ile
 1               5                  10                  15

Gly Lys Glu Val Ile Pro Ala Gly Arg Arg Ile Leu Glu Ala Leu Pro
            20                  25                  30

Ala Ser Leu Gly Leu Lys Phe Glu Phe Ile Asp Leu Lys Ala Gly Trp
```

```
            35                  40                  45
Glu Thr Phe Glu Gln Thr Gly Asn Ala Leu Pro Glu Glu Thr Val Ser
 50                  55                  60

Ile Leu Lys Ser Glu Cys Asp Gly Ala Leu Phe Gly Ala Val Ser Ser
 65                  70                  75                  80

Pro Thr Lys Ala Val Lys Gly Tyr Ser Ser Pro Ile Val Ala Leu His
                 85                  90                  95

Lys Lys Leu Asp Leu Tyr Ala Asn Val Arg Pro Val Lys Ser Val Arg
                100                 105                 110

Gly Pro Gly Val Lys Pro Ile Asp Met Val Ile Val His Glu Asn Thr
                115                 120                 125

Glu Asp Leu Tyr Val Lys Glu Lys Thr Tyr Asp Thr Pro Glu Gly
                130                 135                 140

Lys Val Ala Glu Ala Ile Lys Arg Ile Ser Gln Arg Ala Ser Ser Arg
145                 150                 155                 160

Ile Ala Thr Ile Ala Gly Glu Ile Ala Leu Arg Arg Gln Lys Ile Arg
                165                 170                 175

Glu Gly Gly Ser Pro Ser Ile His Lys Gly Pro Leu Val Thr Val Thr
                180                 185                 190

His Lys Ser Asn Val Leu Ser Gln Thr Asp Gly Leu Phe Arg Ser Thr
                195                 200                 205

Ala Arg Glu Ala Leu Ala Ala Gly Arg Phe Thr Ser Val Ala Val Glu
                210                 215                 220

Glu Gln Ile Val Asp Ser Met Val Tyr Lys Leu Phe Arg Gln Pro Glu
225                 230                 235                 240

Ala Tyr Asp Val Ile Val Ala Pro Asn Leu Tyr Gly Asp Ile Leu Ser
                245                 250                 255

Asp Gly Ala Ala Ala Leu Val Gly Ser Leu Gly Leu Val Pro Ser Ala
                260                 265                 270

Asn Val Gly Glu Gly Phe Ala Ile Gly Glu Pro Cys His Gly Ser Ala
                275                 280                 285

Pro Asp Ile Gln Gly Gln Asn Ile Ala Asn Pro Ile Ala Thr Leu Arg
                290                 295                 300

Ser Ala Ala Leu Met Leu Glu Phe Leu Asn Glu Glu Ala Ala
305                 310                 315                 320

Lys Ile Tyr Ala Ala Val Asp Ala Asn Leu Glu Glu Gly Lys Leu Leu
                325                 330                 335

Ser Pro Asp Leu Gly Lys Ala Lys Thr Glu Glu Val Gln Asp
                340                 345                 350

Ile Leu Arg Arg Leu
                355

<210> SEQ ID NO 85
<211> LENGTH: 341
<212> TYPE: PRT
<213> ORGANISM: Oceanithermus profundus

<400> SEQUENCE: 85

Met Glu Asn Arg Val Tyr Lys Ile Thr Leu Ile Glu Gly Asp Gly Ile
  1               5                  10                  15

Gly His Glu Val Ile Pro Ala Ala Arg Thr Val Leu Glu Ala Thr Gly
                 20                  25                  30

Leu Ser Phe Val Phe Asp Glu Ala Glu Ala Gly Trp Glu Thr Phe Glu
                 35                  40                  45

Arg Ile Gly Thr Ser Val Pro Glu Glu Thr Val Glu Lys Ile Glu Arg
```

```
                50                  55                  60
Ser Asp Ala Thr Leu Phe Gly Ala Ala Thr Ser Pro Thr Lys Lys Val
 65                  70                  75                  80

Glu Gly Phe Phe Gly Ala Ile Arg Tyr Leu His Arg Arg Leu Asp Leu
                 85                  90                  95

Phe Ala Asn Val Arg Pro Ala Lys Tyr His Pro Val Pro Gly Ala Thr
                100                 105                 110

Pro Gly Thr Asp Leu Ile Val Val His Glu Asn Thr Glu Gly Leu Tyr
                115                 120                 125

Val Glu Gln Glu Arg Arg Tyr Ala Arg Gly Arg Val Ala Ile Ala Asp
                130                 135                 140

Arg Val Ile Thr Tyr Asp Ala Ser Tyr Arg Ile Val Glu Phe Ala Leu
145                 150                 155                 160

Glu Leu Ala Glu Arg Arg Gly Gln Leu Ala Leu Val His Lys Ala
                165                 170                 175

Asn Val Leu Pro Leu Ser Asp Gly Leu Phe Leu Glu Ala Ala Tyr Asp
                180                 185                 190

Ala Ala Lys Arg His Pro Thr Val Glu Ile Glu Val Ile Val Asp
                195                 200                 205

Ala Cys Ala Met Arg Leu Val Arg Asp Pro Ser Gln Phe Asp Val Leu
            210                 215                 220

Val Met Glu Asn Leu Phe Gly Asp Ile Ile Ser Asp Leu Thr Ala Gly
225                 230                 235                 240

Leu Val Gly Gly Leu Gly Ile Ala Pro Ser Gly Asn Ile Gly Glu Arg
                245                 250                 255

Ala Ala Ile Phe Glu Pro Val His Gly Ser Ala Pro Asp Ile Ala Gly
                260                 265                 270

Lys Gly Ile Ala Asn Pro Thr Ala Thr Ile Leu Ser Ala Ala Met Met
            275                 280                 285

Leu Asp His Leu Gly Glu Ser Arg Val Ala Arg Val Ile Glu Glu Ala
            290                 295                 300

Val Asp Arg Val Leu Glu Ser Gly Pro Arg Thr Pro Asp Leu Gly Gly
305                 310                 315                 320

Arg Ala Thr Thr Gln Glu Phe Ala Glu Ala Val Ala Ala Lys Val Gln
                325                 330                 335

Glu Leu Leu Ser Ala
            340

<210> SEQ ID NO 86
<211> LENGTH: 341
<212> TYPE: PRT
<213> ORGANISM: Oceanithermus profundus

<400> SEQUENCE: 86

Met Glu Asn Arg Val Tyr Lys Ile Thr Leu Ile Glu Gly Asp Gly Ile
  1               5                  10                  15

Gly His Glu Val Ile Pro Ala Ala Arg Thr Val Leu Glu Ala Thr Gly
                 20                  25                  30

Leu Ser Phe Val Phe Asp Glu Ala Glu Ala Gly Trp Glu Thr Phe Glu
                 35                  40                  45

Arg Ile Gly Thr Ser Val Pro Glu Glu Thr Val Glu Lys Ile Glu Arg
             50                  55                  60

Ser Asp Ala Thr Leu Phe Gly Ala Ala Thr Ser Pro Thr Lys Lys Val
 65                  70                  75                  80

Glu Gly Phe Phe Gly Ala Ile Arg Tyr Leu His Arg Arg Leu Asp Leu
```

```
                    85                  90                  95
Phe Ala Asn Val Arg Pro Ala Lys Tyr His Pro Val Pro Gly Ala Thr
                100                 105                 110
Pro Gly Thr Asp Leu Ile Val Val His Glu Asn Thr Glu Gly Leu Tyr
            115                 120                 125
Val Glu Gln Glu Arg Arg Tyr Ala Arg Gly Arg Val Ala Ile Ala Asp
        130                 135                 140
Arg Val Ile Thr Tyr Asp Ala Ser Tyr Arg Ile Val Glu Phe Ala Leu
145                 150                 155                 160
Glu Leu Ala Glu Arg Arg Gly Gln Leu Ala Leu Val His Lys Ala
                165                 170                 175
Asn Val Leu Pro Leu Ser Asp Gly Leu Phe Leu Glu Ala Ala Tyr Asp
                180                 185                 190
Ala Ala Lys Arg His Pro Thr Val Glu Ile Glu Val Ile Val Asp
            195                 200                 205
Ala Cys Ala Met Arg Leu Val Arg Asp Pro Ser Gln Phe Asp Val Leu
        210                 215                 220
Val Met Glu Asn Leu Phe Gly Asp Ile Ile Ser Asp Leu Thr Ala Gly
225                 230                 235                 240
Leu Val Gly Gly Leu Gly Ile Ala Pro Ser Gly Asn Ile Gly Glu Arg
                245                 250                 255
Ala Ala Ile Phe Glu Pro Val His Gly Ser Ala Pro Asp Ile Ala Gly
            260                 265                 270
Lys Gly Ile Ala Asn Pro Thr Ala Thr Ile Leu Ser Ala Ala Met Met
        275                 280                 285
Leu Asp His Leu Gly Glu Ser Arg Val Ala Arg Val Ile Glu Glu Ala
        290                 295                 300
Val Asp Arg Val Leu Glu Ser Gly Pro Arg Thr Pro Asp Leu Gly Gly
305                 310                 315                 320
Arg Ala Thr Thr Gln Glu Phe Ala Glu Ala Val Ala Ala Lys Val Gln
                325                 330                 335
Glu Leu Leu Ser Ala
            340

<210> SEQ ID NO 87
<211> LENGTH: 357
<212> TYPE: PRT
<213> ORGANISM: Ogataea parapolymorpha

<400> SEQUENCE: 87

Met Ser Pro Ala Asn Ile Ala Gly Leu Ile Pro Gly Asp Gly Ile Gly
1               5                   10                  15
Arg Glu Val Ile Pro Ala Gly Lys Gln Val Leu Glu Ala Leu Pro Ser
                20                  25                  30
Asp Leu Gly Leu Lys Phe Glu Phe Thr Glu Leu Lys Ala Gly Phe Glu
            35                  40                  45
Leu Phe Lys Gln Thr Gly Thr Ala Leu Pro Asp Glu Thr Val Glu Val
        50                  55                  60
Leu Gln Lys Ser Cys Asp Gly Ala Leu Phe Gly Ala Val Ser Ser Pro
65                  70                  75                  80
Thr Thr Lys Val Glu Gly Tyr Ser Ser Pro Ile Val Ala Leu His Lys
                85                  90                  95
Lys Leu Gly Leu Tyr Ala Asn Val Arg Pro Val Lys Ser Val Glu Gly
            100                 105                 110
Ile Gly Arg Pro Val Asp Met Val Ile Val His Glu Asn Thr Glu Asp
```

```
            115                 120                 125
Leu Tyr Ile Lys Glu Glu Lys Leu Tyr Glu Lys Asp Gly Gln Lys Val
    130                 135                 140

Ala Glu Ala Ile Lys Arg Ile Thr Glu Arg Ala Thr Thr Lys Ile Gly
145                 150                 155                 160

Ala Ile Ala Leu Glu Ile Ala Leu Gln Arg Gln Ala Ile Arg Glu Leu
                165                 170                 175

Gly Gly Ala Ser Leu His Ser Gln Pro Thr Leu Thr Val Thr His Lys
            180                 185                 190

Ser Asn Val Leu Ser Val Ser Asp Gly Leu Phe Arg Glu Thr Val Arg
        195                 200                 205

Lys Leu Tyr Asp Ser Asn Pro Ala Lys Tyr Ser Gly Val Gln Tyr Lys
    210                 215                 220

Glu Gln Ile Val Asp Ser Met Val Tyr Arg Met Phe Arg Glu Pro Glu
225                 230                 235                 240

Ile Phe Asp Val Val Ala Pro Asn Leu Tyr Gly Asp Ile Leu Ser
                245                 250                 255

Asp Gly Ala Ala Ala Leu Val Gly Ser Leu Gly Val Val Pro Ser Ala
            260                 265                 270

Asn Val Gly Asp Asn Phe Ala Ile Gly Glu Pro Cys His Gly Ser Ala
        275                 280                 285

Pro Asp Ile Glu Gly Lys Gly Ile Ala Asn Pro Ile Ala Thr Ile Arg
    290                 295                 300

Ser Thr Ala Leu Met Leu Glu Phe Met Gly His Pro Glu Ala Ala Ser
305                 310                 315                 320

Lys Ile Tyr Ala Ala Val Asp Ala Asn Leu Lys Glu Asp Val Ile Lys
                325                 330                 335

Thr Pro Asp Leu Gly Gly Lys Ser Ser Thr Gln Glu Val Val Ala Asp
            340                 345                 350

Val Ile Arg Arg Leu
        355

<210> SEQ ID NO 88
<211> LENGTH: 361
<212> TYPE: PRT
<213> ORGANISM: Paracoccidioides brasiliensis

<400> SEQUENCE: 88

Met Ala Ala Arg Thr Leu Arg Ile Gly Leu Ile Pro Gly Asp Gly Ile
1               5                   10                  15

Gly Arg Glu Val Ile Pro Ala Gly Arg Arg Leu Leu Glu Ala Leu Pro
            20                  25                  30

Ser Ser Leu Gly Leu Lys Phe Ser Phe Val Asp Leu Ala Gly Phe
        35                  40                  45

Asp Thr Phe Lys Lys Thr Gly Ala Ala Leu Pro Asp Lys Thr Val Glu
    50                  55                  60

Val Leu Lys Lys Glu Cys Asp Gly Ala Leu Phe Gly Ala Val Ser Ser
65                  70                  75                  80

Pro Ser Thr Lys Val Ala Gly Tyr Ser Ser Pro Ile Val Ala Leu His
                85                  90                  95

Lys Arg Leu Asp Leu Tyr Ala Asn Val Arg Pro Val Arg Thr Thr Thr
            100                 105                 110

Gly Ser Ser Gly Thr Pro Ile Asp Leu Val Ile Val His Glu Asn Thr
        115                 120                 125

Glu Asp Leu Tyr Val Lys Glu Glu Lys Thr Arg Asp Thr Pro Asn Gly
```

```
            130                 135                 140
Lys Val Ala Glu Ala Ile Lys Arg Ile Ser Glu His Ala Ser Phe Arg
145                 150                 155                 160

Ile Ala Thr Met Ala Gly Asp Ile Ala Leu Arg Arg Gln Lys Ile Arg
                165                 170                 175

Asp Ala Asp Pro Ser Thr Gln Ser Asn Ala Arg Ser Lys Pro Met Val
                180                 185                 190

Thr Ile Thr His Lys Ser Asn Val Leu Ser Gln Thr Asp Gly Leu Phe
                195                 200                 205

Arg Glu Thr Ala Arg Arg Ala Leu Ala Gln Thr Arg Phe Ala Glu Thr
            210                 215                 220

Val Ala Val Glu Glu Gln Ile Val Asp Ser Met Val Tyr Lys Leu Phe
225                 230                 235                 240

Arg Gln Pro Ser Tyr Tyr Asp Val Ile Val Ala Pro Asn Leu Tyr Gly
                245                 250                 255

Asp Ile Leu Ser Asp Gly Ala Ala Ala Leu Val Gly Ser Leu Gly Leu
                260                 265                 270

Val Pro Ser Ala Asn Val Gly Asp Asn Phe Ala Ile Gly Glu Pro Cys
            275                 280                 285

His Gly Ser Ala Pro Asp Ile Glu Gly Lys Gly Ile Ala Asn Pro Ile
            290                 295                 300

Ala Thr Leu Arg Ser Val Ala Leu Met Leu Glu Phe Leu Gly Glu Gly
305                 310                 315                 320

Lys Ala Ala Ser Ile Tyr Lys Ala Val Asp Glu Asn Leu Asp Ala
                325                 330                 335

Gly Thr Phe Leu Ser Pro Asp Leu Gly Gly Lys Ala Lys Thr Asp Glu
                340                 345                 350

Val Leu Glu Asp Val Leu Lys Arg Leu
                355                 360

<210> SEQ ID NO 89
<211> LENGTH: 361
<212> TYPE: PRT
<213> ORGANISM: Paracoccidioides brasiliensis

<400> SEQUENCE: 89

Met Ala Ala Arg Thr Leu Arg Ile Gly Leu Ile Pro Gly Asp Gly Ile
1               5                   10                  15

Gly Arg Glu Val Ile Pro Ala Gly Arg Arg Leu Leu Glu Ala Leu Pro
                20                  25                  30

Ser Ser Leu Gly Leu Lys Phe Ser Phe Val Asp Leu Glu Ala Gly Phe
            35                  40                  45

Asp Thr Phe Lys Lys Thr Gly Ala Ala Leu Pro Asp Lys Thr Val Glu
        50                  55                  60

Val Leu Lys Lys Glu Cys Asp Gly Ala Leu Phe Gly Ala Val Ser Ser
65                  70                  75                  80

Pro Ser Thr Lys Val Ala Gly Tyr Ser Ser Pro Ile Val Ala Leu His
                85                  90                  95

Lys Arg Leu Asp Leu Tyr Ala Asn Val Arg Pro Val Arg Thr Thr Thr
                100                 105                 110

Gly Ser Ser Gly Thr Pro Ile Asp Leu Val Ile Val His Glu Asn Thr
            115                 120                 125

Glu Asp Leu Tyr Val Lys Glu Glu Lys Thr Arg Asp Thr Pro Asn Gly
        130                 135                 140

Lys Val Ala Glu Ala Ile Lys Arg Ile Ser Glu His Ala Ser Phe Arg
```

```
                    145                 150                 155                 160
Ile Ala Thr Met Ala Gly Asp Ile Ala Leu Arg Arg Gln Lys Ile Arg
                165                 170                 175

Asp Ala Asp Pro Ser Thr Gln Ser Asn Ala Arg Ser Lys Pro Met Val
            180                 185                 190

Thr Ile Thr His Lys Ser Asn Val Leu Ser Gln Thr Asp Gly Leu Phe
        195                 200                 205

Arg Glu Thr Ala Arg Arg Leu Ala Gln Thr Arg Phe Ala Glu Thr
    210                 215                 220

Val Ala Val Glu Glu Gln Ile Val Asp Ser Met Val Tyr Lys Leu Phe
225                 230                 235                 240

Arg Gln Pro Ser Tyr Tyr Asp Val Ile Val Ala Pro Asn Leu Tyr Gly
                245                 250                 255

Asp Ile Leu Ser Asp Gly Ala Ala Leu Val Gly Ser Leu Gly Leu
            260                 265                 270

Val Pro Ser Ala Asn Val Gly Asp Asn Phe Ala Ile Gly Glu Pro Cys
            275                 280                 285

His Gly Ser Ala Pro Asp Ile Glu Gly Lys Gly Ile Ala Asn Pro Ile
        290                 295                 300

Ala Thr Leu Arg Ser Val Ala Leu Met Leu Glu Phe Leu Gly Glu Gly
305                 310                 315                 320

Lys Ala Ala Ser Ile Tyr Lys Ala Val Asp Glu Asn Leu Asp Ala
                325                 330                 335

Gly Thr Phe Leu Ser Pro Asp Leu Gly Gly Lys Ala Lys Thr Asp Glu
            340                 345                 350

Val Leu Glu Asp Val Leu Lys Arg Leu
            355                 360

<210> SEQ ID NO 90
<211> LENGTH: 361
<212> TYPE: PRT
<213> ORGANISM: Paracoccidioides brasiliensis

<400> SEQUENCE: 90

Met Ala Ala Arg Thr Leu Arg Ile Gly Leu Ile Pro Gly Asp Gly Ile
1               5                   10                  15

Gly Arg Glu Val Ile Pro Ala Gly Arg Arg Leu Leu Glu Ala Leu Pro
            20                  25                  30

Ser Ser Leu Gly Leu Lys Phe Ser Phe Val Asp Leu Glu Ala Gly Phe
        35                  40                  45

Asp Thr Phe Lys Lys Thr Gly Ala Ala Leu Pro Asp Lys Thr Val Glu
    50                  55                  60

Val Leu Lys Lys Glu Cys Asp Gly Ala Leu Phe Gly Ala Val Ser Ser
65                  70                  75                  80

Pro Ser Thr Lys Val Ala Gly Tyr Ser Ser Pro Ile Val Ala Leu His
                85                  90                  95

Lys Arg Leu Asp Leu Tyr Ala Asn Val Arg Pro Val Arg Thr Thr Thr
            100                 105                 110

Gly Ser Ser Gly Thr Pro Ile Asp Leu Val Ile Val His Glu Asn Thr
        115                 120                 125

Glu Asp Leu Tyr Val Lys Glu Lys Thr Ser Asp Thr Pro Asn Gly
    130                 135                 140

Lys Val Ala Glu Ala Ile Lys Arg Ile Ser Glu His Ala Ser Phe Arg
145                 150                 155                 160

Ile Ala Thr Met Ala Gly Asp Ile Ala Leu Arg Arg Gln Lys Ile Arg
```

```
                    165                 170                 175
Asp Ala Asp Pro Ser Thr Lys Ser Asn Ala Arg Ser Lys Pro Met Val
            180                 185                 190

Thr Ile Thr His Lys Ser Asn Val Leu Ser Gln Thr Asp Gly Leu Phe
            195                 200                 205

Arg Glu Thr Ala Arg Arg Ala Leu Ala Gln Thr Arg Phe Ala Gly Thr
            210                 215                 220

Val Ala Val Glu Glu Gln Ile Val Asp Ser Met Val Tyr Lys Leu Phe
225                 230                 235                 240

Arg Gln Pro Ser Tyr Tyr Asp Val Ile Val Ala Pro Asn Leu Tyr Gly
            245                 250                 255

Asp Ile Leu Ser Asp Gly Ala Ala Leu Val Gly Ser Leu Gly Leu
            260                 265                 270

Val Pro Ser Ala Asn Val Gly Asp Asn Phe Ala Ile Gly Glu Pro Cys
            275                 280                 285

His Gly Ser Ala Pro Asp Ile Glu Gly Lys Gly Ile Ala Asn Pro Ile
            290                 295                 300

Ala Thr Leu Arg Ser Val Ala Leu Met Leu Glu Phe Leu Gly Glu Glu
305                 310                 315                 320

Lys Ala Ala Ala Ile Ile Tyr Lys Ala Val Asp Ala Asn Leu Asp Ala
                    325                 330                 335

Gly Ala Phe Leu Ser Pro Asp Leu Gly Gly Lys Ala Lys Thr Asp Glu
            340                 345                 350

Val Leu Glu Asp Val Leu Arg Arg Leu
            355                 360

<210> SEQ ID NO 91
<211> LENGTH: 345
<212> TYPE: PRT
<213> ORGANISM: Pyrococcus horikoshii

<400> SEQUENCE: 91

Met Tyr Lys Val Ala Val Ile Lys Gly Asp Gly Ile Gly Pro Glu Val
1               5                   10                  15

Ile Asp Ala Ala Ile Arg Val Val Lys Ser Val Thr Asp Lys Ile Lys
            20                  25                  30

Phe Tyr Glu Phe Glu Gly Gly Leu Ser Val Phe Lys Lys Tyr Gly Val
            35                  40                  45

Pro Ile Arg Glu Glu Asp Leu Glu Glu Ile Arg Lys Met Asp Ala Ile
        50                  55                  60

Leu Phe Gly Ala Thr Thr Thr Pro Phe Asp Val Pro Arg Tyr Lys Ser
65                  70                  75                  80

Leu Ile Ile Thr Leu His Lys Glu Leu Asp Leu Tyr Ala Asn Leu Arg
                85                  90                  95

Ile Ile Pro Asn Phe Lys Leu Arg Lys Glu Ile Ile Val His Glu
            100                 105                 110

Asn Ser Glu Gly Leu Tyr Ser Gly Glu Gly Ala Tyr Asp Ser Asn Lys
            115                 120                 125

Val Val Asp Phe Arg Ile Ile Thr Arg Lys Gly Ala Glu Arg Ile Ala
        130                 135                 140

Lys Phe Ala Val Lys Leu Ala Lys Asp Arg Ser Thr Phe Leu Thr Phe
145                 150                 155                 160

Val His Lys Ala Asn Ile Leu Glu Ser Asp Arg Phe Phe Arg Lys Ile
                165                 170                 175

Val Leu Asp Ile Ala Arg Lys Glu Asp Val Lys Val Arg Glu Glu Ile
```

```
                        180                 185                 190
Val Asp Ser Phe Thr Ile Lys Leu Val Lys Asp Pro Trp Asn Leu Gly
                195                 200                 205

Ile Ile Leu Ser Glu Asn Met Phe Gly Asp Ile Leu Ser Asp Leu Ala
            210                 215                 220

Thr Ile His Ala Gly Ser Ile Gly Ile Val Pro Ser Gly Asn Tyr Gly
225                 230                 235                 240

Glu Asp Ile Ala Leu Phe Glu Pro Ile His Gly Ser Ala Pro Asp Ile
                245                 250                 255

Ala Gly Lys Gly Ile Ala Asn Pro Ile Gly Ala Ile Leu Ser Ala Ala
            260                 265                 270

Met Met Leu Asp Tyr Leu Gly Leu Asp Gly Ser Ile Ile Trp Lys Ala
275                 280                 285

Val Gly Arg Tyr Val Arg Arg Gly Asn Leu Thr Pro Asp Met Glu Gly
        290                 295                 300

Arg Ala Thr Thr Leu Glu Val Thr Asn Gly Ile Ile Ser Glu Ile Tyr
305                 310                 315                 320

Arg Leu Asp Glu Tyr Glu Ile Asp Glu Val Trp Arg Asp Glu Val Arg
                325                 330                 335

Leu Gly Arg Ile Leu Leu Glu Ile Ser
                340                 345

<210> SEQ ID NO 92
<211> LENGTH: 362
<212> TYPE: PRT
<213> ORGANISM: Roseiflexus sp.

<400> SEQUENCE: 92

Met Ser Ala Ala Pro Tyr Thr Ile Leu Val Ile Pro Gly Asp Gly Ile
1               5                   10                  15

Gly Arg Glu Val Ile Pro Ala Val Ala Val Leu Arg Ala Thr Gly
            20                  25                  30

Leu Pro Phe His Phe Glu Asn Ala Asp Ala Gly Trp Glu Cys Phe Gln
        35                  40                  45

Arg Gln Gly Glu Ala Leu Pro Ser Ala Thr Leu Thr Ala Ala Arg Ala
    50                  55                  60

Ala Asp Ala Ile Leu Phe Gly Ala Val Ala Ser Pro Gly Tyr Pro Val
65                  70                  75                  80

Ala Gly Tyr Arg Ser Pro Ile Val Arg Leu His Arg Glu Leu Asp Leu
                85                  90                  95

Tyr Ala Asn Ile Arg Pro Val Phe Asp Asp Leu Pro Glu Asn Gly Ser
            100                 105                 110

Asn Pro Arg Arg Arg Lys Val Asp Leu Val Val Val His Glu Asn Thr
        115                 120                 125

Glu Asp Val Tyr Ala Gly Arg Glu Arg Val Glu Asp Asp Gly Ala Thr
    130                 135                 140

Ala Ile Ala Glu Arg Val Ile Thr Arg Arg Ala Ser Ala Arg Ile Met
145                 150                 155                 160

Arg Val Ala Cys Asp Leu Ala Arg Ala Arg Arg Ser Ala Arg Asn Gly
                165                 170                 175

Ser Asp Ala Pro Pro Gly Arg Val Thr Val Val His Lys Ala Asn Val
            180                 185                 190

Leu Arg Glu Thr Cys Gly Leu Phe Arg Ser Val Ala Leu Glu Val Ala
        195                 200                 205

Gln Ala Tyr Pro Asp Leu Gln Ile Asp Glu Met Leu Val Asp Thr Cys
```

```
               210                 215                 220
Ala Leu Gln Leu Ala Thr Arg Pro Glu Arg Phe Asp Val Ile Val Thr
225                 230                 235                 240

Thr Asn Leu Phe Gly Asp Ile Leu Ser Asp Val Ala Cys Ala Trp Gly
                245                 250                 255

Gly Gly Leu Gly Leu Ala Pro Ser Ala Asn Leu Gly Glu Arg His Ala
            260                 265                 270

Leu Phe Glu Pro Val His Gly Ala Ala Pro Asp Ile Ala Gly Lys Gly
                275                 280                 285

Ile Ala Asn Pro Leu Ala Ala Ile Gly Cys Thr Ala Leu Leu Leu Asp
        290                 295                 300

His Leu Ala Gly Arg Ala Pro Ala Asp Leu Ala Ser Ala Met Arg Gly
305                 310                 315                 320

Trp Ser Ala Arg Ile Gln Arg Ala Ile Arg His Val Arg Ala Ala Gly
                325                 330                 335

Pro His Thr Pro Asp Leu Gly Gly Ser Ala Val Thr Thr Asp Ile Thr
                340                 345                 350

Asn Ala Val Leu Ser His Met Leu Thr Thr
                355                 360

<210> SEQ ID NO 93
<211> LENGTH: 371
<212> TYPE: PRT
<213> ORGANISM: Saccharomyces cerevisiae

<400> SEQUENCE: 93

Met Phe Arg Ser Val Ala Thr Arg Leu Ser Ala Cys Arg Gly Leu Ala
1               5                   10                  15

Ser Asn Ala Ala Arg Lys Ser Leu Thr Ile Gly Leu Ile Pro Gly Asp
                20                  25                  30

Gly Ile Gly Lys Glu Val Ile Pro Ala Gly Lys Gln Val Leu Glu Asn
            35                  40                  45

Leu Asn Ser Lys His Gly Leu Ser Phe Asn Phe Ile Asp Leu Tyr Ala
    50                  55                  60

Gly Phe Gln Thr Phe Gln Glu Thr Gly Lys Ala Leu Pro Asp Glu Thr
65                  70                  75                  80

Val Lys Val Leu Lys Glu Gln Cys Gln Gly Ala Leu Phe Gly Ala Val
                85                  90                  95

Gln Ser Pro Thr Thr Lys Val Glu Gly Tyr Ser Ser Pro Ile Val Ala
                100                 105                 110

Leu His Arg Glu Met Gly Leu Phe Ala Asn Val Arg Pro Val Lys Ser
            115                 120                 125

Val Glu Gly Glu Lys Gly Lys Pro Ile Asp Met Val Ile Val His Glu
        130                 135                 140

Asn Thr Glu Asp Leu Tyr Ile Lys Ile Glu Lys Thr Tyr Ile Asp Lys
145                 150                 155                 160

Ala Thr Gly Thr Arg Val Ala Asp Ala Thr Lys Arg Ile Ser Glu Ile
                165                 170                 175

Ala Thr Arg Arg Ile Ala Thr Ile Ala Leu Asp Ile Ala Leu Lys Arg
                180                 185                 190

Leu Gln Thr Arg Gly Gln Ala Thr Leu Thr Val Thr His Lys Ser Asn
            195                 200                 205

Val Leu Ser Gln Ser Asp Gly Leu Phe Arg Glu Ile Cys Lys Glu Val
        210                 215                 220

Tyr Glu Ser Asn Lys Asp Lys Tyr Gly Gln Ile Lys Tyr Asn Glu Gln
```

```
                    225                 230                 235                 240
Ile Val Asp Ser Met Val Tyr Arg Leu Phe Arg Glu Pro Gln Cys Phe
                245                 250                 255

Asp Val Ile Val Ala Pro Asn Leu Tyr Gly Asp Ile Leu Ser Asp Gly
                260                 265                 270

Ala Ala Ala Leu Val Gly Ser Leu Gly Val Val Pro Ser Ala Asn Val
                275                 280                 285

Gly Pro Glu Ile Val Ile Gly Glu Pro Cys His Gly Ser Ala Pro Asp
                290                 295                 300

Ile Ala Gly Lys Gly Ile Ala Asn Pro Ile Ala Thr Ile Arg Ser Thr
305                 310                 315                 320

Ala Leu Met Leu Glu Phe Leu Gly His Asn Glu Ala Ala Gln Asp Ile
                325                 330                 335

Tyr Lys Ala Val Asp Ala Asn Leu Arg Glu Gly Ser Ile Lys Thr Pro
                340                 345                 350

Asp Leu Gly Gly Lys Ala Ser Thr Gln Gln Val Val Asp Asp Val Leu
                355                 360                 365

Ser Arg Leu
        370

<210> SEQ ID NO 94
<211> LENGTH: 361
<212> TYPE: PRT
<213> ORGANISM: Schizosaccharomyces japonicus

<400> SEQUENCE: 94

Met Ala Ala Ile Arg Lys Ile Ile Leu Gly Leu Ile Pro Ala Asp Gly
1               5                   10                  15

Ile Gly Arg Glu Val Val Pro Ala Ala Val Arg Met Met Lys Asn Leu
                20                  25                  30

Pro Ala Lys His Asn Leu Gln Phe Asp Phe Val Asp Leu Asp Ala Gly
                35                  40                  45

Trp Gly Thr Phe Glu Arg Thr Gly Val Ala Leu Pro Glu Lys Thr Val
            50                  55                  60

Glu Arg Leu Lys Thr Glu Cys Asn Ala Ala Leu Phe Gly Ala Val Gln
65                  70                  75                  80

Ser Pro Thr His Lys Val Ala Gly Tyr Ser Ser Pro Ile Val Ala Leu
                85                  90                  95

His Lys Leu Leu Gly Leu Tyr Ala Asn Val Arg Pro Val Lys Ser Leu
                100                 105                 110

Ala Asn Thr Lys Gly Lys Thr Val Asp Met Val Ile Val His Glu Asn
            115                 120                 125

Thr Glu Cys Leu Tyr Ile Lys Glu Glu Arg Met Val Val Glu Thr Pro
130                 135                 140

Gly Arg Arg Val Ser Glu Ala Ile Arg Arg Ile Ser Glu Glu Ala Ser
145                 150                 155                 160

Val Lys Ile Gly Lys Met Ala Tyr Gln Ile Ala Leu Ser Arg Gln Arg
                165                 170                 175

Ile Arg Asp Ala Gly Ala Ala Ser Ile His Ser Lys Pro Asn Val Thr
                180                 185                 190

Ile Ile His Lys Ser Asn Val Met Ser Val Thr Asp Gly Leu Phe Arg
            195                 200                 205

Glu Ser Cys Arg Tyr Ala Gln Thr Leu Asp Pro Ala Phe Ala Ser Val
210                 215                 220

Ser Val Asp Glu Gln Ile Val Asp Ser Met Val Tyr Arg Leu Phe Arg
```

```
                 225                 230                 235                 240

Glu Pro Gln Cys Phe Asp Val Val Ala Pro Asn Leu Tyr Gly Asp
            245                 250                 255

Ile Leu Ser Asp Gly Ala Ala Ser Leu Ile Gly Ser Leu Gly Leu Val
            260                 265                 270

Pro Ser Ala Asn Val Gly Asp Phe Val Met Ser Glu Pro Val His
        275                 280                 285

Gly Ser Ala Pro Asp Ile Ala Gly Arg Gly Ile Ala Asn Pro Val Ala
    290                 295                 300

Thr Phe Arg Ser Val Ala Leu Met Leu Glu Phe Met Gly His Gln Glu
305                 310                 315                 320

Ala Ala Ala Asp Ile Tyr Arg Ala Val Asp Ser Val Leu Met Glu Gly
                325                 330                 335

Lys Val Leu Thr Pro Asp Leu Gly Gly Lys Ser Gly Thr Asn Glu Ile
                340                 345                 350

Thr Asp Ala Val Ile Ala Lys Met Asn
                355                 360

<210> SEQ ID NO 95
<211> LENGTH: 361
<212> TYPE: PRT
<213> ORGANISM: Schizosaccharomyces japonicus

<400> SEQUENCE: 95

Met Ala Ala Ile Arg Lys Ile Ile Leu Gly Leu Ile Pro Ala Asp Gly
1               5                   10                  15

Ile Gly Arg Glu Val Val Pro Ala Ala Val Arg Met Met Lys Asn Leu
            20                  25                  30

Pro Ala Lys His Asn Leu Gln Phe Asp Phe Val Asp Leu Asp Ala Gly
        35                  40                  45

Trp Gly Thr Phe Glu Arg Thr Gly Val Ala Leu Pro Glu Lys Thr Val
    50                  55                  60

Glu Arg Leu Lys Thr Glu Cys Asn Ala Ala Leu Phe Gly Ala Val Gln
65                  70                  75                  80

Ser Pro Thr His Lys Val Ala Gly Tyr Ser Ser Pro Ile Val Ala Leu
                85                  90                  95

His Lys Leu Leu Gly Leu Tyr Ala Asn Val Arg Pro Val Lys Ser Leu
            100                 105                 110

Ala Asn Thr Lys Gly Lys Thr Val Asp Met Val Ile Val His Glu Asn
        115                 120                 125

Thr Glu Cys Leu Tyr Ile Lys Glu Glu Arg Met Val Val Glu Thr Pro
    130                 135                 140

Gly Arg Arg Val Ser Glu Ala Ile Arg Ile Ser Glu Glu Ala Ser
145                 150                 155                 160

Val Lys Ile Gly Lys Met Ala Tyr Gln Ile Ala Leu Ser Arg Gln Arg
                165                 170                 175

Ile Arg Asp Ala Gly Ala Ala Ser Ile His Ser Lys Pro Asn Val Thr
            180                 185                 190

Ile Ile His Lys Ser Asn Val Met Ser Val Thr Asp Gly Leu Phe Arg
        195                 200                 205

Glu Ser Cys Arg Tyr Ala Gln Thr Leu Asp Pro Ala Phe Ala Ser Val
    210                 215                 220

Ser Val Asp Glu Gln Ile Val Asp Ser Met Val Tyr Arg Leu Phe Arg
225                 230                 235                 240

Glu Pro Gln Cys Phe Asp Val Val Val Ala Pro Asn Leu Tyr Gly Asp
```

-continued

```
                245                 250                 255
Ile Leu Ser Asp Gly Ala Ala Ser Leu Ile Gly Ser Leu Gly Leu Val
            260                 265                 270

Pro Ser Ala Asn Val Gly Asp Asp Phe Val Met Ser Glu Pro Val His
        275                 280                 285

Gly Ser Ala Pro Asp Ile Ala Gly Arg Gly Ile Ala Asn Pro Val Ala
        290                 295                 300

Thr Phe Arg Ser Val Ala Leu Met Leu Glu Phe Met Gly His Gln Glu
305                 310                 315                 320

Ala Ala Ala Asp Ile Tyr Arg Ala Val Asp Ser Val Leu Met Glu Gly
                325                 330                 335

Lys Val Leu Thr Pro Asp Leu Gly Gly Lys Ser Gly Thr Asn Glu Ile
                340                 345                 350

Thr Asp Ala Val Ile Ala Lys Met Asn
                355                 360

<210> SEQ ID NO 96
<211> LENGTH: 362
<212> TYPE: PRT
<213> ORGANISM: Schizosaccharomyces pombe

<400> SEQUENCE: 96

Met Ser Ala Thr Arg Arg Ile Val Leu Gly Leu Ile Pro Ala Asp Gly
1               5                   10                  15

Ile Gly Lys Glu Val Val Pro Ala Ala Arg Arg Leu Met Glu Asn Leu
            20                  25                  30

Pro Ala Lys His Lys Leu Lys Phe Asp Phe Ile Asp Leu Asp Ala Gly
        35                  40                  45

Trp Gly Thr Phe Glu Arg Thr Gly Lys Ala Leu Pro Glu Arg Thr Val
    50                  55                  60

Glu Arg Leu Lys Thr Glu Cys Asn Ala Ala Leu Phe Gly Ala Val Gln
65                  70                  75                  80

Ser Pro Thr His Lys Val Ala Gly Tyr Ser Ser Pro Ile Val Ala Leu
                85                  90                  95

His Lys Lys Met Gly Leu Tyr Ala Asn Val Arg Pro Val Lys Ser Leu
            100                 105                 110

Asp Gly Ala Lys Gly Lys Pro Val Asp Leu Val Ile Val His Glu Asn
        115                 120                 125

Thr Glu Cys Leu Tyr Val Lys Glu Glu Arg Met Val Gln Asn Thr Pro
130                 135                 140

Gly Lys Arg Val Ala Glu Ala Ile Arg Arg Ile Ser Glu Glu Ala Ser
145                 150                 155                 160

Thr Lys Ile Gly Lys Met Ala Phe Glu Ile Ala Lys Ser Arg Gln Lys
                165                 170                 175

Ile Arg Glu Ser Gly Thr Tyr Ser Ile His Lys Lys Pro Leu Val Thr
            180                 185                 190

Ile Ile His Lys Ser Asn Val Met Ser Val Thr Asp Gly Leu Phe Arg
        195                 200                 205

Glu Ser Cys Arg His Ala Gln Ser Leu Asp Pro Ser Tyr Ala Ser Ile
    210                 215                 220

Asn Val Asp Glu Gln Ile Val Asp Ser Met Val Tyr Arg Leu Phe Arg
225                 230                 235                 240

Glu Pro Glu Cys Phe Asp Val Val Ala Pro Asn Leu Tyr Gly Asp
                245                 250                 255

Ile Leu Ser Asp Gly Ala Ala Ser Leu Ile Gly Ser Leu Gly Leu Val
```

-continued

```
            260                 265                 270
Pro Ser Ala Asn Val Gly Asp Asn Phe Val Met Ser Glu Pro Val His
            275                 280                 285
Gly Ser Ala Pro Asp Ile Ala Gly Arg Gly Ile Ala Asn Pro Val Ala
            290                 295                 300
Thr Phe Arg Ser Val Ala Leu Met Leu Glu Phe Met Gly His Gln Asp
305                 310                 315                 320
Ala Ala Ala Asp Ile Tyr Thr Ala Val Asp Lys Val Leu Thr Glu Gly
                325                 330                 335
Lys Val Leu Thr Pro Asp Leu Gly Gly Lys Ser Gly Thr Asn Glu Ile
                340                 345                 350
Thr Asp Ala Val Leu Ala Asn Ile His Asn
                355                 360

<210> SEQ ID NO 97
<211> LENGTH: 362
<212> TYPE: PRT
<213> ORGANISM: Schizosaccharomyces pombe

<400> SEQUENCE: 97

Met Ser Ala Thr Arg Arg Ile Val Leu Gly Leu Ile Pro Ala Asp Gly
1               5                   10                  15
Ile Gly Lys Glu Val Val Pro Ala Ala Arg Arg Leu Met Glu Asn Leu
                20                  25                  30
Pro Ala Lys His Lys Leu Lys Phe Asp Phe Ile Asp Leu Asp Ala Gly
                35                  40                  45
Trp Gly Thr Phe Glu Arg Thr Gly Lys Ala Leu Pro Glu Arg Thr Val
    50                  55                  60
Glu Arg Leu Lys Thr Glu Cys Asn Ala Ala Leu Phe Gly Ala Val Gln
65                  70                  75                  80
Ser Pro Thr His Lys Val Ala Gly Tyr Ser Ser Pro Ile Val Ala Leu
                85                  90                  95
His Lys Lys Met Gly Leu Tyr Ala Asn Val Arg Pro Val Lys Ser Leu
                100                 105                 110
Asp Gly Ala Lys Gly Lys Pro Val Asp Leu Val Ile Val His Glu Asn
                115                 120                 125
Thr Glu Cys Leu Tyr Val Lys Glu Glu Arg Met Val Gln Asn Thr Pro
                130                 135                 140
Gly Lys Arg Val Ala Glu Ala Ile Arg Arg Ile Ser Glu Glu Ala Ser
145                 150                 155                 160
Thr Lys Ile Gly Lys Met Ala Phe Glu Ile Ala Lys Ser Arg Gln Lys
                165                 170                 175
Ile Arg Glu Ser Gly Thr Tyr Ser Ile His Lys Lys Pro Leu Val Thr
                180                 185                 190
Ile Ile His Lys Ser Asn Val Met Ser Val Thr Asp Gly Leu Phe Arg
                195                 200                 205
Glu Ser Cys Arg His Ala Gln Ser Leu Asp Pro Ser Tyr Ala Ser Ile
                210                 215                 220
Asn Val Asp Glu Gln Ile Val Asp Ser Met Val Tyr Arg Leu Phe Arg
225                 230                 235                 240
Glu Pro Glu Cys Phe Asp Val Val Ala Pro Asn Leu Tyr Gly Asp
                245                 250                 255
Ile Leu Ser Asp Gly Ala Ala Ser Leu Ile Gly Ser Leu Gly Leu Val
                260                 265                 270
Pro Ser Ala Asn Val Gly Asp Asn Phe Val Met Ser Glu Pro Val His
```

```
                275                 280                 285
Gly Ser Ala Pro Asp Ile Ala Gly Arg Gly Ile Ala Asn Pro Val Ala
            290                 295                 300

Thr Phe Arg Ser Val Ala Leu Met Leu Glu Phe Met Gly His Gln Asp
305                 310                 315                 320

Ala Ala Ala Asp Ile Tyr Thr Ala Val Asp Lys Val Leu Thr Glu Gly
                325                 330                 335

Lys Val Leu Thr Pro Asp Leu Gly Gly Lys Ser Gly Thr Asn Glu Ile
            340                 345                 350

Thr Asp Ala Val Leu Ala Asn Ile His Asn
            355                 360

<210> SEQ ID NO 98
<211> LENGTH: 366
<212> TYPE: PRT
<213> ORGANISM: Schizosaccharomyces pombe

<400> SEQUENCE: 98

Gly Ser Thr Ser Met Ser Ala Thr Arg Arg Ile Val Leu Gly Leu Ile
1               5                   10                  15

Pro Ala Asp Gly Ile Gly Lys Glu Val Val Pro Ala Ala Arg Arg Leu
            20                  25                  30

Met Glu Asn Leu Pro Ala Lys His Lys Leu Lys Phe Asp Phe Ile Asp
        35                  40                  45

Leu Asp Ala Gly Trp Gly Thr Phe Glu Arg Thr Gly Lys Ala Leu Pro
    50                  55                  60

Glu Arg Thr Val Glu Arg Leu Lys Thr Glu Cys Asn Ala Ala Leu Phe
65                  70                  75                  80

Gly Ala Val Gln Ser Pro Thr His Lys Val Ala Gly Tyr Ser Ser Pro
                85                  90                  95

Ile Val Ala Leu His Lys Lys Met Gly Leu Tyr Ala Asn Val Arg Pro
            100                 105                 110

Val Lys Ser Leu Asp Gly Ala Lys Gly Lys Pro Val Asp Leu Val Ile
        115                 120                 125

Val His Glu Asn Thr Glu Cys Leu Tyr Val Lys Glu Glu Arg Met Val
    130                 135                 140

Gln Asn Thr Pro Gly Lys Arg Val Ala Glu Ala Ile Arg Arg Ile Ser
145                 150                 155                 160

Glu Glu Ala Ser Thr Lys Ile Gly Lys Met Ala Phe Glu Ile Ala Lys
                165                 170                 175

Ser Arg Gln Lys Ile Arg Glu Ser Gly Thr Tyr Ser Ile His Lys Lys
            180                 185                 190

Pro Leu Val Thr Ile Ile His Lys Ser Asn Val Met Ser Val Thr Asp
        195                 200                 205

Gly Leu Phe Arg Glu Ser Cys Arg His Ala Gln Ser Leu Asp Pro Ser
    210                 215                 220

Tyr Ala Ser Ile Asn Val Asp Glu Gln Ile Val Asp Ser Met Val Tyr
225                 230                 235                 240

Arg Leu Phe Arg Glu Pro Glu Cys Phe Asp Val Val Ala Pro Asn
                245                 250                 255

Leu Tyr Gly Asp Ile Leu Ser Asp Gly Ala Ala Ser Leu Ile Gly Ser
            260                 265                 270

Leu Gly Leu Val Pro Ser Ala Asn Val Gly Asp Asn Phe Val Met Ser
        275                 280                 285

Glu Pro Val His Gly Ser Ala Pro Asp Ile Ala Gly Arg Gly Ile Ala
```

```
                  290                 295                 300
Asn Pro Val Ala Thr Phe Arg Ser Val Ala Leu Met Leu Glu Phe Met
305                 310                 315                 320

Gly His Gln Asp Ala Ala Asp Ile Tyr Thr Ala Val Asp Lys Val
                325                 330                 335

Leu Thr Glu Gly Lys Val Leu Thr Pro Asp Leu Gly Gly Lys Ser Gly
                340                 345                 350

Thr Asn Glu Ile Thr Asp Ala Val Leu Ala Asn Ile His Asn
                355                 360                 365

<210> SEQ ID NO 99
<211> LENGTH: 366
<212> TYPE: PRT
<213> ORGANISM: Schizosaccharomyces pombe

<400> SEQUENCE: 99

Gly Ser Thr Ser Met Ser Ala Thr Arg Arg Ile Val Leu Gly Leu Ile
1               5                   10                  15

Pro Ala Asp Gly Ile Gly Lys Glu Val Pro Ala Ala Arg Arg Leu
                20                  25                  30

Met Glu Asn Leu Pro Ala Lys His Lys Leu Lys Phe Asp Phe Ile Asp
                35                  40                  45

Leu Asp Ala Gly Trp Gly Thr Phe Glu Arg Thr Gly Lys Ala Leu Pro
50                  55                  60

Glu Arg Thr Val Glu Arg Leu Lys Thr Glu Cys Asn Ala Ala Leu Phe
65                  70                  75                  80

Gly Ala Val Gln Ser Pro Thr His Lys Val Ala Gly Tyr Ser Ser Pro
                85                  90                  95

Ile Val Ala Leu His Lys Lys Met Gly Leu Tyr Ala Asn Val Arg Pro
                100                 105                 110

Val Lys Ser Leu Asp Gly Ala Lys Gly Lys Pro Val Asp Leu Val Ile
                115                 120                 125

Val His Glu Asn Thr Glu Cys Leu Tyr Val Lys Glu Glu Arg Met Val
130                 135                 140

Gln Asn Thr Pro Gly Lys Arg Val Ala Glu Ala Ile Arg Arg Ile Ser
145                 150                 155                 160

Glu Glu Ala Ser Thr Lys Ile Gly Lys Met Ala Phe Glu Ile Ala Lys
                165                 170                 175

Ser Arg Gln Lys Ile Arg Glu Ser Gly Thr Tyr Ser Ile His Lys Lys
                180                 185                 190

Pro Leu Val Thr Ile Ile His Lys Ser Asn Val Met Ser Val Thr Asp
                195                 200                 205

Gly Leu Phe Arg Glu Ser Cys Arg His Ala Gln Ser Leu Asp Pro Ser
210                 215                 220

Tyr Ala Ser Ile Asn Val Asp Glu Gln Ile Val Asp Ser Met Val Tyr
225                 230                 235                 240

Arg Leu Phe Arg Glu Pro Glu Cys Phe Asp Val Val Ala Pro Asn
                245                 250                 255

Leu Tyr Gly Asp Ile Leu Ser Asp Gly Ala Ala Ser Leu Ile Gly Ser
                260                 265                 270

Leu Gly Leu Val Pro Ser Ala Asn Val Gly Asp Asn Phe Val Met Ser
                275                 280                 285

Glu Pro Val His Gly Ser Ala Pro Asp Ile Ala Gly Arg Gly Ile Ala
                290                 295                 300

Asn Pro Val Ala Thr Phe Arg Ser Val Ala Leu Met Leu Glu Phe Met
```

```
                    305                 310                 315                 320
Gly His Gln Asp Ala Ala Ala Asp Ile Tyr Thr Ala Val Asp Lys Val
                325                 330                 335

Leu Thr Glu Gly Lys Val Leu Thr Pro Asp Leu Gly Gly Lys Ser Gly
            340                 345                 350

Thr Asn Glu Ile Thr Asp Ala Val Leu Ala Asn Ile His Asn
            355                 360                 365

<210> SEQ ID NO 100
<211> LENGTH: 366
<212> TYPE: PRT
<213> ORGANISM: Schizosaccharomyces pombe

<400> SEQUENCE: 100

Gly Ser Thr Ser Met Ser Ala Thr Arg Arg Ile Val Leu Gly Leu Ile
1               5                   10                  15

Pro Ala Asp Gly Ile Gly Lys Glu Val Val Pro Ala Ala Arg Arg Leu
            20                  25                  30

Met Glu Asn Leu Pro Ala Lys His Lys Leu Lys Phe Asp Phe Ile Asp
        35                  40                  45

Leu Asp Ala Gly Trp Gly Thr Phe Glu Arg Thr Gly Lys Ala Leu Pro
    50                  55                  60

Glu Arg Thr Val Glu Arg Leu Lys Thr Glu Cys Asn Ala Ala Leu Phe
65                  70                  75                  80

Gly Ala Val Gln Ser Pro Thr His Lys Val Ala Gly Tyr Ser Ser Pro
                85                  90                  95

Ile Val Ala Leu His Lys Lys Met Gly Leu Tyr Ala Asn Val Arg Pro
            100                 105                 110

Val Lys Ser Leu Asp Gly Ala Lys Gly Lys Pro Val Asp Leu Val Ile
        115                 120                 125

Val His Glu Asn Thr Glu Cys Leu Tyr Val Lys Glu Glu Arg Met Val
    130                 135                 140

Gln Asn Thr Pro Gly Lys Arg Val Ala Glu Ala Ile Arg Arg Ile Ser
145                 150                 155                 160

Glu Glu Ala Ser Thr Lys Ile Gly Lys Met Ala Phe Glu Ile Ala Lys
                165                 170                 175

Ser Arg Gln Lys Ile Arg Glu Ser Gly Thr Tyr Ser Ile His Lys Lys
            180                 185                 190

Pro Leu Val Thr Ile Ile His Lys Ser Asn Val Met Ser Val Thr Asp
        195                 200                 205

Gly Leu Phe Arg Glu Ser Cys Arg His Ala Gln Ser Leu Asp Pro Ser
    210                 215                 220

Tyr Ala Ser Ile Asn Val Asp Glu Gln Ile Val Asp Ser Met Val Tyr
225                 230                 235                 240

Arg Leu Phe Arg Glu Pro Glu Cys Phe Asp Val Val Ala Pro Asn
                245                 250                 255

Leu Tyr Gly Asp Ile Leu Ser Asp Gly Ala Ala Ser Leu Ile Gly Ser
            260                 265                 270

Leu Gly Leu Val Pro Ser Ala Asn Val Gly Asp Asn Phe Val Met Ser
        275                 280                 285

Glu Pro Val His Gly Ser Ala Pro Asp Ile Ala Gly Arg Gly Ile Ala
    290                 295                 300

Asn Pro Val Ala Thr Phe Arg Ser Val Ala Leu Met Leu Glu Phe Met
305                 310                 315                 320

Gly His Gln Asp Ala Ala Ala Asp Ile Tyr Thr Ala Val Asp Lys Val
```

```
                    325                 330                 335
Leu Thr Glu Gly Lys Val Leu Thr Pro Asp Leu Gly Gly Lys Ser Gly
                340                 345                 350

Thr Asn Glu Ile Thr Asp Ala Val Leu Ala Asn Ile His Asn
            355                 360                 365

<210> SEQ ID NO 101
<211> LENGTH: 366
<212> TYPE: PRT
<213> ORGANISM: Schizosaccharomyces pombe

<400> SEQUENCE: 101

Gly Ser Thr Ser Met Ser Ala Thr Arg Arg Ile Val Leu Gly Leu Ile
1               5                   10                  15

Pro Ala Asp Gly Ile Gly Lys Glu Val Pro Ala Ala Arg Arg Leu
            20                  25                  30

Met Glu Asn Leu Pro Ala Lys His Lys Leu Lys Phe Asp Phe Ile Asp
        35                  40                  45

Leu Asp Ala Gly Trp Gly Thr Phe Glu Arg Thr Gly Lys Ala Leu Pro
    50                  55                  60

Glu Arg Thr Val Glu Arg Leu Lys Thr Glu Cys Asn Ala Ala Leu Phe
65                  70                  75                  80

Gly Ala Val Gln Ser Pro Thr His Lys Val Ala Gly Tyr Ser Ser Pro
                85                  90                  95

Ile Val Ala Leu His Lys Lys Met Gly Leu Tyr Ala Asn Val Arg Pro
            100                 105                 110

Val Lys Ser Leu Asp Gly Ala Lys Gly Lys Pro Val Asp Leu Val Ile
        115                 120                 125

Val His Glu Asn Thr Glu Cys Leu Tyr Val Lys Glu Glu Arg Met Val
130                 135                 140

Gln Asn Thr Pro Gly Lys Arg Val Ala Glu Ala Ile Arg Arg Ile Ser
145                 150                 155                 160

Glu Glu Ala Ser Thr Lys Ile Gly Lys Met Ala Phe Glu Ile Ala Lys
                165                 170                 175

Ser Arg Gln Lys Ile Arg Glu Ser Gly Thr Tyr Ser Ile His Lys Lys
            180                 185                 190

Pro Leu Val Thr Ile Ile His Lys Ser Asn Val Met Ser Val Thr Asp
        195                 200                 205

Gly Leu Phe Arg Glu Ser Cys Arg His Ala Gln Ser Leu Asp Pro Ser
    210                 215                 220

Tyr Ala Ser Ile Asn Val Asp Glu Gln Ile Val Asp Ser Met Val Tyr
225                 230                 235                 240

Arg Leu Phe Arg Glu Pro Glu Cys Phe Asp Val Val Ala Pro Asn
                245                 250                 255

Leu Tyr Gly Asp Ile Leu Ser Asp Gly Ala Ala Ser Leu Ile Gly Ser
            260                 265                 270

Leu Gly Leu Val Pro Ser Ala Asn Val Gly Asp Asn Phe Val Met Ser
        275                 280                 285

Glu Pro Val His Gly Ser Ala Pro Asp Ile Ala Gly Arg Gly Ile Ala
    290                 295                 300

Asn Pro Val Ala Thr Phe Arg Ser Val Ala Leu Met Leu Glu Phe Met
305                 310                 315                 320

Gly His Gln Asp Ala Ala Ala Asp Ile Tyr Thr Ala Val Asp Lys Val
                325                 330                 335

Leu Thr Glu Gly Lys Val Leu Thr Pro Asp Leu Gly Gly Lys Ser Gly
```

```
                340             345             350
Thr Asn Glu Ile Thr Asp Ala Val Leu Ala Asn Ile His Asn
            355             360             365

<210> SEQ ID NO 102
<211> LENGTH: 362
<212> TYPE: PRT
<213> ORGANISM: Schizosaccharomyces pombe

<400> SEQUENCE: 102

Met Ser Ala Thr Arg Arg Ile Val Leu Gly Leu Ile Pro Ala Asp Gly
1               5                   10                  15

Ile Gly Lys Glu Val Val Pro Ala Ala Arg Arg Leu Met Glu Asn Leu
            20                  25                  30

Pro Ala Lys His Lys Leu Lys Phe Asp Phe Ile Asp Leu Asp Ala Gly
        35                  40                  45

Trp Gly Thr Phe Glu Arg Thr Gly Lys Ala Leu Pro Glu Arg Thr Val
    50                  55                  60

Glu Arg Leu Lys Thr Glu Cys Asn Ala Ala Leu Phe Gly Ala Val Gln
65                  70                  75                  80

Ser Pro Thr His Lys Val Ala Gly Tyr Ser Ser Pro Ile Val Ala Leu
                85                  90                  95

His Lys Lys Met Gly Leu Tyr Ala Asn Val Arg Pro Val Lys Ser Leu
            100                 105                 110

Asp Gly Ala Lys Gly Lys Pro Val Asp Leu Val Ile Val His Glu Asn
        115                 120                 125

Thr Glu Cys Leu Tyr Val Lys Glu Glu Arg Met Val Gln Asn Thr Pro
    130                 135                 140

Gly Lys Arg Val Ala Glu Ala Ile Arg Ile Ser Glu Glu Ala Ser
145                 150                 155                 160

Thr Lys Ile Gly Lys Met Ala Phe Glu Ile Ala Lys Ser Arg Gln Lys
                165                 170                 175

Ile Arg Glu Ser Gly Thr Tyr Ser Ile His Lys Lys Pro Leu Val Thr
            180                 185                 190

Ile Ile His Lys Ser Asn Val Met Ser Val Thr Asp Gly Leu Phe Arg
        195                 200                 205

Glu Ser Cys Arg His Ala Gln Ser Leu Asp Pro Ser Tyr Ala Ser Ile
    210                 215                 220

Asn Val Asp Glu Gln Ile Val Asp Ser Met Val Tyr Arg Leu Phe Arg
225                 230                 235                 240

Glu Pro Glu Cys Phe Asp Val Val Ala Pro Asn Leu Tyr Gly Asp
                245                 250                 255

Ile Leu Ser Asp Gly Ala Ala Ser Leu Ile Gly Ser Leu Gly Leu Val
            260                 265                 270

Pro Ser Ala Asn Val Gly Asp Asn Phe Val Met Ser Glu Pro Val His
        275                 280                 285

Gly Ser Ala Pro Asp Ile Ala Gly Arg Gly Ile Ala Asn Pro Val Ala
    290                 295                 300

Thr Phe Arg Ser Val Ala Leu Met Leu Glu Phe Met Gly His Gln Asp
305                 310                 315                 320

Ala Ala Ala Asp Ile Tyr Thr Ala Val Asp Lys Val Leu Thr Glu Gly
                325                 330                 335

Lys Val Leu Thr Pro Asp Leu Gly Gly Lys Ser Gly Thr Asn Glu Ile
            340                 345                 350

Thr Asp Ala Val Leu Ala Asn Ile His Asn
```

```
                    355                 360

<210> SEQ ID NO 103
<211> LENGTH: 361
<212> TYPE: PRT
<213> ORGANISM: Starkeya novella

<400> SEQUENCE: 103

Met Gln Leu Leu Val Leu Pro Gly Asp Gly Ile Gly Pro Glu Ile Thr
1               5                   10                  15

Ala Ala Thr Leu Arg Ala Leu Asn Val Leu Asn Asp Arg Cys Ala Val
            20                  25                  30

Asp Val Arg Trp Ser Glu Ala Asp Ile Gly Leu Lys Ser Leu Arg Glu
        35                  40                  45

Gln Gly Thr Thr Leu Pro Gly Ala Ile Ile Asp Gly Val Gln Thr Ala
    50                  55                  60

Asp Gly Val Leu Leu Gly Pro Val Ser His Tyr Glu Tyr Pro Ser Arg
65                  70                  75                  80

Gln Glu Gly Ser Ile Asn Pro Ser Gly Glu Leu His Thr Arg Phe Glu
                85                  90                  95

Leu Phe Ala Asn Ile Arg Pro Cys Arg Ser Leu Ser Asp Leu Ser Ile
            100                 105                 110

Leu Arg Arg Pro Met Asp Leu Ile Ile Val His Glu Asn Thr Glu Gly
        115                 120                 125

Phe Tyr Ser Asp Arg Ser Met Ala Ala Gly Thr Gly Glu Leu Met Pro
    130                 135                 140

Asp Glu Asn Met Ala Leu Ser Val Arg Lys Ile Thr Ala Arg Ala Ser
145                 150                 155                 160

Gly Gln Val Ala Arg Ala Ala Phe Glu Leu Ala Arg Gly Arg Arg Lys
                165                 170                 175

Lys Val Thr Ala Val His Lys Ala Asn Val Leu Lys Leu Ser Asp Gly
            180                 185                 190

Leu Phe Leu Arg Glu Val Arg Lys Val Ala Ala Asp Tyr Pro Asp Val
        195                 200                 205

Ala Leu Glu Glu Leu Ile Val Asp Ala Thr Ala Ala His Leu Ile Arg
    210                 215                 220

Thr Pro Asp Ser Phe Asp Val Ile Val Thr Thr Asn Met Phe Gly Asp
225                 230                 235                 240

Ile Leu Ser Asp Glu Ala Ser Glu Leu Cys Gly Ser Leu Gly Leu Ala
                245                 250                 255

Gly Ser Ile Ser Ile Gly Asp Gly Val Cys Val Ala Gln Ala Gln His
            260                 265                 270

Gly Ser Ala Pro Asp Ile Ala Ser Arg Gly Ile Ala Asn Pro Thr Ser
        275                 280                 285

Leu Met Leu Ser Ala Ala Met Leu Leu Asp Trp Arg Gly Arg Arg Asp
    290                 295                 300

Gly Ser Lys Pro Leu Ile Asp Ala Ala Ala Leu Asp Gln Ala Val
305                 310                 315                 320

Ser Lys Val Leu Val Asp Pro Ala Thr Arg Thr Pro Asp Leu Gly Gly
                325                 330                 335

Thr Leu Ser Thr Glu Ala Phe Asp Ala Val Arg Ala Ala Ile Thr
        340                 345                 350

Arg Ser Ser Ala Ala Gly Arg Ala Ala
    355                 360
```

<210> SEQ ID NO 104
<211> LENGTH: 361
<212> TYPE: PRT
<213> ORGANISM: Starkeya novella

<400> SEQUENCE: 104

```
Met Gln Leu Leu Val Leu Pro Gly Asp Gly Ile Gly Pro Glu Ile Thr
 1               5                  10                  15

Ala Ala Thr Leu Arg Ala Leu Asn Val Leu Asn Asp Arg Cys Ala Val
                20                  25                  30

Asp Val Arg Trp Ser Glu Ala Asp Ile Gly Leu Lys Ser Leu Arg Glu
            35                  40                  45

Gln Gly Thr Thr Leu Pro Gly Ala Ile Ile Asp Gly Val Gln Thr Ala
        50                  55                  60

Asp Gly Val Leu Leu Gly Pro Val Ser His Tyr Glu Tyr Pro Ser Arg
65                  70                  75                  80

Gln Glu Gly Ser Ile Asn Pro Ser Gly Glu Leu His Thr Arg Phe Glu
                85                  90                  95

Leu Phe Ala Asn Ile Arg Pro Cys Arg Ser Leu Ser Asp Leu Ser Ile
            100                 105                 110

Leu Arg Arg Pro Met Asp Leu Ile Ile Val His Glu Asn Thr Glu Gly
        115                 120                 125

Phe Tyr Ser Asp Arg Ser Met Ala Ala Gly Thr Gly Glu Leu Met Pro
    130                 135                 140

Asp Glu Asn Met Ala Leu Ser Val Arg Lys Ile Thr Ala Arg Ala Ser
145                 150                 155                 160

Gly Gln Val Ala Arg Ala Ala Phe Glu Leu Ala Arg Gly Arg Arg Lys
                165                 170                 175

Lys Val Thr Ala Val His Lys Ala Asn Val Leu Lys Leu Ser Asp Gly
            180                 185                 190

Leu Phe Leu Arg Glu Val Arg Lys Val Ala Ala Asp Tyr Pro Asp Val
        195                 200                 205

Ala Leu Glu Glu Leu Ile Val Asp Ala Thr Ala Ala His Leu Ile Arg
    210                 215                 220

Thr Pro Asp Ser Phe Asp Val Ile Val Thr Thr Asn Met Phe Gly Asp
225                 230                 235                 240

Ile Leu Ser Asp Glu Ala Ser Glu Leu Cys Gly Ser Leu Gly Leu Ala
                245                 250                 255

Gly Ser Ile Ser Ile Gly Asp Gly Val Cys Val Ala Gln Ala Gln His
            260                 265                 270

Gly Ser Ala Pro Asp Ile Ala Ser Arg Gly Ile Ala Asn Pro Thr Ser
        275                 280                 285

Leu Met Leu Ser Ala Ala Met Leu Leu Asp Trp Arg Gly Arg Arg Asp
    290                 295                 300

Gly Ser Lys Pro Leu Ile Asp Ala Ala Ala Leu Asp Gln Ala Val
305                 310                 315                 320

Ser Lys Val Leu Val Asp Pro Ala Thr Arg Thr Pro Asp Leu Gly Gly
                325                 330                 335

Thr Leu Ser Thr Glu Ala Phe Thr Asp Ala Val Arg Ala Ala Ile Thr
            340                 345                 350

Arg Ser Ser Ala Ala Gly Arg Ala Ala
        355                 360
```

<210> SEQ ID NO 105
<211> LENGTH: 368
<212> TYPE: PRT

<213> ORGANISM: Streptococcus vestibularis

<400> SEQUENCE: 105

| | | | | | | | | | | | | | | |
|---|---|---|---|---|---|---|---|---|---|---|---|---|---|---|
| Met | Lys | Ser | Ile | Ala | Val | Leu | Pro | Gly | Asp | Gly | Ile | Gly | Ile | Glu | Val |
| 1 | | | | 5 | | | | | 10 | | | | | 15 | |
| Met | Glu | Ala | Cys | Val | Pro | Ile | Phe | Lys | Glu | Leu | Asn | Leu | Asp | Ile | Lys |
| | | | 20 | | | | | 25 | | | | | 30 | | |
| Leu | Lys | Tyr | Gly | Glu | Ile | Gly | Trp | Lys | Cys | Trp | Ile | Asn | Ser | Ala | Asn |
| | | | 35 | | | | 40 | | | | | 45 | | | |
| Pro | Val | Pro | Asn | Glu | Thr | Trp | Asn | Leu | Ile | Lys | Asn | Cys | Asp | Ala | Val |
| | 50 | | | | | 55 | | | | 60 | | | | | |
| Leu | Val | Gly | Ala | Ile | Thr | Ser | Lys | Pro | Lys | His | Glu | Ala | Glu | Gln | Glu |
| 65 | | | | | 70 | | | | | 75 | | | | | 80 |
| Leu | Lys | Val | Lys | Ser | Ser | Asn | Thr | Thr | Asp | Tyr | Val | Ser | Pro | Val | Ile |
| | | | | 85 | | | | | 90 | | | | | 95 | |
| Gln | Leu | His | Gln | Lys | Leu | Gln | Leu | Phe | Ala | Asn | Val | Arg | Pro | Ile | Val |
| | | | 100 | | | | | 105 | | | | | 110 | | |
| Ser | Leu | Ile | Asn | Asn | Lys | Ser | Phe | Glu | Val | Tyr | Ile | Ile | His | Glu | Asn |
| | | | 115 | | | | | 120 | | | | | 125 | | |
| Thr | Glu | Gly | Leu | Tyr | Ser | Gly | Leu | Asp | Phe | Asn | Pro | Ile | Pro | Glu | Pro |
| | 130 | | | | | 135 | | | | | 140 | | | | |
| Leu | Glu | Asn | Phe | Ile | Asn | Glu | Ser | Thr | Ser | Lys | Tyr | Ser | Asn | Lys | Leu |
| 145 | | | | | 150 | | | | | 155 | | | | | 160 |
| Lys | Asn | Gly | Ala | Ala | Thr | Ile | Arg | Ile | Ile | Thr | Glu | Glu | Gly | Phe | Asn |
| | | | | 165 | | | | | 170 | | | | | 175 | |
| Arg | Leu | Leu | Lys | Phe | Ser | Ser | Glu | Trp | Ala | Leu | Lys | His | Gly | Lys | Ser |
| | | | 180 | | | | | 185 | | | | | 190 | | |
| Asn | Ile | Val | Ile | Ala | Asp | Lys | Pro | Asn | Val | Phe | Arg | Asn | Ser | Ser | Asp |
| | | | 195 | | | | | 200 | | | | | 205 | | |
| Ile | Ile | Phe | Arg | Leu | Ile | Lys | Lys | Tyr | Ser | Leu | Asp | Tyr | Pro | Met | Leu |
| | 210 | | | | | 215 | | | | | 220 | | | | |
| Asn | Tyr | Thr | Val | Glu | Asn | Ile | Asp | Ala | Val | Ala | Met | Trp | Leu | Val | Lys |
| 225 | | | | | 230 | | | | | 235 | | | | | 240 |
| Lys | Pro | Gln | Lys | Tyr | Glu | Ile | Val | Ile | Cys | Glu | Asn | Gln | Phe | Gly | Asp |
| | | | | 245 | | | | | 250 | | | | | 255 | |
| Ile | Leu | Ser | Asp | Val | Gly | Ala | Val | Met | Gly | Gly | Leu | Gly | Leu | Ala |
| | | | 260 | | | | | 265 | | | | | 270 | | |
| Tyr | Ser | Gly | Asn | Tyr | Gly | Leu | Lys | Glu | Thr | Ala | Tyr | Phe | Glu | Pro | Val |
| | | 275 | | | | | 280 | | | | | 285 | | | |
| His | Gly | Ser | Ala | Pro | Lys | Tyr | Ser | Gly | Gln | Asn | Lys | Val | Asn | Pro | Met |
| | 290 | | | | | 295 | | | | | 300 | | | | |
| Ala | Met | Phe | Leu | Ser | Ile | Ala | Met | Leu | Leu | Asn | Phe | Leu | Gly | Tyr | Lys |
| 305 | | | | | 310 | | | | | 315 | | | | | 320 |
| Glu | Ala | Ser | Gln | Ser | Ile | Gln | Lys | Ala | Val | Glu | Tyr | Thr | Ala | Lys | Asp |
| | | | | 325 | | | | | 330 | | | | | 335 | |
| Lys | Arg | Phe | Cys | Thr | Phe | Asp | Leu | Ser | Gly | Ala | Ala | Thr | Leu | Ser | Glu |
| | | | 340 | | | | | 345 | | | | | 350 | | |
| Ser | Ala | Lys | His | Ile | Ile | Glu | Glu | Ala | Val | Lys | Ile | Tyr | Gly | Asn | Leu |
| | | | 355 | | | | | 360 | | | | | 365 | | |

<210> SEQ ID NO 106
<211> LENGTH: 368
<212> TYPE: PRT
<213> ORGANISM: Streptococcus vestibularis

<400> SEQUENCE: 106

Met Lys Ser Ile Ala Val Leu Pro Gly Asp Gly Ile Gly Ile Glu Val
1               5                   10                  15

Met Glu Ala Cys Val Pro Ile Phe Lys Glu Leu Asn Leu Asp Ile Lys
            20                  25                  30

Leu Lys Tyr Gly Glu Ile Gly Trp Lys Cys Trp Ile Asn Ser Ala Asn
        35                  40                  45

Pro Val Pro Asn Glu Thr Trp Asn Leu Ile Lys Asn Cys Asp Ala Val
    50                  55                  60

Leu Val Gly Ala Ile Thr Ser Lys Pro Lys His Glu Ala Glu Gln Glu
65                  70                  75                  80

Leu Lys Val Lys Ser Ser Asn Thr Thr Asp Tyr Val Ser Pro Val Ile
                85                  90                  95

Gln Leu His Gln Lys Leu Gln Leu Phe Ala Asn Val Arg Pro Ile Val
                100                 105                 110

Ser Leu Ile Asn Asn Lys Ser Phe Glu Val Tyr Ile Ile His Glu Asn
            115                 120                 125

Thr Glu Gly Leu Tyr Ser Gly Leu Asp Phe Asn Pro Ile Pro Glu Pro
    130                 135                 140

Leu Glu Asn Phe Ile Asn Glu Ser Thr Ser Lys Tyr Ser Asn Lys Leu
145                 150                 155                 160

Lys Asn Gly Ala Ala Thr Ile Arg Ile Ile Thr Glu Glu Gly Phe Asn
                165                 170                 175

Arg Leu Leu Lys Phe Ser Ser Glu Trp Ala Leu Lys His Gly Lys Ser
            180                 185                 190

Asn Ile Val Ile Ala Asp Lys Pro Asn Val Phe Arg Asn Ser Ser Asp
        195                 200                 205

Ile Ile Phe Arg Leu Ile Lys Lys Tyr Ser Leu Asp Tyr Pro Met Leu
    210                 215                 220

Asn Tyr Thr Val Glu Asn Ile Asp Ala Val Ala Met Trp Leu Val Lys
225                 230                 235                 240

Lys Pro Gln Lys Tyr Glu Ile Val Ile Cys Glu Asn Gln Phe Gly Asp
                245                 250                 255

Ile Leu Ser Asp Val Gly Ala Ala Val Met Gly Gly Leu Gly Leu Ala
            260                 265                 270

Tyr Ser Gly Asn Tyr Gly Leu Lys Glu Thr Ala Tyr Phe Glu Pro Val
        275                 280                 285

His Gly Ser Ala Pro Lys Tyr Ser Gly Gln Asn Lys Val Asn Pro Met
    290                 295                 300

Ala Met Phe Leu Ser Ile Ala Met Leu Leu Asn Phe Leu Gly Tyr Lys
305                 310                 315                 320

Glu Ala Ser Gln Ser Ile Gln Lys Ala Val Glu Tyr Thr Ala Lys Asp
                325                 330                 335

Lys Arg Phe Cys Thr Phe Asp Leu Ser Gly Ala Ala Thr Leu Ser Glu
            340                 345                 350

Ser Ala Lys His Ile Ile Glu Glu Ala Val Lys Ile Tyr Gly Asn Leu
        355                 360                 365

<210> SEQ ID NO 107
<211> LENGTH: 347
<212> TYPE: PRT
<213> ORGANISM: Thermococcus kodakarensis

<400> SEQUENCE: 107

Met Tyr Arg Val Ala Val Ile Pro Gly Asp Gly Ile Gly Pro Glu Val
1               5                   10                  15

Ile Asp Gly Ala Val Arg Val Leu Lys Ala Val Thr Gly Arg Val Arg
            20                  25                  30

Phe Glu Tyr Tyr Glu Gly Gly Val Asp Val Phe Gln Glu Cys Gly Ser
        35                  40                  45

Pro Ile Arg Glu Glu Asp Leu Glu Glu Ile Arg Arg Ser Asp Ala Val
50                  55                  60

Leu Phe Gly Ala Thr Thr Thr Pro Phe Asp Leu Pro Gly Tyr Arg Ser
65                  70                  75                  80

Leu Ile Leu Thr Leu His Lys Glu Leu Gly Leu Tyr Ala Asn Leu Arg
                85                  90                  95

Ile Ile Pro Asp Leu Arg Thr Gly Arg Glu Ile Val Ile Val His Glu
            100                 105                 110

Asn Ser Glu Gly Leu Tyr Phe Gly Ile Gly Ala Val Val Asn Gly Arg
        115                 120                 125

Ala Val Asp Val Arg Leu Ile Thr Arg Glu Gly Ala Glu Arg Ile Ala
130                 135                 140

Arg Phe Ala Val Glu Gln Ala Lys Ala Arg Gly Ser Phe Ile Thr Phe
145                 150                 155                 160

Val His Lys Ala Asn Val Leu Thr Gly Asp Lys Phe Phe Arg Arg Ile
                165                 170                 175

Val Arg Glu Val Ala Gly Glu Glu Gly Val Glu Val Arg Asp Ala Ile
            180                 185                 190

Ile Asp Ser Phe Thr Ile Lys Leu Val Arg Asn Pro Trp Glu His Gly
        195                 200                 205

Val Ile Leu Ser Glu Asn Leu Phe Gly Asp Ile Leu Ser Asp Leu Ala
210                 215                 220

Thr Val His Ala Gly Ser Ile Gly Ile Val Pro Ser Gly Asn Tyr Gly
225                 230                 235                 240

Asp Gly Ile Ala Leu Phe Glu Pro Val His Gly Ser Ala Pro Asp Ile
                245                 250                 255

Ala Gly Lys Gly Ile Ala Asn Pro Ile Gly Ala Ile Leu Ser Gly Ala
            260                 265                 270

Met Leu Leu Asp Tyr Leu Gly Leu Asp Gly Ser Leu Ile Arg Ala Ala
        275                 280                 285

Val Arg Gly Tyr Val Val Asn Gly Glu Leu Thr Pro Asp Met Gly Gly
290                 295                 300

Arg Ala Arg Thr Glu Asp Val Val Arg Gly Ile Ile Gly Glu Ile Glu
305                 310                 315                 320

Asp Leu Leu Ser Met Asp Glu Val Trp Arg Asp Ile Arg Leu Ser
                325                 330                 335

Arg Leu Glu Ser Asp Ile Ser Arg Met Ala Gly
            340                 345

<210> SEQ ID NO 108
<211> LENGTH: 334
<212> TYPE: PRT
<213> ORGANISM: Thermus aquaticus

<400> SEQUENCE: 108

Met Ala Tyr Arg Ile Cys Leu Ile Glu Gly Asp Gly Ile Gly His Glu
1               5                   10                  15

Val Val Pro Ala Ala Arg Arg Val Leu Glu Ala Thr Gly Leu Pro Leu
            20                  25                  30

Glu Phe Val Glu Ala Glu Ala Gly Trp Glu Thr Phe Glu Arg Arg Gly
        35                  40                  45

Val Ser Val Pro Glu Glu Thr Val Glu Lys Ile Leu Ser Cys His Ala
    50                  55                  60

Thr Leu Phe Gly Ala Ala Thr Ser Pro Thr Arg Lys Val Pro Gly Phe
65                  70                  75                  80

Phe Gly Ala Ile Arg Tyr Leu His Arg Arg Leu Asp Leu Tyr Ala Asn
                85                  90                  95

Val Arg Pro Ala Lys Ser Arg Pro Ile Pro Gln Ser Arg Pro Gly Val
            100                 105                 110

Asp Leu Ile Ile Val His Glu Asn Thr Glu Gly Leu Tyr Val Glu Gln
        115                 120                 125

Glu Arg Arg Tyr Leu Asp Val Ala Ile Ala Asp Ala Val Ile Ser Lys
    130                 135                 140

Lys Ala Ser Glu Arg Ile Gly Arg Val Ala Leu Lys Ile Ala Glu Gly
145                 150                 155                 160

Arg Pro Cys Lys Thr Leu His Ile Ala His Lys Ala Asn Val Leu Pro
                165                 170                 175

Val Thr Gln Gly Leu Phe Leu Asp Thr Val Lys Glu Ala Ala Arg Asp
            180                 185                 190

Phe Pro Leu Val Asn Val Gln Asp Ile Ile Val Asp Asn Cys Ala Met
        195                 200                 205

Gln Leu Val Met Arg Pro Glu Arg Phe Asp Val Ile Val Thr Thr Asn
    210                 215                 220

Leu Leu Gly Asp Ile Leu Ser Asp Leu Thr Ala Gly Leu Val Gly Gly
225                 230                 235                 240

Leu Gly Leu Ala Pro Ser Ala Asn Ile Gly Asp Thr Thr Ala Val Phe
                245                 250                 255

Glu Pro Val His Gly Ser Ala Pro Asp Ile Ala Gly Lys Gly Ile Ala
            260                 265                 270

Asn Pro Thr Ala Thr Ile Leu Ser Ala Ala Met Met Leu Asp Tyr Leu
        275                 280                 285

Gly Glu Arg Glu Val Ala Arg Lys Val Glu Arg Ala Val Asp Leu Val
    290                 295                 300

Leu Glu Lys Gly Pro Arg Thr Pro Asp Leu Gly Gly Glu Ala Thr Thr
305                 310                 315                 320

Glu Thr Phe Thr Gln Ala Val Ile Glu Ala Leu Lys Ala Leu
                325                 330

<210> SEQ ID NO 109
<211> LENGTH: 334
<212> TYPE: PRT
<213> ORGANISM: Thermus aquaticus

<400> SEQUENCE: 109

Met Ala Tyr Arg Ile Cys Leu Ile Glu Gly Asp Gly Ile Gly His Glu
1               5                   10                  15

Val Val Pro Ala Ala Arg Lys Val Leu Glu Ala Thr Gly Leu Pro Leu
            20                  25                  30

Glu Phe Val Glu Ala Glu Ala Gly Trp Glu Thr Phe Glu Arg Arg Gly
        35                  40                  45

Val Ser Val Pro Glu Glu Thr Val Glu Lys Ile Leu Ser Cys His Ala
    50                  55                  60

Thr Leu Phe Gly Ala Ala Thr Ser Pro Thr Arg Lys Val Pro Gly Phe
65                  70                  75                  80

Phe Gly Ala Ile Arg Tyr Leu His Arg Arg Leu Asp Leu Tyr Ala Asn
                85                  90                  95

```
Val Arg Pro Ala Lys Ser Arg Pro Ile Pro Gln Ser Arg Pro Gly Val
            100                 105                 110

Asp Leu Ile Ile Val His Glu Asn Thr Glu Gly Leu Tyr Val Glu Gln
            115                 120                 125

Glu Arg Arg Tyr Leu Asp Val Ala Ile Ala Asp Ala Val Ile Ser Lys
130                 135                 140

Lys Ala Ser Glu Arg Ile Gly Arg Val Ala Leu Lys Ile Ala Glu Gly
145                 150                 155                 160

Arg Pro Arg Lys Thr Leu His Ile Ala His Lys Ala Asn Val Leu Pro
                165                 170                 175

Val Thr Gln Gly Leu Phe Leu Asp Thr Val Lys Glu Ala Ala Arg Asp
            180                 185                 190

Phe Pro Leu Val Asn Val Gln Asp Ile Ile Val Asp Asn Cys Ala Met
            195                 200                 205

Gln Leu Val Met Arg Pro Glu Arg Phe Asp Val Ile Val Thr Thr Asn
210                 215                 220

Leu Leu Gly Asp Ile Leu Ser Asp Leu Thr Ala Gly Leu Val Gly Gly
225                 230                 235                 240

Leu Gly Leu Ala Pro Ser Ala Asn Ile Gly Asp Thr Thr Ala Val Phe
                245                 250                 255

Glu Pro Val His Gly Ser Ala Pro Asp Ile Ala Gly Lys Gly Ile Ala
            260                 265                 270

Asn Pro Thr Ala Thr Ile Leu Ser Ala Ala Met Met Leu Asp Tyr Leu
            275                 280                 285

Gly Glu Arg Glu Val Ala Arg Lys Val Glu Arg Ala Val Asp Leu Val
290                 295                 300

Leu Glu Lys Gly Pro Arg Thr Pro Asp Leu Gly Gly Glu Ala Thr Thr
305                 310                 315                 320

Glu Thr Phe Thr Gln Ala Val Ile Glu Ala Leu Lys Ala Leu
                325                 330

<210> SEQ ID NO 110
<211> LENGTH: 334
<212> TYPE: PRT
<213> ORGANISM: Thermus aquaticus

<400> SEQUENCE: 110

Met Ala Tyr Arg Ile Cys Leu Ile Glu Gly Asp Gly Ile Gly His Glu
1               5                   10                  15

Val Val Pro Ala Ala Arg Lys Val Leu Glu Ala Thr Gly Leu Pro Leu
            20                  25                  30

Glu Phe Val Glu Ala Glu Ala Gly Trp Glu Thr Phe Glu Arg Arg Gly
        35                  40                  45

Val Ser Val Pro Glu Glu Thr Val Glu Lys Ile Leu Ser Cys His Ala
50                  55                  60

Thr Leu Phe Gly Ala Ala Thr Ser Pro Thr Arg Lys Val Pro Gly Phe
65                  70                  75                  80

Phe Gly Ala Ile Arg Tyr Leu His Arg Arg Leu Asp Leu Tyr Ala Asn
                85                  90                  95

Val Arg Pro Ala Lys Ser Arg Pro Ile Pro Gln Ser Arg Pro Gly Val
            100                 105                 110

Asp Leu Ile Ile Val His Glu Asn Thr Glu Gly Leu Tyr Val Glu Gln
            115                 120                 125

Glu Arg Arg Tyr Leu Asp Val Ala Ile Ala Asp Ala Val Ile Ser Lys
130                 135                 140
```

Lys Ala Ser Glu Arg Ile Gly Arg Val Ala Leu Lys Ile Ala Glu Gly
145                 150                 155                 160

Arg Pro Arg Lys Thr Leu His Ile Ala His Lys Ala Asn Val Leu Pro
            165                 170                 175

Val Thr Gln Gly Leu Phe Leu Asp Thr Val Lys Glu Ala Ala Arg Asp
        180                 185                 190

Phe Pro Leu Val Asn Val Gln Asp Ile Ile Val Asp Asn Cys Ala Met
    195                 200                 205

Gln Leu Val Met Arg Pro Glu Arg Phe Asp Val Ile Val Thr Thr Asn
210                 215                 220

Leu Leu Gly Asp Ile Leu Ser Asp Leu Thr Ala Gly Leu Val Gly Gly
225                 230                 235                 240

Leu Gly Leu Ala Pro Ser Ala Asn Ile Gly Asp Thr Thr Ala Val Phe
                245                 250                 255

Glu Pro Val His Gly Ser Ala Pro Asp Ile Ala Gly Lys Gly Ile Ala
            260                 265                 270

Asn Pro Thr Ala Thr Ile Leu Ser Ala Ala Met Met Leu Asp Tyr Leu
        275                 280                 285

Gly Glu Arg Glu Val Ala Arg Lys Val Glu Arg Ala Val Asp Leu Val
    290                 295                 300

Leu Glu Lys Gly Pro Arg Thr Pro Asp Leu Gly Gly Glu Ala Thr Thr
305                 310                 315                 320

Glu Thr Phe Thr Gln Ala Val Ile Glu Ala Leu Lys Ala Leu
                325                 330

<210> SEQ ID NO 111
<211> LENGTH: 334
<212> TYPE: PRT
<213> ORGANISM: Thermus sp. CCB US3 UF1

<400> SEQUENCE: 111

Met Ala Tyr Arg Ile Cys Leu Ile Glu Gly Asp Gly Ile Gly His Glu
1               5                   10                  15

Val Val Pro Ala Ala Arg Lys Val Leu Glu Ala Thr Gly Leu Pro Leu
            20                  25                  30

Glu Phe Val Glu Ala Glu Ala Gly Trp Glu Thr Phe Glu Arg Arg Gly
        35                  40                  45

Thr Ser Val Pro Glu Glu Thr Val Glu Lys Ile Leu Ser Ser His Ala
    50                  55                  60

Thr Leu Phe Gly Ala Ala Thr Ser Pro Thr Arg Lys Val Pro Gly Phe
65                  70                  75                  80

Phe Gly Ala Ile Arg Tyr Leu His Arg Arg Leu Asp Leu Tyr Ala Asn
                85                  90                  95

Val Arg Pro Ala Lys Ser Arg Pro Ile Pro Gly Ser Arg Pro Gly Val
            100                 105                 110

Asp Leu Ile Ile Val His Glu Asn Thr Glu Gly Leu Tyr Val Glu Gln
        115                 120                 125

Glu Arg Arg Tyr Leu Asp Val Ala Ile Ala Asp Ala Val Ile Ser Lys
    130                 135                 140

Lys Ala Ser Glu Arg Ile Gly Arg Val Ala Leu Lys Leu Ala Glu Ser
145                 150                 155                 160

Arg Pro Arg Lys Thr Leu His Ile Ala His Lys Ala Asn Val Leu Pro
            165                 170                 175

Val Thr Gln Gly Leu Phe Leu Asp Thr Val Arg Glu Val Ala Lys Glu
        180                 185                 190

Tyr Pro Leu Val Asn Val Gln Asp Ile Ile Val Asp Asn Cys Ala Met
            195                 200                 205

Gln Leu Val Met Arg Pro Glu Arg Phe Asp Val Val Thr Thr Asn
    210                 215                 220

Leu Leu Gly Asp Ile Leu Ser Asp Leu Thr Ala Gly Leu Val Gly Gly
225                 230                 235                 240

Leu Gly Leu Ala Pro Ser Ala Asn Ile Gly Asp Thr Thr Ala Val Phe
                245                 250                 255

Glu Pro Val His Gly Ser Ala Pro Asp Ile Ala Gly Lys Gly Ile Ala
            260                 265                 270

Asn Pro Thr Ala Thr Ile Leu Ser Ala Ala Met Met Leu Asp Tyr Leu
        275                 280                 285

Gly Glu Lys Glu Ala Ala Gln Arg Val Glu Lys Ala Val Asp Leu Val
        290                 295                 300

Leu Glu Lys Gly Pro Arg Thr Pro Asp Leu Gly Gly Thr Ala Thr Thr
305                 310                 315                 320

Glu Thr Phe Thr Gln Ala Val Val Glu Ala Leu Gln Ala Leu
                325                 330

<210> SEQ ID NO 112
<211> LENGTH: 334
<212> TYPE: PRT
<213> ORGANISM: Thermus thermophilus

<400> SEQUENCE: 112

Met Ala Tyr Arg Ile Cys Leu Ile Glu Gly Asp Gly Ile Gly His Glu
1               5                   10                  15

Val Ile Pro Ala Ala Arg Arg Val Leu Glu Ala Thr Gly Leu Pro Leu
            20                  25                  30

Glu Phe Val Glu Ala Glu Ala Gly Trp Glu Thr Phe Glu Arg Arg Gly
        35                  40                  45

Thr Ser Val Pro Glu Glu Thr Val Glu Lys Ile Leu Ser Cys His Ala
    50                  55                  60

Thr Leu Phe Gly Ala Ala Thr Ser Pro Thr Arg Lys Val Pro Gly Phe
65                  70                  75                  80

Phe Gly Ala Ile Arg Tyr His Arg Arg Leu Asp Leu Tyr Ala Asn
                85                  90                  95

Val Arg Pro Ala Lys Ser Arg Pro Val Pro Gly Ser Arg Pro Gly Val
            100                 105                 110

Asp Leu Val Ile Val His Glu Asn Thr Glu Gly Leu Tyr Val Glu Gln
        115                 120                 125

Glu Arg Arg Tyr Leu Asp Val Ala Ile Ala Asp Ala Val Ile Ser Lys
        130                 135                 140

Lys Ala Ser Glu Arg Ile Gly Arg Ala Ala Leu Arg Ile Ala Glu Gly
145                 150                 155                 160

Arg Pro Arg Lys Thr Leu His Ile Ala His Lys Ala Asn Val Leu Pro
                165                 170                 175

Leu Thr Gln Gly Leu Phe Leu Asp Thr Val Lys Glu Val Ala Lys Asp
            180                 185                 190

Phe Pro Leu Val Asn Val Gln Asp Ile Ile Val Asp Asn Cys Ala Met
        195                 200                 205

Gln Leu Val Met Arg Pro Glu Arg Phe Asp Val Ile Val Thr Thr Asn
    210                 215                 220

Leu Leu Gly Asp Ile Leu Ser Asp Leu Ala Ala Gly Leu Val Gly Gly
225                 230                 235                 240

Leu Gly Leu Ala Pro Ser Gly Asn Ile Gly Asp Thr Thr Ala Val Phe
            245                 250                 255

Glu Pro Val His Gly Ser Ala Pro Asp Ile Ala Gly Lys Gly Ile Ala
            260                 265                 270

Asn Pro Thr Ala Ala Ile Leu Ser Ala Ala Met Met Leu Asp Tyr Leu
            275                 280                 285

Gly Glu Lys Glu Ala Ala Lys Arg Val Glu Lys Ala Val Asp Leu Val
290                 295                 300

Leu Glu Arg Gly Pro Arg Thr Pro Asp Leu Gly Gly Asp Ala Thr Thr
305                 310                 315                 320

Glu Ala Phe Thr Glu Ala Val Val Glu Ala Leu Lys Ser Leu
            325                 330

<210> SEQ ID NO 113
<211> LENGTH: 334
<212> TYPE: PRT
<213> ORGANISM: Thermus thermophilus

<400> SEQUENCE: 113

Met Ala Tyr Arg Ile Cys Leu Ile Glu Gly Asp Gly Ile Gly His Glu
1               5                   10                  15

Val Ile Pro Ala Ala Arg Arg Val Leu Glu Ala Thr Gly Leu Pro Leu
            20                  25                  30

Glu Phe Val Glu Ala Glu Ala Gly Trp Glu Thr Phe Glu Arg Arg Gly
        35                  40                  45

Thr Ser Val Pro Glu Glu Thr Val Glu Lys Ile Leu Ser Cys His Ala
    50                  55                  60

Thr Leu Phe Gly Ala Ala Thr Ser Pro Thr Arg Lys Val Pro Gly Phe
65                  70                  75                  80

Phe Gly Ala Ile Arg Tyr Leu His Arg Leu Asp Leu Tyr Ala Asn
                85                  90                  95

Val Arg Pro Ala Lys Ser Arg Pro Val Pro Gly Ser Arg Pro Gly Val
            100                 105                 110

Asp Leu Val Ile Val His Glu Asn Thr Glu Gly Leu Tyr Val Glu Gln
            115                 120                 125

Glu Arg Arg Tyr Leu Asp Val Ala Ile Ala Asp Ala Val Ile Ser Lys
130                 135                 140

Lys Ala Ser Glu Arg Ile Gly Arg Ala Ala Leu Arg Ile Ala Glu Gly
145                 150                 155                 160

Arg Pro Arg Lys Thr Leu His Ile Ala His Lys Ala Asn Val Leu Pro
            165                 170                 175

Leu Thr Gln Gly Leu Phe Leu Asp Thr Val Lys Glu Val Ala Lys Asp
            180                 185                 190

Phe Pro Leu Val Asn Val Gln Asp Ile Ile Val Asp Asn Cys Ala Met
            195                 200                 205

Gln Leu Val Met Arg Pro Glu Arg Phe Asp Val Ile Val Thr Thr Asn
        210                 215                 220

Leu Leu Gly Asp Ile Leu Ser Asp Leu Ala Ala Gly Leu Val Gly Gly
225                 230                 235                 240

Leu Gly Leu Ala Pro Ser Gly Asn Ile Gly Asp Thr Thr Ala Val Phe
            245                 250                 255

Glu Pro Val His Gly Ser Ala Pro Asp Ile Ala Gly Lys Gly Ile Ala
            260                 265                 270

Asn Pro Thr Ala Ala Ile Leu Ser Ala Ala Met Met Leu Asp Tyr Leu
            275                 280                 285

Gly Glu Lys Glu Ala Ala Lys Arg Val Glu Lys Ala Val Asp Leu Val
            290                 295                 300

Leu Glu Arg Gly Pro Arg Thr Pro Asp Leu Gly Gly Asp Ala Thr Thr
305                 310                 315                 320

Glu Ala Phe Thr Glu Ala Val Val Glu Ala Leu Lys Ser Leu
            325                 330

<210> SEQ ID NO 114
<211> LENGTH: 334
<212> TYPE: PRT
<213> ORGANISM: Thermus thermophilus

<400> SEQUENCE: 114

Met Ala Tyr Arg Ile Cys Leu Ile Glu Gly Asp Gly Ile Gly His Glu
1               5                   10                  15

Val Ile Pro Ala Ala Arg Arg Val Leu Glu Ala Thr Gly Leu Pro Leu
            20                  25                  30

Glu Phe Val Glu Ala Glu Ala Gly Trp Glu Thr Phe Glu Arg Arg Gly
        35                  40                  45

Thr Ser Val Pro Glu Thr Val Glu Lys Ile Leu Ser Cys His Ala
    50                  55                  60

Thr Leu Phe Gly Ala Ala Thr Ser Pro Thr Arg Lys Val Pro Gly Phe
65                  70                  75                  80

Phe Gly Ala Ile Arg Tyr Leu His Arg Leu Asp Leu Tyr Ala Asn
                85                  90                  95

Val Arg Pro Ala Lys Ser Arg Pro Val Pro Gly Ser Arg Pro Gly Val
            100                 105                 110

Asp Leu Val Ile Val His Glu Asn Thr Glu Gly Leu Tyr Val Glu Gln
            115                 120                 125

Glu Arg Arg Tyr Leu Asp Val Ala Ile Ala Asp Ala Val Ile Ser Lys
130                 135                 140

Lys Ala Ser Glu Arg Ile Gly Arg Ala Ala Leu Arg Ile Ala Glu Gly
145                 150                 155                 160

Arg Pro Arg Lys Thr Leu His Ile Ala His Lys Ala Asn Val Leu Pro
                165                 170                 175

Leu Thr Gln Gly Leu Phe Leu Asp Thr Val Lys Glu Val Ala Lys Asp
            180                 185                 190

Phe Pro Leu Val Asn Val Gln Asp Ile Ile Val Asp Asn Cys Ala Met
        195                 200                 205

Gln Leu Val Met Arg Pro Glu Arg Phe Asp Val Ile Val Thr Thr Asn
210                 215                 220

Leu Leu Gly Asp Ile Leu Ser Asp Leu Ala Ala Gly Leu Val Gly Gly
225                 230                 235                 240

Leu Gly Leu Ala Pro Ser Gly Asn Ile Gly Asp Thr Thr Ala Val Phe
                245                 250                 255

Glu Pro Val His Gly Ser Ala Pro Asp Ile Ala Gly Lys Gly Ile Ala
            260                 265                 270

Asn Pro Thr Ala Ala Ile Leu Ser Ala Ala Met Met Leu Asp Tyr Leu
        275                 280                 285

Gly Glu Lys Glu Ala Ala Lys Arg Val Glu Lys Ala Val Asp Leu Val
            290                 295                 300

Leu Glu Arg Gly Pro Arg Thr Pro Asp Leu Gly Gly Asp Ala Thr Thr
305                 310                 315                 320

Glu Ala Phe Thr Glu Ala Val Val Glu Ala Leu Lys Ser Leu
            325                 330

<210> SEQ ID NO 115
<211> LENGTH: 334
<212> TYPE: PRT
<213> ORGANISM: Thermus thermophilus

<400> SEQUENCE: 115

```
Met Ala Tyr Arg Ile Cys Leu Ile Glu Gly Asp Gly Ile Gly His Glu
1               5                   10                  15

Val Ile Pro Ala Ala Arg Arg Val Leu Glu Ala Thr Gly Leu Pro Leu
            20                  25                  30

Glu Phe Val Glu Ala Glu Ala Gly Trp Glu Thr Phe Glu Arg Arg Gly
        35                  40                  45

Thr Ser Val Pro Glu Glu Thr Val Glu Lys Ile Leu Ser Cys His Ala
    50                  55                  60

Thr Leu Phe Gly Ala Ala Thr Ser Pro Thr Arg Lys Val Pro Gly Phe
65                  70                  75                  80

Phe Gly Ala Ile Arg Tyr Leu His Arg Arg Leu Asp Leu Tyr Ala Asn
                85                  90                  95

Val Arg Pro Ala Lys Ser Arg Pro Val Pro Gly Ser Arg Pro Gly Val
            100                 105                 110

Asp Leu Val Ile Val His Glu Asn Thr Glu Gly Leu Tyr Val Glu Gln
        115                 120                 125

Glu Arg Arg Tyr Leu Asp Val Ala Ile Ala Asp Ala Val Ile Ser Lys
    130                 135                 140

Lys Ala Ser Glu Arg Ile Gly Arg Ala Ala Leu Arg Ile Ala Glu Gly
145                 150                 155                 160

Arg Pro Arg Lys Thr Leu His Ile Ala His Lys Ala Asn Val Leu Pro
                165                 170                 175

Leu Thr Gln Gly Leu Phe Leu Asp Thr Val Lys Glu Val Ala Lys Asp
            180                 185                 190

Phe Pro Leu Val Asn Val Gln Asp Ile Ile Val Asp Asn Cys Ala Met
        195                 200                 205

Gln Leu Val Met Arg Pro Glu Arg Phe Asp Val Ile Val Thr Thr Asn
    210                 215                 220

Leu Leu Gly Asp Ile Leu Ser Asp Leu Ala Ala Gly Leu Val Gly Gly
225                 230                 235                 240

Leu Gly Leu Ala Pro Ser Gly Asn Ile Gly Asp Thr Thr Ala Val Phe
                245                 250                 255

Glu Pro Val His Gly Ser Ala Pro Asp Ile Ala Gly Lys Gly Ile Ala
            260                 265                 270

Asn Pro Thr Ala Ala Ile Leu Ser Ala Ala Met Met Leu Asp Tyr Leu
        275                 280                 285

Gly Glu Lys Glu Ala Ala Lys Arg Val Glu Lys Ala Val Asp Leu Val
    290                 295                 300

Leu Glu Arg Gly Pro Arg Thr Pro Asp Leu Gly Gly Asp Ala Thr Thr
305                 310                 315                 320

Glu Ala Phe Thr Glu Ala Val Val Glu Ala Leu Lys Ser Leu
                325                 330
```

<210> SEQ ID NO 116
<211> LENGTH: 334
<212> TYPE: PRT
<213> ORGANISM: Thermus thermophilus

<400> SEQUENCE: 116

```
Met Ala Tyr Arg Ile Cys Leu Ile Glu Gly Asp Gly Ile Gly His Glu
1               5                   10                  15

Val Ile Pro Ala Arg Arg Val Leu Glu Ala Thr Gly Leu Pro Leu
            20                  25                  30

Glu Phe Val Glu Ala Glu Ala Gly Trp Glu Thr Phe Glu Arg Arg Gly
            35                  40                  45

Thr Ser Val Pro Glu Glu Thr Val Glu Lys Ile Leu Ser Cys His Ala
    50                  55                  60

Thr Leu Phe Gly Ala Ala Thr Ser Pro Thr Arg Lys Val Pro Gly Phe
65                  70                  75                  80

Phe Gly Ala Ile Arg Tyr Leu His Arg Arg Leu Asp Leu Tyr Ala Asn
                85                  90                  95

Val Arg Pro Ala Lys Ser Arg Pro Val Pro Gly Ser Arg Pro Gly Val
            100                 105                 110

Asp Leu Val Ile Val His Glu Asn Thr Glu Gly Leu Tyr Val Glu Gln
            115                 120                 125

Glu Arg Arg Tyr Leu Asp Val Ala Ile Ala Asp Ala Val Ile Ser Lys
    130                 135                 140

Lys Ala Ser Glu Arg Ile Gly Arg Ala Ala Leu Arg Ile Ala Glu Gly
145                 150                 155                 160

Arg Pro Arg Lys Thr Leu His Ile Ala His Lys Ala Asn Val Leu Pro
                165                 170                 175

Leu Thr Gln Gly Leu Phe Leu Asp Thr Val Lys Glu Val Ala Lys Asp
            180                 185                 190

Phe Pro Leu Val Asn Val Gln Asp Ile Ile Val Asp Asn Cys Ala Met
            195                 200                 205

Gln Leu Val Met Arg Pro Glu Arg Phe Asp Val Ile Val Thr Thr Asn
    210                 215                 220

Leu Leu Gly Asp Ile Leu Ser Asp Leu Ala Ala Gly Leu Val Gly Gly
225                 230                 235                 240

Leu Gly Leu Ala Pro Ser Gly Asn Ile Gly Asp Thr Ala Val Phe
                245                 250                 255

Glu Pro Val His Gly Ser Ala Pro Asp Ile Ala Gly Lys Gly Ile Ala
            260                 265                 270

Asn Pro Thr Ala Ala Ile Leu Ser Ala Ala Met Met Leu Asp Tyr Leu
    275                 280                 285

Gly Glu Lys Glu Ala Ala Lys Arg Val Glu Lys Ala Val Asp Leu Val
290                 295                 300

Leu Glu Arg Gly Pro Arg Thr Pro Asp Leu Gly Gly Asp Ala Thr Thr
305                 310                 315                 320

Glu Ala Phe Thr Glu Ala Val Val Glu Ala Leu Lys Ser Leu
                325                 330

<210> SEQ ID NO 117
<211> LENGTH: 333
<212> TYPE: PRT
<213> ORGANISM: Thermus thermophilus

<400> SEQUENCE: 117

Ala Tyr Arg Ile Cys Leu Ile Glu Gly Asp Gly Ile Gly His Glu Val
1               5                   10                  15

Ile Pro Ala Ala Arg Arg Val Leu Glu Ala Thr Gly Leu Pro Leu Glu
            20                  25                  30

Phe Val Glu Ala Glu Ala Gly Trp Glu Thr Phe Glu Arg Arg Gly Thr
        35                  40                  45
```

```
Ser Val Pro Glu Glu Thr Val Glu Lys Ile Leu Ser Cys His Ala Thr
    50                  55                  60

Leu Phe Gly Ala Ala Thr Ser Pro Thr Arg Lys Val Pro Gly Phe Phe
 65                  70                  75                  80

Gly Ala Ile Arg Tyr Leu His Arg Arg Leu Asp Leu Tyr Ala Asn Val
                 85                  90                  95

Arg Pro Ala Lys Ser Arg Pro Val Pro Gly Ser Arg Pro Gly Val Asp
                100                 105                 110

Leu Val Ile Val His Glu Asn Thr Glu Gly Leu Tyr Val Glu Gln Glu
            115                 120                 125

Arg Arg Tyr Leu Asp Val Ala Ile Ala Asp Ala Val Ile Ser Lys Lys
        130                 135                 140

Ala Ser Glu Arg Ile Gly Arg Ala Ala Leu Arg Ile Ala Glu Gly Arg
145                 150                 155                 160

Pro Arg Lys Thr Leu His Ile Ala His Lys Ala Asn Val Leu Pro Leu
                165                 170                 175

Thr Gln Gly Leu Phe Leu Asp Thr Val Lys Glu Val Ala Lys Asp Phe
            180                 185                 190

Pro Leu Val Asn Val Gln Asp Ile Ile Val Asp Asn Cys Ala Met Gln
        195                 200                 205

Leu Val Met Arg Pro Glu Arg Phe Asp Val Ile Val Thr Thr Asn Leu
210                 215                 220

Leu Gly Asp Ile Leu Ser Asp Leu Ala Ala Gly Leu Val Gly Gly Leu
225                 230                 235                 240

Gly Leu Ala Pro Ser Gly Asn Ile Gly Asp Thr Thr Ala Val Phe Glu
                245                 250                 255

Pro Val His Gly Ser Ala Pro Asp Ile Ala Gly Lys Gly Ile Ala Asn
            260                 265                 270

Pro Thr Ala Ala Ile Leu Ser Ala Ala Met Met Leu Asp Tyr Leu Gly
        275                 280                 285

Glu Lys Glu Ala Ala Lys Arg Val Glu Lys Ala Val Asp Leu Val Leu
290                 295                 300

Glu Arg Gly Pro Arg Thr Pro Asp Leu Gly Gly Asp Ala Thr Thr Glu
305                 310                 315                 320

Ala Phe Thr Glu Ala Val Val Glu Ala Leu Lys Ser Leu
                325                 330

<210> SEQ ID NO 118
<211> LENGTH: 333
<212> TYPE: PRT
<213> ORGANISM: Thermus thermophilus

<400> SEQUENCE: 118

Ala Tyr Arg Ile Cys Leu Ile Glu Gly Asp Gly Ile Gly His Glu Val
 1               5                  10                  15

Ile Pro Ala Ala Arg Arg Val Leu Glu Ala Thr Gly Leu Pro Leu Glu
                 20                  25                  30

Phe Val Glu Ala Glu Ala Gly Trp Glu Thr Phe Glu Arg Arg Gly Thr
             35                  40                  45

Ser Val Pro Glu Glu Thr Val Glu Lys Ile Leu Ser Cys His Ala Thr
    50                  55                  60

Leu Phe Gly Ala Ala Thr Ser Pro Thr Arg Lys Val Pro Gly Phe Phe
 65                  70                  75                  80

Gly Ala Ile Arg Tyr Leu His Arg Arg Leu Asp Leu Tyr Ala Asn Val
                 85                  90                  95
```

Arg Pro Ala Lys Ser Arg Pro Val Pro Gly Ser Arg Pro Gly Val Asp
            100                 105                 110

Leu Val Ile Val His Glu Asn Thr Glu Gly Leu Tyr Val Glu Gln Glu
        115                 120                 125

Arg Arg Tyr Leu Asp Val Ala Ile Ala Asp Ala Val Ile Ser Lys Lys
130                 135                 140

Ala Ser Glu Arg Ile Gly Arg Ala Ala Leu Arg Ile Ala Glu Gly Arg
145                 150                 155                 160

Pro Arg Lys Thr Leu His Ile Ala His Lys Ala Asn Val Leu Pro Leu
                165                 170                 175

Thr Gln Gly Leu Phe Leu Asp Thr Val Lys Glu Val Ala Lys Asp Phe
            180                 185                 190

Pro Leu Val Asn Val Gln Asp Ile Ile Val Asp Asn Cys Ala Met Gln
        195                 200                 205

Leu Val Met Arg Pro Glu Arg Phe Asp Val Ile Val Thr Thr Asn Leu
210                 215                 220

Leu Gly Asp Ile Leu Ser Asp Leu Ala Ala Gly Leu Val Gly Gly Leu
225                 230                 235                 240

Gly Leu Ala Pro Ser Gly Asn Ile Gly Asp Thr Thr Ala Val Phe Glu
                245                 250                 255

Pro Val His Gly Ser Ala Pro Asp Ile Ala Gly Lys Gly Ile Ala Asn
            260                 265                 270

Pro Thr Ala Ala Ile Leu Ser Ala Ala Met Met Leu Asp Tyr Leu Gly
        275                 280                 285

Glu Lys Glu Ala Ala Lys Arg Val Glu Lys Ala Val Asp Leu Val Leu
290                 295                 300

Glu Arg Gly Pro Arg Thr Pro Asp Leu Gly Gly Asp Ala Thr Thr Glu
305                 310                 315                 320

Ala Phe Thr Glu Ala Val Val Glu Ala Leu Lys Ser Leu
                325                 330

<210> SEQ ID NO 119
<211> LENGTH: 334
<212> TYPE: PRT
<213> ORGANISM: Thermus thermophilus

<400> SEQUENCE: 119

Met Ala Tyr Arg Ile Cys Leu Ile Glu Gly Asp Gly Ile Gly His Glu
1               5                   10                  15

Val Ile Pro Ala Ala Arg Arg Val Leu Glu Ala Thr Gly Leu Pro Leu
            20                  25                  30

Glu Phe Val Glu Ala Glu Ala Gly Trp Glu Thr Phe Glu Arg Arg Gly
        35                  40                  45

Thr Ser Val Pro Glu Glu Thr Val Glu Lys Ile Leu Ser Cys His Ala
50                  55                  60

Thr Leu Phe Gly Ala Ala Thr Ser Pro Thr Arg Lys Val Pro Gly Phe
65                  70                  75                  80

Phe Gly Ala Ile Arg Tyr Leu His Arg Arg Leu Asp Leu Tyr Ala Asn
                85                  90                  95

Val Arg Pro Ala Lys Ser Arg Pro Val Pro Gly Ser Arg Pro Gly Val
            100                 105                 110

Asp Leu Val Ile Val His Glu Asn Thr Glu Gly Leu Tyr Val Glu Gln
        115                 120                 125

Glu Arg Arg Tyr Leu Asp Val Ala Ile Ala Asp Ala Val Ile Ser Lys
    130                 135                 140

```
Lys Ala Ser Glu Arg Ile Gly Arg Ala Ala Leu Arg Ile Ala Glu Gly
145                 150                 155                 160

Arg Pro Arg Lys Thr Leu His Ile Ala His Lys Ala Asn Val Leu Pro
                165                 170                 175

Leu Thr Gln Gly Leu Phe Leu Asp Thr Val Lys Glu Val Ala Lys Asp
            180                 185                 190

Phe Pro Leu Val Asn Val Gln Asp Ile Ile Val Asp Asn Cys Ala Met
        195                 200                 205

Gln Leu Val Met Arg Pro Glu Arg Phe Asp Val Ile Val Thr Thr Asn
210                 215                 220

Leu Leu Gly Asp Ile Leu Ser Asp Leu Ala Ala Gly Leu Val Gly Gly
225                 230                 235                 240

Leu Gly Leu Ala Pro Ser Gly Asn Ile Gly Asp Thr Thr Ala Val Phe
                245                 250                 255

Glu Pro Val His Gly Ser Ala Pro Asp Ile Ala Gly Lys Gly Ile Ala
            260                 265                 270

Asn Pro Thr Ala Ala Ile Leu Ser Ala Ala Met Met Leu Asp Tyr Leu
        275                 280                 285

Gly Glu Lys Glu Ala Ala Lys Arg Val Glu Lys Ala Val Asp Leu Val
290                 295                 300

Leu Glu Arg Gly Pro Arg Thr Pro Asp Leu Gly Gly Asp Ala Thr Thr
305                 310                 315                 320

Glu Ala Phe Thr Glu Ala Val Val Glu Ala Leu Lys Ser Leu
                325                 330

<210> SEQ ID NO 120
<211> LENGTH: 334
<212> TYPE: PRT
<213> ORGANISM: Thermus thermophilus

<400> SEQUENCE: 120

Met Ala Tyr Arg Ile Cys Leu Ile Glu Gly Asp Gly Ile Gly His Glu
1               5                   10                  15

Val Ile Pro Ala Ala Arg Arg Val Leu Glu Ala Thr Gly Leu Pro Leu
            20                  25                  30

Glu Phe Val Glu Ala Glu Ala Gly Trp Glu Thr Phe Glu Arg Arg Gly
        35                  40                  45

Thr Ser Val Pro Glu Glu Thr Val Glu Lys Ile Leu Ser Cys His Ala
50                  55                  60

Thr Leu Phe Gly Ala Ala Thr Ser Pro Thr Arg Lys Val Pro Gly Phe
65                  70                  75                  80

Phe Gly Ala Ile Arg Tyr Leu His Arg Leu Asp Leu Tyr Ala Asn
                85                  90                  95

Val Arg Pro Ala Lys Ser Arg Pro Val Pro Gly Ser Arg Pro Gly Val
            100                 105                 110

Asp Leu Val Ile Val His Glu Asn Thr Glu Gly Leu Tyr Val Glu Gln
        115                 120                 125

Glu Arg Arg Tyr Leu Asp Val Ala Ile Ala Asp Ala Val Ile Ser Lys
130                 135                 140

Lys Ala Ser Glu Arg Ile Gly Arg Ala Ala Leu Arg Ile Ala Glu Gly
145                 150                 155                 160

Arg Pro Arg Lys Thr Leu His Ile Ala His Lys Ala Asn Val Leu Pro
                165                 170                 175

Leu Thr Gln Gly Leu Phe Leu Asp Thr Val Lys Glu Val Ala Lys Asp
            180                 185                 190
```

```
Phe Pro Leu Val Asn Val Gln Asp Ile Ile Val Asp Asn Cys Ala Met
        195                 200                 205

Gln Leu Val Met Arg Pro Glu Arg Phe Asp Val Ile Val Thr Thr Asn
        210                 215                 220

Leu Leu Gly Asp Ile Leu Ser Asp Leu Ala Ala Gly Leu Val Gly Gly
225                 230                 235                 240

Leu Gly Leu Ala Pro Ser Gly Asn Ile Gly Asp Thr Thr Ala Val Phe
                245                 250                 255

Glu Pro Val His Gly Ser Ala Pro Asp Ile Ala Gly Lys Gly Ile Ala
                260                 265                 270

Asn Pro Thr Ala Ala Ile Leu Ser Ala Ala Met Met Leu Asp Tyr Leu
            275                 280                 285

Gly Glu Lys Glu Ala Ala Lys Arg Val Glu Lys Ala Val Asp Leu Val
        290                 295                 300

Leu Glu Arg Gly Pro Arg Thr Pro Asp Leu Gly Gly Asp Ala Thr Thr
305                 310                 315                 320

Glu Ala Phe Thr Glu Ala Val Val Glu Ala Leu Lys Ser Leu
                325                 330
```

<210> SEQ ID NO 121
<211> LENGTH: 345
<212> TYPE: PRT
<213> ORGANISM: Thermus thermophilus

<400> SEQUENCE: 121

```
Met Lys Val Ala Val Leu Pro Gly Asp Gly Ile Gly Pro Glu Val Thr
1               5                   10                  15

Glu Ala Ala Leu Lys Val Leu Arg Ala Leu Asp Glu Ala Glu Gly Leu
                20                  25                  30

Gly Leu Ala Tyr Glu Val Phe Pro Phe Gly Ala Ala Ile Asp Ala
            35                  40                  45

Phe Gly Glu Pro Phe Pro Glu Pro Thr Arg Lys Gly Val Glu Glu Ala
        50                  55                  60

Glu Ala Val Leu Leu Gly Ser Val Gly Gly Pro Lys Trp Asp Gly Leu
65                  70                  75                  80

Pro Arg Lys Ile Arg Pro Glu Thr Gly Leu Leu Ser Leu His Lys Ser
                85                  90                  95

Gln Asp Leu Phe Ala Asn Leu Arg Pro Ala Lys Val Phe Pro Gly Leu
            100                 105                 110

Glu Arg Leu Ser Pro Leu Lys Glu Glu Ile Ala Arg Gly Val Asp Val
        115                 120                 125

Leu Ile Val His Glu Leu Thr Gly Gly Ile Tyr Phe Gly Glu Pro Arg
        130                 135                 140

Gly Met Ser Glu Ala Glu Ala Trp Asn Thr Glu Arg Tyr Ser Lys Pro
145                 150                 155                 160

Glu Val Glu Arg Val Ala Arg Val Ala Phe Glu Ala Ala Arg Lys Arg
                165                 170                 175

Arg Lys His Val Val Ser Val Asp Lys Ala Asn Val Leu Glu Val Gly
            180                 185                 190

Glu Phe Trp Arg Lys Thr Val Glu Glu Val Gly Arg Gly Tyr Pro Asp
        195                 200                 205

Val Ala Leu Glu His Gln Tyr Val Asp Ala Met Ala Met His Leu Val
        210                 215                 220

Arg Ser Pro Ala Arg Phe Asp Val Val Val Thr Gly Asn Ile Phe Gly
225                 230                 235                 240
```

-continued

```
Asp Ile Leu Ser Asp Leu Ala Ser Val Leu Pro Gly Ser Leu Gly Leu
                245                 250                 255

Leu Pro Ser Ala Ser Leu Gly Arg Gly Thr Pro Val Phe Glu Pro Val
            260                 265                 270

His Gly Ser Ala Pro Asp Ile Ala Gly Lys Gly Leu Ala Asn Pro Thr
        275                 280                 285

Ala Ala Ile Leu Ser Ala Ala Met Met Leu Glu His Ala Phe Gly Leu
    290                 295                 300

Val Glu Leu Ala Arg Lys Val Glu Asp Ala Val Ala Lys Ala Leu Leu
305                 310                 315                 320

Glu Ala Pro Pro Pro Asp Leu Gly Gly Ser Ala Gly Thr Glu Ala Phe
                325                 330                 335

Thr Ala Thr Val Leu Arg His Leu Ala
                340                 345

<210> SEQ ID NO 122
<211> LENGTH: 496
<212> TYPE: PRT
<213> ORGANISM: Thermus thermophilus

<400> SEQUENCE: 122

Met Pro Leu Ile Thr Thr Glu Thr Gly Lys Lys Met His Val Leu Glu
1               5                   10                  15

Asp Gly Arg Lys Leu Ile Thr Val Ile Pro Gly Asp Gly Val Gly Pro
            20                  25                  30

Glu Cys Val Glu Ala Thr Leu Lys Val Leu Glu Ala Ala Lys Ala Pro
        35                  40                  45

Leu Ala Tyr Glu Val Arg Glu Ala Gly Ala Ser Val Phe Arg Arg Gly
    50                  55                  60

Ile Ala Ser Gly Val Pro Gln Glu Thr Ile Glu Ser Ile Arg Lys Thr
65                  70                  75                  80

Arg Val Val Leu Lys Gly Pro Leu Glu Thr Pro Val Gly Tyr Gly Glu
                85                  90                  95

Lys Ser Ala Asn Val Thr Leu His Lys Leu Phe Glu Thr Tyr Ala Asn
            100                 105                 110

Val Arg Pro Val Arg Glu Phe Pro Asn Val Pro Thr Pro Tyr Ala Gly
        115                 120                 125

Arg Gly Ile Asp Leu Val Val Val His Glu Asn Val Glu Asp Leu Tyr
    130                 135                 140

Ala Gly Ile Glu His Met Gln Thr Pro Ser Val Ala Gln Thr Leu Lys
145                 150                 155                 160

Leu Ile Ser Trp Lys Gly Ser Glu Lys Ile Val Arg Phe Ala Phe Glu
                165                 170                 175

Leu Ala Arg Ala Glu Gly Arg Lys Lys Val His Cys Ala Thr Lys Ser
            180                 185                 190

Asn Ile Met Lys Leu Ala Glu Gly Thr Leu Lys Arg Ala Phe Glu Gln
        195                 200                 205

Val Ala Gln Glu Tyr Pro Asp Ile Glu Ala Val His Ile Ile Val Asp
    210                 215                 220

Asn Ala Ala His Gln Leu Val Lys Arg Pro Glu Gln Phe Glu Val Ile
225                 230                 235                 240

Val Thr Thr Asn Met Asn Gly Asp Ile Leu Ser Asp Leu Thr Ser Gly
                245                 250                 255

Leu Ile Gly Gly Leu Gly Phe Ala Pro Ser Ala Asn Ile Gly Asn Glu
            260                 265                 270
```

```
Val Ala Ile Phe Glu Ala Val His Gly Ser Ala Pro Lys Tyr Ala Gly
            275                 280                 285

Lys Asn Val Ile Asn Pro Thr Ala Val Leu Leu Ser Ala Val Met Met
290                 295                 300

Leu Arg Tyr Leu Glu Glu Phe Ala Thr Ala Asp Leu Ile Glu Asn Ala
305                 310                 315                 320

Leu Leu Tyr Thr Leu Glu Glu Gly Arg Val Leu Thr Gly Asp Val Val
            325                 330                 335

Gly Tyr Asp Arg Gly Ala Lys Thr Thr Glu Tyr Thr Glu Ala Ile Ile
            340                 345                 350

Gln Asn Leu Gly Lys Thr Pro Arg Lys Thr Gln Val Arg Gly Tyr Lys
            355                 360                 365

Pro Phe Arg Leu Pro Gln Val Asp Gly Ala Ile Ala Pro Ile Val Pro
370                 375                 380

Arg Ser Arg Arg Val Val Gly Val Asp Val Phe Val Glu Thr Asn Leu
385                 390                 395                 400

Leu Pro Glu Ala Leu Gly Lys Ala Leu Glu Asp Leu Ala Ala Gly Thr
            405                 410                 415

Pro Phe Arg Leu Lys Met Ile Ser Asn Arg Gly Thr Gln Val Tyr Pro
            420                 425                 430

Pro Thr Gly Gly Leu Thr Asp Leu Val Asp His Tyr Arg Cys Arg Phe
            435                 440                 445

Leu Tyr Thr Gly Glu Gly Glu Ala Lys Asp Pro Glu Ile Leu Asp Leu
            450                 455                 460

Val Ser Arg Val Ala Ser Arg Phe Arg Trp Met His Leu Glu Lys Leu
465                 470                 475                 480

Gln Glu Phe Asp Gly Glu Pro Gly Phe Thr Lys Ala Gln Gly Glu Asp
            485                 490                 495

<210> SEQ ID NO 123
<211> LENGTH: 334
<212> TYPE: PRT
<213> ORGANISM: Thermus thermophilus

<400> SEQUENCE: 123

Met Ala Tyr Arg Ile Cys Leu Ile Glu Gly Asp Gly Ile Gly His Glu
1               5                   10                  15

Val Ile Pro Ala Ala Arg Arg Val Leu Glu Ala Thr Gly Leu Pro Leu
            20                  25                  30

Glu Phe Val Glu Ala Glu Ala Gly Trp Glu Thr Phe Glu Arg Arg Gly
            35                  40                  45

Thr Ser Val Pro Glu Glu Thr Val Glu Lys Ile Leu Ser Cys His Ala
50                  55                  60

Thr Leu Phe Gly Ala Ala Thr Ser Pro Thr Arg Lys Val Pro Gly Phe
65                  70                  75                  80

Phe Gly Ala Ile Arg Tyr Leu Arg His Arg Leu Asp Leu Tyr Ala Asn
                85                  90                  95

Val Arg Pro Ala Lys Ser Arg Pro Val Pro Gly Ser Arg Pro Gly Val
            100                 105                 110

Asp Leu Val Ile Val His Glu Asn Thr Glu Gly Leu Tyr Val Glu Gln
            115                 120                 125

Glu Arg Arg Tyr Leu Asp Val Ala Ile Ala Asp Ala Val Ile Ser Lys
            130                 135                 140

Lys Ala Ser Glu Arg Ile Gly Arg Ala Ala Leu Arg Ile Ala Glu Gly
145                 150                 155                 160
```

```
Arg Pro Arg Lys Thr Leu His Ile Ala His Lys Ala Asn Val Leu Pro
            165                 170                 175

Leu Thr Gln Gly Leu Phe Leu Asp Thr Val Lys Glu Val Ala Lys Asp
        180                 185                 190

Phe Pro Leu Val Asn Val Gln Asp Ile Ile Val Asp Asn Cys Ala Met
        195                 200                 205

Gln Leu Val Met Arg Pro Glu Arg Phe Asp Val Ile Val Thr Thr Asn
        210                 215                 220

Leu Leu Gly Asp Ile Leu Ser Asp Leu Ala Ala Gly Leu Val Gly Gly
225                 230                 235                 240

Leu Gly Leu Ala Pro Ser Gly Asn Ile Gly Asp Thr Thr Ala Val Phe
                245                 250                 255

Glu Pro Val His Gly Ser Ala Pro Asp Ile Ala Gly Lys Gly Ile Ala
                260                 265                 270

Asn Pro Thr Ala Ala Ile Leu Ser Ala Ala Met Met Leu Asp Tyr Leu
                275                 280                 285

Gly Glu Lys Glu Ala Ala Lys Arg Val Glu Lys Ala Val Asp Leu Val
                290                 295                 300

Leu Glu Arg Gly Pro Arg Thr Pro Asp Leu Gly Gly Asp Ala Thr Thr
305                 310                 315                 320

Glu Ala Phe Thr Glu Ala Val Val Glu Ala Leu Lys Ser Leu
                325                 330

<210> SEQ ID NO 124
<211> LENGTH: 334
<212> TYPE: PRT
<213> ORGANISM: Thermus thermophilus

<400> SEQUENCE: 124

Met Ala Tyr Arg Ile Cys Leu Ile Glu Gly Asp Gly Ile Gly His Glu
1               5                   10                  15

Val Ile Pro Ala Ala Arg Arg Val Leu Glu Ala Thr Gly Leu Pro Leu
                20                  25                  30

Glu Phe Val Glu Ala Glu Ala Gly Trp Glu Thr Phe Glu Arg Arg Gly
            35                  40                  45

Thr Ser Val Pro Glu Glu Thr Val Glu Lys Ile Leu Ser Cys His Ala
50                  55                  60

Thr Leu Phe Gly Ala Ala Thr Ser Pro Thr Arg Lys Val Pro Gly Phe
65                  70                  75                  80

Phe Gly Ala Ile Arg Tyr Leu His Arg Arg Leu Asp Leu Tyr Ala Asn
                85                  90                  95

Val Arg Pro Ala Lys Ser Arg Pro Val Pro Gly Ser Arg Pro Gly Val
                100                 105                 110

Asp Leu Val Ile Val His Glu Asn Thr Glu Gly Leu Tyr Val Glu Gln
                115                 120                 125

Glu Arg Arg Tyr Leu Asp Val Ala Ile Ala Asp Ala Val Ile Ser Lys
            130                 135                 140

Lys Ala Ser Glu Arg Ile Gly Arg Ala Ala Leu Arg Ile Ala Glu Gly
145                 150                 155                 160

Arg Pro Arg Lys Thr Leu His Ile Ala His Lys Ala Asn Val Leu Pro
                165                 170                 175

Leu Thr Gln Gly Leu Phe Leu Asp Thr Val Lys Glu Val Ala Lys Asp
            180                 185                 190

Phe Pro Leu Val Asn Val Gln Asp Ile Ile Val Asp Asn Cys Ala Met
            195                 200                 205
```

```
Gln Leu Val Met Arg Pro Glu Arg Phe Asp Val Ile Val Thr Thr Asn
    210                 215                 220

Leu Leu Gly Asp Ile Leu Ser Asp Leu Ala Ala Gly Leu Val Gly Gly
225                 230                 235                 240

Leu Gly Leu Ala Pro Ser Gly Asn Ile Gly Asp Thr Thr Ala Val Phe
                245                 250                 255

Glu Pro Val His Gly Ser Ala Pro Asp Ile Ala Gly Lys Gly Ile Ala
            260                 265                 270

Asn Pro Thr Ala Ala Ile Leu Ser Ala Ala Met Met Leu Asp Tyr Leu
        275                 280                 285

Gly Glu Lys Glu Ala Ala Lys Arg Val Glu Lys Ala Val Asp Leu Val
    290                 295                 300

Leu Glu Arg Gly Pro Arg Thr Pro Asp Leu Gly Gly Asp Ala Thr Thr
305                 310                 315                 320

Glu Ala Phe Thr Glu Ala Val Val Glu Ala Leu Lys Ser Leu
                325                 330

<210> SEQ ID NO 125
<211> LENGTH: 334
<212> TYPE: PRT
<213> ORGANISM: Thermus thermophilus

<400> SEQUENCE: 125

Met Ala Tyr Arg Ile Cys Leu Ile Glu Gly Asp Gly Ile Gly His Glu
1               5                   10                  15

Val Ile Pro Ala Ala Arg Arg Val Leu Glu Ala Thr Gly Leu Pro Leu
            20                  25                  30

Glu Phe Val Glu Ala Glu Ala Gly Trp Glu Thr Phe Glu Arg Arg Gly
        35                  40                  45

Thr Ser Val Pro Glu Glu Thr Val Glu Lys Ile Leu Ser Cys His Ala
    50                  55                  60

Thr Leu Phe Gly Ala Ala Thr Ser Pro Thr Arg Lys Val Pro Gly Phe
65                  70                  75                  80

Phe Gly Ala Ile Arg Tyr Leu His Arg Arg Leu Asp Leu Tyr Ala Asn
                85                  90                  95

Val Arg Pro Ala Lys Ser Arg Pro Val Pro Gly Ser Arg Pro Gly Val
            100                 105                 110

Asp Leu Val Ile Val His Glu Asn Thr Glu Gly Leu Tyr Val Glu Gln
        115                 120                 125

Glu Arg Arg Tyr Leu Asp Val Ala Ile Ala Asp Ala Val Ile Ser Lys
    130                 135                 140

Lys Ala Ser Glu Arg Ile Gly Arg Ala Ala Leu Arg Ile Ala Glu Gly
145                 150                 155                 160

Arg Pro Arg Lys Thr Leu His Ile Ala His Lys Ala Asn Val Leu Pro
                165                 170                 175

Leu Thr Gln Gly Leu Phe Leu Asp Thr Val Lys Glu Val Ala Lys Asp
            180                 185                 190

Phe Pro Leu Val Asn Val Gln Asp Ile Ile Val Asp Asn Cys Ala Met
        195                 200                 205

Gln Leu Val Met Arg Pro Glu Arg Phe Asp Val Ile Val Thr Thr Asn
    210                 215                 220

Leu Leu Gly Asp Ile Leu Ser Asp Leu Ala Ala Gly Leu Val Gly Gly
225                 230                 235                 240

Leu Gly Leu Ala Pro Ser Gly Asn Ile Gly Asp Thr Thr Ala Val Phe
                245                 250                 255
```

```
Glu Pro Val His Gly Ser Ala Pro Asp Ile Ala Gly Lys Gly Ile Ala
            260                 265                 270

Asn Pro Thr Ala Ala Ile Leu Ser Ala Ala Met Met Leu Asp Tyr Leu
        275                 280                 285

Gly Glu Lys Glu Ala Ala Lys Arg Val Glu Lys Ala Val Asp Leu Val
    290                 295                 300

Leu Glu Arg Gly Pro Arg Thr Pro Asp Leu Gly Gly Asp Ala Thr Thr
305                 310                 315                 320

Glu Ala Phe Thr Glu Ala Val Val Glu Ala Leu Lys Ser Leu
                325                 330

<210> SEQ ID NO 126
<211> LENGTH: 334
<212> TYPE: PRT
<213> ORGANISM: Thermus thermophilus

<400> SEQUENCE: 126

Met Ala Tyr Arg Ile Cys Leu Ile Glu Gly Asp Gly Ile Gly His Glu
1               5                   10                  15

Val Ile Pro Ala Ala Arg Arg Val Leu Glu Ala Thr Gly Leu Pro Leu
            20                  25                  30

Glu Phe Val Glu Ala Glu Ala Gly Trp Glu Thr Phe Glu Arg Arg Gly
        35                  40                  45

Thr Ser Val Pro Glu Glu Thr Val Glu Lys Ile Leu Ser Cys His Ala
50                  55                  60

Thr Leu Phe Gly Ala Ala Thr Ser Pro Thr Arg Lys Val Pro Gly Phe
65                  70                  75                  80

Phe Gly Ala Ile Arg Tyr Leu His Arg Leu Asp Leu Tyr Ala Asn
                85                  90                  95

Val Arg Pro Ala Lys Ser Arg Pro Ile Pro Gly Ser Arg Pro Gly Val
            100                 105                 110

Asp Leu Ile Ile Val His Glu Asn Thr Glu Gly Leu Tyr Val Glu Gln
        115                 120                 125

Glu Arg Arg Tyr Leu Asp Val Ala Ile Ala Asp Ala Val Ile Ser Lys
130                 135                 140

Lys Ala Ser Glu Arg Ile Gly Arg Ala Ala Leu Arg Ile Ala Glu Gly
145                 150                 155                 160

Arg Pro Arg Lys Thr Leu His Ile Ala His Lys Ala Asn Val Leu Pro
                165                 170                 175

Leu Thr Gln Gly Leu Phe Leu Asp Thr Val Lys Glu Val Ala Lys Asp
            180                 185                 190

Phe Pro Leu Val Asn Val Gln Asp Ile Ile Val Asp Asn Cys Ala Met
        195                 200                 205

Gln Leu Val Met Arg Pro Glu Arg Phe Asp Val Ile Val Thr Thr Asn
210                 215                 220

Leu Leu Gly Asp Ile Leu Ser Asp Leu Ala Ala Gly Leu Val Gly Gly
225                 230                 235                 240

Leu Gly Leu Ala Pro Ser Gly Asn Ile Gly Asp Thr Thr Ala Val Phe
                245                 250                 255

Glu Pro Val His Gly Ser Ala Pro Asp Ile Ala Gly Lys Gly Ile Ala
            260                 265                 270

Asn Pro Thr Ala Ala Ile Leu Ser Ala Ala Met Met Leu Asp Tyr Leu
        275                 280                 285

Gly Glu Lys Glu Ala Ala Lys Arg Val Glu Lys Ala Val Asp Leu Val
    290                 295                 300
```

```
Leu Glu Arg Gly Pro Arg Thr Pro Asp Leu Gly Gly Asp Ala Thr Thr
305                 310                 315                 320

Glu Ala Phe Thr Lys Ala Val Val Glu Ala Leu Lys Ser Leu
                325                 330

<210> SEQ ID NO 127
<211> LENGTH: 334
<212> TYPE: PRT
<213> ORGANISM: Thermus thermophilus

<400> SEQUENCE: 127

Met Ala Tyr Arg Ile Cys Leu Ile Glu Gly Asp Gly Ile Gly Tyr Glu
1               5                   10                  15

Val Ile Pro Ala Ala Arg Arg Val Leu Glu Ala Thr Gly Leu Pro Leu
                20                  25                  30

Glu Phe Val Glu Ala Glu Ala Gly Trp Glu Thr Phe Glu Arg Arg Gly
            35                  40                  45

Thr Ser Val Pro Glu Gly Thr Val Val Lys Ile Leu Ser Cys His Ala
        50                  55                  60

Thr Leu Phe Gly Ala Ala Thr Ile Pro Thr Arg Lys Val Pro Gly Phe
65                  70                  75                  80

Phe Gly Ala Ile Met Ala Leu His Arg Arg Leu Asp Leu Tyr Ala Asn
                85                  90                  95

Val Arg Pro Ala Lys Ser Arg Pro Val Pro Gly Ser Arg Pro Gly Val
                100                 105                 110

Asp Leu Val Ile Val His Glu Asn Thr Glu Gly Leu Tyr Val Glu Gln
            115                 120                 125

Glu Arg Arg Tyr Leu Asp Val Ala Ile Ala Asp Ala Val Ile Ser Lys
        130                 135                 140

Lys Ala Ser Glu Arg Ile Gly Arg Ala Ala Leu Arg Ile Ala Glu Gly
145                 150                 155                 160

Arg Pro Arg Lys Thr Leu His Ile Ala His Lys Ala Asn Val Leu Pro
                165                 170                 175

Leu Thr Gln Gly Leu Phe Leu Asp Thr Val Lys Glu Val Ala Lys Asp
            180                 185                 190

Phe Pro Leu Val Asn Val Gln Asp Ile Ile Val Asp Asn Cys Ala Thr
        195                 200                 205

Gln Leu Val Met Arg Pro Glu Arg Tyr Asp Val Ile Val Thr Thr Asn
    210                 215                 220

Leu Leu Gly Asp Ile Leu Ser Asp Leu Ala Ala Gly Leu Met Gly Gly
225                 230                 235                 240

Leu Gly Leu Ala Pro Ser Gly Asn Ile Gly Asp Thr Thr Ala Val Phe
                245                 250                 255

Glu Pro Val His Gly Ser Ala Pro Asp Ile Ala Gly Lys Gly Ile Ala
            260                 265                 270

Asn Pro Thr Ala Ala Ile Leu Ser Ala Ala Met Met Leu Asp Tyr Leu
        275                 280                 285

Gly Glu Lys Glu Ala Ala Lys Arg Val Glu Lys Ala Val Asp Leu Val
    290                 295                 300

Leu Glu Arg Gly Pro Met Thr Pro Asp Leu Gly Gly Asp Ala Thr Thr
305                 310                 315                 320

Glu Ala Phe Thr Glu Ala Val Val Glu Ala Leu Lys Ser Leu
                325                 330

<210> SEQ ID NO 128
<211> LENGTH: 334
```

<212> TYPE: PRT
<213> ORGANISM: Thermus thermophilus

<400> SEQUENCE: 128

```
Met Ala Tyr Arg Ile Cys Leu Ile Glu Gly Asp Gly Ile Gly Tyr Glu
1               5                   10                  15

Val Ile Pro Ala Ala Arg Arg Val Leu Glu Ala Thr Gly Leu Pro Leu
            20                  25                  30

Glu Phe Val Glu Ala Glu Ala Gly Trp Glu Thr Phe Glu Arg Arg Gly
        35                  40                  45

Thr Ser Val Pro Glu Glu Thr Val Val Lys Ile Leu Ser Cys His Ala
    50                  55                  60

Thr Leu Phe Gly Ala Ala Thr Ile Pro Thr Arg Lys Val Pro Gly Phe
65                  70                  75                  80

Phe Gly Ala Ile Met Ala Leu His Arg Arg Leu Asp Leu Tyr Ala Asn
                85                  90                  95

Val Arg Pro Ala Lys Ser Arg Pro Val Pro Gly Ser Arg Pro Gly Val
            100                 105                 110

Asp Leu Val Ile Val His Glu Asn Thr Glu Gly Leu Tyr Val Glu Gln
        115                 120                 125

Glu Arg Arg Tyr Leu Asp Val Ala Ile Ala Asp Ala Val Ile Ser Lys
    130                 135                 140

Lys Ala Ser Glu Arg Ile Gly Arg Ala Ala Leu Arg Ile Ala Glu Gly
145                 150                 155                 160

Arg Pro Arg Lys Thr Leu His Ile Ala His Lys Ala Asn Val Leu Pro
                165                 170                 175

Leu Thr Gln Gly Leu Phe Leu Asp Thr Val Lys Glu Val Ala Lys Asp
            180                 185                 190

Phe Pro Leu Val Asn Val Gln Asp Ile Ile Val Asp Asn Cys Ala Thr
        195                 200                 205

Gln Leu Val Met Arg Pro Glu Arg Tyr Asp Val Ile Val Thr Thr Asn
    210                 215                 220

Leu Leu Gly Asp Ile Leu Ser Asp Leu Ala Ala Gly Leu Met Gly Gly
225                 230                 235                 240

Leu Gly Leu Ala Pro Ser Gly Asn Ile Gly Asp Thr Thr Ala Val Phe
                245                 250                 255

Glu Pro Val His Gly Ser Ala Pro Asp Ile Ala Gly Lys Gly Ile Ala
            260                 265                 270

Asn Pro Thr Ala Ala Ile Leu Ser Ala Ala Met Met Leu Asp Tyr Leu
        275                 280                 285

Gly Glu Lys Glu Ala Ala Lys Arg Val Glu Lys Ala Val Asp Leu Val
    290                 295                 300

Leu Glu Arg Gly Pro Met Thr Pro Asp Leu Gly Gly Asp Ala Thr Thr
305                 310                 315                 320

Glu Ala Phe Thr Glu Ala Val Val Glu Ala Leu Lys Ser Leu
                325                 330
```

<210> SEQ ID NO 129
<211> LENGTH: 334
<212> TYPE: PRT
<213> ORGANISM: Thermus thermophilus

<400> SEQUENCE: 129

```
Met Ala Tyr Arg Ile Cys Leu Ile Glu Gly Asp Gly Ile Gly Tyr Glu
1               5                   10                  15

Val Ile Pro Ala Ala Arg Arg Val Leu Glu Ala Thr Gly Leu Pro Leu
```

-continued

```
                20                  25                  30
Glu Phe Val Glu Ala Glu Ala Gly Trp Glu Thr Phe Glu Arg Arg Gly
            35                  40                  45

Thr Ser Val Pro Glu Glu Thr Val Val Lys Ile Leu Ser Cys His Ala
        50                  55                  60

Thr Leu Phe Gly Ala Ala Thr Ile Pro Thr Arg Lys Val Pro Gly Phe
65                  70                  75                  80

Phe Gly Ala Ile Met Ala Leu His Arg Arg Leu Asp Leu Tyr Ala Asn
                85                  90                  95

Val Arg Pro Ala Lys Ser Arg Pro Val Pro Gly Ser Arg Pro Gly Val
            100                 105                 110

Asp Leu Val Ile Val His Glu Asn Thr Glu Gly Leu Tyr Val Glu Gln
        115                 120                 125

Glu Arg Arg Tyr Leu Asp Val Ala Ile Ala Asp Ala Val Ile Ser Lys
            130                 135                 140

Lys Ala Ser Glu Arg Ile Gly Arg Ala Ala Leu Arg Ile Ala Glu Gly
145                 150                 155                 160

Arg Pro Arg Lys Thr Leu His Ile Ala His Lys Ala Asn Val Leu Pro
                165                 170                 175

Leu Thr Gln Gly Leu Phe Leu Asp Thr Val Lys Glu Val Ala Lys Asp
            180                 185                 190

Phe Pro Leu Val Asn Val Gln Asp Ile Ile Val Asp Asn Cys Ala Thr
        195                 200                 205

Gln Leu Val Met Arg Pro Glu Arg Tyr Asp Val Ile Val Thr Thr Asn
    210                 215                 220

Leu Leu Gly Asp Ile Leu Ser Asp Leu Ala Ala Gly Leu Met Gly Gly
225                 230                 235                 240

Leu Gly Leu Ala Pro Ser Gly Asn Ile Gly Asp Thr Thr Ala Val Phe
                245                 250                 255

Glu Pro Val His Gly Ser Ala Pro Asp Ile Ala Gly Lys Gly Ile Ala
            260                 265                 270

Asn Pro Thr Ala Ala Ile Leu Ser Ala Ala Met Met Leu Asp Tyr Leu
        275                 280                 285

Gly Glu Lys Glu Ala Ala Lys Arg Val Glu Lys Ala Val Asp Leu Val
    290                 295                 300

Leu Glu Arg Gly Pro Met Thr Pro Asp Leu Gly Gly Asp Ala Thr Thr
305                 310                 315                 320

Glu Ala Phe Thr Glu Ala Val Val Glu Ala Leu Lys Ser Leu
                325                 330

<210> SEQ ID NO 130
<211> LENGTH: 334
<212> TYPE: PRT
<213> ORGANISM: Thermus thermophilus

<400> SEQUENCE: 130

Met Ala Tyr Arg Ile Cys Leu Ile Glu Gly Asp Gly Ile Gly Tyr Glu
1               5                   10                  15

Val Ile Pro Ala Ala Arg Arg Val Leu Glu Ala Thr Gly Leu Pro Leu
            20                  25                  30

Glu Phe Val Glu Ala Glu Ala Gly Trp Glu Thr Phe Glu Arg Arg Gly
            35                  40                  45

Thr Ser Val Pro Glu Glu Thr Val Val Lys Ile Leu Ser Cys His Ala
        50                  55                  60

Thr Leu Phe Gly Ala Ala Thr Ile Pro Thr Arg Lys Val Pro Gly Phe
```

```
                65                  70                  75                  80
Phe Gly Ala Ile Met Ala Leu His Arg Arg Leu Asp Leu Tyr Ala Asn
                    85                  90                  95
Val Arg Pro Ala Lys Ser Arg Pro Val Pro Gly Ser Arg Pro Gly Val
                100                 105                 110
Asp Leu Val Ile Val His Glu Asn Thr Glu Gly Leu Tyr Val Glu Gln
                115                 120                 125
Glu Arg Arg Tyr Leu Asp Val Ala Ile Ala Asp Val Ile Ser Lys
            130                 135                 140
Lys Ala Ser Glu Arg Ile Gly Arg Ala Ala Leu Arg Ile Ala Glu Gly
145                 150                 155                 160
Arg Pro Arg Lys Thr Leu His Ile Ala His Lys Ala Asn Val Leu Pro
                165                 170                 175
Leu Thr Gln Gly Leu Phe Leu Asp Thr Val Lys Glu Val Ala Lys Asp
                180                 185                 190
Phe Pro Leu Val Asn Val Gln Asp Ile Ile Val Asp Asn Cys Ala Thr
                195                 200                 205
Gln Leu Val Met Arg Pro Glu Arg Tyr Asp Val Ile Val Thr Thr Asn
            210                 215                 220
Leu Leu Gly Asp Ile Leu Ser Asp Leu Ala Ala Gly Leu Met Gly Gly
225                 230                 235                 240
Leu Gly Leu Ala Pro Ser Gly Asn Ile Gly Asp Thr Thr Ala Val Phe
                245                 250                 255
Glu Pro Val His Gly Ser Ala Pro Asp Ile Ala Gly Lys Gly Ile Ala
                260                 265                 270
Asn Pro Thr Ala Ala Ile Leu Ser Ala Met Met Leu Asp Tyr Leu
                275                 280                 285
Gly Glu Lys Glu Ala Ala Lys Arg Val Glu Lys Ala Val Asp Leu Val
            290                 295                 300
Leu Glu Arg Gly Pro Met Thr Pro Asp Leu Gly Gly Asp Ala Thr Thr
305                 310                 315                 320
Glu Ala Phe Thr Glu Ala Val Val Glu Ala Leu Lys Ser Leu
                325                 330

<210> SEQ ID NO 131
<211> LENGTH: 360
<212> TYPE: PRT
<213> ORGANISM: Trichophyton equinum

<400> SEQUENCE: 131

Met Ala Ala Arg Thr Leu Arg Ile Gly Leu Ile Pro Gly Asp Gly Ile
1               5                   10                  15
Gly Arg Glu Val Ile Pro Ala Gly Arg Ile Leu Glu Ala Leu Pro
                20                  25                  30
Ala Ser Leu Gly Leu Lys Phe Ser Phe Val Asp Leu Asp Ala Gly Tyr
            35                  40                  45
Asp Thr Phe Leu Arg Thr Lys Thr Ala Leu Pro Asp Lys Thr Val Glu
        50                  55                  60
Thr Leu Lys Lys Glu Cys Asp Gly Ala Leu Phe Gly Ala Val Ser Ser
65                  70                  75                  80
Pro Ser Thr Lys Val Ala Gly Tyr Ser Ser Pro Ile Val Ala Leu His
                85                  90                  95
Lys Lys Leu Asp Leu Tyr Ala Asn Val Arg Pro Val Lys Thr Thr Ala
                100                 105                 110
Gly Ala Asn Thr Ser Ala Arg Pro Ile Asp Leu Val Ile Val His Glu
```

```
                115                 120                 125
Asn Thr Glu Asp Leu Tyr Val Lys Glu Lys Thr Tyr Asp Thr Pro
130                 135                 140
Asn Gly Lys Val Ala Glu Ala Ile Lys Arg Ile Ser Glu Asn Ala Ser
145                 150                 155                 160
Phe Arg Ile Gly Thr Met Ala Gly Glu Ile Ala Leu Arg Arg Gln Lys
                165                 170                 175
Ile Arg Gln Ala Gln Ser Ala Asn Thr Thr Thr Ser Pro Met Val
                180                 185                 190
Thr Ile Thr His Lys Ser Asn Val Leu Ser Gln Ser Asp Gly Leu Phe
                195                 200                 205
Arg Glu Thr Cys Arg Lys Ala Leu Ala Asn Glu Lys Phe Ser Gly Val
                210                 215                 220
Asn Val Glu Glu Gln Ile Val Asp Ser Met Val Tyr Lys Leu Phe Arg
225                 230                 235                 240
Gln Pro Ser Tyr Tyr Asp Val Ile Val Ala Pro Asn Leu Tyr Gly Asp
                245                 250                 255
Ile Leu Ser Asp Gly Ala Ala Ala Leu Val Gly Ser Leu Gly Leu Val
                260                 265                 270
Pro Ser Ala Asn Val Gly Asp Gly Phe Ala Ile Gly Glu Pro Cys His
                275                 280                 285
Gly Ser Ala Pro Asp Ile Glu Gly Lys Gly Ile Ala Asn Pro Ile Ala
                290                 295                 300
Thr Ile Arg Ser Thr Ala Leu Met Leu Glu Phe Leu Gly Glu Gly Ala
305                 310                 315                 320
Ala Ala Ala Lys Ile Tyr Ala Ala Val Asp Ala Asn Leu Asp Glu Gly
                325                 330                 335
Lys Leu Leu Ser Pro Asp Leu Gly Gly Lys Ala Thr Thr Ala Glu Val
                340                 345                 350
Leu Glu Asp Val Leu Lys Lys Leu
                355                 360

<210> SEQ ID NO 132
<211> LENGTH: 344
<212> TYPE: PRT
<213> ORGANISM: Truepera radiovictrix

<400> SEQUENCE: 132

Met Thr Arg Arg Ala Tyr Thr Ile Thr Leu Ile Pro Gly Asp Gly Ile
1               5                   10                  15
Gly Gln Glu Val Val Pro Ala Ala Glu Arg Leu Leu Arg Glu Thr Gly
                20                  25                  30
Leu Pro Leu Glu Met His Tyr Ala Glu Ala Gly Trp Asp Thr Phe Gln
                35                  40                  45
Lys Val Gly Lys Ser Val Pro Asp Glu Thr Leu Glu Arg Val Lys Ala
                50                  55                  60
Ser Asp Ala Thr Leu Ala Gly Ala Phe Thr Ser Pro Ser Gly Ser Gln
65                  70                  75                  80
Lys Val Pro Gly Phe Gln Gly Ala Ile Arg Tyr Leu His Arg Thr Leu
                85                  90                  95
Asp Leu Phe Ala Asn Leu Arg Pro Thr Lys Ser Arg Pro Ile Pro Gly
                100                 105                 110
Ser Met Lys Asn Val Asp Met Leu Met Val His Glu Asn Thr Gln Gly
                115                 120                 125
Leu Tyr Val Glu Gln Glu Arg Arg Tyr Gly Asp Val Ala Ile Ala Asp
```

```
                130                 135                 140
Cys Val Ile Thr Lys Gly Ala Ser Glu Arg Ile Ala Lys Val Ala Leu
145                 150                 155                 160

Lys Glu Ala Gln Arg Arg Arg Lys Leu Ala Val Ile His Lys Ala
                165                 170                 175

Asn Val Leu Pro Leu Thr Thr Gly Leu Phe Leu Glu Thr Ala Leu Glu
                180                 185                 190

Ala Ala Lys Ala Phe Pro Glu Val Glu Thr Tyr Asp Ile Ile Val Asp
                195                 200                 205

Ala Ala Ala Met Lys Leu Val Arg Asp Pro Gln Ser Phe Asp Val Leu
210                 215                 220

Val Thr Thr Asn Leu Phe Gly Asp Ile Leu Ser Asp Leu Met Ala Gly
225                 230                 235                 240

Leu Val Gly Gly Leu Gly Leu Ala Pro Ser Ala Asn Ile Gly Glu Arg
                245                 250                 255

Thr Ala Ile Phe Glu Pro Val His Gly Ser Ala Pro Asp Ile Ala Gly
                260                 265                 270

Lys Gly Val Ala Asn Pro Ala Ala Thr Phe Leu Thr Ala Ala Met Met
                275                 280                 285

Leu Asp Tyr Leu Gly Glu Ala Ala Thr Ala Lys Arg Ile Asp Arg Ala
290                 295                 300

Val Asp Thr Val Leu Glu Gly Pro Arg Thr Ala Asp Leu Gly Gly
305                 310                 315                 320

Lys Ala Asp Thr Glu Glu Phe Thr Asp Ala Val Ile Glu Ala Phe Arg
                325                 330                 335

Ser Leu Ala Pro His Glu Ala Ala
            340

<210> SEQ ID NO 133
<211> LENGTH: 344
<212> TYPE: PRT
<213> ORGANISM: Truepera radiovictrix

<400> SEQUENCE: 133

Met Thr Arg Arg Ala Tyr Thr Ile Thr Leu Ile Pro Gly Asp Gly Ile
1               5                   10                  15

Gly Gln Glu Val Val Pro Ala Ala Glu Arg Leu Leu Arg Glu Thr Gly
                20                  25                  30

Leu Pro Leu Glu Met His Tyr Ala Glu Ala Gly Trp Asp Thr Phe Gln
            35                  40                  45

Lys Val Gly Lys Ser Val Pro Asp Glu Thr Leu Glu Arg Val Lys Ala
50                  55                  60

Ser Asp Ala Thr Leu Ala Gly Phe Thr Ser Pro Ser Gly Ser Gln
65                  70                  75                  80

Lys Val Pro Gly Phe Gln Gly Ala Ile Arg Tyr Leu His Arg Thr Leu
                85                  90                  95

Asp Leu Phe Ala Asn Leu Arg Pro Thr Lys Ser Arg Pro Ile Pro Gly
                100                 105                 110

Ser Met Lys Asn Val Asp Met Leu Met Val His Glu Asn Thr Gln Gly
            115                 120                 125

Leu Tyr Val Glu Gln Glu Arg Arg Tyr Gly Asp Val Ala Ile Ala Asp
            130                 135                 140

Cys Val Ile Thr Lys Gly Ala Ser Glu Arg Ile Ala Lys Val Ala Leu
145                 150                 155                 160

Lys Glu Ala Gln Arg Arg Arg Arg Lys Leu Ala Val Ile His Lys Ala
```

```
                165                 170                 175
Asn Val Leu Pro Leu Thr Thr Gly Leu Phe Leu Glu Thr Ala Leu Glu
            180                 185                 190

Ala Ala Lys Ala Phe Pro Glu Val Glu Thr Tyr Asp Ile Ile Val Asp
            195                 200                 205

Ala Ala Ala Met Lys Leu Val Arg Asp Pro Gln Ser Phe Asp Val Leu
            210                 215                 220

Val Thr Thr Asn Leu Phe Gly Asp Ile Leu Ser Asp Leu Met Ala Gly
225                 230                 235                 240

Leu Val Gly Gly Leu Gly Leu Ala Pro Ser Ala Asn Ile Gly Glu Arg
                245                 250                 255

Thr Ala Ile Phe Glu Pro Val His Gly Ser Ala Pro Asp Ile Ala Gly
            260                 265                 270

Lys Gly Val Ala Asn Pro Ala Ala Thr Phe Leu Thr Ala Ala Met Met
            275                 280                 285

Leu Asp Tyr Leu Gly Glu Ala Ala Thr Ala Lys Arg Ile Asp Arg Ala
            290                 295                 300

Val Asp Thr Val Leu Glu Glu Gly Pro Arg Thr Ala Asp Leu Gly Gly
305                 310                 315                 320

Lys Ala Asp Thr Glu Glu Phe Thr Asp Ala Val Ile Glu Ala Phe Arg
                325                 330                 335

Ser Leu Ala Pro His Glu Ala Ala
            340

<210> SEQ ID NO 134
<211> LENGTH: 359
<212> TYPE: PRT
<213> ORGANISM: Uncinocarpus reesii

<400> SEQUENCE: 134

Met Ala Ala Ser Arg Thr Leu Arg Ile Gly Leu Ile Pro Gly Asp Gly
1               5                   10                  15

Ile Gly Arg Glu Val Ile Pro Ala Gly Arg Arg Ile Leu Glu Ala Leu
                20                  25                  30

Pro Ala Ser Leu Gly Leu Lys Phe Ser Phe Val Asp Leu Glu Ala Gly
            35                  40                  45

Phe Asp Thr Phe Lys Gln Thr Lys Thr Ala Leu Pro Asp Lys Thr Val
        50                  55                  60

Glu Thr Leu Lys Lys Glu Cys Asp Gly Ala Leu Phe Gly Ala Val Ser
65                  70                  75                  80

Ser Pro Thr Thr Lys Val Ala Gly Tyr Ser Ser Pro Ile Val Ala Leu
                85                  90                  95

His Lys Arg Leu Asp Leu Tyr Ala Asn Val Arg Pro Val Lys Thr Thr
            100                 105                 110

Ala Gly Ala Lys Leu Ala Ala Pro Ile Asp Leu Val Ile Val His Glu
            115                 120                 125

Asn Thr Glu Asp Leu Tyr Val Lys Asp Glu Lys Thr Tyr Asp Thr Pro
        130                 135                 140

Glu Gly Lys Val Ala Glu Ala Ile Lys Arg Ile Ser Glu Arg Ala Ser
145                 150                 155                 160

Ser Arg Ile Ala Thr Ile Ala Gly Asp Ile Ala Leu Arg Arg Gln Lys
                165                 170                 175

Ile Arg Asp Ala Gly His Pro Ala Ala Arg Ser Ser Pro Met Val Thr
            180                 185                 190

Ile Thr His Lys Ser Asn Val Leu Ser Gln Thr Asp Gly Leu Phe Arg
```

-continued

```
            195                 200                 205
Glu Ala Ala Arg Lys Ala Leu Ser Gln Gln Lys Phe Ser Ala Val Glu
210                 215                 220

Val Glu Glu Gln Ile Val Asp Ser Met Val Tyr Lys Leu Phe Arg Gln
225                 230                 235                 240

Pro Ser Tyr Tyr Asp Val Ile Val Ala Pro Asn Leu Tyr Gly Asp Ile
                245                 250                 255

Leu Ser Asp Gly Ala Ala Ala Leu Val Gly Ser Leu Gly Leu Val Pro
            260                 265                 270

Ser Ala Asn Val Gly Asp Gly Phe Ala Ile Gly Glu Pro Cys His Gly
        275                 280                 285

Ser Ala Pro Asp Ile Glu Gly Lys Gly Ile Ala Asn Pro Ile Ala Thr
    290                 295                 300

Leu Arg Ser Ala Gly Leu Met Leu Glu Phe Leu Gly Glu Glu Lys Ala
305                 310                 315                 320

Ala Ala Lys Ile Tyr Ala Ala Val Asp Ala Asn Leu Asp Glu Gly Lys
                325                 330                 335

Tyr Leu Ser Pro Asp Leu Gly Gly Lys Ala Thr Thr Gln Glu Val Leu
            340                 345                 350

Asp Asp Val Leu Arg Arg Leu
            355
```

<210> SEQ ID NO 135
<211> LENGTH: 359
<212> TYPE: PRT
<213> ORGANISM: Uncinocarpus reesii

<400> SEQUENCE: 135

```
Met Ala Ala Ser Arg Thr Leu Arg Ile Gly Leu Ile Pro Gly Asp Gly
1               5                   10                  15

Ile Gly Arg Glu Val Ile Pro Ala Gly Arg Arg Ile Leu Glu Ala Leu
                20                  25                  30

Pro Ala Ser Leu Gly Leu Lys Phe Ser Phe Val Asp Leu Glu Ala Gly
            35                  40                  45

Phe Asp Thr Phe Lys Gln Thr Lys Thr Ala Leu Pro Asp Lys Thr Val
50                  55                  60

Glu Thr Leu Lys Lys Glu Cys Asp Gly Ala Leu Phe Gly Ala Val Ser
65                  70                  75                  80

Ser Pro Thr Thr Lys Val Ala Gly Tyr Ser Ser Pro Ile Val Ala Leu
                85                  90                  95

His Lys Arg Leu Asp Leu Tyr Ala Asn Val Arg Pro Val Lys Thr Thr
            100                 105                 110

Ala Gly Ala Lys Leu Ala Ala Pro Ile Asp Leu Val Ile Val His Glu
        115                 120                 125

Asn Thr Glu Asp Leu Tyr Val Lys Asp Glu Lys Thr Tyr Asp Thr Pro
    130                 135                 140

Glu Gly Lys Val Ala Glu Ala Ile Lys Arg Ile Ser Glu Arg Ala Ser
145                 150                 155                 160

Ser Arg Ile Ala Thr Ile Ala Gly Asp Ile Ala Leu Arg Arg Gln Lys
                165                 170                 175

Ile Arg Asp Ala Gly His Pro Ala Ala Arg Ser Ser Pro Met Val Thr
            180                 185                 190

Ile Thr His Lys Ser Asn Val Leu Ser Gln Thr Asp Gly Leu Phe Arg
        195                 200                 205

Glu Ala Ala Arg Lys Ala Leu Ser Gln Gln Lys Phe Ser Ala Val Glu
```

```
                210                 215                 220
Val Glu Glu Gln Ile Val Asp Ser Met Val Tyr Lys Leu Phe Arg Gln
225                 230                 235                 240

Pro Ser Tyr Tyr Asp Val Ile Val Ala Pro Asn Leu Tyr Gly Asp Ile
                245                 250                 255

Leu Ser Asp Gly Ala Ala Leu Val Gly Ser Leu Gly Leu Val Pro
                260                 265                 270

Ser Ala Asn Val Gly Asp Gly Phe Ala Ile Gly Glu Pro Cys His Gly
                275                 280                 285

Ser Ala Pro Asp Ile Glu Gly Lys Gly Ile Ala Asn Pro Ile Ala Thr
                290                 295                 300

Leu Arg Ser Ala Gly Leu Met Leu Glu Phe Leu Gly Glu Glu Lys Ala
305                 310                 315                 320

Ala Ala Lys Ile Tyr Ala Ala Val Asp Ala Asn Leu Asp Glu Gly Lys
                325                 330                 335

Tyr Leu Ser Pro Asp Leu Gly Gly Lys Ala Thr Thr Gln Glu Val Leu
                340                 345                 350

Asp Asp Val Leu Arg Arg Leu
                355

<210> SEQ ID NO 136
<211> LENGTH: 316
<212> TYPE: PRT
<213> ORGANISM: Verticillium albo-atrum

<400> SEQUENCE: 136

Met Ser Ile Arg Thr Leu Arg Ile Gly Leu Ile Pro Gly Asp Gly Ile
1               5                   10                  15

Gly Lys Glu Val Ile Pro Ala Gly Arg Arg Ile Leu Glu Ala Leu Pro
                20                  25                  30

Ser Tyr Leu Gly Leu Lys Phe Glu Phe Thr Asp Leu His Ala Gly Phe
            35                  40                  45

Glu Thr Phe Glu Arg Thr Gly Ala Ala Leu Pro Asp Lys Thr Val Glu
        50                  55                  60

Ile Leu Arg Asn Glu Cys Asp Gly Ala Leu Phe Gly Ala Val Ser Ser
65                  70                  75                  80

Pro Ser Ser Pro Val Lys Gly Tyr Ser Ser Pro Ile Val Ala Leu His
                85                  90                  95

Lys Lys Leu Asp Leu Tyr Ala Asn Val Arg Pro Val Lys Thr Val Leu
                100                 105                 110

Ser Ala Ala Lys Pro Ile Asp Met Val Ile Val His Glu Asn Thr Glu
            115                 120                 125

Asp Leu Tyr Val Lys Glu Thr Thr Arg Asp Thr Pro Asp Gly Lys
        130                 135                 140

Val Ala Glu Ala Ile Lys Arg Ile Ser Glu Arg Ala Ser His Arg Ile
145                 150                 155                 160

Ala Thr Met Ala Gly Asp Ile Ala Leu Arg Arg Gln Lys Ile Arg Ala
                165                 170                 175

Ala Gly Ala Pro Ser Ile His Gln Ser Pro Leu Val Thr Ile Thr His
            180                 185                 190

Lys Ser Asn Val Leu Leu Arg Leu Lys Asn Val Ile Asp Pro Asn
        195                 200                 205

Leu Tyr Gly Asp Ile Leu Ser Asp Asp Ala Ala Leu Val Gly Ser
    210                 215                 220

Leu Gly Leu Val Pro Ser Ala Asn Val Gly Glu Gly Phe Ala Ile Gly
```

-continued

```
                225                 230                 235                 240
Glu Pro Cys His Gly Ser Ala Pro Asp Ile Met Gly Gln Asn Ile Ala
            245                 250                 255

Asn Pro Ile Ala Thr Leu Arg Ser Ala Ala Leu Met Leu Glu Phe Leu
            260                 265                 270

Asp Glu Glu Ala Ala Ala Lys Ile Tyr Ala Ala Val Asp Ala Asn
        275                 280                 285

Leu Thr Glu Gly Lys Leu Leu Ser Pro Asp Leu Gly Gly Thr Ala Lys
        290                 295                 300

Thr Thr Glu Val Ile Glu Asp Ile Leu Arg Arg Leu
305                 310                 315

<210> SEQ ID NO 137
<211> LENGTH: 316
<212> TYPE: PRT
<213> ORGANISM: Verticillium albo-atrum

<400> SEQUENCE: 137

Met Ser Ile Arg Thr Leu Arg Ile Gly Leu Ile Pro Gly Asp Gly Ile
1               5                   10                  15

Gly Lys Glu Val Ile Pro Ala Gly Arg Arg Ile Leu Glu Ala Leu Pro
            20                  25                  30

Ser Tyr Leu Gly Leu Lys Phe Glu Phe Thr Asp Leu His Ala Gly Phe
        35                  40                  45

Glu Thr Phe Glu Arg Thr Gly Ala Ala Leu Pro Asp Lys Thr Val Glu
    50                  55                  60

Ile Leu Arg Asn Glu Cys Asp Gly Ala Leu Phe Gly Ala Val Ser Ser
65                  70                  75                  80

Pro Ser Ser Pro Val Lys Gly Tyr Ser Ser Pro Ile Val Ala Leu His
                85                  90                  95

Lys Lys Leu Asp Leu Tyr Ala Asn Val Arg Pro Val Lys Thr Val Leu
            100                 105                 110

Ser Ala Ala Lys Pro Ile Asp Met Val Ile Val His Glu Asn Thr Glu
        115                 120                 125

Asp Leu Tyr Val Lys Glu Glu Thr Thr Arg Asp Thr Pro Asp Gly Lys
    130                 135                 140

Val Ala Glu Ala Ile Lys Arg Ile Ser Glu Arg Ala Ser His Arg Ile
145                 150                 155                 160

Ala Thr Met Ala Gly Asp Ile Ala Leu Arg Arg Gln Lys Ile Arg Ala
                165                 170                 175

Ala Gly Ala Pro Ser Ile His Gln Ser Pro Leu Val Thr Ile Thr His
            180                 185                 190

Lys Ser Asn Val Leu Leu Arg Leu Lys Asn Val Ile Val Asp Pro Asn
        195                 200                 205

Leu Tyr Gly Asp Ile Leu Ser Asp Ala Ala Ala Leu Val Gly Ser
    210                 215                 220

Leu Gly Leu Val Pro Ser Ala Asn Val Gly Glu Gly Phe Ala Ile Gly
225                 230                 235                 240

Glu Pro Cys His Gly Ser Ala Pro Asp Ile Met Gly Gln Asn Ile Ala
                245                 250                 255

Asn Pro Ile Ala Thr Leu Arg Ser Ala Ala Leu Met Leu Glu Phe Leu
            260                 265                 270

Asp Glu Glu Ala Ala Ala Lys Ile Tyr Ala Ala Val Asp Ala Asn
        275                 280                 285

Leu Thr Glu Gly Lys Leu Leu Ser Pro Asp Leu Gly Gly Thr Ala Lys
```

```
                  290                 295                 300
Thr Thr Glu Val Ile Glu Asp Ile Leu Arg Arg Leu
305                 310                 315

<210> SEQ ID NO 138
<211> LENGTH: 357
<212> TYPE: PRT
<213> ORGANISM: Verticillium dahliae

<400> SEQUENCE: 138

Met Ser Ile

<210> SEQ ID NO 139
<211> LENGTH: 406
<212> TYPE: PRT
<213> ORGANISM: Sphingobium yanoikuyae

<400> SEQUENCE: 139

Met Ala Lys Ile Lys Val Lys Asn Pro Val Val Glu Ile Asp Gly Asp
1               5                   10                  15

Glu Met Thr Arg Ile Ile Trp Glu Trp Ile Arg Glu Arg Leu Ile Leu
            20                  25                  30

Pro Tyr Leu Asp Val Asp Leu Lys Tyr Tyr Asp Leu Ser Val Glu Lys
        35                  40                  45

Arg Asp Glu Thr Ser Asp Gln Ile Thr Ile Asp Ala Ala Asn Ala Ile
    50                  55                  60

Lys Glu Tyr Gly Val Gly Val Lys Cys Ala Thr Ile Thr Pro Asp Glu
65                  70                  75                  80

Ala Arg Val Glu Glu Phe Gly Leu Lys Lys Met Trp Lys Ser Pro Asn
                85                  90                  95

Gly Thr Ile Arg Asn Ile Leu Gly Gly Val Val Phe Arg Glu Pro Ile
            100                 105                 110

Val Ile Lys Asn Val Pro Arg Leu Val Pro Gly Trp Thr Asp Pro Ile
        115                 120                 125

Val Val Gly Arg His Ala Phe Gly Asp Gln Tyr Lys Ala Thr Asp Phe
    130                 135                 140

Lys Val Pro Gly Ala Gly Thr Leu Thr Met Lys Trp Val Gly Thr Asn
145                 150                 155                 160

Gly Glu Glu Leu Glu Tyr Glu Val Phe Glu Phe Pro Ser Ala Gly Val
                165                 170                 175

Ala Met Gly Met Tyr Asn Leu Asp Glu Ser Ile Arg Asp Phe Ala Lys
            180                 185                 190

Ala Ser Phe Asn Tyr Gly Leu Asn Arg Gly Trp Pro Val Tyr Leu Ser
        195                 200                 205

Thr Lys Asn Thr Ile Leu Lys Ala Tyr Asp Gly Arg Phe Lys Asp Leu
    210                 215                 220

Phe Gln Glu Val Phe Asp Ala Glu Phe Asp Lys Phe Lys Ala Ala
225                 230                 235                 240

Gly Ile Val Tyr Glu His Arg Leu Ile Asp Asp Met Val Ala Ser Ala
                245                 250                 255

Leu Lys Trp Ser Gly Lys Phe Val Trp Ala Cys Lys Asn Tyr Asp Gly
            260                 265                 270

Asp Val Gln Ser Asp Thr Val Ala Gln Gly Phe Gly Ser Leu Gly Leu
        275                 280                 285

Met Thr Ser Val Leu Leu Ser Pro Asp Gly Lys Thr Val Glu Ala Glu
    290                 295                 300

Ala Ala His Gly Thr Val Thr Arg His Tyr Arg Gln His Gln Gln Gly
305                 310                 315                 320

Lys Ala Thr Ser Thr Asn Pro Ile Ala Ser Ile Phe Ala Trp Thr Gln
                325                 330                 335

Gly Leu Ser Phe Arg Gly Lys Phe Asp Asp Thr Pro Val Val Lys
            340                 345                 350

Phe Ala Glu Thr Leu Glu Gln Val Cys Ile Lys Thr Val Glu Gly Gly
        355                 360                 365

Ala Met Thr Lys Asp Leu Ala Leu Leu Ile Gly Pro Asp Gln Ala Trp

-continued

```
                  370                 375                 380
Met Thr Thr Glu Gln Phe Phe Glu Ala Ile Arg Val Asn Leu Glu Ala
385                 390                 395                 400

Glu Met Ala Lys Trp Ala
                405

<210> SEQ ID NO 140
<211> LENGTH: 414
<212> TYPE: PRT
<213> ORGANISM: Homo sapiens

<400> SEQUENCE: 140

Met Ser Lys Lys Ile Ser Gly Gly Ser Val Glu Met Gln Gly Asp
1               5                   10                  15

Glu Met Thr Arg Ile Ile Trp Glu Leu Ile Lys Glu Lys Leu Ile Phe
                20                  25                  30

Pro Tyr Val Glu Leu Asp Leu His Ser Tyr Asp Leu Gly Ile Glu Asn
                35                  40                  45

Arg Asp Ala Thr Asn Asp Gln Val Thr Lys Asp Ala Ala Glu Ala Ile
50                  55                  60

Lys Lys His Asn Val Gly Val Lys Cys Ala Thr Ile Thr Pro Asp Glu
65                  70                  75                  80

Lys Arg Val Glu Glu Phe Lys Leu Lys Gln Met Trp Lys Ser Pro Asn
                85                  90                  95

Gly Thr Ile Arg Asn Ile Leu Gly Gly Thr Val Phe Arg Glu Ala Ile
                100                 105                 110

Ile Cys Lys Asn Ile Pro Arg Leu Val Ser Gly Trp Val Lys Pro Ile
                115                 120                 125

Ile Ile Gly Arg His Ala Tyr Gly Asp Gln Tyr Arg Ala Thr Asp Phe
                130                 135                 140

Val Val Pro Gly Pro Gly Lys Val Glu Met Thr Tyr Thr Pro Ser Asp
145                 150                 155                 160

Gly Thr Gln Lys Val Thr Tyr Leu Val His Asn Phe Glu Glu Gly Gly
                165                 170                 175

Gly Val Ala Met Gly Met Tyr Asn Gln Asp Lys Ser Ile Glu Asp Phe
                180                 185                 190

Ala His Ser Ser Phe Gln Met Ala Leu Ser Lys Gly Trp Pro Leu Tyr
                195                 200                 205

Leu Ser Thr Lys Asn Thr Ile Leu Lys Lys Tyr Asp Gly Arg Phe Lys
                210                 215                 220

Asp Ile Phe Gln Glu Ile Tyr Asp Lys Gln Tyr Lys Ser Gln Phe Glu
225                 230                 235                 240

Ala Gln Lys Ile Trp Tyr Glu His Arg Leu Ile Asp Asp Met Val Ala
                245                 250                 255

Gln Ala Met Lys Ser Glu Gly Gly Phe Ile Trp Ala Cys Lys Asn Tyr
                260                 265                 270

Asp Gly Asp Val Gln Ser Asp Ser Val Ala Gln Gly Tyr Gly Ser Leu
                275                 280                 285

Gly Met Met Thr Ser Val Leu Val Cys Pro Asp Gly Lys Thr Val Glu
                290                 295                 300

Ala Glu Ala Ala His Gly Thr Val Thr Arg His Tyr Arg Met Tyr Gln
305                 310                 315                 320

Lys Gly Gln Glu Thr Ser Thr Asn Pro Ile Ala Ser Ile Phe Ala Trp
                325                 330                 335

Thr Arg Gly Leu Ala His Arg Ala Lys Leu Asp Asn Asn Lys Glu Leu
```

-continued

```
                340                 345                 350
Ala Phe Phe Ala Asn Ala Leu Glu Glu Val Ser Ile Glu Thr Ile Glu
            355                 360                 365

Ala Gly Phe Met Thr Lys Asp Leu Ala Ala Cys Ile Lys Gly Leu Pro
        370                 375                 380

Asn Val Gln Arg Ser Asp Tyr Leu Asn Thr Phe Glu Phe Met Asp Lys
385                 390                 395                 400

Leu Gly Glu Asn Leu Lys Ile Lys Leu Ala Gln Ala Lys Leu
                405                 410

<210> SEQ ID NO 141
<211> LENGTH: 452
<212> TYPE: PRT
<213> ORGANISM: Homo sapiens

<400> SEQUENCE: 141

Met Ala Gly Tyr Leu Arg Val Val Arg Ser Leu Cys Arg Ala Ser Gly
1               5                   10                  15

Ser Arg Pro Ala Trp Ala Pro Ala Ala Leu Thr Ala Pro Thr Ser Gln
                20                  25                  30

Glu Gln Pro Arg Arg His Tyr Ala Asp Lys Arg Ile Lys Val Ala Lys
            35                  40                  45

Pro Val Val Glu Met Asp Gly Asp Glu Met Thr Arg Ile Ile Trp Gln
        50                  55                  60

Phe Ile Lys Glu Lys Leu Ile Leu Pro His Val Asp Ile Gln Leu Lys
65                  70                  75                  80

Tyr Phe Asp Leu Gly Leu Pro Asn Arg Asp Gln Thr Asp Asp Gln Val
                85                  90                  95

Thr Ile Asp Ser Ala Leu Ala Thr Gln Lys Tyr Ser Val Ala Val Lys
            100                 105                 110

Cys Ala Thr Ile Thr Pro Asp Glu Ala Arg Val Glu Glu Phe Lys Leu
        115                 120                 125

Lys Lys Met Trp Lys Ser Pro Asn Gly Thr Ile Arg Asn Ile Leu Gly
    130                 135                 140

Gly Thr Val Phe Arg Glu Pro Ile Ile Cys Lys Asn Ile Pro Arg Leu
145                 150                 155                 160

Val Pro Gly Trp Thr Lys Pro Ile Thr Ile Gly Arg His Ala His Gly
                165                 170                 175

Asp Gln Tyr Lys Ala Thr Asp Phe Val Ala Asp Arg Ala Gly Thr Phe
            180                 185                 190

Lys Met Val Phe Thr Pro Lys Asp Gly Ser Gly Val Lys Glu Trp Glu
        195                 200                 205

Val Tyr Asn Phe Pro Ala Gly Gly Val Gly Met Gly Met Tyr Asn Thr
    210                 215                 220

Asp Glu Ser Ile Ser Gly Phe Ala His Ser Cys Phe Gln Tyr Ala Ile
225                 230                 235                 240

Gln Lys Lys Trp Pro Leu Tyr Met Ser Thr Lys Asn Thr Ile Leu Lys
                245                 250                 255

Ala Tyr Asp Gly Arg Phe Lys Asp Ile Phe Gln Glu Ile Phe Asp Lys
            260                 265                 270

His Tyr Lys Thr Asp Phe Asp Lys Asn Lys Ile Trp Tyr Glu His Arg
        275                 280                 285

Leu Ile Asp Asp Met Val Ala Gln Val Leu Lys Ser Ser Gly Gly Phe
    290                 295                 300

Val Trp Ala Cys Lys Asn Tyr Asp Gly Asp Val Gln Ser Asp Ile Leu
```

```
                305                 310                 315                 320
Ala Gln Gly Phe Gly Ser Leu Gly Leu Met Thr Ser Val Leu Val Cys
                    325                 330                 335

Pro Asp Gly Lys Thr Ile Glu Ala Glu Ala His Gly Thr Val Thr
                340                 345                 350

Arg His Tyr Arg Glu His Gln Lys Gly Arg Pro Thr Ser Thr Asn Pro
                    355                 360                 365

Ile Ala Ser Ile Phe Ala Trp Thr Arg Gly Leu Glu His Arg Gly Lys
                370                 375                 380

Leu Asp Gly Asn Gln Asp Leu Ile Arg Phe Ala Gln Met Leu Glu Lys
385                 390                 395                 400

Val Cys Val Glu Thr Val Glu Ser Gly Ala Met Thr Lys Asp Leu Ala
                    405                 410                 415

Gly Cys Ile His Gly Leu Ser Asn Val Lys Leu Asn Glu His Phe Leu
                420                 425                 430

Asn Thr Thr Asp Phe Leu Asp Thr Ile Lys Ser Asn Leu Asp Arg Ala
                    435                 440                 445

Leu Gly Arg Gln
    450

<210> SEQ ID NO 142
<211> LENGTH: 416
<212> TYPE: PRT
<213> ORGANISM: Escherichia coli

<400> SEQUENCE: 142

Met Glu Ser Lys Val Val Pro Ala Gln Gly Lys Lys Ile Thr Leu
1               5                   10                  15

Gln Asn Gly Lys Leu Asn Val Pro Glu Asn Pro Ile Ile Pro Tyr Ile
                20                  25                  30

Glu Gly Asp Gly Ile Gly Val Asp Val Thr Pro Ala Met Leu Lys Val
                35                  40                  45

Val Asp Ala Ala Val Glu Lys Ala Tyr Lys Gly Glu Arg Lys Ile Ser
        50                  55                  60

Trp Met Glu Ile Tyr Thr Gly Glu Lys Ser Thr Gln Val Tyr Gly Gln
65                  70                  75                  80

Asp Val Trp Leu Pro Ala Glu Thr Leu Asp Leu Ile Arg Glu Tyr Arg
                85                  90                  95

Val Ala Ile Lys Gly Pro Leu Thr Thr Pro Val Gly Gly Gly Ile Arg
                100                 105                 110

Ser Leu Asn Val Ala Leu Arg Gln Glu Leu Asp Leu Tyr Ile Cys Leu
            115                 120                 125

Arg Pro Val Arg Tyr Tyr Gln Gly Thr Pro Ser Pro Val Lys His Pro
        130                 135                 140

Glu Leu Thr Asp Met Val Ile Phe Arg Glu Asn Ser Glu Asp Ile Tyr
145                 150                 155                 160

Ala Gly Ile Glu Trp Lys Ala Asp Ser Ala Asp Ala Glu Lys Val Ile
                165                 170                 175

Lys Phe Leu Arg Glu Glu Met Gly Val Lys Lys Ile Arg Phe Pro Glu
                180                 185                 190

His Cys Gly Ile Gly Ile Lys Pro Cys Ser Glu Glu Gly Thr Lys Arg
            195                 200                 205

Leu Val Arg Ala Ala Ile Glu Tyr Ala Ile Ala Asn Asp Arg Asp Ser
        210                 215                 220

Val Thr Leu Val His Lys Gly Asn Ile Met Lys Phe Thr Glu Gly Ala
```

```
                    225                 230                 235                 240

Phe Lys Asp Trp Gly Tyr Glu Leu Ala Arg Glu Glu Phe Gly Gly Glu
                245                 250                 255

Leu Ile Asp Gly Gly Pro Trp Leu Lys Val Lys Asn Pro Asn Thr Gly
                260                 265                 270

Lys Glu Ile Val Ile Lys Asp Val Ala Asp Ala Phe Leu Gln Gln
            275                 280                 285

Ile Leu Leu Arg Pro Ala Glu Tyr Asp Val Ile Ala Cys Met Asn Leu
        290                 295                 300

Asn Gly Asp Tyr Ile Ser Asp Ala Leu Ala Ala Gln Val Gly Ile
305                 310                 315                 320

Gly Ile Ala Pro Gly Ala Asn Ile Gly Asp Glu Cys Ala Leu Phe Glu
                325                 330                 335

Ala Thr His Gly Thr Ala Pro Lys Tyr Ala Gly Gln Asp Lys Val Asn
            340                 345                 350

Pro Gly Ser Ile Ile Leu Ser Ala Glu Met Met Leu Arg His Met Gly
        355                 360                 365

Trp Thr Glu Ala Ala Asp Leu Ile Val Lys Gly Met Glu Gly Ala Ile
370                 375                 380

Asn Ala Lys Thr Val Thr Tyr Asp Phe Glu Arg Leu Met Glu Gly Ala
385                 390                 395                 400

Lys Leu Leu Lys Cys Ser Glu Phe Gly Asp Ala Ile Ile Lys Asn Met
                405                 410                 415

<210> SEQ ID NO 143
<211> LENGTH: 423
<212> TYPE: PRT
<213> ORGANISM: Bacillus subtilis

<400> SEQUENCE: 143

Met Ala Gln Gly Glu Lys Ile Thr Val Ser Asn Gly Val Leu Asn Val
1               5                   10                  15

Pro Asn Asn Pro Ile Ile Pro Phe Ile Glu Gly Asp Gly Thr Gly Pro
                20                  25                  30

Asp Ile Trp Asn Ala Ala Ser Lys Val Leu Glu Ala Ala Val Glu Lys
            35                  40                  45

Ala Tyr Lys Gly Glu Lys Lys Ile Thr Trp Lys Glu Val Tyr Ala Gly
        50                  55                  60

Glu Lys Ala Tyr Asn Lys Thr Gly Glu Trp Leu Pro Ala Glu Thr Leu
65                  70                  75                  80

Asp Val Ile Arg Glu Tyr Phe Ile Ala Ile Lys Gly Pro Leu Thr Thr
                85                  90                  95

Pro Val Gly Gly Gly Ile Arg Ser Leu Asn Val Ala Leu Arg Gln Glu
                100                 105                 110

Leu Asp Leu Phe Val Cys Leu Arg Pro Val Arg Tyr Phe Thr Gly Val
            115                 120                 125

Pro Ser Pro Val Lys Arg Pro Glu Asp Thr Asp Met Val Ile Phe Arg
        130                 135                 140

Glu Asn Thr Glu Asp Ile Tyr Ala Gly Ile Glu Tyr Ala Lys Gly Ser
145                 150                 155                 160

Glu Glu Val Gln Lys Leu Ile Ser Phe Leu Gln Asn Glu Leu Asn Val
                165                 170                 175

Asn Lys Ile Arg Phe Pro Glu Thr Ser Gly Ile Gly Ile Lys Pro Val
            180                 185                 190

Ser Glu Glu Gly Thr Ser Arg Leu Val Arg Ala Ala Ile Asp Tyr Ala
```

```
               195                 200                 205
Ile Glu His Gly Arg Lys Ser Val Thr Leu Val His Lys Gly Asn Ile
            210                 215                 220

Met Lys Phe Thr Glu Gly Ala Phe Lys Asn Trp Gly Tyr Glu Leu Ala
225                 230                 235                 240

Glu Lys Glu Tyr Gly Asp Lys Val Phe Thr Trp Ala Gln Tyr Asp Arg
                245                 250                 255

Ile Ala Glu Glu Gln Gly Lys Asp Ala Ala Asn Lys Ala Gln Ser Glu
            260                 265                 270

Ala Glu Ala Ala Gly Lys Ile Ile Lys Asp Ser Ile Ala Asp Ile
            275                 280                 285

Phe Leu Gln Gln Ile Leu Thr Arg Pro Asn Glu Phe Asp Val Val Ala
290                 295                 300

Thr Met Asn Leu Asn Gly Asp Tyr Ile Ser Asp Ala Leu Ala Ala Gln
305                 310                 315                 320

Val Gly Gly Ile Gly Ile Ala Pro Gly Ala Asn Ile Asn Tyr Glu Thr
                325                 330                 335

Gly His Ala Ile Phe Glu Ala Thr His Gly Thr Ala Pro Lys Tyr Ala
                340                 345                 350

Gly Leu Asp Lys Val Asn Pro Ser Ser Val Ile Leu Ser Gly Val Leu
            355                 360                 365

Leu Leu Glu His Leu Gly Trp Asn Glu Ala Ala Asp Leu Val Ile Lys
370                 375                 380

Ser Met Glu Lys Thr Ile Ala Ser Lys Val Val Thr Tyr Asp Phe Ala
385                 390                 395                 400

Arg Leu Met Asp Gly Ala Thr Glu Val Lys Cys Ser Glu Phe Gly Glu
                405                 410                 415

Glu Leu Ile Lys Asn Met Asp
            420

<210> SEQ ID NO 144
<211> LENGTH: 366
<212> TYPE: PRT
<213> ORGANISM: Homo sapiens

<400> SEQUENCE: 144

Met Ala Gly Pro Ala Trp Ile Ser Lys Val Ser Arg Leu Leu Gly Ala
1               5                   10                  15

Phe His Asn Pro Lys Gln Val Thr Arg Gly Phe Thr Gly Gly Val Gln
                20                  25                  30

Thr Val Thr Leu Ile Pro Gly Asp Gly Ile Gly Pro Glu Ile Ser Ala
            35                  40                  45

Ala Val Met Lys Ile Phe Asp Ala Ala Lys Ala Pro Ile Gln Trp Glu
        50                  55                  60

Glu Arg Asn Val Thr Ala Ile Gln Gly Pro Gly Gly Lys Trp Met Ile
65                  70                  75                  80

Pro Ser Glu Ala Lys Glu Ser Met Asp Lys Asn Lys Met Gly Leu Lys
                85                  90                  95

Gly Pro Leu Lys Thr Pro Ile Ala Ala Gly His Pro Ser Met Asn Leu
            100                 105                 110

Leu Leu Arg Lys Thr Phe Asp Leu Tyr Ala Asn Val Arg Pro Cys Val
        115                 120                 125

Ser Ile Glu Gly Tyr Lys Thr Pro Tyr Asp Val Asn Ile Val Thr
    130                 135                 140

Ile Arg Glu Asn Thr Glu Gly Glu Tyr Ser Gly Ile Glu His Val Ile
```

```
                145                 150                 155                 160
Val Asp Gly Val Val Gln Ser Ile Lys Leu Ile Thr Glu Gly Val Ser
                    165                 170                 175

Lys Arg Ile Ala Glu Phe Ala Phe Glu Tyr Ala Arg Asn Asn His Arg
                180                 185                 190

Ser Asn Val Thr Ala Val His Lys Ala Asn Ile Met Arg Met Ser Asp
            195                 200                 205

Gly Leu Phe Leu Gln Lys Cys Arg Glu Val Ala Glu Ser Cys Lys Asp
        210                 215                 220

Ile Lys Phe Asn Glu Met Tyr Leu Asp Thr Val Cys Leu Asn Met Val
225                 230                 235                 240

Gln Asp Pro Ser Gln Phe Asp Val Leu Val Met Pro Asn Leu Tyr Gly
                245                 250                 255

Asp Ile Leu Ser Asp Leu Cys Ala Gly Leu Ile Gly Gly Leu Gly Val
                260                 265                 270

Thr Pro Ser Gly Asn Ile Gly Ala Asn Gly Val Ala Ile Phe Glu Ser
            275                 280                 285

Val His Gly Thr Ala Pro Asp Ile Ala Gly Lys Asp Met Ala Asn Pro
        290                 295                 300

Thr Ala Leu Leu Leu Ser Ala Val Met Met Leu Arg His Met Gly Leu
305                 310                 315                 320

Phe Asp His Ala Ala Arg Ile Glu Ala Ala Cys Phe Ala Thr Ile Lys
                325                 330                 335

Asp Gly Lys Ser Leu Thr Lys Asp Leu Gly Gly Asn Ala Lys Cys Ser
            340                 345                 350

Asp Phe Thr Glu Glu Ile Cys Arg Arg Val Lys Asp Leu Asp
        355                 360                 365

<210> SEQ ID NO 145
<211> LENGTH: 362
<212> TYPE: PRT
<213> ORGANISM: Schizosaccharomyces pombe

<400> SEQUENCE: 145

Met Ser Ala Thr Arg Arg Ile Val Leu Gly Leu Ile Pro Ala Asp Gly
1               5                   10                  15

Ile Gly Lys Glu Val Val Pro Ala Ala Arg Arg Leu Met Glu Asn Leu
                20                  25                  30

Pro Ala Lys His Lys Leu Lys Phe Asp Phe Ile Asp Leu Asp Ala Gly
            35                  40                  45

Trp Gly Thr Phe Glu Arg Thr Gly Lys Ala Leu Pro Glu Arg Thr Val
        50                  55                  60

Glu Arg Leu Lys Thr Glu Cys Asn Ala Ala Leu Phe Gly Ala Val Gln
65                  70                  75                  80

Ser Pro Thr His Lys Val Ala Gly Tyr Ser Ser Pro Ile Val Ala Leu
                85                  90                  95

Arg Lys Lys Met Gly Leu Tyr Ala Asn Val Arg Pro Val Lys Ser Leu
                100                 105                 110

Asp Gly Ala Lys Gly Lys Pro Val Asp Leu Val Ile Val Arg Glu Asn
            115                 120                 125

Thr Glu Cys Leu Tyr Val Lys Glu Glu Arg Met Val Gln Asn Thr Pro
        130                 135                 140

Gly Lys Arg Val Ala Glu Ala Ile Arg Arg Ile Ser Glu Glu Ala Ser
145                 150                 155                 160

Thr Lys Ile Gly Lys Met Ala Phe Glu Ile Ala Lys Ser Arg Gln Lys
```

```
                    165                 170                 175
Ile Arg Glu Ser Gly Thr Tyr Ser Ile His Lys Lys Pro Leu Val Thr
            180                 185                 190

Ile Ile His Lys Ser Asn Val Met Ser Val Thr Asp Gly Leu Phe Arg
            195                 200                 205

Glu Ser Cys Arg His Ala Gln Ser Leu Asp Pro Ser Tyr Ala Ser Ile
            210                 215                 220

Asn Val Asp Glu Gln Ile Val Asp Ser Met Val Tyr Arg Leu Phe Arg
225                 230                 235                 240

Glu Pro Glu Cys Phe Asp Val Val Ala Pro Asn Leu Tyr Gly Asp
                245                 250                 255

Ile Leu Ser Asp Gly Ala Ala Ser Leu Ile Gly Ser Leu Gly Leu Val
            260                 265                 270

Pro Ser Ala Asn Val Gly Asp Asn Phe Val Met Ser Glu Pro Val His
            275                 280                 285

Gly Ser Ala Pro Asp Ile Ala Gly Arg Gly Ile Ala Asn Pro Val Ala
            290                 295                 300

Thr Phe Arg Ser Val Ala Leu Met Leu Glu Phe Met Gly His Gln Asp
305                 310                 315                 320

Ala Ala Ala Asp Ile Tyr Thr Ala Val Asp Lys Val Leu Thr Glu Gly
                325                 330                 335

Lys Val Leu Thr Pro Asp Leu Gly Gly Lys Ser Gly Thr Asn Glu Ile
                340                 345                 350

Thr Asp Ala Val Leu Ala Asn Ile His Asn
            355                 360

<210> SEQ ID NO 146
<211> LENGTH: 371
<212> TYPE: PRT
<213> ORGANISM: Saccharomyces cerevisiae

<400> SEQUENCE: 146

Met Phe Arg Ser Val Ala Thr Arg Leu Ser Ala Cys Arg Gly Leu Ala
1               5                   10                  15

Ser Asn Ala Ala Arg Lys Ser Leu Thr Ile Gly Leu Ile Pro Gly Asp
            20                  25                  30

Gly Ile Gly Lys Glu Val Ile Pro Ala Gly Lys Gln Val Leu Glu Asn
        35                  40                  45

Leu Asn Ser Lys His Gly Leu Ser Phe Asn Phe Ile Asp Leu Tyr Ala
    50                  55                  60

Gly Phe Gln Thr Phe Gln Glu Thr Gly Lys Ala Leu Pro Asp Glu Thr
65                  70                  75                  80

Val Lys Val Leu Lys Glu Gln Cys Gln Gly Ala Leu Phe Gly Ala Val
                85                  90                  95

Gln Ser Pro Thr Thr Lys Val Glu Gly Tyr Ser Ser Pro Ile Val Ala
            100                 105                 110

Leu Arg Arg Glu Met Gly Leu Phe Ala Asn Val Arg Pro Val Lys Ser
        115                 120                 125

Val Glu Gly Glu Lys Gly Lys Pro Ile Asp Met Val Ile Val Arg Glu
    130                 135                 140

Asn Thr Glu Asp Leu Tyr Ile Lys Ile Glu Lys Thr Tyr Ile Asp Lys
145                 150                 155                 160

Ala Thr Gly Thr Arg Val Ala Asp Ala Thr Lys Arg Ile Ser Glu Ile
                165                 170                 175

Ala Thr Arg Arg Ile Ala Thr Ile Ala Leu Asp Ile Ala Leu Lys Arg
```

```
                    180                 185                 190
Leu Gln Thr Arg Gly Gln Ala Thr Leu Thr Val Thr His Lys Ser Asn
                195                 200                 205

Val Leu Ser Gln Ser Asp Gly Leu Phe Arg Glu Ile Cys Lys Glu Val
            210                 215                 220

Tyr Glu Ser Asn Lys Asp Lys Tyr Gly Gln Ile Lys Tyr Asn Glu Gln
225                 230                 235                 240

Ile Val Asp Ser Met Val Tyr Arg Leu Phe Arg Glu Pro Gln Cys Phe
                245                 250                 255

Asp Val Ile Val Ala Pro Asn Leu Tyr Gly Asp Ile Leu Ser Asp Gly
            260                 265                 270

Ala Ala Ala Leu Val Gly Ser Leu Gly Val Val Pro Ser Ala Asn Val
                275                 280                 285

Gly Pro Glu Ile Val Ile Gly Glu Pro Cys His Gly Ser Ala Pro Asp
            290                 295                 300

Ile Ala Gly Lys Gly Ile Ala Asn Pro Ile Ala Thr Ile Arg Ser Thr
305                 310                 315                 320

Ala Leu Met Leu Glu Phe Leu Gly His Asn Glu Ala Ala Gln Asp Ile
                325                 330                 335

Tyr Lys Ala Val Asp Ala Asn Leu Arg Glu Gly Ser Ile Lys Thr Pro
            340                 345                 350

Asp Leu Gly Gly Lys Ala Ser Thr Gln Gln Val Val Asp Asp Val Leu
                355                 360                 365

Ser Arg Leu
        370

<210> SEQ ID NO 147
<211> LENGTH: 376
<212> TYPE: PRT
<213> ORGANISM: Candida albicans

<400> SEQUENCE: 147

Met Leu Ala Ala Arg Ser Ser Ile Arg Arg Cys Phe Ser Thr Ser Ser
1               5                   10                  15

Thr Thr Leu Lys Ser Leu Lys Ile Gly Leu Ile Ser Gly Asp Gly Ile
                20                  25                  30

Gly Arg Glu Val Ile Pro Ala Gly Lys Ala Val Leu Glu Asn Leu Pro
            35                  40                  45

Ser Lys His Asp Leu Gln Phe Glu Phe Val Asn Leu Asp Ala Gly Phe
    50                  55                  60

Glu Leu Phe Lys Lys Thr Gly Thr Ala Leu Pro Asp Glu Thr Val Asp
65                  70                  75                  80

Val Leu Lys Lys Glu Cys Asp Gly Ala Leu Phe Gly Ala Val Ser Ser
                85                  90                  95

Pro Thr Thr Lys Val Ala Gly Tyr Ser Ser Pro Ile Val Ala Leu Arg
            100                 105                 110

Lys Lys Leu Gly Leu Tyr Ala Asn Val Arg Pro Val Lys Ser Val Glu
        115                 120                 125

Gly Ile Gly Arg Pro Val Asp Met Val Ile Val Arg Glu Asn Thr Glu
    130                 135                 140

Asp Leu Tyr Ile Lys Glu Glu Arg Val Tyr Lys Lys Glu Asp Gly Thr
145                 150                 155                 160

Lys Val Ala Glu Ala Ile Lys Arg Ile Thr Glu Thr Ala Ser Thr Arg
                165                 170                 175

Ile Ala Lys Met Ala Tyr Glu Ile Ala Leu Gln Arg Glu Ala Val Arg
```

-continued

```
            180                 185                 190
Lys Gly Thr Ser Gly Lys Gln Leu His Glu Lys Pro Ser Val Thr Val
            195                 200                 205
Thr His Lys Ser Asn Val Leu Ser Gln Ser Asp Gly Leu Phe Arg Glu
            210                 215                 220
Thr Cys Arg Ala Val Tyr Asp Ala Asn Ala Asn Glu Tyr Gly Gly Ile
225                 230                 235                 240
Glu Tyr Lys Glu Gln Ile Val Asp Ser Met Val Tyr Arg Met Phe Arg
            245                 250                 255
Glu Pro Glu Ile Phe Asp Val Val Ala Pro Asn Leu Tyr Gly Asp
            260                 265                 270
Ile Leu Ser Asp Gly Ala Ala Ala Leu Val Gly Ser Leu Gly Val Val
            275                 280                 285
Pro Ser Ala Asn Val Gly Asp Asn Phe Ala Ile Gly Glu Pro Cys His
            290                 295                 300
Gly Ser Ala Pro Asp Ile Glu Gly Lys Gly Ile Ser Asn Pro Val Ala
305                 310                 315                 320
Thr Ile Arg Ser Thr Ala Leu Met Leu Glu Phe Met Gly Tyr Pro Glu
            325                 330                 335
Ala Ala Ala Thr Ile Tyr Gln Ala Val Asp Ala Asn Leu Ala Glu Asp
            340                 345                 350
Lys Ile Lys Thr Pro Asp Leu Gly Gly Asn Ser Thr Thr Gln Glu Val
            355                 360                 365
Ile Asp Asp Ile Ile Arg Arg Phe
            370                 375

<210> SEQ ID NO 148
<211> LENGTH: 334
<212> TYPE: PRT
<213> ORGANISM: Thermus thermophilus

<400> SEQUENCE: 148

Met Ala Tyr Arg Ile Cys Leu Ile Glu Gly Asp Gly Ile Gly His Glu
1               5                   10                  15
Val Ile Pro Ala Ala Arg Arg Val Leu Glu Ala Thr Gly Leu Pro Leu
            20                  25                  30
Glu Phe Val Glu Ala Glu Ala Gly Trp Glu Thr Phe Glu Arg Arg Gly
            35                  40                  45
Thr Ser Val Pro Glu Glu Thr Val Glu Lys Ile Leu Ser Cys His Ala
            50                  55                  60
Thr Leu Phe Gly Ala Ala Thr Ser Pro Thr Arg Lys Val Pro Gly Phe
65              70                  75                  80
Phe Gly Ala Ile Arg Tyr Leu Arg Arg Arg Leu Asp Leu Tyr Ala Asn
            85                  90                  95
Val Arg Pro Ala Lys Ser Arg Pro Val Pro Gly Ser Arg Pro Gly Val
            100                 105                 110
Asp Leu Val Ile Val Arg Glu Asn Thr Glu Gly Leu Tyr Val Glu Gln
            115                 120                 125
Glu Arg Arg Tyr Leu Asp Val Ala Ile Ala Asp Ala Val Ile Ser Lys
            130                 135                 140
Lys Ala Ser Glu Arg Ile Gly Arg Ala Ala Leu Arg Ile Ala Glu Gly
145                 150                 155                 160
Arg Pro Arg Lys Thr Leu His Ile Ala His Lys Ala Asn Val Leu Pro
            165                 170                 175
Leu Thr Gln Gly Leu Phe Leu Asp Thr Val Lys Glu Val Ala Lys Asp
```

```
                        180                 185                 190
Phe Pro Leu Val Asn Val Gln Asp Ile Ile Val Asp Asn Cys Ala Met
                195                 200                 205

Gln Leu Val Met Arg Pro Glu Arg Phe Asp Val Ile Val Thr Thr Asn
            210                 215                 220

Leu Leu Gly Asp Ile Leu Ser Asp Leu Ala Ala Gly Leu Val Gly Gly
225                 230                 235                 240

Leu Gly Leu Ala Pro Ser Gly Asn Ile Gly Asp Thr Thr Ala Val Phe
                245                 250                 255

Glu Pro Val His Gly Ser Ala Pro Asp Ile Ala Gly Lys Gly Ile Ala
            260                 265                 270

Asn Pro Thr Ala Ala Ile Leu Ser Ala Ala Met Met Leu Asp Tyr Leu
        275                 280                 285

Gly Glu Lys Glu Ala Ala Lys Arg Val Glu Lys Ala Val Asp Leu Val
    290                 295                 300

Leu Glu Arg Gly Pro Arg Thr Pro Asp Leu Gly Gly Asp Ala Thr Thr
305                 310                 315                 320

Glu Ala Phe Thr Glu Ala Val Val Glu Ala Leu Lys Ser Leu
                325                 330

<210> SEQ ID NO 149
<211> LENGTH: 361
<212> TYPE: PRT
<213> ORGANISM: Escherichia coli

<400> SEQUENCE: 149

Met Met Lys Thr Met Arg Ile Ala Ala Ile Pro Gly Asp Gly Ile Gly
1               5                   10                  15

Lys Glu Val Leu Pro Glu Gly Ile Arg Val Leu Gln Ala Ala Ala Glu
                20                  25                  30

Arg Trp Gly Phe Ala Leu Ser Phe Glu Gln Met Glu Trp Ala Ser Cys
            35                  40                  45

Glu Tyr Tyr Ser His His Gly Lys Met Met Pro Asp Asp Trp His Glu
        50                  55                  60

Gln Leu Ser Arg Phe Asp Ala Ile Tyr Phe Gly Ala Val Gly Trp Pro
65                  70                  75                  80

Asp Thr Val Pro Asp His Ile Ser Leu Trp Gly Ser Leu Leu Lys Phe
                85                  90                  95

Arg Arg Glu Phe Asp Gln Tyr Val Asn Leu Arg Pro Val Arg Leu Phe
            100                 105                 110

Pro Gly Val Pro Cys Pro Leu Ala Gly Lys Gln Pro Gly Asp Ile Asp
        115                 120                 125

Phe Tyr Val Val Arg Glu Asn Thr Glu Gly Glu Tyr Ser Ser Leu Gly
    130                 135                 140

Gly Arg Val Asn Glu Gly Thr Glu His Glu Val Val Ile Gln Glu Ser
145                 150                 155                 160

Val Phe Thr Arg Arg Gly Val Asp Arg Ile Leu Arg Tyr Ala Phe Glu
                165                 170                 175

Leu Ala Gln Ser Arg Pro Arg Lys Thr Leu Thr Ser Ala Thr Lys Ser
            180                 185                 190

Asn Gly Leu Ala Ile Ser Met Pro Tyr Trp Asp Glu Arg Val Glu Ala
        195                 200                 205

Met Ala Glu Asn Tyr Pro Glu Ile Arg Trp Asp Lys Gln His Ile Asp
    210                 215                 220

Ile Leu Cys Ala Arg Phe Val Met Gln Pro Glu Arg Phe Asp Val Val
```

| | | | | | | | | | | | | | | |
|---|---|---|---|---|---|---|---|---|---|---|---|---|---|---|
| | | 225 | | | | 230 | | | | 235 | | | | 240 |

Val Ala Ser Asn Leu Phe Gly Asp Ile Leu Ser Asp Leu Gly Pro Ala
                    245                    250                    255

Cys Thr Gly Thr Ile Gly Ile Ala Pro Ser Ala Asn Leu Asn Pro Glu
              260                    265                    270

Arg Thr Phe Pro Ser Leu Phe Glu Pro Val His Gly Ser Ala Pro Asp
        275                    280                    285

Ile Tyr Gly Lys Asn Ile Ala Asn Pro Ile Ala Thr Ile Trp Ala Gly
290                    295                    300

Ala Met Met Leu Asp Phe Leu Gly Asn Gly Asp Glu Arg Phe Gln Gln
305              310                    315                    320

Ala His Asn Gly Ile Leu Ala Val Ile Glu Glu Val Ile Ala His Gly
              325                    330                    335

Pro Lys Thr Pro Asp Met Lys Gly Ser Ala Thr Pro Gln Val Ala
        340                    345                    350

Asp Ala Ile Cys Lys Ile Leu Arg
        355                    360

<210> SEQ ID NO 150
<211> LENGTH: 363
<212> TYPE: PRT
<213> ORGANISM: Pseudomonas putida

<400> SEQUENCE: 150

Met Ser Lys Pro Phe Arg Ile Ala Ala Ile Pro Gly Asp Gly Ile Gly
1                 5                    10                    15

Asn Glu Val Leu Pro Glu Gly Ile Arg Val Val Glu Ala Ala Ala Arg
              20                    25                    30

Lys His Gly Leu Asp Ile Ser Phe Glu Phe Phe Glu Trp Ala Ser Cys
        35                    40                    45

Asp Tyr Tyr Leu Ala His Gly Lys Met Met Pro Asp Asp Trp Phe Glu
    50                    55                    60

Gln Leu Lys Gly Phe Asp Ala Leu Tyr Phe Gly Ala Val Gly Trp Pro
65                    70                    75                    80

Asp Lys Val Pro Asp His Ile Ser Leu Trp Gly Ser Leu Leu Lys Phe
              85                    90                    95

Arg Arg Asp Phe Asp Gln Tyr Val Asn Ile Arg Pro Val Arg Leu Phe
            100                    105                  110

Pro Gly Val Pro Cys Pro Leu Ala Gly Arg Glu Pro Gly Asp Ile Asp
        115                    120                    125

Phe Val Val Ile Arg Glu Asn Thr Glu Gly Glu Tyr Ser Ser Leu Gly
    130                    135                    140

Gly Arg Met Phe Glu Gly Thr Glu Asn Glu Phe Val Leu Gln Glu Ser
145                    150                    155                    160

Val Phe Thr Arg Arg Gly Val Asp Arg Ile Leu Lys Tyr Ala Phe Asp
              165                    170                    175

Val Ala Gln Thr Arg Glu Arg Lys His Val Thr Ser Ala Thr Lys Ser
        180                    185                    190

Asn Gly Met Ala Val Ser Met Pro Tyr Trp Asp Glu Arg Thr Ala Ala
            195                    200                    205

Met Ala Ala Asn Tyr Pro Glu Ile Ser Trp Asp Lys Gln His Ile Asp
    210                    215                    220

Ile Leu Cys Ala Arg Phe Val Leu Gln Pro Asp Arg Phe Asp Val Val
225                    230                    235                    240

Val Ala Ser Asn Leu Phe Gly Asp Ile Leu Ser Asp Leu Gly Pro Ala

```
                   245                 250                 255
Cys Ala Gly Thr Ile Gly Ile Ala Pro Ser Ala Asn Leu Asn Pro Glu
                260                 265                 270

Arg Lys Phe Pro Ser Leu Phe Glu Pro Val His Gly Ser Ala Pro Asp
            275                 280                 285

Ile Tyr Gly Lys Asn Ile Ala Asn Pro Ile Ala Met Ile Trp Ser Gly
        290                 295                 300

Ala Leu Met Leu Asp Phe Leu Gly Asn Asp Gly Ala Asp Pro Arg Tyr
305                 310                 315                 320

Arg Ala Ala His Asp Asp Ile Leu Lys Ala Ile Glu Gln Val Ile Ala
                325                 330                 335

Ala Gly Asp Val Thr Arg Asp Met Gly Gly Gln Gln Ser Thr Gln Gln
                340                 345                 350

Val Gly Gln Ala Ile Thr Ala Leu Val Glu Ala
                355                 360

<210> SEQ ID NO 151
<211> LENGTH: 345
<212> TYPE: PRT
<213> ORGANISM: Thermus thermophilus

<400> SEQUENCE: 151

Met Lys Val Ala Val Leu Pro Gly Asp Gly Ile Gly Pro Glu Val Thr
1               5                   10                  15

Glu Ala Ala Leu Lys Val Leu Arg Ala Leu Asp Glu Ala Glu Gly Leu
                20                  25                  30

Gly Leu Ala Tyr Glu Val Phe Pro Phe Gly Ala Ala Ile Asp Ala
            35                  40                  45

Phe Gly Glu Pro Phe Pro Glu Pro Thr Arg Lys Gly Val Glu Glu Ala
        50                  55                  60

Glu Ala Val Leu Leu Gly Ser Val Gly Gly Pro Lys Trp Asp Gly Leu
65                  70                  75                  80

Pro Arg Lys Ile Arg Pro Glu Thr Gly Leu Leu Ser Leu Arg Lys Ser
                85                  90                  95

Gln Asp Leu Phe Ala Asn Leu Arg Pro Ala Lys Val Phe Pro Gly Leu
            100                 105                 110

Glu Arg Leu Ser Pro Leu Lys Glu Glu Ile Ala Arg Gly Val Asp Val
        115                 120                 125

Leu Ile Val Arg Glu Leu Thr Gly Gly Ile Tyr Phe Gly Glu Pro Arg
130                 135                 140

Gly Met Ser Glu Ala Glu Ala Trp Asn Thr Glu Arg Tyr Ser Lys Pro
145                 150                 155                 160

Glu Val Glu Arg Val Ala Arg Val Ala Phe Glu Ala Ala Arg Lys Arg
                165                 170                 175

Arg Lys His Val Val Ser Val Asp Lys Ala Asn Val Leu Glu Val Gly
            180                 185                 190

Glu Phe Trp Arg Lys Thr Val Glu Glu Val Gly Arg Gly Tyr Pro Asp
        195                 200                 205

Val Ala Leu Glu His Gln Tyr Val Asp Ala Met Ala Met His Leu Val
210                 215                 220

Arg Ser Pro Ala Arg Phe Asp Val Val Thr Gly Asn Ile Phe Gly
225                 230                 235                 240

Asp Ile Leu Ser Asp Leu Ala Ser Val Leu Pro Gly Ser Leu Gly Leu
            245                 250                 255

Leu Pro Ser Ala Ser Leu Gly Arg Gly Thr Pro Val Phe Glu Pro Val
```

```
                       260                 265                 270
His Gly Ser Ala Pro Asp Ile Ala Gly Lys Gly Ile Ala Asn Pro Thr
            275                 280                 285

Ala Ala Ile Leu Ser Ala Ala Met Met Leu Glu His Ala Phe Gly Leu
        290                 295                 300

Val Glu Leu Ala Arg Lys Val Glu Asp Ala Val Ala Lys Ala Leu Leu
305                 310                 315                 320

Glu Thr Pro Pro Asp Leu Gly Gly Ser Ala Gly Thr Glu Ala Phe
                325                 330                 335

Thr Ala Thr Val Leu Arg His Leu Ala
            340                 345

<210> SEQ ID NO 152
<211> LENGTH: 358
<212> TYPE: PRT
<213> ORGANISM: Acidithiobacillus ferrooxidans

<400> SEQUENCE: 152

Met Lys Lys Ile Ala Ile Phe Ala Gly Asp Gly Ile Gly Pro Glu Ile
1               5                   10                  15

Val Ala Ala Ala Arg Gln Val Leu Ala Val Asp Gln Ala Ala Arg
            20                  25                  30

Leu Gly Leu His Cys Ser Glu Gly Leu Val Gly Gly Ala Ala Leu Asp
        35                  40                  45

Ala Ser Asp Asp Pro Leu Pro Ala Ala Ser Leu Gln Leu Ala Leu Glu
    50                  55                  60

Ala Asp Ala Val Ile Leu Gly Ala Val Gly Gly Pro Arg Trp Asp Ala
65                  70                  75                  80

Tyr Pro Pro Ala Lys Arg Pro Glu Gln Gly Leu Leu Arg Leu Arg Lys
                85                  90                  95

Gly Leu Asp Leu Tyr Ala Asn Leu Arg Pro Ala Gln Ile Phe Pro Gln
            100                 105                 110

Leu Leu Asp Ala Ser Pro Leu Arg Pro Glu Leu Val Arg Asp Val Asp
        115                 120                 125

Ile Leu Val Val Arg Glu Leu Thr Gly Asp Ile Tyr Phe Gly Gln Pro
    130                 135                 140

Arg Gly Leu Glu Val Val Asp Gly Lys Arg Arg Gly Phe Asn Thr Met
145                 150                 155                 160

Val Tyr Asp Glu Asp Glu Ile Arg Arg Ile Ala His Val Ala Phe Arg
                165                 170                 175

Ala Ala Gln Gly Arg Arg Lys Gln Leu Cys Ser Val Asp Lys Ala Asn
            180                 185                 190

Val Leu Glu Thr Thr Arg Leu Trp Arg Glu Val Val Thr Glu Val Ala
        195                 200                 205

Gln Asp Tyr Pro Asp Val Gln Leu Ser His Met Tyr Val Asp Asn Ala
    210                 215                 220

Ala Met Gln Leu Ile Arg Ala Pro Ala Gln Phe Asp Val Leu Leu Thr
225                 230                 235                 240

Gly Asn Met Phe Gly Asp Ile Leu Ser Asp Glu Ala Ser Gln Leu Thr
                245                 250                 255

Gly Ser Ile Gly Met Leu Pro Ser Ala Ser Leu Gly Glu Gly Arg Ala
            260                 265                 270

Met Tyr Glu Pro Ile His Gly Ser Ala Pro Asp Ile Ala Gly Gln Asp
        275                 280                 285

Lys Ala Asn Pro Leu Ala Thr Ile Leu Ser Val Ala Met Met Leu Arg
```

```
                 290                 295                 300
Tyr Ser Leu Gly Ala Glu Leu Trp Ala Gln Arg Val Glu Ala Val
305                 310                 315                 320

Gln Arg Val Leu Asp Gln Gly Leu Arg Thr Ala Asp Ile Ala Ala Pro
            325                 330                 335

Gly Ala Pro Val Ile Gly Thr Lys Ala Met Gly Ala Ala Val Val Asp
            340                 345                 350

Ala Leu Asn Phe Lys Asp
        355

<210> SEQ ID NO 153
<211> LENGTH: 364
<212> TYPE: PRT
<213> ORGANISM: Saccharomyces cerevisiae

<400> SEQUENCE: 153

Met Ser Gly Pro Lys Lys Ile Val Val Leu Pro Gly Asp His Val Gly
1               5                   10                  15

Gln Glu Ile Thr Ala Glu Ala Ile Lys Val Leu Lys Ala Ile Ser Asp
            20                  25                  30

Val Arg Ser Asn Val Lys Phe Asp Phe Glu Asn His Leu Ile Gly Gly
        35                  40                  45

Ala Ala Ile Asp Ala Thr Gly Val Pro Leu Pro Asp Glu Ala Leu Glu
    50                  55                  60

Ala Ser Lys Lys Ala Asp Ala Val Leu Leu Gly Ala Val Gly Gly Pro
65                  70                  75                  80

Lys Trp Gly Thr Gly Ser Val Arg Pro Glu Gln Gly Leu Leu Lys Ile
                85                  90                  95

Arg Lys Glu Leu Gln Leu Tyr Ala Asn Leu Arg Pro Cys Asn Phe Ala
            100                 105                 110

Ser Asp Ser Leu Leu Asp Leu Ser Pro Ile Lys Pro Gln Phe Ala Lys
        115                 120                 125

Gly Thr Asp Phe Val Val Val Arg Glu Leu Val Gly Gly Ile Tyr Phe
    130                 135                 140

Gly Lys Arg Lys Glu Asp Asp Gly Asp Gly Val Ala Trp Asp Ser Glu
145                 150                 155                 160

Gln Tyr Thr Val Pro Glu Val Gln Arg Ile Thr Arg Met Ala Ala Phe
                165                 170                 175

Met Ala Leu Gln His Glu Pro Pro Leu Pro Ile Trp Ser Leu Asp Lys
            180                 185                 190

Ala Asn Val Leu Ala Ser Ser Arg Leu Trp Arg Lys Thr Val Glu Glu
        195                 200                 205

Thr Ile Lys Asn Glu Phe Pro Thr Leu Lys Val Gln His Gln Leu Ile
    210                 215                 220

Asp Ser Ala Ala Met Ile Leu Val Lys Asn Pro Thr His Leu Asn Gly
225                 230                 235                 240

Ile Ile Ile Thr Ser Asn Met Phe Gly Asp Ile Ile Ser Asp Glu Ala
                245                 250                 255

Ser Val Ile Pro Gly Ser Leu Gly Leu Leu Pro Ser Ala Ser Leu Ala
            260                 265                 270

Ser Leu Pro Asp Lys Asn Thr Ala Phe Gly Leu Tyr Glu Pro Cys His
        275                 280                 285

Gly Ser Ala Pro Asp Leu Pro Lys Asn Lys Val Asn Pro Ile Ala Thr
    290                 295                 300

Ile Leu Ser Ala Ala Met Met Leu Lys Leu Ser Leu Asn Leu Pro Glu
```

```
305            310              315              320
Glu Gly Lys Ala Ile Glu Asp Ala Val Lys Val Leu Asp Ala Gly
            325              330              335

Ile Arg Thr Gly Asp Leu Gly Gly Ser Asn Ser Thr Thr Glu Val Gly
            340              345              350

Asp Ala Val Ala Glu Glu Val Lys Lys Ile Leu Ala
            355              360
```

```
<210> SEQ ID NO 154
<211> LENGTH: 1053
<212> TYPE: DNA
<213> ORGANISM: Saccharomyces cerevisiae

<400> SEQUENCE: 154
atgaaatcac tcactattgg tcttatcccc ggtgacggta tcggtaagga agtcattcct      60
gctggtaagc aagttttgga aaaccttaac tccaagcacg gcctaagctt caactttatt     120
gatctctacg ccggtttcca acattccaa gaaacaggaa aggcgttgcc tgatgagact     180
gttaaagtgt tgaaggaaca atgtcaaggt gctcttttcg gtgcagttca gtctccaact     240
actaaggtgg aaggttactc ctcaccaatt gttgctctaa ggagggaaat gggccttttc     300
gctaatgttc gtcctgttaa gtctgtagag ggagaaaagg gtaaaccaat tgacatggtt     360
atcgtctgtg aaaatactga ggacctgtac attaaaattg aaaaaacata cattgacaag     420
gccacaggta caagagttgc tgatgccaca agagaatat ccgaaattgc aacaagaaga     480
attgcaacca ttgcattaga tattgccttg aaaagattac aaacaagagg ccaagccact     540
ttgacagtga ctcataaatc aaatgttcta tctcaaagtg atggtctatt cagagaaatc     600
tgtaaggaag tctacgaatc taacaaggac aagtacggtc aaatcaaata taacgaacaa     660
attgtggatt ccatggttta taggctgttc agagaaccac aatgttttga tgtgatagtg     720
gcaccaaacc tatacgggga tatattatct gacggtgctg ctgctttagt cggttcatta     780
ggtgttgttc aagcgccaa cgtaggtcca gaaattgtca ttggtgaacc atgccatggt     840
tctgcaccag atattgctgg taaaggtatt gctaacccaa tcgccactat aagatctact     900
gctttgatgt tggaattctt gggccacaac gaagctgccc aagatatcta caaggctgtt     960
gatgctaact aagagagggg ttctatcaag acaccagatt taggtggtaa ggcttctact    1020
caacaagtcg ttgacgacgt tttgtcgaga tta                                 1053
```

```
<210> SEQ ID NO 155
<211> LENGTH: 351
<212> TYPE: PRT
<213> ORGANISM: Saccharomyces cerevisiae

<400> SEQUENCE: 155

Met Lys Ser Leu Thr Ile Gly Leu Ile Pro Gly Asp Gly Ile Gly Lys
1               5                   10                  15

Glu Val Ile Pro Ala Gly Lys Gln Val Leu Glu Asn Leu Asn Ser Lys
            20                  25                  30

His Gly Leu Ser Phe Asn Phe Ile Asp Leu Tyr Ala Gly Phe Gln Thr
        35                  40                  45

Phe Gln Glu Thr Gly Lys Ala Leu Pro Asp Glu Thr Val Lys Val Leu
    50                  55                  60

Lys Glu Gln Cys Gln Gly Ala Leu Phe Gly Ala Val Gln Ser Pro Thr
65                  70                  75                  80

Thr Lys Val Glu Gly Tyr Ser Ser Pro Ile Val Ala Leu Arg Arg Glu
                85                  90                  95
```

Met Gly Leu Phe Ala Asn Val Arg Pro Val Lys Ser Val Glu Gly Glu
            100                 105                 110

Lys Gly Lys Pro Ile Asp Met Val Ile Val Cys Glu Asn Thr Glu Asp
        115                 120                 125

Leu Tyr Ile Lys Ile Glu Lys Thr Tyr Ile Asp Lys Ala Thr Gly Thr
    130                 135                 140

Arg Val Ala Asp Ala Thr Lys Arg Ile Ser Glu Ile Ala Thr Arg Arg
145                 150                 155                 160

Ile Ala Thr Ile Ala Leu Asp Ile Ala Leu Lys Arg Leu Gln Thr Arg
                165                 170                 175

Gly Gln Ala Thr Leu Thr Val Thr His Lys Ser Asn Val Leu Ser Gln
            180                 185                 190

Ser Asp Gly Leu Phe Arg Glu Ile Cys Lys Glu Val Tyr Glu Ser Asn
        195                 200                 205

Lys Asp Lys Tyr Gly Gln Ile Lys Tyr Asn Glu Gln Ile Val Asp Ser
    210                 215                 220

Met Val Tyr Arg Leu Phe Arg Glu Pro Gln Cys Phe Asp Val Ile Val
225                 230                 235                 240

Ala Pro Asn Leu Tyr Gly Asp Ile Leu Ser Asp Gly Ala Ala Ala Leu
                245                 250                 255

Val Gly Ser Leu Gly Val Val Pro Ser Ala Asn Val Gly Pro Glu Ile
            260                 265                 270

Val Ile Gly Glu Pro Cys His Gly Ser Ala Pro Asp Ile Ala Gly Lys
        275                 280                 285

Gly Ile Ala Asn Pro Ile Ala Thr Ile Arg Ser Thr Ala Leu Met Leu
    290                 295                 300

Glu Phe Leu Gly His Asn Glu Ala Ala Gln Asp Ile Tyr Lys Ala Val
305                 310                 315                 320

Asp Ala Asn Leu Arg Glu Gly Ser Ile Lys Thr Pro Asp Leu Gly Gly
                325                 330                 335

Lys Ala Ser Thr Gln Gln Val Val Asp Asp Val Leu Ser Arg Leu
            340                 345                 350

<210> SEQ ID NO 156
<211> LENGTH: 972
<212> TYPE: DNA
<213> ORGANISM: Acidaminococcus fermentans

<400> SEQUENCE: 156
ggatccatga gtaaagtaat gacgttaaaa gacgcaatcg ccaagtatgt gcacagtggt      60
gatcacattg ctctgggtgg tttttacgacg gaccgtaaac cctatgcggc tgtgttcgaa    120
atcctgagac agggtatcac ggatctgacc ggtctgggcg gcgctgccgg cggcgactgg    180
gatatgctga tcggcaacgg ccgtgtgaaa gcctacatca actgctacac cgccaactcc    240
ggtgtgacca acgtttccag acggttcaga aaatggttcg aagccggcaa actgaccatg    300
gaagactatt cccaggatgt tatctacatg atgtggcatg ccgccgctct gggcctgccc    360
ttcctgcctg taaccctgat gcagggctcc ggcctgaccg atgaatgggg catcagcaag    420
gaagtccgta aaaccctgga caaagttcct gatgacaaat caaatacat cgacaacccc    480 ttcaaaccgg gtgaaaaagt cgtggctgtt cctgttccgc aggttgatgt ggccatcatc    540
catgcccagc aggcttctcc cgatggcacc gttcgcatct ggggcggcaa attccaggat    600
gtggatattg ctgaagcagc caatacacc atcgttacct gcgaagaaat catttctgat    660
gaagaaatca aagagatcc caccaagaac gatatccccg gcatgtgcgt agatgctgtt    720

```
gtcctggctc cttacggtgc acatccttct cagtgctatg gcctgtacga ctacgacaat      780
ccgttcctga aagtctatga caaggtctcc aagacccagg aagacttcga tgccttctgc      840
aaggaatggg tgttcgacct gaaggatcat gacgaatacc tgaacaaact gggtgccact      900
cgtctgatca acctgaaggt tgttcctggt ctgggctacc acatcgacat gacgaaggag      960
gacaaagtcg ac                                                          972

<210> SEQ ID NO 157
<211> LENGTH: 972
<212> TYPE: DNA
<213> ORGANISM: Artificial Sequence
<220> FEATURE:
<223> OTHER INFORMATION: Codon optimized glutaconate CoA-transferase
      subunit A polynucleotide

<400> SEQUENCE: 157
ggatccatgt caaaagttat gacattaaag gacgctattg ctaaatacgt ccactcaggt       60
gaccacatag ctttgggtgg tttcacaact gacaggaagc cttacgctgc agtcttcgag      120
attttgaggc agggtattac tgacttgact ggtttgggtg gtgctgcagg tggtgactgg      180
gacatgttga taggaaacgg aagggttaag gcatacataa actgttacac agcaaactca      240
ggtgtcacaa acgtctctag gaggttcagg aagtggttcg aggctggtaa gttgacaatg      300
gaagattatt cacaggatgt tatttacatg atgtggcacg cagcagcatt gggtttgcct      360
ttcttgcctg tcacattgat gcagggatca ggtttgactg acgagtgggg tatttctaag      420
gaggttagaa agactttgga taaagtccct gacgacaagt tcaagtatat agacaaccca      480
ttcaagccag gtgagaaggt cgtcgctgtc ccagtcccac aagttgacgt cgctattatt      540
cacgctcagc aggcatctcc agacggaact gtcaggatat ggggaggtaa gttccaggac      600
gttgacattg cagaggcagc aaagtacaca attgtcacat gcgaggaaat aatttctgac      660
gaggagataa ggagggaccc tacaaagaat gacattcctg gaatgtgcgt tgacgcagtc      720
gtcttggctc catatggtgc acacccatca cagtgctacg gtttgtacga ctacgataac      780
ccttttttga aggtctacga caaagtctca aagactcagg aagacttcga cgctttctgc      840
aaggaatggg tcttcgactt gaaggatcac gacgagtatt tgaacaagtt aggagcaaca      900
aggttaataa acttgaaagt cgtcccaggt ttgggttacc acatagacat gactaaggaa      960
gacaaggtcg ac                                                          972

<210> SEQ ID NO 158
<211> LENGTH: 322
<212> TYPE: PRT
<213> ORGANISM: Acidaminococcus fermentans

<400> SEQUENCE: 158

Met Ser Lys Val Met Thr Leu Lys Asp Ala Ile Ala Lys Tyr Val His
1               5                   10                  15

Ser Gly Asp His Ile Ala Leu Gly Gly Phe Thr Thr Asp Arg Lys Pro
            20                  25                  30

Tyr Ala Ala Val Phe Glu Ile Leu Arg Gln Gly Ile Thr Asp Leu Thr
        35                  40                  45

Gly Leu Gly Gly Ala Ala Gly Gly Asp Trp Asp Met Leu Ile Gly Asn
    50                  55                  60

Gly Arg Val Lys Ala Tyr Ile Asn Cys Tyr Thr Ala Asn Ser Gly Val
65                  70                  75                  80

Thr Asn Val Ser Arg Arg Phe Arg Lys Trp Phe Glu Ala Gly Lys Leu
```

```
                    85                  90                  95
Thr Met Glu Asp Tyr Ser Gln Asp Val Ile Tyr Met Met Trp His Ala
                100                 105                 110

Ala Ala Leu Gly Leu Pro Phe Leu Pro Val Thr Leu Met Gln Gly Ser
            115                 120                 125

Gly Leu Thr Asp Glu Trp Gly Ile Ser Lys Glu Val Arg Lys Thr Leu
        130                 135                 140

Asp Lys Val Pro Asp Lys Phe Lys Tyr Ile Asp Asn Pro Phe Lys
145                 150                 155                 160

Pro Gly Glu Lys Val Val Ala Val Pro Val Pro Gln Val Asp Val Ala
                165                 170                 175

Ile Ile His Ala Gln Gln Ala Ser Pro Asp Gly Thr Val Arg Ile Trp
            180                 185                 190

Gly Gly Lys Phe Gln Asp Val Asp Ile Ala Glu Ala Ala Lys Tyr Thr
        195                 200                 205

Ile Val Thr Cys Glu Glu Ile Ile Ser Asp Glu Ile Arg Arg Asp
210                 215                 220

Pro Thr Lys Asn Asp Ile Pro Gly Met Cys Val Asp Ala Val Val Leu
225                 230                 235                 240

Ala Pro Tyr Gly Ala His Pro Ser Gln Cys Tyr Gly Leu Tyr Asp Tyr
                245                 250                 255

Asp Asn Pro Phe Leu Lys Val Tyr Asp Lys Val Ser Lys Thr Gln Glu
            260                 265                 270

Asp Phe Asp Ala Phe Cys Lys Glu Trp Val Phe Asp Leu Lys Asp His
        275                 280                 285

Asp Glu Tyr Leu Asn Lys Leu Gly Ala Thr Arg Leu Ile Asn Leu Lys
    290                 295                 300

Val Val Pro Gly Leu Gly Tyr His Ile Asp Met Thr Lys Glu Asp Lys
305                 310                 315                 320

Val Asp

<210> SEQ ID NO 159
<211> LENGTH: 814
<212> TYPE: DNA
<213> ORGANISM: Acidaminococcus fermentans

<400> SEQUENCE: 159
gcggccgcat ggctgattac acgaattata ccaataaaga aatgcaggct gtgaccattg     60
ccaagcagat caaaaatggt caggttgtaa cggttggtac cggtctgcct ctgatcggcg    120
ccagcgtggc caagagagtc tatgctcctg actgccacat catcgtggaa agcggtctga    180
tggactgctc cccggtggaa gttccccgtt ccgtaggtga cctgcggttc atggctcact    240
gcggctgcat ctggccgaac gtccggttcg tgggcttcga atcaacgaa tacctgcaca    300 aggccaaccg tctgatcgcc ttcatcggcg ggcccagat cgatccgtac ggcaacgtga    360
actccacttc catcggtgat taccatcatc cgaaaacccg tttcaccggg tccggcggtg    420
ccaacggcat tgccacctac tccaacacca tcatcatgat gcagcatgaa aaacgcagat    480
tcatgaacaa aatcgactac gtgaccagcc cgggctggat cgacggccct ggcggacggg    540
aaagactggg tctgccccggc gatgtgggac ctcagctggt agtaaccgat aaagggatcc    600
tgaaattcga cgaaaagacc aaacggatgt acctggctgc ctactatccc acttcttctc    660
cggaagatgt actggaaaac accgggttcg acctggatgt atccaaggct gtggaactgg    720
aagctccgga tccggccgtc atcaaactga tccgtgaaga aatcgatccg ggcaggcct    780
```

```
ttatccaggt ccccacggaa gcaaaagcac tagt                                814
```

<210> SEQ ID NO 160
<211> LENGTH: 814
<212> TYPE: DNA
<213> ORGANISM: Artificial Sequence
<220> FEATURE:
<223> OTHER INFORMATION: Codon optimized gctB glutaconate
     CoA-transferase subunit B polynucleotide

<400> SEQUENCE: 160

```
gcggccgcat ggctgattat acaaactaca caaacaagga gatgcaggca gttacaattg    60
caaaacagat taagaacggt caggtcgtta cagtcggtac tggattgcca ttgattggtg   120
catcagtcgc taagagggtc tacgcaccag actgccacat tattgtcgag tcaggtttga   180
tggactgctc accagtcgag gtcccaaggt cagtcggtga tttgaggttc atggctcact   240
gcggttgcat ttggccaaac gtcaggttcg tcggtttcga gattaatgag tacttgcaca   300
aggcaaacag attgattgca ttcattggtg gtgctcagat agacccatac ggtaatgtca   360
attctacttc aattggtgac taccatcacc ctaagactag gttcactgga tctggtggtg   420
ctaacggtat agcaacttac tctaacacaa taataatgat gcaacatgag aagagaaggt   480
tcatgaataa gattgattac gtcacatcac caggttggat tgacggacca ggtggtaggg   540
agagattggg attgccaggt gacgtcggtc cacagttggt tgtcactgac aagggaattt   600
taaagttcga cgaaaagact aagagaatgt atttggcagc atactaccca acttcttctc   660
ctgaggacgt cttggagaac actggtttcg acttggatgt ctcaaaggca gtcgaattag   720
aggctcctga cccagcagtc ataaagttga taaggaggag gattgaccct ggtcaggctt   780
tcatacaggt cccaactgaa gctaaggcac tagt                               814
```

<210> SEQ ID NO 161
<211> LENGTH: 268
<212> TYPE: PRT
<213> ORGANISM: Acidaminococcus fermentans

<400> SEQUENCE: 161

```
Met Ala Asp Tyr Thr Asn Tyr Thr Asn Lys Glu Met Gln Ala Val Thr
1               5                   10                  15

Ile Ala Lys Gln Ile Lys Asn Gly Gln Val Val Thr Val Gly Thr Gly
            20                  25                  30

Leu Pro Leu Ile Gly Ala Ser Val Ala Lys Arg Val Tyr Ala Pro Asp
        35                  40                  45

Cys His Ile Ile Val Glu Ser Gly Leu Met Asp Cys Ser Pro Val Glu
    50                  55                  60

Val Pro Arg Ser Val Gly Asp Leu Arg Phe Met Ala His Cys Gly Cys
65                  70                  75                  80

Ile Trp Pro Asn Val Arg Phe Val Gly Phe Glu Ile Asn Glu Tyr Leu
                85                  90                  95

His Lys Ala Asn Arg Leu Ile Ala Phe Ile Gly Gly Ala Gln Ile Asp
            100                 105                 110

Pro Tyr Gly Asn Val Asn Ser Thr Ser Ile Gly Asp Tyr His His Pro
        115                 120                 125

Lys Thr Arg Phe Thr Gly Ser Gly Gly Ala Asn Gly Ile Ala Thr Tyr
    130                 135                 140

Ser Asn Thr Ile Ile Met Met Gln His Glu Lys Arg Arg Phe Met Asn
145                 150                 155                 160

Lys Ile Asp Tyr Val Thr Ser Pro Gly Trp Ile Asp Gly Pro Gly Gly
```

```
                    165                 170                 175
Arg Glu Arg Leu Gly Leu Pro Gly Asp Val Gly Pro Gln Leu Val Val
            180                 185                 190

Thr Asp Lys Gly Ile Leu Lys Phe Asp Glu Lys Thr Lys Arg Met Tyr
            195                 200                 205

Leu Ala Ala Tyr Tyr Pro Thr Ser Ser Pro Glu Asp Val Leu Glu Asn
            210                 215                 220

Thr Gly Phe Asp Leu Asp Val Ser Lys Ala Val Glu Leu Glu Ala Pro
225                 230                 235                 240

Asp Pro Ala Val Ile Lys Leu Ile Arg Glu Glu Ile Asp Pro Gly Gln
                245                 250                 255

Ala Phe Ile Gln Val Pro Thr Glu Ala Lys Ala Leu
            260                 265

<210> SEQ ID NO 162
<211> LENGTH: 1452
<212> TYPE: DNA
<213> ORGANISM: Clostridium symbiosum

<400> SEQUENCE: 162
ggatccatgg caaaacaagt tagtcctggc gttctcgcac ttcgcaaggt cgttgatgac      60
gtacacaaag aggcgcgcga ggccaaagca agaggcgagt tagtcggctg gtcctcatcc     120
aagttcccct tgtgagcttgc agcagctttt gatctgaatg ttatgtatcc ggagaaccag    180
gctgccggca tcgctgcaaa ccgttacggt gagatgatgt gccaggccgc tgaggatctt    240
ggctatgaca acgatatctg cggatatgcc cgtatcagtc tggcttatgc agccggtgtg    300
cgtgtatcac gcaaatatga tgctgaaacc ggtgaataca tcatcgatcc tgctacaggc    360
aaaccgttaa agacgcaga aggcaatgtg gtaatcgacg aagcaaccgg taaaccaaag    420
aaagatccaa agacacagac tccttatctt gtactggaca atctgcttga gattgaagct    480
cttccggacg gcccggagaa agaaagacgt ctggaggcaa tctctccaat ccgtcagatg    540
cgtattccgc agccggactt cgttctctgc tgtaacaata tctgcaactg tatgaccaaa    600
tggtatgaga atattgcccg tatgtgcaac gtaccgctga tcatgattga tattccgtat    660
aacaatacag tagaggttca tgacgataat gtaaaatatg tacgcgctca gttcgataag    720
gcaattaagc agttagaaga actcacaggc aagaaatttg acgagaagaa gtttgaaaaa    780
gcctgttcca tgctaaccg taccgcacag gcatggttaa aggtttgcga ttatcttcag    840
tataaaccgg ctccatacag cggtttcgac ctgttcaacc atatggctga cgtcgtaact    900
gcacgtgcca gagtggaagc cgctgaggca tttgagcttc tggcagacga tctggaagag    960
acagttaaga agggtgagac gacaactccg ttcccggaga ataccgtgt tatgttcgag   1020 ggtattcctt gctggccgaa gctgcctaac ctgttcaaac ctctgaaaga gcatggcgtc  1080
aacgttactg ccgttgttta tgcaccagct ttcggttttg tttataacaa catcgatgag   1140
atggcccgcg cttactacaa agctccgaac tccgtctgca tcgaacaggg tgttgactgg  1200
cgtgaaggta tctgccgcga caataaggta gatggcgttc ttgttcatta taacagaagc  1260
tgtaaaccgt ggagcggtta tatggctgag atgcagcggc gtttcactga agatctgggc  1320
gttccatgcg caggttttcga cggtgaccag gctgacccgc gtaacttcaa tgccgctcag  1380
tatgagaccc gagtacaggg ccttgtggag gcaatggaag caaataagca ggcaaaggag  1440
gcaaaggtcg ac                                                        1452

<210> SEQ ID NO 163
```

<211> LENGTH: 1452
<212> TYPE: DNA
<213> ORGANISM: Artificial Sequence
<220> FEATURE:
<223> OTHER INFORMATION: Codon optimized hgdA, (R)-2-hydroxyglutaryl-CoA
      dehydratase subunit A polynucleotide

<400> SEQUENCE: 163

```
ggatccatgg ctaaacaggt ctctccagga gtcttagcat taaggaaggt cgtcgatgac    60
gtccacaaag aggctaggga agcaaaggct aggggtgagt tggtcggttg gtcatcttca   120
aagttcccat gcgagttggc agcagctttc gacttgaacg tcatgtaccc agagaaccag   180
gcagctggta tagcagcaaa caggtacggt gagatgatgt gtcaggcagc tgaggacttg   240
ggatacgaca acgacatttg cggttacgct aggatttctt tggcatacgc agcaggtgtc   300
agggtctcaa gaaagtacga cgcagagaca ggagagtaca ttattgaccc agcaacagga   360
aagcctttga aggacgctga gggtaacgtc gtcattgatg aggcaactgg aaagccaaag   420
aaggacccaa agactcagac tccatacttg gtcttagata tttgttgga gatagaggct   480
ttgcctgacg gtccagagaa ggagaggagg ttggaagcaa tttctcctat aagacaaatg   540
aggattcctc aacctgactt tgtcttgtgt tgtaacaaca tatgtaattg catgacaaaa   600
tggtacgaga acattgctag gatgtgtaac gttcctttaa ttatgataga cataccttac   660
aacaatactg ttgaggtcca tgacgacaac gtcaagtacg tcagggcaca gtttgacaag   720
gcaataaaac aattggagga gttgactgga aagaaattcg acgagaagaa gtttgaaaag   780
gcttgctcta cgctaacag aactgctcag gcatggttga aggtctgcga ctacttgcag   840
tataagcctg ctccatactc tggatttgat ttattcaacc acatggctga cgtcgtcact   900
gctagggcta gagttgaggc tgcagaggca ttcgagttgt tggcagacga cttggaggag   960
acagttaaga agggagaaac tactactcct ttccctgaga agtacagggt catgttcgag  1020
ggaattcctt gctggccaaa gttgcctaac ttatttaaac cattgaagga gcacggagtc  1080
aacgttacag ctgtcgtcta cgctccagct ttcggttttg tttacaataa tattgacgag  1140
atggcaagag cttattacaa agctccaaac tctgtctgta tagaacaggg agttgactgg  1200
agagagggta tatgcagaga caacaaggtt gacggagtct tagtccacta caacaggtct  1260
tgcaagccat ggtctggata catggcagag atgcagagga ggtttacaga agacttggga  1320
gtcccttgcg ctggtttcga tggagaccaa gctgacccaa ggaacttcaa cgctgctcag  1380
tacgagacaa gggtccaagg attagtcgag gctatggagg ctaacaagca ggcaaaggaa  1440
gctaaggtcg ac                                                     1452
```

<210> SEQ ID NO 164
<211> LENGTH: 482
<212> TYPE: PRT
<213> ORGANISM: Clostridium symbiosum

<400> SEQUENCE: 164

```
Met Ala Lys Gln Val Ser Pro Gly Val Leu Ala Leu Arg Lys Val Val
 1               5                  10                  15

Asp Asp Val His Lys Glu Ala Arg Glu Ala Lys Ala Arg Gly Glu Leu
                20                  25                  30

Val Gly Trp Ser Ser Ser Lys Phe Pro Cys Glu Leu Ala Ala Ala Phe
            35                  40                  45

Asp Leu Asn Val Met Tyr Pro Glu Asn Gln Ala Ala Gly Ile Ala Ala
        50                  55                  60

Asn Arg Tyr Gly Glu Met Met Cys Gln Ala Ala Glu Asp Leu Gly Tyr
```

```
            65                  70                  75                  80
Asp Asn Asp Ile Cys Gly Tyr Ala Arg Ile Ser Leu Ala Tyr Ala Ala
                    85                  90                  95

Gly Val Arg Val Ser Arg Lys Tyr Asp Ala Glu Thr Gly Glu Tyr Ile
                100                 105                 110

Ile Asp Pro Ala Thr Gly Lys Pro Leu Lys Asp Ala Glu Gly Asn Val
            115                 120                 125

Val Ile Asp Glu Ala Thr Gly Lys Pro Lys Asp Pro Lys Thr Gln
        130                 135                 140

Thr Pro Tyr Leu Val Leu Asp Asn Leu Leu Glu Ile Glu Ala Leu Pro
145                 150                 155                 160

Asp Gly Pro Glu Lys Glu Arg Arg Leu Glu Ala Ile Ser Pro Ile Arg
                165                 170                 175

Gln Met Arg Ile Pro Gln Pro Asp Phe Val Leu Cys Cys Asn Asn Ile
                180                 185                 190

Cys Asn Cys Met Thr Lys Trp Tyr Glu Asn Ile Ala Arg Met Cys Asn
                195                 200                 205

Val Pro Leu Ile Met Ile Asp Ile Pro Tyr Asn Asn Thr Val Glu Val
        210                 215                 220

His Asp Asp Asn Val Lys Tyr Val Arg Ala Gln Phe Asp Lys Ala Ile
225                 230                 235                 240

Lys Gln Leu Glu Glu Leu Thr Gly Lys Lys Phe Asp Glu Lys Lys Phe
                245                 250                 255

Glu Lys Ala Cys Ser Asn Ala Asn Arg Thr Ala Gln Ala Trp Leu Lys
                260                 265                 270

Val Cys Asp Tyr Leu Gln Tyr Lys Pro Ala Pro Tyr Ser Gly Phe Asp
        275                 280                 285

Leu Phe Asn His Met Ala Asp Val Val Thr Ala Arg Ala Arg Val Glu
        290                 295                 300

Ala Ala Glu Ala Phe Glu Leu Leu Ala Asp Asp Leu Glu Glu Thr Val
305                 310                 315                 320

Lys Lys Gly Glu Thr Thr Thr Pro Phe Pro Glu Lys Tyr Arg Val Met
                325                 330                 335

Phe Glu Gly Ile Pro Cys Trp Pro Lys Leu Pro Asn Leu Phe Lys Pro
                340                 345                 350

Leu Lys Glu His Gly Val Asn Val Thr Ala Val Val Tyr Ala Pro Ala
                355                 360                 365

Phe Gly Phe Val Tyr Asn Asn Ile Asp Glu Met Ala Arg Ala Tyr Tyr
                370                 375                 380

Lys Ala Pro Asn Ser Val Cys Ile Glu Gln Gly Val Asp Trp Arg Glu
385                 390                 395                 400

Gly Ile Cys Arg Asp Asn Lys Val Asp Gly Val Leu Val His Tyr Asn
                405                 410                 415

Arg Ser Cys Lys Pro Trp Ser Gly Tyr Met Ala Glu Met Gln Arg Arg
                420                 425                 430

Phe Thr Glu Asp Leu Gly Val Pro Cys Ala Gly Phe Asp Gly Asp Gln
                435                 440                 445

Ala Asp Pro Arg Asn Phe Asn Ala Ala Gln Tyr Glu Thr Arg Val Gln
        450                 455                 460

Gly Leu Val Glu Ala Met Glu Ala Asn Lys Gln Ala Lys Glu Ala Lys
465                 470                 475                 480

Val Asp
```

<210> SEQ ID NO 165
<211> LENGTH: 1161
<212> TYPE: DNA
<213> ORGANISM: Clostridium symbiosum

<400> SEQUENCE: 165

```
ggatccatga gtatcaacgc attattggat gaatttaaag taaaggctgc cactccaaaa      60
cagcagcttg ctgaatataa agctcagggc aagaaagtaa tcggtgttct gccgtattac     120
gcaccggaag agcttgttta tgccgcaggt atggtgccga tgggaatctg gggttccaat     180
aacaagacta tcagccgtgc taaagaatac tgtgcaactt tctactgcac tatcgcacag     240
cttgctctgg agatgctgtt agacggcaca atggatcagc tggacggaat cattactcca     300
accatctgtg atacactgcg cccaatgagc cagaacttcc gtgttgctat gggagataag     360
atggcagtta tcttccttgc tcagcctcag aaccgttttg aagatttcgg tcttcagttc     420
agtgttgacc agtatacaaa tgttaagaaa gaactggaaa agttgccgg taaagagatt     480
accaacgagg cgattcagga tgccatcaaa gtatacaata gagccgtgc ggcccgccgt     540
aaattcgtag aactggcaag cgcacactgc gatgtcatta caccaaccaa gcgttctgca     600
gtactgaaat ccttcttctt tatggagaaa ccggaataca tagagaagct ggaagaattg     660
aacgcagagc ttgaaaaact tcctgtctgt gactggcagg gaaccaaggt tgttacatcc     720
ggtattatct gtgacaatcc aaagcttctt gaaatcttcg aagagaacaa cattgccatc     780
gccgcagacg acgttggcca tgagagccgt tccttccgtg tagacgctcc ggaggatgag     840
gcagatgcat taatgcact ggcaaaacag tttgccaata tggactatga cgttcttctg     900
tacgatccaa aatctacaga gaaccgccgc ggcgaattca ttgccaacat ggtaaaggaa     960
agcggcgctc agggactggt attgttcatg caacagttct gtgacccgga ggaaatggag    1020
tatccatact aaagaaggc attaaataat gcaggtattc cgcatatcaa actgggtatc    1080
gatcagcaga tgcgtgactt cggtcaggca agcacagcta tccaggcatt gcagatgta    1140
ctcgagatgc agaaagtcga c                                             1161
```

<210> SEQ ID NO 166
<211> LENGTH: 1161
<212> TYPE: DNA
<213> ORGANISM: Artificial Sequence
<220> FEATURE:
<223> OTHER INFORMATION: Codon optimized hgdB, (R)-2-hydroxyglutaryl-CoA dehydratase subunit B polynucleotide

<400> SEQUENCE: 166

```
ggatccatgt ctattaatgc attgttagac gagttcaagg tcaaggcagc tactccaaag      60
cagcagttgg cagagtataa ggctcagggt aagaaggtca taggagtctt gccttactac     120
gcacctgagg aattggtcta cgctgctggt atggtcccaa tgggtatatg gggttctaat     180
aataagacta tttctagagc taaggaatat tgtgctacat tctactgtac aattgctcag     240
ttggcattag aaatgttgtt ggatggtaca atggaccagt ggacggaat aataacacca     300
acaatttgtg acactttgag gccaatgtct cagaacttca gggtcgcaat gggtgataaa     360
atggctgtca tatttttagc tcagccacag aacaggttcg aggacttcgg tttgcagttc     420
tcagttgacc agtatacaaa cgtcaagaag gaattggaga aggtcgctgg taaggagata     480
actaacgagg ctatacagga cgctataaag gtttacaaca agtcaagggc tgcaaggaga     540
aagttcgtcg agtggcatc agctcactgc gacgtcatta ctccaacaaa gagatctgct     600
gtcttaaagt cttctttttt catggaaaag cctgagtaca ttgaaaagtt ggaagagttg     660
```

```
aacgcagagt tggaaaagtt gcctgtctgc gattggcagg gtactaaggt tgtcacatct    720
ggtataatat gcgacaatcc aaagttattg gaaattttcg aggaaaacaa cattgctata    780
gctgctgacg acgtcggtca cgagtctagg tcatttaggg ttgacgctcc tgaagacgag    840
gcagacgctt tgatggcatt ggctaagcag ttcgctaata tggattacga tgtcttattg    900
tacgacccta aatctactga aaataggaga ggagaattca ttgctaacat ggtcaaggag    960
tctggtgctc agggtttggt cttgttcatg caacagttct gcgacccaga ggagatggaa   1020 taccctttact taaagaaggc attgaataac gctggaatac cacacataaa attaggaatt   1080
gaccagcaga tgagggactt cggtcaggct tcaactgcaa tacaggcttt cgctgacgtc   1140
ttggagatgc agaaagtcga c                                             1161
```

<210> SEQ ID NO 167
<211> LENGTH: 385
<212> TYPE: PRT
<213> ORGANISM: Clostridium symbiosum

<400> SEQUENCE: 167

```
Met Ser Ile Asn Ala Leu Leu Asp Glu Phe Lys Val Lys Ala Ala Thr
1               5                   10                  15

Pro Lys Gln Gln Leu Ala Glu Tyr Lys Ala Gln Gly Lys Lys Val Ile
            20                  25                  30

Gly Val Leu Pro Tyr Tyr Ala Pro Glu Glu Leu Val Tyr Ala Ala Gly
        35                  40                  45

Met Val Pro Met Gly Ile Trp Gly Ser Asn Asn Lys Thr Ile Ser Arg
    50                  55                  60

Ala Lys Glu Tyr Cys Ala Thr Phe Tyr Cys Thr Ile Ala Gln Leu Ala
65                  70                  75                  80

Leu Glu Met Leu Leu Asp Gly Thr Met Asp Gln Leu Asp Gly Ile Ile
                85                  90                  95

Thr Pro Thr Ile Cys Asp Thr Leu Arg Pro Met Ser Gln Asn Phe Arg
            100                 105                 110

Val Ala Met Gly Asp Lys Met Ala Val Ile Phe Leu Ala Gln Pro Gln
        115                 120                 125

Asn Arg Phe Glu Asp Phe Gly Leu Gln Phe Ser Val Asp Gln Tyr Thr
    130                 135                 140

Asn Val Lys Lys Glu Leu Glu Lys Val Ala Gly Lys Glu Ile Thr Asn
145                 150                 155                 160

Glu Ala Ile Gln Asp Ala Ile Lys Val Tyr Asn Lys Ser Arg Ala Ala
                165                 170                 175

Arg Arg Lys Phe Val Glu Leu Ala Ser Ala His Cys Asp Val Ile Thr
            180                 185                 190

Pro Thr Lys Arg Ser Ala Val Leu Lys Ser Phe Phe Met Glu Lys
        195                 200                 205

Pro Glu Tyr Ile Glu Lys Leu Glu Glu Leu Asn Ala Glu Leu Glu Lys
    210                 215                 220

Leu Pro Val Cys Asp Trp Gln Gly Thr Lys Val Val Thr Ser Gly Ile
225                 230                 235                 240

Ile Cys Asp Asn Pro Lys Leu Leu Glu Ile Phe Glu Glu Asn Asn Ile
                245                 250                 255

Ala Ile Ala Ala Asp Asp Val Gly His Glu Ser Arg Ser Phe Arg Val
            260                 265                 270

Asp Ala Pro Glu Asp Glu Ala Asp Ala Leu Met Ala Leu Ala Lys Gln
        275                 280                 285
```

```
Phe Ala Asn Met Asp Tyr Asp Val Leu Leu Tyr Asp Pro Lys Ser Thr
    290                 295                 300
Glu Asn Arg Arg Gly Glu Phe Ile Ala Asn Met Val Lys Glu Ser Gly
305                 310                 315                 320
Ala Gln Gly Leu Val Leu Phe Met Gln Gln Phe Cys Asp Pro Glu Glu
                325                 330                 335
Met Glu Tyr Pro Tyr Leu Lys Lys Ala Leu Asn Asn Ala Gly Ile Pro
            340                 345                 350
His Ile Lys Leu Gly Ile Asp Gln Gln Met Arg Asp Phe Gly Gln Ala
        355                 360                 365
Ser Thr Ala Ile Gln Ala Phe Ala Asp Val Leu Glu Met Gln Lys Val
    370                 375                 380
Asp
385

<210> SEQ ID NO 168
<211> LENGTH: 794
<212> TYPE: DNA
<213> ORGANISM: Acidaminococcus fermentans

<400> SEQUENCE: 168
gaattcatga gtatctatac cttgggaatc gatgttggat ctactgcatc caagtgcatt      60
atcctgaaag atgaaaaga aatcgtggcg aaatccctgg tagccgtggg gaccggaact     120
tccggtcccg cacggtctat ttcggaagtc ctggaaaatg cccacatgaa aaagaagac     180 atggccttta ccctggctac cggctacgga cgcaattcgc tggaaggcat tgccgacaag     240
cagatgagcg aactgagctg ccatgccatg ggcgccagct ttatctggcc caacgtccat     300
accgtcatcg atatcggcgg gcaggatgtg aaggtcatcc atgtggaaaa cgggaccatg     360
accaatttcc agatgaatga taaatgcgct gccgggactg gccgtttcct ggatgttatg     420
gccaatatcc tggaagtgaa ggtttccgac ctggctgagc tgggagccaa atccaccaaa     480
cgggtggcta tcagctccac ctgtactgtg tttgcagaaa gtgaagtcat cagccagctg     540
tccaaaggaa ccgacaagat cgacatcatt gccgggatcc atcgttctgt agccagccgg     600
gtcattggtc ttgccaatcg ggtggggatt gtgaaagacg tggtcatgac cggcggtgta     660
gcccagaact atggcgtgag aggagccctg gaagaaggcc ttggcgtgga aatcaagacg     720
tctcccctgg ctcagtacaa cggtgccctg ggtgccgctc tgtatgcgta taaaaaagca     780
gccaaagcac tagt                                                      794

<210> SEQ ID NO 169
<211> LENGTH: 794
<212> TYPE: DNA
<213> ORGANISM: Artificial Sequence
<220> FEATURE:
<223> OTHER INFORMATION: Codon optimized hgdC (R)-2-hydroxyglutaryl-CoA
      dehydratase subunit C polynucleotide

<400> SEQUENCE: 169
gaattcatgt ctatatacac attgggtata gacgtcggtt ctactgcttc aaagtgcatt      60
attttgaagg acggaaagga gatagtcgca agtcattgg tcgctgtcgg tactggtaca     120
tctggtccag ctaggtctat atcagaggtc ttggaaaacg cacacatgaa gaaggaggac     180
atggctttca ctttagctac aggttacggt aggaactctt tggaaggaat agctgacaag     240
cagatgtctg agttgtcttg ccacgcaatg ggtgcttctt tcatatggcc aaacgtccac     300
actgtcatag acataggagg tcaggacgtc aaggtcattc acgtcgagaa cggaactatg     360
```

-continued

```
actaacttcc agatgaacga taagtgcgct gctggtacag gtagattctt ggacgttatg    420
gctaacatat tagaagtcaa ggtctctgac ttggctgagt tgggtgctaa gtcaactaag    480
agggtcgcaa tttcatcaac atgcactgtc ttcgctgagt ctgaggtcat atcacagtta    540 tcaaaggta cagacaagat agacataata gcaggtattc acaggtctgt cgcatctagg    600
gtcattggtt tggcaaatag ggtcggtatt gtcaaggacg tcgtcatgac aggaggagtc    660
gctcagaact acggtgtcag gggtgcattg gaggagggtt tgggtgtcga gataaagact    720
tctcctttgg ctcagtacaa cggagctttg ggtgcagcat tgtacgctta caagaaagct    780
gcaaaggcac tagt                                                      794
```

<210> SEQ ID NO 170
<211> LENGTH: 262
<212> TYPE: PRT
<213> ORGANISM: Acidaminococcus fermentans

<400> SEQUENCE: 170

```
Met Ser Ile Tyr Thr Leu Gly Ile Asp Val Gly Ser Thr Ala Ser Lys
1               5                   10                  15

Cys Ile Ile Leu Lys Asp Gly Lys Glu Ile Val Ala Lys Ser Leu Val
            20                  25                  30

Ala Val Gly Thr Gly Thr Ser Gly Pro Ala Arg Ser Ile Ser Glu Val
        35                  40                  45

Leu Glu Asn Ala His Met Lys Lys Glu Asp Met Ala Phe Thr Leu Ala
    50                  55                  60

Thr Gly Tyr Gly Arg Asn Ser Leu Glu Gly Ile Ala Asp Lys Gln Met
65                  70                  75                  80

Ser Glu Leu Ser Cys His Ala Met Gly Ala Ser Phe Ile Trp Pro Asn
                85                  90                  95

Val His Thr Val Ile Asp Ile Gly Gly Gln Asp Val Lys Val Ile His
            100                 105                 110

Val Glu Asn Gly Thr Met Thr Asn Phe Gln Met Asn Asp Lys Cys Ala
        115                 120                 125

Ala Gly Thr Gly Arg Phe Leu Asp Val Met Ala Asn Ile Leu Glu Val
    130                 135                 140

Lys Val Ser Asp Leu Ala Glu Leu Gly Ala Lys Ser Thr Lys Arg Val
145                 150                 155                 160

Ala Ile Ser Ser Thr Cys Thr Val Phe Ala Glu Ser Glu Val Ile Ser
                165                 170                 175

Gln Leu Ser Lys Gly Thr Asp Lys Ile Asp Ile Ala Gly Ile His
            180                 185                 190

Arg Ser Val Ala Ser Arg Val Ile Gly Leu Ala Asn Arg Val Gly Ile
        195                 200                 205

Val Lys Asp Val Val Met Thr Gly Gly Val Ala Gln Asn Tyr Gly Val
    210                 215                 220

Arg Gly Ala Leu Glu Glu Gly Leu Gly Val Glu Ile Lys Thr Ser Pro
225                 230                 235                 240

Leu Ala Gln Tyr Asn Gly Ala Leu Gly Ala Ala Leu Tyr Ala Tyr Lys
                245                 250                 255

Lys Ala Ala Lys Ala Leu
            260
```

<210> SEQ ID NO 171
<211> LENGTH: 1170
<212> TYPE: DNA
<213> ORGANISM: Desulfococcus multivorans

<400> SEQUENCE: 171

```
atggatttca acttatccaa agaactacag atgctgcaga agaggtccg caacttcgtc        60
aacaagaaga tcgtcccctt cgccgaccag tgggacaacg agaatcactt cccatacgag      120
gaggccgtcc ggcccatggg cgagctgggc ttcttcggga cggtgattcc cgaggagtac      180
ggcggcgaag gcatggacca gggatggctc gcggccatga tcgtcaccga ggagatcgca      240
aggggctcct ccgcactccg tgtccagctc aacatggagg tgctggggtg cgcctatacc      300
atcctgacct acgggagcga ggccctcaaa aagaaatacg tccccaagct ctccagcgcc      360
gaattcctgg gcggcttcgg catcaccgag cccgacgccg gctccgacgt catggccatg      420
tcctccacgg ccgaggacaa ggggaccac tggctcctca acggctccaa gacctggatc      480
tccaacgcgg cccaggccga cgtgctgatc tactatgcct acaccgacaa ggcggcgggc      540
tcccgggggc tttcggcctt cgtcatcgaa cccagaaact tccccggcat caagacctcc      600
aacctggaga agctgggatc ccacgcctcc cccaccggga gctcttcct cgacaacgtc       660
aaggtgccca aggagaacat cctcggcaag cccggcgacg gcgccaggat cgtcttcgga      720
tccctcaacc acaccggct tcagccgcc gccggcggc ttgggctcgc ccaggcctgc         780
ctggacgccg ccatcaagta ctgcaacgag cgccgccagt tcggcaagcc catcggcgat      840
ttccagatga accaggacat gatcgcccag atggccgtcg aggtggaggc ggcccgtctt      900
ctggcctaca aggctgccgc ggcaaaggac gagggccggc tcaacaacgg cctcgacgtg      960
gccatggcca agtatgccgc cggcgaagcc gtgagcaagt gcgccaatta cgccatgcgc     1020
atcctcgggg cctacggcta ctccaccgag taccccgtcg cccgcttcta ccgcgacgca     1080
cccacctatt acatggtgga gggctcggcc aacatctgca agatgatcat cgccctggat     1140
cagctggggg tcagaaaggc caaccggtaa                                      1170
```

<210> SEQ ID NO 172
<211> LENGTH: 1170
<212> TYPE: DNA
<213> ORGANISM: Artificial Sequence
<220> FEATURE:
<223> OTHER INFORMATION: Codon optimized gdh, glutaryl-CoA dehydrogenase polynucleotide

<400> SEQUENCE: 172

```
atggatttca atttgtctaa agaattgcaa atgttgcaaa agaagttag aaatttcgtt        60
aataaaaaaa ttgttccatt cgctgatcaa tgggataatg aaaatcattt cccatatgaa      120
gaagctgtta gaccaatggg tgaattgggt ttcttcggta ctgttattcc agaagaatat      180
ggtggtgaag gtatggatca aggttggttg gctgctatga tcgttactga agaaattgct      240
agaggttctt ctgctttgag agttcaattg aatatggaag ttttggttg tgcttatact      300
atcctgactt atggttctga agctttgaaa aaaaaatatg ttccaaaatt gtcttctgct      360
gaattcttgg gtggtttcgg tattactgaa ccagatgctg gttctgatgt tatggctatg      420
tcttctactg ctgaagataa aggtgatcat tggttgttga atggttctaa aacttggatt      480
tctaatgctg ctcaagctga tgttttgatt tattatgctt atactgataa ggctgctggt      540
tctagaggtt tgtctgcttt cgttattgaa ccaagaaatt tcccaggtat taaaacttct      600
aatttggaaa aattgggttc tcatgcttct ccaactggtg aattgttctt ggataatgtt      660
aaagttccaa aagaaaatat tttgggtaaa ccaggtgatg gtgctagaat tgttttcggt      720
tctttgaatc atactagatt gtctgctgct gctggtggtg ttggtttggc tcaagcttgt      780
```

```
ttggatgctg ctattaaata ttgtaatgaa agaagacaat tcggtaaacc aattggtgat    840
ttccaaatga atcaagatat gattgctcaa atggctgttg aagttgaagc tgctagattg    900
ttggcttata agctgctgc tgctaaagat gaaggtagat tgaataatgg tttggatgtt     960
gctatggcta aatatgctgc tggtgaagct gtttctaaat gtgctaatta tgctatgaga   1020
attttgggtg cttatggtta ttctactgaa tatccagttg ctagattcta tagagatgct   1080
ccaacttatt atatggttga aggttctgct aatatttgta aaatgattat tgctttggat   1140
caattgggtg ttagaaaagc taatagataa                                    1170

<210> SEQ ID NO 173
<211> LENGTH: 389
<212> TYPE: PRT
<213> ORGANISM: Desulfococcus multivorans

<400> SEQUENCE: 173
```

Met Asp Phe Asn Leu Ser Lys Glu Leu Gln Met Leu Gln Lys Glu Val
1               5                   10                  15

Arg Asn Phe Val Asn Lys Lys Ile Val Pro Phe Ala Asp Gln Trp Asp
            20                  25                  30

Asn Glu Asn His Phe Pro Tyr Glu Ala Val Arg Pro Met Gly Glu
        35                  40                  45

Leu Gly Phe Phe Gly Thr Val Ile Pro Glu Glu Tyr Gly Gly Glu Gly
    50                  55                  60

Met Asp Gln Gly Trp Leu Ala Ala Met Ile Val Thr Glu Glu Ile Ala
65                  70                  75                  80

Arg Gly Ser Ser Ala Leu Arg Val Gln Leu Asn Met Glu Val Leu Gly
                85                  90                  95

Cys Ala Tyr Thr Ile Leu Thr Tyr Gly Ser Glu Ala Leu Lys Lys Lys
            100                 105                 110

Tyr Val Pro Lys Leu Ser Ser Ala Glu Phe Leu Gly Gly Phe Gly Ile
        115                 120                 125

Thr Glu Pro Asp Ala Gly Ser Asp Val Met Ala Met Ser Ser Thr Ala
    130                 135                 140

Glu Asp Lys Gly Asp His Trp Leu Leu Asn Gly Ser Lys Thr Trp Ile
145                 150                 155                 160

Ser Asn Ala Ala Gln Ala Asp Val Leu Ile Tyr Tyr Ala Tyr Thr Asp
                165                 170                 175

Lys Ala Ala Gly Ser Arg Gly Leu Ser Ala Phe Val Ile Glu Pro Arg
            180                 185                 190

Asn Phe Pro Gly Ile Lys Thr Ser Asn Leu Glu Lys Leu Gly Ser His
        195                 200                 205

Ala Ser Pro Thr Gly Glu Leu Phe Leu Asp Asn Val Lys Val Pro Lys
    210                 215                 220

Glu Asn Ile Leu Gly Lys Pro Gly Asp Gly Ala Arg Ile Val Phe Gly
225                 230                 235                 240

Ser Leu Asn His Thr Arg Leu Ser Ala Ala Gly Gly Val Gly Leu
                245                 250                 255

Ala Gln Ala Cys Leu Asp Ala Ala Ile Lys Tyr Cys Asn Glu Arg Arg
            260                 265                 270

Gln Phe Gly Lys Pro Ile Gly Asp Phe Gln Met Asn Gln Asp Met Ile
        275                 280                 285

Ala Gln Met Ala Val Glu Val Glu Ala Ala Arg Leu Leu Ala Tyr Lys
    290                 295                 300

Ala Ala Ala Ala Lys Asp Glu Gly Arg Leu Asn Asn Gly Leu Asp Val

```
                305                 310                 315                 320
Ala Met Ala Lys Tyr Ala Ala Gly Glu Ala Val Ser Lys Cys Ala Asn
                325                 330                 335

Tyr Ala Met Arg Ile Leu Gly Ala Tyr Gly Tyr Ser Thr Glu Tyr Pro
                340                 345                 350

Val Ala Arg Phe Tyr Arg Asp Ala Pro Thr Tyr Tyr Met Val Glu Gly
                355                 360                 365

Ser Ala Asn Ile Cys Lys Met Ile Ile Ala Leu Asp Gln Leu Gly Val
                370                 375                 380

Arg Lys Ala Asn Arg
385
```